United States Patent [19]
Wityak et al.

[11] Patent Number: 6,130,231
[45] Date of Patent: Oct. 10, 2000

[54] INTEGRIN RECEPTOR ANTAGONISTS

[75] Inventors: John Wityak, West Grove; Aleksandra Ewa Tobin, Lincoln University, both of Pa.

[73] Assignee: DuPont Pharmaceuticals, Wilmington, Del.

[21] Appl. No.: 08/980,016

[22] Filed: Nov. 26, 1997

Related U.S. Application Data

[60] Provisional application No. 60/033,208, Nov. 27, 1996.

[51] Int. Cl.$^7$ .................. A61K 31/4709; A61K 31/472; A61K 31/496; A61K 31/5355; C07D 215/12; C07D 401/02; C07D 413/02; C07D 417/02

[52] U.S. Cl. .............................. 514/312; 514/63; 514/82; 514/183; 514/212; 514/218; 514/228.2; 514/235.2; 514/255; 514/256; 514/269; 514/272; 514/274; 514/275; 514/300; 514/303; 514/307; 540/487; 540/492; 540/542; 540/553; 540/597; 544/57; 544/62; 544/69; 544/128; 544/180; 544/212; 544/219; 544/229; 544/243; 544/297; 544/310; 544/312; 544/316; 544/319; 544/320; 544/328; 544/329; 544/331; 544/332; 544/333; 544/335; 544/337; 544/363; 546/14; 546/23; 546/118; 546/122; 546/146; 546/156

[58] Field of Search ................................. 514/63, 82, 183, 514/212, 218, 228.2, 235.2, 255, 256, 269, 272, 274, 275, 300, 303, 307, 312; 540/487, 492, 542, 553, 597; 544/57, 62, 69, 128, 180, 212, 219, 229, 243, 297, 310, 312, 316, 319, 320, 328, 329, 331, 332, 333, 335, 337, 363; 546/14, 23, 118, 122, 146, 156

[56] References Cited

U.S. PATENT DOCUMENTS 5,622,967   4/1997   Dolle et al. .............................. 514/312

FOREIGN PATENT DOCUMENTS

| 0614664 | 9/1994 | European Pat. Off. . |
| 0635492 | 1/1995 | European Pat. Off. . |
| WO 9422835 | 10/1994 | WIPO . |
| WO 9429273 | 12/1994 | WIPO . |
| WO 9618602 | 6/1996 | WIPO . |
| WO 9622288 | 7/1996 | WIPO . |
| 9626190 | 8/1996 | WIPO . |

*Primary Examiner*—Richard L. Raymond
*Assistant Examiner*—Brenda Coleman

[57] ABSTRACT

This invention relates to novel fused heterocycles which are useful as antagonists of the $\alpha_v\beta_3$ and related integrin receptors, to pharmaceutical compositions containing such compounds, processes for preparing such compounds, and to methods of using these compounds, alone or in combination with other therapeutic agents, for the inhibition of cell adhesion, the treatment of angiogenic disorders, inflammation, bone degradation, cancer metastasis, diabetic retinopathy, thrombosis, restenosis, macular degeneration, and other conditions mediated by cell adhesion and/or cell migration and/or angiogenesis.

18 Claims, No Drawings

INTEGRIN RECEPTOR ANTAGONISTS

This application claims the benefit of U.S. Provisional Application No. 60/033,208 filed Nov. 27, 1996.

FIELD OF THE INVENTION

This invention relates to novel fused heterocycles which are useful as antagonists of the $\alpha_v\beta_3$ and related integrin receptors, to pharmaceutical compositions containing such compounds, processes for preparing such compounds, and to methods of using these compounds, alone or in combination with other therapeutic agents, for the inhibition of cell adhesion and the treatment of angiogenic disorders, inflammation, bone degradation, tumors, metastases, thrombosis, and other cell aggregation-related conditions.

BACKGROUND OF THE INVENTION

Angiogenesis or neovascularization is critical for normal physiological processes such as embryonic development and wound repair (Folkman and Shing, J. Biol. Chem. 1992, 267:10931–10934; D'Amore and Thompson, Ann. Rev. Physiol. 1987, 49:453–464). However, angiogenesis occurs pathologically, for example, in ocular neovascularization (leading to diabetic retinopathy, neovascular glaucoma, retinal vein occlusion and blindness), in rheumatoid arthritis and in solid tumors (Folkman and Shing, J. Biol. Chem., 1992, 267:10931–10934; Blood and Zetter, Biochim. Biophys. Acta 1990, 1032:118–128).

Tumor dissemination, or metastasis, involves several distinct and complementary components, including the penetration and transversion of tumor cells through basement membranes and the establishment of self-sustaining tumor foci in diverse organ systems. To this end, the development and proliferation of new blood vessels, or angiogenesis, is critical to tumor survival. Without neovascularization, tumor cells lack the nourishment to divide and will not be able to leave the primary tumor site (Folkman and Shing, J. Biol. Chem. 1992, 267:10931–10934).

Inhibition of angiogenesis in animal models of cancer has been shown to result in tumor growth suppression and prevention of metastatic growth (Herblin et al., Exp. Opin. Ther. Patents. 1994, 1–14). Many angiogenic inhibitors have been directed toward blocking initial cytokine-dependent induction of new vessel growth, e.g. antibodies to endothelial cell growth factors. However, these approaches are problematic because tumor and inflammatory cells can secrete multiple activators of angiogenesis (Brooks, et al., Cell 1994, 79:1157–1164). Therefore, a more general approach that would allow inhibition of angiogenesis due to a variety of stimuli would be of benefit.

The integrin $\alpha_v\beta_3$ is preferentially expressed on angiogenic blood vessels in chick and man (Brooks, et al., Science 1994, 264:569–571; Enenstein and Kramer, J. Invest. Dermatol. 1994, 103:381–386). Integrin $\alpha_v\beta_3$ is the most promiscuous member of the integrin family, allowing endothelial cells to interact with a wide variety of extracellular matrix components (Hynes, Cell 1992, 69:11–25). These adhesive interactions are considered to be critical for angiogenesis since vascular cells must ultimately be capable of invading virtually all tissues.

While integrin $\alpha_v\beta_3$ promotes adhesive events important for angiogenesis, this receptor also transmits signals from the extracellular environment to the intracellular compartment (Leavesley, et al., J. Cell Biol. 1993, 121:163–170, 1993). For example, the interaction between the $\alpha_v\beta_3$ integrin and extracellular matrix components promotes a calcium signal required for cell motility.

During endothelium injury, the basement membrane zones of blood vessels express several adhesive proteins, including but not limited to von Willebrand factor, fibronectin, and fibrin. Additionally, several members of the integrin family of adhesion receptors are expressed on the surface of endothelial, smooth muscle and on other circulating cells. Among these integrins is $\alpha_v\beta_3$, the endothelial cell, fibroblast, and smooth muscle cell receptor for adhesive proteins including von Willebrand factor, fibrinogen (fibrin), vitronectin, thrombospondin, and osteopontin. These integrins initiate a calcium-dependent signaling pathway that can lead to endothelial cell, smooth muscle cell migration and, therefore, may play a fundamental role in vascular cell biology.

An antibody to the $\alpha_v\beta_3$ integrin has been developed that inhibits the interaction of this integrin with agonists such as vitronectin (Brooks, et al., Science 1994, 264:569–571). Application of this antibody has been shown to disrupt ongoing angiogenesis on the chick chorioallantoic membrane (CAM), leading to rapid regression of histologically distinct human tumor transplanted onto the CAM (Brooks, et al., Cell 1994, 79:1157–1164). In this model, antagonists of the $\alpha_v\beta_3$ integrin induced apoptosis of the proliferating angiogenic vascular cells, leaving pre-existing quiescent blood vessels unaffected. Thus, $\alpha_v\beta_3$ integrin antagonists have been shown to inhibit angiogenesis. Based on this property, therapeutic utility of such agents is expected in human diseases such as cancer, rheumatoid arthritis and ocular vasculopathies (Folkman and Shing, J. Biol. Chem. 1992, 267:10931–10934).

Increasing numbers of other cell surface receptors have been identified which bind to extracellular matrix ligands or other cell adhesion ligands thereby mediating cell-cell and cell-matrix adhesion processes. These receptors belong to a gene superfamily called integrins and are composed of heterodimeric transmembrane glycoproteins containing $\alpha$- and $\beta$-subunits. Integrin subfamilies contain a common $\beta$-subunit combined with different $\alpha$-subunits to form adhesion receptors with unique specificity. The genes for eight distinct $\beta$-subunits have been cloned and sequenced to date.

Two members of the $\beta_1$ subfamily, $\alpha_4\beta_1$ and $\alpha_5\beta_1$ have been implicated in various inflammatory processes. Antibodies to $\alpha 4$ prevent adhesion of lymphocytes to synovial endothelial cells in vitro, a process which may be of importance in rheumatoid arthritis (VanDinther-Janssen, et al., J. Immunol. 1991, 147:4207). Additional studies with monoclonal anti-$\alpha 4$ antibodies provide evidence that $\alpha_4\beta_1$ may additionally have a role in allergy, asthma, and autoimmune disorders (Walsh, et al., J. Immunol. 1991, 146:3419; Bochner, et al., J. Exp. Med. 1991 173:1553; Yednock, et al., Nature 1992, 356:63). Anti-$\alpha 4$ antibodies also block the migration of leukocytes to the site of inflammation (Issedutz, et al., J. Immunol. 1991, 147:4178).

The $\alpha_v\beta_3$ heterodimer is a member of the $\beta_3$ integrin subfamily and has been identified on platelets, endothelial cells, melanoma, smooth muscle cells, and osteoclasts (Horton and Davies, J. Bone Min. Res. 1989, 4:803–808; Davies, et al., J. Cell. Biol. 1989, 109:1817–1826; Horton, Int. J. Exp. Pathol. 1990, 71:741–759). Like GPIIb/IIIa, the vitronectin receptor binds a variety of RGD-containing adhesive proteins such as vitronectin, fibronectin, VWF, fibrinogen, osteopontin, bone sialo protein II and thrombospondin in a manner mediated by the RGD sequence. A key event in bone resorption is the adhesion of osteoclasts to the matrix of bone. Studies with monoclonal antibodies have implicated the $\alpha_v\beta_3$ receptor in this process and suggest that a selective $\alpha_v\beta_3$ antagonist would have utility in blocking bone resorption (Horton, et al., J. Bone Miner. Res. 1993, 8:239–247; Helfrich, et al., J. Bone Miner. Res. 1992, 7:335–343)

PCT Patent Application WO 94/22835 discloses compounds having the general formula:

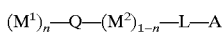

European Patent Application Publication Number 614664 discloses compounds having the general formula:

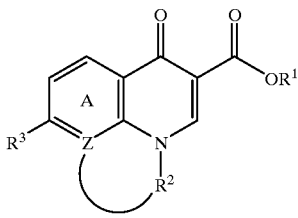

PCT Patent Application WO 94/29273 discloses compounds having the general formula:

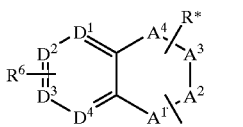

R, R* = carboxy bearing alkyl group
R$^6$ = amine bearing group

PCT Patent Application WO 96/18602 discloses compounds having the general formula:

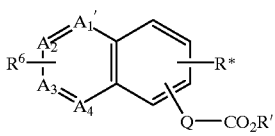

European Patent Application Publication Number EP 635492 discloses compounds having the general formula:

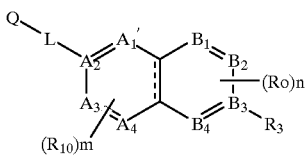

Q = amine bearing group
L = optional linker

PCT Patent Application WO 96/22288 discloses compounds having the general formula:

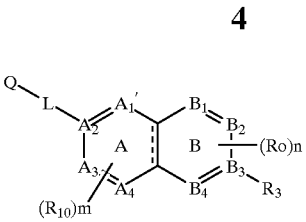

None of the above references teaches or suggests the compounds of the present invention which are described in detail below.

SUMMARY OF THE INVENTION

The present invention provides novel compounds which bind to integrin receptors thereby altering cell-matrix and cell-cell adhesion processes. The compounds of the present invention are useful for the treatment of angiogenic disorders, inflammation, bone degradation, tumors, metastases, thrombosis, and other cell aggregation-related conditions in a mammal.

One aspect of this invention provides novel compounds of Formulae I–IV (described below) which are useful as antagonists of the $\alpha_v\beta_3$ receptor. The compounds of this invention inhibit the binding of vitronectin to $\alpha_v\beta_3$ and inhibit cell adhesion. This invention also includes pharmaceutical compositions containing such compounds of Formulae I–IV, and methods of their use for the inhibition of angiogenesis, and/or for the treatment of angiogenic disorders.

The present invention also provides novel compounds, pharmaceutical compositions and methods which may be used in the treatment or prevention of diseases which involve cell adhesion processes, including, but not limited to, rheumatoid arthritis, asthma, allergies, adult respiratory distress syndrome, graft versus host disease, organ transplantation, septic shock, psoriasis, eczema, contact dermatitis, osteoporosis, osteoarthritis, atherosclerosis, metastasis, wound healing, diabetic retinopathy, ocular vasculopathies, thrombosis, inflammatory bowel disease and other autoimmune diseases.

Also included in this invention are pharmaceutical kits containing dosage units of a compound of Formulae I–IV, for the treatment of cell adhesion related disorders, including, but not limited to, angiogenic disorders.

DETAILED DESCRIPTION OF THE INVENTION

The present invention provides novel compounds of Formulae I–IV (described below) which bind to integrin receptors thereby altering cell-matrix and cell-cell adhesion processes. The compounds of this invention are useful for the treatment of angiogenic disorders, inflammation, bone degradation, tumors, metastases, thrombosis, and other cell aggregation-related conditions in a mammal.

One aspect of this invention provides novel compounds of Formulae I–IV (described below) which are useful as antagonists of the $\alpha_v\beta_3$ receptor. The compounds of this invention inhibit the binding of vitronectin to $\alpha_v\beta_3$ and inhibit cell adhesion. This invention also includes pharmaceutical compositions containing such compounds of Formulae I–IV, and methods of using such compounds for the inhibition of angiogenesis, and/or for the treatment of angiogenic disorders.

[1a] In a first embodiment the present invention comprises compounds of Formula I:

including stereoisomeric forms thereof, or mixtures of stereoisomeric forms thereof, or pharmaceutically acceptable salt or prodrug forms thereof wherein:

$R^1$ is selected from:

D is $-N(R^{12})-$ or $-S-$;
J is $-C(R^2)-$ or $-N-$;
K, L and M are independently $-C(R^2)-$ or $-C(R^3)-$;
$R^2$ and $R^3$ are independently selected from:
  H, $C_1-C_4$ alkoxy, $NR^{11}R^{12}$, halogen, $NO_2$, CN, $CF_3$, $C_1-C_6$ alkyl, $C_3-C_6$ alkenyl, $C_3-C_7$ cycloalkyl, $C_3-C_7$ cycloalkyl($C_1-C_4$ alkyl), aryl($C_1-C_6$ alkyl)-, ($C_1-C_6$ alkyl)carbonyl, ($C_1-C_6$ alkoxy)carbonyl, arylcarbonyl, and aryl substituted with 0–4 $R^7$,
  alternatively, when $R^2$ and $R^3$ are substituents on adjacent atoms, they can be taken together with the carbon atoms to which they are attached to form a 5–7 membered carbocyclic or 5–7 membered heterocyclic aromatic or nonaromatic ring system, said carbocyclic or heterocyclic ring being substituted with 0–2 groups selected from $C_1-C_4$ alkyl, $C_1-C_4$ alkoxy, halo, cyano, amino, $CF_3$ and $NO_2$;
$R^{2a}$ is selected from:
  H, $C_1-C_{10}$ alkyl, $C_2-C_6$ alkenyl, $C_3-C_{11}$ cycloalkyl, $C_3-C_7$ cycloalkyl($C_1-C_4$ alkyl), aryl, aryl($C_1-C_4$ alkyl)-, ($C_2-C_7$ alkyl)carbonyl, arylcarbonyl, ($C_2-C_{10}$ alkoxy) carbonyl, $C_3-C_7$ cycloalkoxycarbonyl, $C_7-C_{11}$ bicycloalkoxycarbonyl, aryloxycarbonyl, aryl($C_1-C_{10}$ alkoxy)carbonyl, $C_1-C_6$ alkylcarbonyloxy ($C_1-C_4$ alkoxy)carbonyl, arylcarbonyloxy($C_1-C_4$ alkoxy)carbonyl, and $C_3-C_7$ cycloalkylcarbonyloxy ($C_1-C_4$ alkoxy)carbonyl;

$R^4$ is selected from:
  H, $C_1-C_{10}$ alkyl, ($C_1-C_{10}$ alkyl)carbonyl, aryl, aryl ($C_1-C_4$ alkyl)-, $C_3-C_{11}$ cycloalkyl, and $C_3-C_{11}$ cycloalkyl($C_1-C_4$ alkyl)-;
U is selected from:
  $-(CH_2)_n-$, $-(CH_2)_nO(CH_2)_m-$, $-(CH_2)_nN(R^{12})(CH_2)_m-$, $-N(H)(CH_2)_n-$, $-(CH_2)_nC(=O)(CH_2)_m-$, $-(CH_2)_nS(O)_p(CH_2)_m-$, $-(CH_2)_nNHNH(CH_2)_m-$, $-N(R^{10})C(=O)-$, $-NHC(=O)(CH_2)_n-$, $-C(=O)N(R^{10})-$, and $-N(R^{10})S(O)_p-$;
W is $-C(=O)-N(R^{10})-(C_1-C_3$ alkylene)-, in which the alkylene group is substituted by $R^8$ and by $R^9$:
$R^8$ and $R^9$ are independently selected from:
  H, $CO_2R^{18b}$, $C(=O)R^{18b}$, $CONR^{17}R^{18b}$,
  hydroxy, $C_5-C_{10}$ alkoxy, nitro, $-N(R^{10})R^{11}$, $-N(R^{16})R^{17}$, aryl($C_0-C_6$ alkyl) carbonyl, aryl($C_3-C_6$ alkyl), heteroaryl($C_1-C_6$ alkyl), $CONR^{18a}R^{20}$, $SO_2R^{18a}$, $SO_2NR^{18a}R^{20}$,
  $C_1-C_{10}$ alkyl substituted with 0–1 $R^6$,
  $C_5-C_{10}$ alkenyl substituted with 0–1 $R^6$,
  $C_5-C_{10}$ alkynyl substituted with 0–1 $R^6$,
  $C_3-C_8$ cycloalkyl substituted with 0–1 $R^6$,
  $C_5-C_6$ cycloalkenyl substituted with 0–1 $R^6$,
  $C_1-C_{10}$ alkylcarbonyl,
  $C_3-C_{10}$ cycloalkyl($C_1-C_4$ alkyl)-,
  phenyl substituted with 1–3 $R^6$,
  naphthyl substituted with 0–3 $R^6$,
  a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$, and
  $C_5-C_{10}$ alkyl substituted with 0–3 $R^7$,
  providing that any of the above alkyl, cycloalkyl, aryl or heteroaryl groups may be unsubstituted or substituted independently with 1–2 $R^7$;
$R^6$ is selected from:
  H, $C_1-C_{10}$ alkyl, hydroxy, $C_1-C_{10}$ alkoxy, nitro, $C_1-C_{10}$ alkylcarbonyl, $-N(R^{11})R^{12}$, cyano, halo, $CF_3$, CHO, $CO_2R^{18b}$, $C(=O)R^{18b}$, $CONR^{17}R^{18b}$, $OC(=O)R^{10}$, $OR^{10}$, $OC(=O)NR^{10}R^{11}$, $NR^{10}C(=O)R^{10}$, $NR^{10}C(=O)OR^{21}$, $NR^{10}C(=O)NR^{10}R^{11}$, $NR^{10}SO_2NR^{10}R^{11}$, $NR^{10}SO_2R^{21}$, $S(O)_pR^{11}$, $SO_2NR^{10}R^{11}$,
  aryl substituted with 0–3 groups selected from halogen, $C_1-C_6$ alkoxy, $C_1-C_6$ alkyl, $CF_3$, $S(O)_mMe$, and $-NMe_2$,
  aryl($C_1-C_4$ alkyl)-, said aryl being substituted with 0–3 groups selected from halogen, $C_1-C_6$ alkoxy, $C_1-C_6$ alkyl, $CF_3$, $S(O)_pMe$, and $-NMe_2$, and
  a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$;
$R^7$ is selected from:
  H, hydroxy, $C_1-C_4$ alkyl, $C_1-C_4$ alkoxy, aryl, aryl ($C_1-C_4$ alkyl)-, ($C_1-C_4$ alkyl)carbonyl, $CO_2R^{18a}$, $SO_2R^{11}$, $SO_2NR^{10}R^{11}$, $OR^{10}$, and $N(R^{11})R^{12}$;
$R^{10}$ is selected from:
  H, $C_3-C_6$ alkenyl, $C_3-C_{11}$ cycloalkyl, aryl, ($C_3-C_{11}$ cycloalkyl)methyl, aryl($C_1-C_4$ alkyl), and $C_1-C_{10}$ alkyl substituted with 0–2 $R^6$;
$R^{11}$ is selected from:
  H, hydroxy, $C_1-C_8$ alkyl, $C_3-C_6$ alkenyl, $C_3-C_{11}$ cycloalkyl, ($C_3-C_{11}$ cycloalkyl)methyl, $C_1-C_6$ alkoxy, benzyloxy, aryl, heteroaryl, heteroaryl($C_1$–$C_4$ alkyl)-, aryl($C_1$–$C_4$ alkyl), adamantylmethyl, and $C_1$–$C_{10}$ alkyl substituted with 0–2 $R^4$, alternatively, when $R^{10}$ and $R^{11}$ are both substituents on the same nitrogen atom (as in —$NR^{10}R^{11}$) they may be taken together with the nitrogen atom to which they are attached to form a heterocycle selected from:

3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl, and 1-piperazinyl;

said heterocycle being substituted with 0–3 groups selected from: $C_1$–$C_6$ alkyl, aryl, heteroaryl, aryl($C_1$–$C_4$ alkyl)-, ($C_1$–$C_6$ alkyl)carbonyl, ($C_3$–$C_7$ cycloalkyl)carbonyl, ($C_1$–$C_6$ alkoxy)carbonyl, aryl($C_1$–$C_4$ alkoxy)carbonyl, $C_1$–$C_6$ alkylsulfonyl, and arylsulfonyl;

$R^{12}$ is selected from:
H, $C_1$–$C_6$ alkyl, triphenylmethyl, methoxymethyl, methoxyphenyldiphenylmethyl, trimethylsilylethoxymethyl, ($C_1$–$C_6$ alkyl)carbonyl, ($C_1$–$C_6$ alkoxy)carbonyl, ($C_1$–$C_6$ alkyl)aminocarbonyl, $C_3$–$C_6$ alkenyl, $C_3$–$C_7$ cycloalkyl, $C_3$–$C_7$ cycloalkyl($C_1$–$C_4$ alkyl)-, aryl, heteroaryl($C_1$–$C_6$ alkyl)carbonyl, heteroarylcarbonyl, aryl($C_1$–$C_6$ alkyl)-, ($C_1$–$C_6$ alkyl)carbonyl, arylcarbonyl, $C_1$–$C_6$ alkylsulfonyl, arylsulfonyl, aryl($C_1$–$C_6$ alkyl)sulfonyl, heteroarylsulfonyl, heteroaryl($C_1$–$C_6$ alkyl)sulfonyl, aryloxycarbonyl, and aryl($C_1$–$C_6$ alkoxy)carbonyl, wherein said aryl groups are substituted with 0–2 substituents selected from the group consisting of $C_1$–$C_4$ alkyl, $C_1$–$C_4$ alkoxy, halo, $CF_3$, and nitro;

$R^{14}$ is selected from H, $C_1$–$C_4$ alkyl, and phenyl($C_1$–$C_4$ alkyl);

$R^{16}$ is selected from:
—C(=O)O$R^{18a}$, —C(=O)$R^{18b}$, —C(=O)N($R^{18b}$)$_2$, —C(=O)NHSO$_2R^{18a}$, —C(=O)NHC(=O)$R^{18b}$, —C(=O)NHC(=O)O$R^{18a}$, —(=O)NHSO$_2$NH$R^{18b}$, —SO$_2R^{18a}$, —SO$_2$N($R^{18b}$)$_2$, and —SO$_2$NHC(=O)O$R^{18b}$;

$R^{17}$ is selected from:
H, $C_1$–$C_6$ alkyl, $C_3$–$C_7$ cycloalkyl, $C_3$–$C_7$ cycloalkyl($C_1$–$C_4$ alkyl)-, aryl, aryl($C_1$–$C_6$ alkyl)-, and heteroaryl($C_1$–$C_6$ alkyl);

$R^{18a}$ is selected from:
$C_7$–$C_8$ alkyl, $C_3$–$C_{11}$ cycloalkyl,
aryl($C_1$–$C_6$ alkyl)-, said aryl substituted with 0–4 $R^{19}$,
heteroaryl($C_1$–$C_6$ alkyl)-, said heteroaryl substituted with 0–4 $R^{19}$,
($C_1$–$C_6$ alkyl)heteroaryl, said heteroaryl substituted with 0–4 $R^{19}$,
heteroaryl substituted with 0–4 $R^{19}$,
phenyl substituted with 3–4 $R^{19}$, and
naphthyl substituted with 0–4 $R^{19}$;

$R^{18b}$ is H or $R^{18a}$;

$R^{19}$ is selected from:
H, halogen, $CF_3$, $CO_2H$, CN, $NO_2$, —$NR^{11}R^{12}$, $OCF_3$, $C_1$–$C_8$ alkyl, $C_2$–$C_6$ alkenyl, $C_2$–$C_6$ alkynyl, $C_3$–$C_{11}$ cycloalkyl, $C_3$–$C_7$ cycloalkyl($C_1$–$C_4$ alkyl)-, aryl($C_1$–$C_6$ alkyl)-, $C_1$–$C_6$ alkoxy, $C_1$–$C_4$ alkoxycarbonyl, aryl, aryl-O—, aryl-SO$_2$—, heteroaryl, and heteroaryl-SO$_2$—, wherein said aryl and heteroaryl groups are substituted with 0–4 groups selected from hydrogen, halogen, $CF_3$, $C_1$–$C_3$ alkyl, and $C_1$–$C_3$ alkoxy;

$R^{20}$ is selected from:
hydroxy, $C_1$–$C_{10}$ alkyloxy, $C_3$–$C_{11}$ cycloalkyloxy, aryloxy, aryl($C_1$–$C_4$ alkyl)oxy,
$C_2$–$C_{10}$ alkylcarbonyloxy($C_1$–$C_2$ alkyl)oxy-,
$C_2$–$C_{10}$ alkoxycarbonyloxy($C_1$–$C_2$ alkyl)oxy-,
$C_2$–$C_{10}$ alkoxycarbonyl($C_1$–$C_2$ alkyl)oxy-,
$C_3$–$C_{10}$ cycloalkylcarbonyloxy($C_1$–$C_2$ alkyl)oxy-,
$C_3$–$C_{10}$ cycloalkoxycarbonyloxy($C_1$–$C_2$ alkyl)oxy-,
$C_3$–$C_{10}$ cycloalkoxycarbonyl($C_1$–$C_2$ alkyl)oxy-,
aryloxycarbonyl($C_1$–$C_2$ alkyl)oxy-,
aryloxycarbonyloxy($C_1$–$C_2$ alkyl)oxy-,
arylcarbonyloxy($C_1$–$C_2$ alkyl)oxy-,
$C_1$–$C_5$ alkoxy($C_1$–$C_5$ alkyl)carbonyloxy($C_1$–$C_2$ alkyl)oxy-,
(5-($C_1$–$C_5$ alkyl)-1,3-dioxa-cyclopenten-2-one-yl)methyloxy,
(5-aryl-1,3-dioxa-cyclopenten-2-one-yl)methyloxy, and
($R^{10}$)($R^{11}$)N—($C_1$–$C_{10}$ alkoxy)-;

$R^{21}$ is selected from:
$C_1$–$C_8$ alkyl, $C_2$–$C_6$ alkenyl, $C_3$–$C_{11}$ cycloalkyl, ($C_3$–$C_{11}$ cycloalkyl)methyl, aryl, aryl($C_1$–$C_4$ alkyl)-, and $C_1$–$C_{10}$ alkyl substituted with 0–2 $R^7$;

Y is selected from:
—COR$^{20}$, —SO$_3$H, —PO$_3$H, —CONHNHSO$_2CF_3$, —CONHSO$_2R^{18a}$, —CONHSO$_2$NH$R^{18b}$, —NHCOCF$_3$, —NHCONHSO$_2R^{18a}$, —NHSO$_2R^{18a}$, —OPO$_3H_2$, —OSO$_3$H, —PO$_3H_2$, —SO$_3$H, —SO$_2$NHCOR$^{18a}$, —SO$_2$NHCO$_2R^{18a}$,

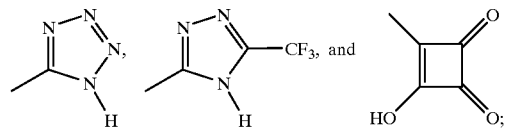

m is 0–2;
n is 0–4;
p is 0–2;

with the following provisos:
(1) n and m are chosen such that the number of atoms connecting $R^1$ and Y is in the range of 8–14;
(2) in W, the alkylene group is substituted with at least one $R^8$ or $R^9$ which is not H;
(3) in the definition of W, when there is only one non-hydrogen substituent on the alkylene group, such substituent may not be an unsubstituted pyridyl radical.

[1b] A preferred embodiment of the present invention are compounds of Formula III:

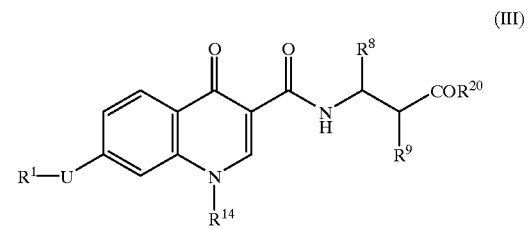

(III)

including stereoisomeric forms thereof, or mixtures of stereoisomeric forms thereof, or pharmaceutically acceptable salt or prodrug forms thereof wherein:

R[1] is selected from:

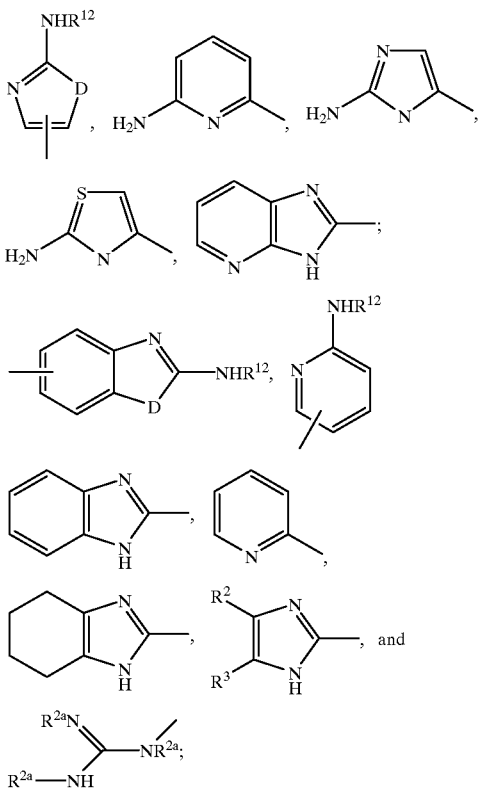

U is selected from —(CH$_2$)$_n$—, —(CH$_2$)$_n$O(CH$_2$)$_m$—, —NH(CH$_2$)$_n$—, —(CH$_2$)$_n$C(=O)(CH$_2$)$_m$—, —N(R$^{10}$)C(=O)—, and —NHC(=O)(CH$_2$)$_n$—;

R[2] and R[3] are independently selected from:
H, C$_1$–C$_4$ alkoxy, NR$^{11}$R$^{12}$, halogen, NO$_2$, CN, CF$_3$, C$_1$–C$_6$ alkyl, C$_3$–C$_6$ alkenyl, C$_3$–C$_7$ cycloalkyl, C$_3$–C$_7$ cycloalkyl(C$_1$–C$_4$ alkyl), aryl(C$_1$–C$_6$ alkyl)-, (C$_1$–C$_6$ alkyl)carbonyl, (C$_1$–C$_6$ alkoxy)carbonyl, arylcarbonyl, and aryl substituted with 0–4 R[7], alternatively, when R[2] and R[3] are substituents on adjacent atoms, they can be taken together with the carbon atoms to which they are attached to form a 5–7 membered carbocyclic or 5–7 membered heterocyclic aromatic or nonaromatic ring system, said carbocyclic or heterocyclic ring being substituted with 0–2 groups selected from C$_1$–C$_4$ alkyl, C$_1$–C$_4$ alkoxy, halo, cyano, amino, CF$_3$ and NO$_2$;

R[4] is selected from:
H, C$_1$–C$_{10}$ alkyl, (C$_1$–C$_{10}$ alkyl)carbonyl, aryl, aryl(C$_1$–C$_4$ alkyl)-, C$_3$–C$_{11}$ cycloalkyl, and C$_3$–C$_{11}$ cycloalkyl(C$_1$–C$_4$ alkyl)-;

R[8] is selected from:
H, CO$_2$R$^{18b}$, C(=O)R$^{18b}$, CONR$^{17}$R$^{18b}$,
C$_1$–C$_{10}$ alkyl substituted with 0–1 R[6],
C$_5$–C$_{10}$ alkenyl substituted with 0–1 R[6],
C$_5$14 C$_{10}$ alkynyl substituted with 0–1 R[6],
C$_3$–C$_8$ cycloalkyl substituted with 0–1 R[6],
C$_5$–C$_6$ cycloalkenyl substituted with 0–1 R[6],
C$_1$–C$_{10}$ alkylcarbonyl,
C$_3$–C$_{10}$ cycloalkyl(C$_1$–C$_4$ alkyl)-,
phenyl substituted with 1–3 R[6],
naphthyl substituted with 0–3 R[6],
a 5–10 membered heterocyclic ring containing 1–3 N, O, or S heteroatoms, wherein said heterocyclic ring may be saturated, partially saturated, or fully unsaturated, said heterocyclic ring being substituted with 0–2 R[7];

R[9] is selected from:
H, hydroxy, C$_5$–C$_{10}$ alkoxy, nitro, N(R$^{10}$)R$^{11}$, N(R$^{16}$)R$^{17}$, aryl(C$_0$–C$_6$ alkyl)carbonyl, aryl(C$_3$–C$_6$ alkyl), heteroaryl(C$_1$–C$_6$ alkyl), CONR$^{18a}$R$^{20}$, SO$_2$R$^{18a}$, SO$_2$NR$^{18a}$R$^{20}$,
C$_1$–C$_{10}$ alkyl substituted with 0–1 R[6],
C$_5$–C$_{10}$ alkenyl substituted with 0–1 R[6],
C$_5$–C$_{10}$ alkynyl substituted with 0–1 R[6],
C$_3$–C$_8$ cycloalkyl substituted with 0–1 R[6],
C$_5$–C$_{10}$ cycloalkenyl substituted with 0–1 R[6],
C$_1$–C$_{10}$ alkylcarbonyl,
C$_3$–C$_{10}$ cycloalkyl(C$_1$–C$_4$ alkyl),
phenyl substituted with 1–3 R[6],
naphthyl substituted with 0–3 R[6], and
a 5–10 membered heterocyclic ring containing 1–3 N, O, or S heteroatoms, wherein said heterocyclic ring may be saturated, partially saturated, or fully unsaturated, said heterocyclic ring being substituted with 0–2 R[7], providing that any of the above alkyl, cycloalkyl, aryl or heteroaryl groups may be unsubstituted or substituted independently with 1–2 R[7];

R[6] is selected from:
H, C$_1$–C$_{10}$ alkyl, hydroxy, C$_1$–C$_{10}$ alkoxy, nitro, C$_1$–C$_{10}$ alkylcarbonyl, —N(R$^{11}$)R$^{12}$, cyano, halo, CF$_3$, CHO, CO$_2$R$^{18b}$, C(=O)R$^{18b}$, CONR$^{17}$R$^{18b}$, OC(=O)R$^{10}$, OR$^{10}$, OC(=O)NR$^{10}$R$^{11}$, NR$^{10}$C(=O)R$^{10}$, NR$^{10}$C(=O)OR$^{21}$, NR$^{10}$C(=O)NR$^{10}$R$^{11}$, NR$^{10}$SO$_2$NR$^{10}$R$^{11}$, NR$^{10}$SO$_2$R$^{21}$, S(O)$_p$R$^{11}$, SO$_2$NR$^{10}$R$^{11}$,
aryl substituted with 0–3 groups selected from halogen, C$_1$–C$_6$ alkoxy, C$_1$–C$_6$ alkyl, CF$_3$, S(O)$_m$Me, and —NMe$_2$,
aryl(C$_1$–C$_4$ alkyl)-, said aryl being substituted with 0–3 groups selected from halogen, C$_1$–C$_6$ alkoxy, C$_1$–C$_6$ alkyl, CF$_3$, S(O)$_p$Me, and —NMe$_2$, and
a 5–10 membered heterocyclic ring containing 1–3 N, O, or S heteroatoms, wherein said heterocyclic ring may be saturated, partially saturated, or fully unsaturated, said heterocyclic ring being substituted with 0–2 R[7];

R[7] is selected from:
H, hydroxy, C$_1$–C$_4$ alkyl, C$_1$–C$_4$ alkoxy, aryl, aryl(C$_1$–C$_4$ alkyl)-, (C$_1$–C$_4$ alkyl)carbonyl, CO$_2$R$^{18a}$, SO$_2$R$^{11}$, SO$_2$NR$^{10}$R$^{11}$, OR$^{10}$, and N(R$^{11}$)R$^{12}$;

R[10] is selected from:
H, C$_3$–C$_6$ alkenyl, C$_3$–C$_{11}$ cycloalkyl, aryl, (C$_3$–C$_{11}$ cycloalkyl)methyl, aryl(C$_1$–C$_4$ alkyl), and C$_1$–C$_{10}$ alkyl substituted with 0–2 R[6];

R[11] is selected from:
H, hydroxy, C$_1$–C$_8$ alkyl, C$_3$–C$_6$ alkenyl, C$_3$–C$_{11}$ cycloalkyl, (C$_3$–C$_{11}$ cycloalkyl)methyl, C$_1$–C$_6$ alkoxy, benzyloxy, aryl, heteroaryl, heteroaryl(C$_1$–C$_4$ alkyl)-, aryl(C$_1$–C$_4$ alkyl), adamantylmethyl, and C$_1$–C$_{10}$ alkyl substituted with 0–2 R[4], alternatively, when R[10] and R[11] are both substituents on the same nitrogen atom (as in —NR$^{10}$R$^{11}$) they may be taken together with the nitrogen atom to which they are attached to form a heterocycle selected from:
3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl, and 1-piperazinyl;

said heterocycle being substituted with 0–3 groups selected from: $C_1$–$C_6$ alkyl, aryl, heteroaryl, aryl($C_1$–$C_4$ alkyl)-, ($C_1$–$C_6$ alkyl)carbonyl, ($C_3$–$C_7$ cycloalkyl)carbonyl, ($C_1$–$C_6$ alkoxy)carbonyl, aryl($C_1$–$C_4$ alkoxy)carbonyl, $C_1$–$C_6$ alkylsulfonyl, and arylsulfonyl;

$R^{12}$ is selected from:
H, $C_1$–$C_6$ alkyl, triphenylmethyl, methoxymethyl, methoxyphenyldiphenylmethyl, trimethylsilylethoxymethyl, ($C_1$–$C_6$ alkyl)carbonyl, ($C_1$–$C_6$ alkoxy)carbonyl, ($C_1$–$C_6$ alkyl) aminocarbonyl, $C_3$–$C_6$ alkenyl, $C_3$–$C_7$ cycloalkyl, $C_3$–$C_7$ cycloalkyl($C_1$–$C_4$ alkyl)-, aryl, heteroaryl ($C_1$–$C_6$ alkyl)carbonyl, heteroarylcarbonyl, aryl ($C_1$–$C_6$ alkyl)-, ($C_1$–$C_6$ alkyl)carbonyl, arylcarbonyl, $C_1$–$C_6$ alkylsulfonyl, arylsulfonyl, aryl($C_1$–$C_6$ alkyl) sulfonyl, heteroarylsulfonyl, heteroaryl($C_1$–$C_6$ alkyl)sulfonyl, aryloxycarbonyl, and aryl($C_1$–$C_6$ alkoxy)carbonyl, wherein said aryl groups are substituted with 0–2 substituents selected from the group consisting of $C_1$–$C_4$ alkyl, $C_1$–$C_4$ alkoxy, halo, $CF_3$, and nitro;

$R^{14}$ is selected from H, $C_1$–$C_4$ alkyl, and phenyl($C_1$–$C_4$ alkyl);

$R^{16}$ is selected from —C(=O)O$R^{18a}$, —C(=O)$R^{18b}$, —C(=O)N($R^{18b}$)$_2$, —SO$_2$$R^{18a}$, and —SO$_2$N($R^{18b}$)$_2$;

$R^{17}$ is selected from:
H, $C_1$–$C_6$ alkyl, $C_3$–$C_7$ cycloalkyl, $C_3$–$C_7$ cycloalkyl ($C_1$–$C_4$ alkyl)-, aryl, aryl($C_1$–$C_6$ alkyl)-, and heteroaryl($C_1$–$C_6$ alkyl);

$R^{18a}$ is selected from:
$C_7$–$C_8$ alkyl, $C_3$–$C_{11}$ cycloalkyl,
aryl($C_1$–$C_6$ alkyl)-, said aryl substituted with 0–4 $R^{19}$,
heteroaryl($C_1$–$C_6$ alkyl)-, said heteroaryl substituted with 0–4 $R^{19}$,
($C_1$–$C_6$ alkyl) heteroaryl, said heteroaryl substituted with 0–4 $R^{19}$,
heteroaryl substituted with 0–4 $R^{19}$,
phenyl substituted with 3–4 $R^{19}$, and
naphthyl substituted with 0–4 $R^{19}$;

$R^{18b}$ is H or $R^{18a}$;

$R^{19}$ is selected from:
H, halogen, $CF_3$, $CO_2$H, CN, $NO_2$, —N$R^{11}R^{12}$, $OCF_3$, $C_1$–$C_8$ alkyl, $C_2$–$C_6$ alkenyl, $C_2$–$C_6$ alkynyl, $C_3$–$C_{11}$ cycloalkyl, $C_3$–$C_7$ cycloalkyl($C_1$–$C_4$ alkyl)-, aryl ($C_1$–$C_6$ alkyl)-, $C_1$–$C_6$ alkoxy, $C_1$–$C_4$ alkoxycarbonyl, aryl, aryl-O—, aryl-SO$_2$—, heteroaryl, and heteroaryl-SO$_2$—, wherein said aryl and heteroaryl groups are substituted with 0–4 groups selected from hydrogen, halogen, $CF_3$, $C_1$–$C_3$ alkyl, and $C_1$–$C_3$ alkoxy;

$R^{20}$ is selected from:
hydroxy, $C_1$–$C_{10}$ alkyloxy, $C_3$–$C_{11}$ cycloalkyloxy, aryloxy, aryl($C_1$–$C_4$ alkyl)oxy,
$C_2$–$C_{10}$ alkylcarbonyloxy($C_1$–$C_2$ alkyl)oxy-,
$C_2$–$C_{10}$ alkoxycarbonyloxy($C_1$–$C_2$ alkyl)oxy-,
$C_2$–$C_{10}$ alkoxycarbonyl($C_1$–$C_2$ alkyl)oxy-,
$C_3$–$C_{10}$ cycloalkylcarbonyloxy($C_1$–$C_2$ alkyl)oxy-,
$C_3$–$C_{10}$ cycloalkoxycarbonyloxy($C_1$–$C_2$ alkyl)oxy-,
$C_3$–$C_{10}$ cycloalkoxycarbonyl($C_1$–$C_2$ alkyl)oxy-,
aryloxycarbonyl($C_1$–$C_2$ alkyl)oxy-,
aryloxycarbonyloxy($C_1$–$C_2$ alkyl)oxy-,
arylcarbonyloxy($C_1$–$C_2$ alkyl)oxy-,
$C_1$–$C_5$ alkoxy($C_1$–$C_5$ alkyl)carbonyloxy($C_1$–$C_2$ alkyl)oxy-,
(5-($C_1$–$C_5$ alkyl)-1,3-dioxa-cyclopenten-2-one-yl) methyloxy,
(5-aryl-1,3-dioxa-cyclopenten-2-one-yl)methyloxy, and
($R^{10}$)($R^{11}$)N—($C_1$–$C_{10}$ alkoxy)-;

$R^{21}$ is selected from:
$C_1$–$C_8$ alkyl, $C_2$–$C_6$ alkenyl, $C_3$–$C_{11}$ cycloalkyl, ($C_3$–$C_{11}$ cycloalkyl)methyl, aryl, aryl($C_1$–$C_4$ alkyl)-, and $C_1$–$C_{10}$ alkyl substituted with 0–2 $R^7$;

m is 0–2;

n is 0–3; and p is 0–2;

with the following provisos:
(1) n and m are chosen such that the number of atoms connecting $R^1$ and —$COR^{20}$ in Formula (III) is in the range of 8–14,
(2) if $R^8$ is H, then $R^9$ may not be an unsubstituted pyridyl radical,
(3) if $R^9$ is H, then $R^8$ may not be an unsubstituted pyridyl radical.

[1c] A more preferred embodiment of the present invention are compounds of Formula III:

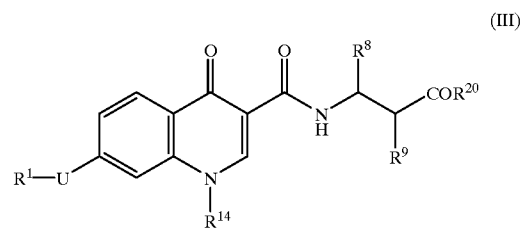

(III)

including stereoisomeric forms thereof, or mixtures of stereoisomeric forms thereof, or pharmaceutically acceptable salt or prodrug forms thereof wherein:

$R^1$ is selected from:

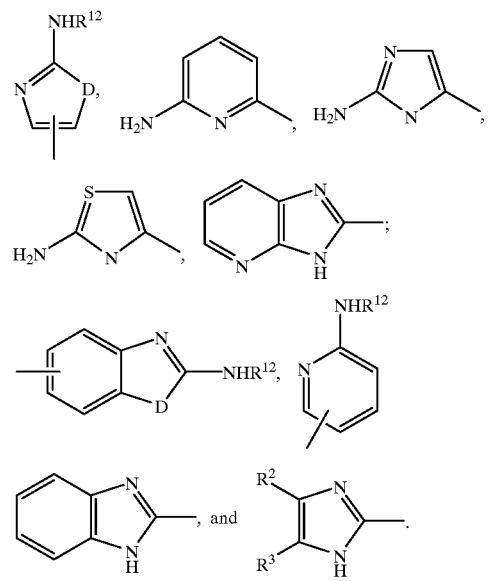

[1d] An even more preferred embodiment of the present invention are compounds of Formula III:

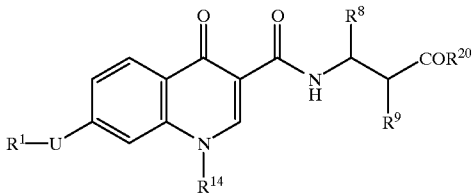

(III)

including stereoisomeric forms thereof, or mixtures of stereoisomeric forms thereof, or pharmaceutically acceptable salt or prodrug forms thereof wherein:

$R^1$ is selected from:

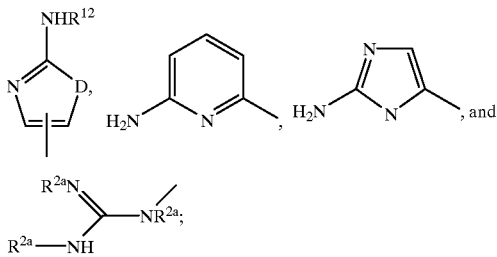

U is selected from $-(CH_2)_n-$, $-NH(CH_2)_n-$, $-N(R^{10})C(=O)-$, and $-NHC(=O)(CH_2)_n-$;

$R^4$ is selected from:
  H, $C_1-C_4$ alkyl, $(C_1-C_4$ alkyl)carbonyl, aryl, aryl$(C_1-C_4$ alkyl)-, $C_3-C_6$ cycloalkyl, and $C_3-C_6$ cycloalkyl$(C_1-C_4$ alkyl)-;

$R^6$ is H;

$R^7$ is selected from:
  H, hydroxy, $C_1-C_4$ alkyl, $C_1-C_4$ alkoxy, aryl, aryl$(C_1-C_4$ alkyl)-, $(C_1-C_4$ alkyl)carbonyl, $CO_2R^{18a}$, $SO_2R^{11}$, $SO_2NR^{10}R^{11}$, $OR^{10}$, and $N(R^{11})R^{12}$;

$R^8$ is H;

$R^9$ is selected from:
  H, hydroxy, $C_5-C_{10}$ alkoxy, nitro, $N(R^{10})R^{11}$, $N(R^{16})R^{17}$, aryl$(C_0-C_6$ alkyl)carbonyl, aryl$(C_3-C_6$ alkyl), heteroaryl$(C_1-C_6$ alkyl), $CONR^{18a}R^{20}$, $SO_2R^{18a}$, $SO_2NR^{18a}R^{20}$,
  providing that any of the above alkyl, cycloalkyl, aryl or heteroaryl groups may be unsubstituted or substituted independently with 1–2 $R^7$;

$R^{10}$ is selected from:
  H, $C_3-C_6$ alkenyl, $C_3-C_6$ cycloalkyl, aryl, $(C_3-C_6$ cycloalkyl)methyl, aryl$(C_1-C_4$ alkyl), and $C_1-C_4$ alkyl;

$R^{11}$ is selected from:
  H, hydroxy, $C_1-C_4$ alkyl, $C_3-C_6$ alkenyl, $C_3-C_6$ cycloalkyl, $(C_3-C_6$ cycloalkyl)methyl, $C_1-C_6$ alkoxy, benzyloxy, aryl, heteroaryl, heteroaryl$(C_1-C_4$ alkyl)-, aryl$(C_1-C_4$ alkyl), adamantylmethyl, and $C_1-C_4$ alkyl substituted with 0–2 $R^4$, $R^{12}$ is selected from:
  H, $C_1-C_4$ alkyl, $(C_1-C_4$ alkyl)carbonyl, $(C_1-C_4$ alkoxy)carbonyl, phenyl$(C_1-C_4$ alkyl)-, phenylsulfonyl, phenyloxycarbonyl, and phenyl$(C_1-C_4$ alkoxy)carbonyl, wherein said phenyl groups are substituted with 0–2 substituents selected from the group consisting of $C_1-C_4$ alkyl, $C_1-C_4$ alkoxy, halo, $CF_3$, and nitro;

$R^{14}$ is selected from H, methyl, ethyl, benzyl and phenylethyl;

$R^{16}$ is selected from $-C(=O)OR^{18a}$, $-C(=O)R^{18b}$, $-C(=O)N(R^{18b})_2$, $-SO_2R^{18a}$, and $-SO_2N(R^{18b})_2$;

$R^{17}$ is selected from:
  H, $C_1-C_6$ alkyl, $C_3-C_7$ cycloalkyl, $C_3-C_7$ cycloalkyl$(C_1-C_4$ alkyl)-, aryl, aryl$(C_1-C_6$ alkyl)-, and heteroaryl$(C_1-C_6$ alkyl);

$R^{18a}$ is selected from:
  $C_7-C_8$ alkyl, $C_3-C_{11}$ cycloalkyl,
  aryl$(C_1-C_6$ alkyl)-, said aryl substituted with 0–4 $R^{19}$,
  heteroaryl$(C_1-C_6$ alkyl)-, said heteroaryl substituted with 0–4 $R^{19}$,
  $(C_1-C_6$ alkyl)heteroaryl, said heteroaryl substituted with 0–4 $R^{19}$,
  heteroaryl substituted with 0–4 $R^{19}$,
  phenyl substituted with 3–4 $R^{19}$, and
  naphthyl substituted with 0–4 $R^{19}$;

$R^{18b}$ is H or $R^{18a}$;

$R^{19}$ is selected from:
  H, halogen, $CF_3$, $CO_2H$, CN, $NO_2$, $-NR^{11}R^{12}$, $OCF_3$, $C_1-C_8$ alkyl, $C_2-C_6$ alkenyl, $C_2-C_6$ alkynyl, $C_3-C_{11}$ cycloalkyl, $C_3-C_7$ cycloalkyl$(C_1-C_4$ alkyl)-, aryl $(C_1-C_6$ alkyl)-, $C_1-C_6$ alkoxy, $C_1-C_4$ alkoxycarbonyl, aryl, aryl-O—, aryl-$SO_2$—, heteroaryl, and heteroaryl-$SO_2$—, wherein said aryl and heteroaryl groups are substituted with 0–4 groups selected from hydrogen, halogen, $CF_3$, $C_1-C_3$ alkyl, and $C_1-C_3$ alkoxy;

$R^{20}$ is selected from:
  hydroxy, $C_1-C_{10}$ alkyloxy, $C_3-C_{11}$ cycloalkyloxy, aryloxy, aryl$(C_1-C_4$ alkyl)oxy,
  $C_2-C_{10}$ alkylcarbonyloxy$(C_1-C_2$ alkyl)oxy-,
  $C_2-C_{10}$ alkoxycarbonyloxy$(C_1-C_2$ alkyl)oxy-,
  $C_2-C_{10}$ alkoxycarbonyl$(C_1-C_2$ alkyl)oxy-,
  $C_3-C_{10}$ cycloalkylcarbonyloxy$(C_1-C_2$ alkyl)oxy-,
  $C_3-C_{10}$ cycloalkoxycarbonyloxy$(C_1-C_2$ alkyl)oxy-,
  $C_3-C_{10}$ cycloalkoxycarbonyl$(C_1-C_2$ alkyl)oxy-,
  aryloxycarbonyl$(C_1-C_2$ alkyl)oxy-,
  arylcarbonyloxy$(C_1-C_2$ alkyl)oxy-,
  arylcarbonyloxy$(C_1-C_2$ alkyl)oxy-,
  $C_1-C_5$ alkoxy$(C_1-C_5$ alkyl)carbonyloxy$(C_1-C_2$ alkyl)oxy-,
  (5-($C_1-C_5$ alkyl)-1,3-dioxa-cyclopenten-2-one-yl) methyloxy,
  (5-aryl-1,3-dioxa-cyclopenten-2-one-yl)methyloxy, and
  $(R^{10})(R^{11})N-(C_1-C_{10}$ alkoxy)-;

$R^{21}$ is selected from:
  $C_1-C_8$ alkyl, $C_2-C_6$ alkenyl, $C_3-C_{11}$ cycloalkyl, $(C_3-C_{10}$ cycloalkyl)methyl, aryl, aryl$(C_1-C_4$ alkyl)-, and $C_1-C_{10}$ alkyl substituted with 0–2 $R^7$;

m is 0–2;

n is 0–3; and p is 0–2;

with the following provisos:
  (1) n and m are chosen such that the number of atoms connecting $R^1$ and $-COR^{20}$ in Formula (III) is in the range of 8–14,
  (2) if $R^8$ is H, then $R^9$ may not be an unsubstituted pyridyl radical,
  (3) if $R^9$ is H, then may not be an unsubstituted pyridyl radical.

[1e] Specifically preferred compounds of Formula III including enantiomeric or diastereomeric forms thereof, or mixtures of enantiomeric or diastereomeric forms thereof, or pharmaceutically acceptable salt or prodrug forms thereof selected from the group consisting of:

3-[7-[(imidazol-2-ylamino)methyl]-1-methylquinoline-4-one-3-ylcarbonylamino]-2-(3,5-dimethylisoxazol-4-ylsulfonylamino)propionic acid, 3-[7-[(imidazol-2-ylamino)methyl]-1-methylquinoline-4-one-3-ylcarbonylamino]-2-((2,4,6-trimethylphenyl)sulfonylamino)propionic acid, 3-[7-[(pyridin-2-ylamino)methyl]-1-methylquinoline-4-one-3-ylcarbonylamino]-2-((2,4,6-trimethylphenyl)sulfonylamino)propionic acid, 3-[7-[(imidazol-2-ylamino)methyl]-1-methylquinoline-4-one-3-ylcarbonylamino]-2-((4-phenylbenzene)sulfonylamino)propionic acid, 3-[7-[(benzimidazol-2-ylamino)methyl]-1-methylquinoline-4-one-3-ylcarbonylamino]-2-((2,4,6-trimethylphenyl)sulfonylamino)propionic acid, 3-[7-[(4-methylimidazol-2-ylamino)methyl]-1-methylquinoline-4-one-3-ylcarbonylamino]-2-((2,4,6-trimethylphenyl)sulfonylamino)propionic acid, 3-[7-[(4,5-dimethylimidazol-2-ylamino)methyl]-1-methylquinoline-4-one-3-ylcarbonylamino]-2 -((2,4,6-trimethylphenyl)sulfonylamino)propionic acid, 3-[7-[(4,5,6,7-tetrahydrobenzimidazol-2-ylamino)methyl]-1-methylquinoline-4-one-3-ylcarbonylamino]-2-((2,4,6-trimethylphenyl)sulfonylamino)propionic acid, 3-[7-(2-aminopyridin-6-yl)quinoline-4-one-3-ylcarbonylamino]-2-((2,4,6-trimethylphenyl)sulfonylamino)propionic acid, 3-[7-[(7-azabenzimidazol-2-yl)methyl]-1-methylquinoline-4-one-3-ylcarbonylamino]-2-((2,4,6-trimethylphenyl)sulfonylamino)propionic acid, 3-[7-[(benzimidazol-2-ylamino)methyl]-1-(2-phenylethyl)quinoline-4-one-3-ylcarbonylamino]-2-((2,4,6-trimethylphenyl)sulfonylamino)propionic acid, 3-[7-[(pyridin-2-ylamino)methyl]-1-(2-phenylethyl)quinoline-4-one-3-ylcarbonylamino]-2-((2,4,6-trimethylphenyl)sulfonylamino)propionic acid, 3-[7-[(imidazol-2-ylamino)methyl]-1-(2-phenylethyl)quinoline-4-one-3-ylcarbonylamino]-2-((2,4,6-trimethylphenyl)sulfonylamino)propionic acid, 3-[7-[(imidazol-2-ylamino)methyl]-(2-phenylethyl)quinoline-4-one-3-ylcarbonylamino]-2-((2,4,6-trimethylphenyl)sulfonylamino)propionic acid, 3-[7-[(pyridin-2-ylamino)methyl]-(2-phenylethyl)quinoline-4-one-3-ylcarbonylamino]-2-((2,4,6-trimethylphenyl)sulfonylamino)propionic acid, 3-[7-[(imidazol-2-ylamino)methyl]-1-(2-phenylethyl)quinoline-4-one-3-ylcarbon-ylamino]-2-((4-phenylbenzene)sulfonylamino)propionic acid, 3-[7-[(benzimidazol-2-ylamino)methyl]-1-(2-phenylethyl)quinoline-4-one-3-ylcarbonylamino]-2 -((2,4,6-trimethylphenyl)sulfonylamino)propionic acid, 3-[7-[(4-methylimidazol-2-ylamino)methyl]-(2-phenylethyl)quinoline-4-one-3-ylcarbonylamino]-2-((2,4,6-trimethylphenyl)sulfonylamino)propionic acid, 3-[7-[(4,5-dimethylimidazol-2-ylamino)methyl]-(2-phenylethyl)quinoline-4-one-3-ylcarbonylamino]-2-((2,4,6-trimethylphenyl)sulfonylamino)propionic acid, 3-[7-[(4,5,6,7-tetrahydrobenzimidazol-2-ylamino)methyl]-1-(2-phenylethyl)quinoline-4-one-3-ylcarbonylamino]-2-((2,4,6-trimethylphenyl)sulfonylamino)propionic acid, 3-[7-(2-aminopyridin-6-yl)1-(2-phenylethyl)quinoline-4-one-3-ylcarbonylamino]-2-((2,4,6-trimethylphenyl)sulfonylamino)propionic acid, 3-[7-[(7-azabenzimidazol-2-yl)methyl]-1-(2-phenylethyl)quinoline-4-one-3-ylcarbonylamino]-2-((2,4,6-trimethylphenyl)sulfonylamino)propionic acid, 3-[7-[(imidazol-2-ylamino)methyl]-1-(2-phenylethyl)quinoline-4-one-3-ylcarbon-ylamino]-2-((2,2-dimethyl-4-phenylbenzene)sulfonylamino)propionic acid, 3-[7-[(imidazol-2-ylamino)methyl]-1-(2-phenylethyl)quinoline-4-one-3-ylcarbon-ylamino]-2-((2,2-dichloro-4-phenylbenzene)sulfonylamino)propionic acid.

[2a] In a second embodiment of the present invention are compounds of Formula II:

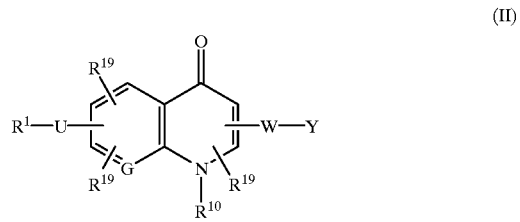

(II)

including stereoisomeric forms thereof, or mixtures of stereoisomeric forms thereof, or pharmaceutically acceptable salt or prodrug forms thereof wherein:

$R^1$ is selected from:

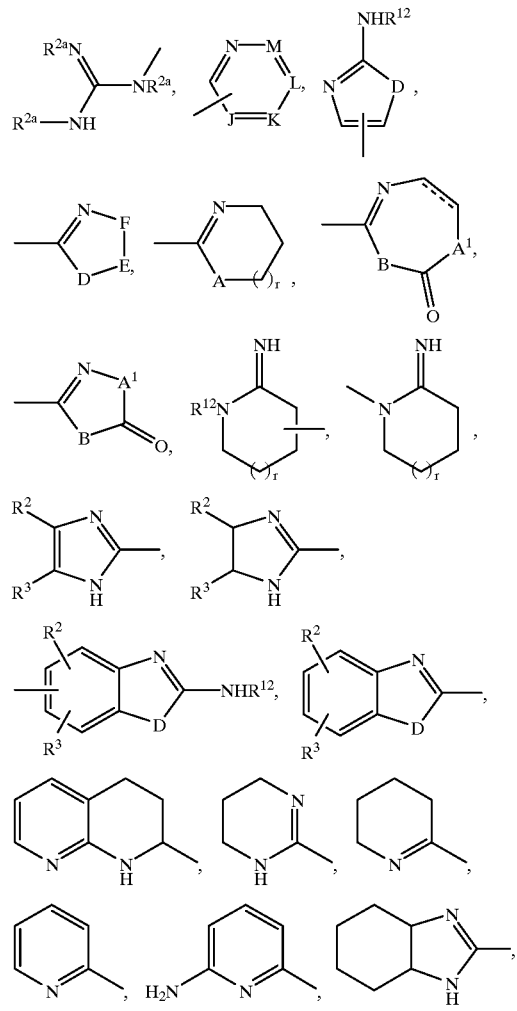

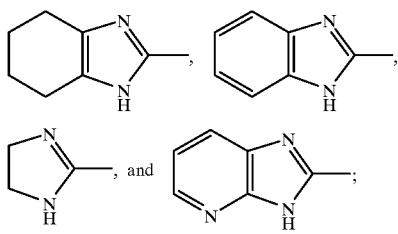

A is —CH$_2$— or —N(R$^{12}$)-;
A$^1$ and B are independently —CH$_2$— or —N(R$^{10}$)—;
D is —N(R$^{12}$)— or —S—;
E—F is —C(R$^2$)=C(R$^3$)— or —C(R$^2$)$_2$C(R$^3$)$_2$—;
J is —C(R$^2$)— or —N—;
K, L and M are independently —C(R$^2$)— or —C(R$^3$)—;
R$^2$ and R$^3$ are independently selected from:
  H, C$_1$–C$_4$ alkoxy, NR$^{11}$R$^{12}$, halogen, NO$_2$, CN, CF$_3$, C$_1$–C$_6$ alkyl, C$_3$–C$_6$ alkenyl, C$_3$–C$_7$ cycloalkyl, C$_3$–C$_7$ cycloalkyl(C$_1$–C$_4$ alkyl), aryl(C$_1$–C$_6$ alkyl)-, (C$_1$–C$_6$ alkyl)carbonyl, (C$_1$–C$_6$ alkoxy)carbonyl, arylcarbonyl, and aryl substituted with 0–4 R$^7$,
  alternatively, when R$^2$ and R$^3$ are substituents on adjacent atoms, they can be taken together with the carbon atoms to which they are attached to form a 5–7 membered carbocyclic or 5–7 membered heterocyclic aromatic or nonaromatic ring system, said carbocyclic or heterocyclic ring being substituted with 0–2 groups selected from C$_1$–C$_4$ alkyl, C$_1$–C$_4$ alkoxy, halo, cyano, amino, CF$_3$ and NO$_2$;
R$^{2a}$ is selected from:
  H, C$_1$–C$_{10}$ alkyl, C$_2$–C$_6$ alkenyl, C$_3$–C$_{11}$ cycloalkyl, C$_3$–C$_7$ cycloalkyl(C$_1$–C$_4$ alkyl), aryl, aryl(C$_1$–C$_4$ alkyl)-, (C$_2$–C$_7$ alkyl)carbonyl, arylcarbonyl, (C$_2$–C$_{10}$ alkoxy)carbonyl, C$_3$–C$_7$ cycloalkoxycarbonyl, C$_7$–C$_{11}$ bicycloalkoxycarbonyl, aryloxycarbonyl, aryl(C$_1$–C$_{10}$ alkoxy)carbonyl, C$_1$–C$_6$ alkylcarbonyloxy(C$_1$–C$_4$ alkoxy)carbonyl, arylcarbonyloxy(C$_1$–C$_4$ alkoxy)carbonyl, and C$_3$–C$_7$ cycloalkylcarbonyloxy(C$_1$–C$_4$ alkoxy)carbonyl;
R$^4$ is selected from:
  H, C$_1$–C$_6$ alkyl, C$_3$–C$_7$ cycloalkyl, C$_3$–C$_7$ cycloalkyl(C$_1$–C$_4$ alkyl)-, (C$_1$–C$_{10}$ alkyl)carbonyl, aryl, heteroaryl, aryl(,-C$_6$ alkyl)-, and heteroaryl(C$_1$–C$_6$ alkyl)-,
  wherein said aryl or heteroaryl groups are substituted with 0–2 substituents independently selected from the group consisting of C$_1$–C$_4$ alkyl, C$_1$–C$_4$ alkoxy, F, Cl, Br, CF$_3$, and NO$_2$,
R$^6$ is selected from:
  H, C$_1$–C$_{10}$ alkyl, hydroxy, C$_1$–C$_{10}$ alkoxy, nitro, C$_1$–C$_{10}$ alkylcarbonyl, —N(R$^{11}$)R$^{12}$, cyano, halo, CF$_3$, CHO, CO$_2$R$^{18b}$, C(=O)R$^{18b}$, CONR$^{17}$R$^{18b}$, OC(=O)R$^{10}$, OR$^{10}$, OC(=O)NR$^{10}$R$^{11}$, NR$^{10}$C(=O)R$^{10}$, NR$^{10}$C(=O)OR$^{21}$, NR$^{10}$C(=O)NR$^{10}$R$^{11}$, NR$^{10}$SO$_2$NR$^{10}$R$^{11}$, NR$^{10}$SO$_2$R$^{21}$, S(O)$_p$R$^{11}$, SO$_2$NR$^{10}$R$^{11}$,
  aryl substituted with 0–3 groups selected from halogen, C$_1$–C$_6$ alkoxy, C$_1$–C$_6$ alkyl, CF$_3$, S(O)$_m$Me, and —NMe$_2$,
  aryl(C$_1$–C$_4$ alkyl)-, said aryl being substituted with 0–3 groups selected from halogen, C$_1$–C$_6$ alkoxy, C$_1$–C$_6$ alkyl, CF$_3$, S(O)$_p$Me, and —NMe$_2$, and a 5–10 membered heterocyclic ring containing 1–3 N, O, or S heteroatoms, wherein said heterocyclic ring may be saturated, partially saturated, or fully unsaturated, said heterocyclic ring being substituted with 0–2 R$^7$;
R$^7$ is selected from:
  H, hydroxy, C$_1$–C$_4$ alkyl, C$_1$–C$_4$ alkoxy, aryl, aryl(C$_1$–C$_4$ alkyl)-, (C$_1$–C$_4$ alkyl)carbonyl, CO$_2$R$^{18a}$, SO$_2$R$^{11}$, SO$_2$NR$^{10}$R$^{11}$, OR$^{10}$, and N(R$^{11}$)R$^{12}$;
U is selected from:
  —(CH$_2$)$_n$—, —(CH$_2$)$_n$O(CH$_2$)$_m$—, —(CH$_2$)$_n$N(R$^{12}$)(CH$_2$)$_m$—, —NH(CH$_2$)$_n$—, —(CH$_2$)$_n$C(=O)(CH$_2$)$_m$—, —(CH$_2$)$_n$S(O)$_p$(CH$_2$)$_m$—, —(CH$_2$)$_n$NHNH(CH$_2$)$_m$—, —N(R$^{10}$)C(=O)—, —NHC(=O)(CH$_2$)$_n$—, —C(=O)N(R$^{10}$)—, and —N(R$^{10}$)S(O)$_p$—;
G is N or CR$^{19}$;
W is —C(=O)—N(R$^{10}$)—(C$_1$–C$_3$ alkylene)-, in which the alkylene group is substituted by R$^8$ and by R$^9$:
R$^8$ and R$^9$ are independently selected from:
  H, CO$_2$R$^{18b}$, C(=O)R$^{18b}$, CONR$^{17}$R$^{18b}$,
  C$_1$–C$_{10}$ alkyl substituted with 0–1 R$^6$,
  C$_2$–C$_{10}$ alkenyl substituted with 0–1 R$^6$,
  C$_2$–C$_{10}$ alkynyl substituted with 0–1 R$^6$,
  C$_3$–C$_8$ cycloalkyl substituted with 0–1 R$^6$,
  C$_5$–C$_6$ cycloalkenyl substituted with 0–1 R$^6$,
  (C$_1$–C$_{10}$ alkyl)carbonyl,
  C$_3$–C$_{10}$ cycloalkyl(C$_1$–C$_4$ alkyl)-,
  phenyl substituted with 0–3 R$^6$,
  naphthyl substituted with 0–3 R$^6$,
  a 5–10 membered heterocyclic ring containing 1–3 N, O, or S heteroatoms, wherein said heterocyclic ring may be saturated, partially saturated, or fully unsaturated, said heterocyclic ring being substituted with 0–2 R$^7$,
  C$_1$–C$_{10}$ alkoxy substituted with 0–2 R$^7$,
  hydroxy, nitro, —N(R$^{10}$)R$^{11}$, —N(R$^{16}$)R$^{17}$, aryl(C$_0$–C$_6$ alkyl)carbonyl, aryl(C$_3$–C$_6$ alkyl), heteroaryl(C$_1$–C$_6$ alkyl), CONR$^{18a}$R$^{20}$, SO$_2$R$^{18a}$, and SO$_2$NR$^{18a}$R$^{20}$,
  providing that any of the above alkyl, cycloalkyl, aryl or heteroaryl groups may be unsubstituted or substituted independently with 1–2 R$^7$;
R$^{10}$ is selected from:
  H, CF$_3$, C$_3$–C$_6$ alkenyl, C$_3$–C$_{11}$ cycloalkyl, aryl, (C$_3$–C$_{11}$ cycloalkyl)methyl, aryl(C$_1$–C$_4$ alkyl), and C$_1$–C$_{10}$ alkyl substituted with 0–2 R$^6$;
R$^{11}$ is selected from:
  H, hydroxy, C$_1$–C$_8$ alkyl, C$_3$–C$_6$ alkenyl, C$_3$–C$_{11}$ cycloalkyl, (C$_3$–C$_{11}$ cycloalkyl)methyl, C$_1$–C$_6$ alkoxy, benzyloxy, aryl, heteroaryl, heteroaryl(C$_1$–C$_4$ alkyl)-, aryl(C$_1$–C$_4$ alkyl), adamantylmethyl, and C$_1$–C$_{10}$ alkyl substituted with 0–2 R$^4$;
  alternatively, when R$^{10}$ and R$^{11}$ are both substituents on the same nitrogen atom (as in —NR$^{10}$R$^{11}$) they may be taken together with the nitrogen atom to which they are attached to form a heterocycle selected from:
    3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl, and 1-piperazinyl;
    said heterocycle being substituted with 0–3 groups selected from: C$_1$–C$_6$ alkyl, aryl, heteroaryl, aryl(C$_1$–C$_4$ alkyl)-, (C$_1$–C$_6$ alkyl)carbonyl, (C$_3$–C$_7$ cycloalkyl)carbonyl, (C$_1$–C$_6$ alkoxy)carbonyl, aryl(C$_1$–C$_4$ alkoxy)carbonyl, C$_1$–C$_6$ alkylsulfonyl, and arylsulfonyl;

$R^{12}$ is selected from:
  H, $C_1$–$C_6$ alkyl, triphenylmethyl, methoxymethyl, methoxyphenyldiphenylmethyl, trimethylsilylethoxymethyl, ($C_1$–$C_6$ alkyl)carbonyl, ($C_1$–$C_6$ alkoxy)carbonyl, ($C_1$–$C_6$ alkyl) aminocarbonyl, $C_3$–$C_6$ alkenyl, $C_3$–$C_7$ cycloalkyl, $C_3$–$C_7$ cycloalkyl($C_1$–$C_4$ alkyl)-, aryl, heteroaryl ($C_1$–$C_6$ alkyl)carbonyl, heteroarylcarbonyl, aryl ($C_1$–$C_6$ alkyl)-, ($C_1$–$C_6$ alkyl)carbonyl, arylcarbonyl, $C_1$–$C_6$ alkylsulfonyl, arylsulfonyl, aryl($C_1$–$C_6$ alkyl) sulfonyl, heteroarylsulfonyl, heteroaryl($C_1$–$C_6$ alkyl)sulfonyl, aryloxycarbonyl, and aryl($C_1$–$C_6$ alkoxy)carbonyl, wherein said aryl groups are substituted with 0–2 substituents selected from the group consisting of $C_1$–$C_4$ alkyl, $C_1$–$C_4$ alkoxy, halo, $CF_3$, and nitro;

$R^{16}$ is selected from:
  —C(=O)$OR^{18a}$, —C(=O)$R^{18b}$, —C(=O)N($R^{18b}$)$_2$, —C(=O)$NHSO_2R^{18a}$, —C(=O)NHC(=O)$R^{18b}$, —C(=O)NHC(=O)$OR^{18a}$, —C(=O)$NHSO_2NHR^{18b}$, $SO_2R^{18a}$, —$SO_2$N($R^{18b}$)$_2$, and —$SO_2$NHC(=O)$OR^{18b}$;

$R^{17}$ is selected from:
  H, $C_1$–$C_6$ alkyl, $C_3$–$C_7$ cycloalkyl, $C_3$–$C_7$ cycloalkyl ($C_1$–$C_4$ alkyl)-, aryl, aryl($C_1$–$C_6$ alkyl)-, and heteroaryl($C_1$–$C_6$ alkyl);

$R^{18a}$ is selected from:
  $C_1$–$C_8$ alkyl, $C_3$–$C_{11}$ cycloalkyl, aryl($C_1$–$C_6$ alkyl)-, said aryl substituted with 0–4 $R^{19}$, heteroaryl($C_1$–$C_6$ alkyl)-, said heteroaryl substituted with 0–4 $R^{19}$, ($C_1$–$C_6$ alkyl)heteroaryl, said heteroaryl substituted with 0–4 $R^{19}$, heteroaryl substituted with 0–4 $R^{19}$, phenyl substituted with 0–4 $R^{19}$, and naphthyl substituted with 0–4 $R^{19}$;

$R^{18b}$ is H or $R^{18a}$;

$R^{19}$ is selected from:
  H, halogen, $CF_3$, $CO_2H$, CN, $NO_2$, —$NR^{11}R^{12}$, $OCF_3$, $C_1$–$C_8$ alkyl, $C_2$–$C_6$ alkenyl, $C_2$–$C_6$ alkynyl, $C_3$–$C_{11}$ cycloalkyl, $C_3$–$C_7$ cycloalkyl ($C_1$–$C_4$ alkyl)-, aryl ($C_1$–$C_6$ alkyl)-, $C_1$–$C_6$ alkoxy, $C_1$–$C_4$ alkoxycarbonyl, aryl, aryl-O—, aryl-$SO_2$—, heteroaryl, and heteroaryl-$SO_2$—, wherein said aryl and heteroaryl groups are substituted with 0–4 groups selected from hydrogen, halogen, $CF_3$, $C_1$–$C_3$ alkyl, and $C_1$–$C_3$ alkoxy;

$R^{20}$ is selected from:
  hydroxy, $C_1$–$C_{10}$ alkyloxy, $C_3$–$C_{11}$ cycloalkyloxy, aryloxy, aryl($C_1$–$C_4$ alkyl)oxy,
  $C_2$–$C_{10}$ alkylcarbonyloxy($C_1$–$C_2$ alkyl)oxy-,
  $C_2$–$C_{10}$ alkoxycarbonyloxy($C_1$–$C_2$ alkyl)oxy-,
  $C_2$–$C_{10}$ alkoxycarbonyl($C_1$–$C_2$ alkyl)oxy-,
  $C_3$–$C_{10}$ cycloalkylcarbonyloxy($C_1$–$C_2$ alkyl)oxy-,
  $C_3$–$C_{10}$ cycloalkoxycarbonyloxy($C_1$–$C_2$ alkyl)oxy-,
  $C_3$–$C_{10}$ cycloalkoxycarbonyl($C_1$–$C_2$ alkyl)oxy-,
  aryloxycarbonyl($C_1$–$C_2$ alkyl)oxy-,
  aryloxycarbonyloxy($C_1$–$C_2$ alkyl)oxy-,
  arylcarbonyloxy($C_1$–$C_2$ alkyl)oxy-,
  $C_1$–$C_5$ alkoxy($C_1$–$C_5$ alkyl)carbonyloxy($C_1$–$C_2$ alkyl) oxy-,
  (5-($C_1$–$C_5$ alkyl)-1,3-dioxa-cyclopenten-2-one-yl) methyloxy,
  (5-aryl-1,3-dioxa-cyclopenten-2-one-yl)methyloxy, and
  ($R^{10}$)($R^{11}$)N—($C_1$–$C_{10}$ alkoxy)-;

$R^{21}$ is selected from:
  $C_1$–$C_8$ alkyl, $C_2$–$C_6$ alkenyl, $C_3$–$C_{11}$ cycloalkyl, ($C_3$–$C_{11}$ cycloalkyl)methyl, aryl, aryl($C_1$–$C_4$ alkyl)-, and $C_1$–$C_{10}$ alkyl substituted with 0–2 $R^7$;

$R^{22}$ is selected from:
  —C(=O)—$R^{18b}$, —C(=O)N($R^{18b}$)$_2$, —C(=O) $NHSO_2R^{18a}$, —C(=O)NHC(=O)$R^{18b}$, —C(=O) NHC(=O)$OR^{18a}$, and —C(=O)$NHSO_2NHR^{18b}$;

Y is selected from:
  —$COR^{20}$, —$SO_3H$, —$PO_3H$, —$CONHNHSO_2CF_3$, —$CONHSO_2R^{18a}$, —$CONHSO_2NHR^{18b}$, —$NHCOCF_3$, —$NHCONHSO_2R^{18a}$, —$NHSO_2R^{18a}$, —$OPO_3H_2$, —$OSO_3H$, —$PO_3H_2$, —$SO_2NHCOR^{18a}$, —$SO_2NHCO_2R^{18a}$,

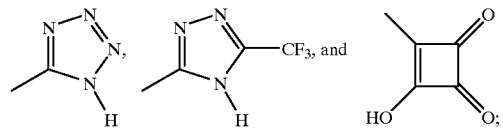

m is 0–2;

n is 0–4;

p is 0–2;

r is 0–2;

with the following provisos:
  (1) n and m are chosen such that the number of atoms connecting $R^1$ and Y is in the range of 8–14,
  (2) when $R^{10}$ is hydrogen, $C_1$–$C_4$ alkyl, or phenyl ($C_1$–$C_4$ alkyl) and all $R^{19}$ groups are H, G is N,
  (3) when G is $CR^{19}$, at least one $R^{19}$ group cannot be H.

[2b] Preferred compounds in the second embodiment are compounds of Formula IV:

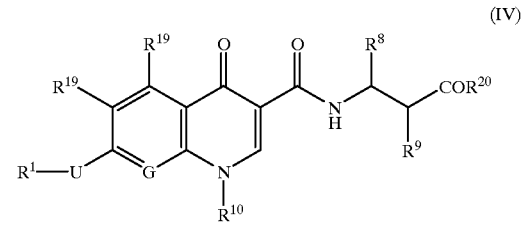

(IV)

including stereoisomeric forms thereof, or mixtures of stereoisomeric forms thereof, or pharmaceutically acceptable salt or prodrug forms thereof wherein:

$R^1$ is selected from:

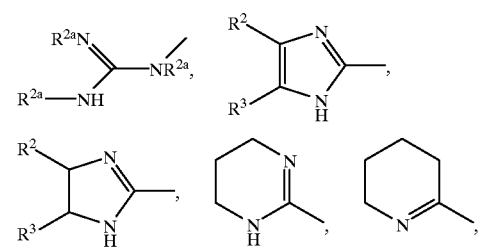

-continued

[chemical structures]

and

R² and R³ are independently selected from:
H, $C_1$–$C_4$ alkoxy, $NR^{11}R^{12}$, halogen, $NO_2$, CN, $CF_3$, $C_1$–$C_6$ alkyl, $C_3$–$C_6$ alkenyl, $C_3$–$C_7$ cycloalkyl, $C_3$–$C_7$ cycloalkyl($C_1$–$C_4$ alkyl), aryl($C_1$–$C_6$ alkyl)-, ($C_1$–$C_6$ alkyl)carbonyl, ($C_1$–$C_6$ alkoxy)carbonyl, arylcarbonyl, and aryl substituted with 0–4 $R^7$,
alternatively, when $R^2$ and $R^3$ are substituents on adjacent atoms, they can be taken together with the carbon atoms to which they are attached to form a 5–7 membered carbocyclic or 5–7 membered heterocyclic aromatic or nonaromatic ring system, said carbocyclic or heterocyclic ring being substituted with 0–2 groups selected from $C_1$–$C_4$ alkyl, $C_1$–$C_4$ alkoxy, halo, cyano, amino, $CF_3$ and $NO_2$;

$R^{2a}$ is selected from:
H, $C_1$–$C_{10}$ alkyl, $C_2$–$C_6$ alkenyl, $C_3$–$C_{11}$ cycloalkyl, $C_3$–$C_7$ cycloalkyl($C_1$–$C_4$ alkyl), aryl, aryl($C_1$–$C_4$ alkyl)-, ($C_2$–$C_7$ alkyl)carbonyl, arylcarbonyl, ($C_2$–$C_{10}$ alkoxy)carbonyl, $C_3$–$C_7$ cycloalkoxycarbonyl, $C_7$–$C_{11}$ bicycloalkoxycarbonyl, aryloxycarbonyl, aryl ($C_1$–$C_{10}$ alkoxy)carbonyl, $C_1$–$C_6$ alkylcarbonyloxy ($C_1$–$C_4$ alkoxy)carbonyl, arylcarbonyloxy($C_1$–$C_4$ alkoxy)carbonyl, and $C_3$–$C_7$ cycloalkylcarbonyloxy ($C_1$–$C_4$ alkoxy)carbonyl;

$R^4$ is selected from:
H, $C_1$–$C_6$ alkyl, $C_3$–$C_7$ cycloalkyl, $C_3$-$c_7$ cycloalkyl ($C_1$–$C_4$ alkyl)-, aryl, heteroaryl, aryl($C_1$–$C_6$ alkyl)-, and heteroaryl($C_1$–$C_6$ alkyl)-, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$, $R^6$ is selected from:
H, $C_1$–$C_{10}$ alkyl, hydroxy, $C_1$–$C_{10}$ alkoxy, nitro, $C_1$–$C_{10}$ alkylcarbonyl, —$N(R^{11})R^{12}$, cyano, halo, $CF_3$, CHO, $CO_2R^{18b}$, $C(=O)R^{18b}$, $CONR^{17}R^{18b}$, $OC(=O)R^{10}$, $OR^{10}$, $OC(=O)NR^{10}R^{11}$, $NR^{10}C$ (=O)$R^{10}$, $NR^{10}C(=O)OR^{21}$, $NR^{10}C(=O)NR^{10}R^{11}$, $NR^{10}SO_2NR^{10}R^{11}$, $NR^{10}SO_2R^{21}$, $S(O)_pR^{11}$, $SO_2NR^{10}R^{11}$,
aryl substituted with 0–3 groups selected from halogen, $C_1$–$C_6$ alkoxy, $C_1$–$C_6$ alkyl, $CF_3$, $S(O)_m$Me, and —$NMe_2$,
aryl($C_1$–$C_4$ alkyl)-, said aryl being substituted with 0–3 groups selected from halogen, $C_1$–$C_6$ alkoxy, $C_1$–$C_6$ alkyl, $CF_3$, $S(O)_p$Me, and —$NMe_2$, and
a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$;

$R^7$ is selected from:
H, hydroxy, $C_1$–$C_4$ alkyl, $C_1$–$C_4$ alkoxy, aryl, aryl ($C_1$–$C_4$ alkyl)-, ($C_1$–$C_4$ alkyl)carbonyl, $CO_2R^{18a}$, $SO_2R^{11}$, $SO_2NR^{10}R^{11}$, $OR^{10}$, and $N(R^{11})R^{12}$;

U is selected from:
—$(CH_2)_n$—, —$(CH_2)_nO(CH_2)_m$—, —$NH(CH_2)_n$—, —$N(R^{10})C(=O)$—, —$NHC(=O)(CH_2)_n$—, and —$C(=O)N(R^{10})$—;

G is N or $CR^{19}$;

$R^8$ is selected from:
H, $CO_2R^{18b}$, $C(=O)R^{18b}$, $CONR^{17}R^{18b}$,
$C_1$–$C_{10}$ alkyl substituted with 0–1 $R^6$,
$C_2$–$C_{10}$ alkenyl substituted with 0–1 $R^6$,
$C_2$–$C_{10}$ alkynyl substituted with 0–1 $R^6$,
$C_3$–$C_8$ cycloalkyl substituted with 0–1 $R^6$,
$C_5$–$C_6$ cycloalkenyl substituted with 0–1 $R^6$,
($C_1$–$C_{10}$ alkyl)carbonyl,
$C_3$–$C_{10}$ cycloalkyl ($C_1$–$C_4$ alkyl)-,
phenyl substituted with 0–3 $R^6$,
naphthyl substituted with 0–3 $R^6$,
a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$;

$R^9$ is selected from:
$C_1$–$C_{10}$ alkyl substituted with 0–1 $R^6$,
$C_1$–$C_{10}$ alkoxy substituted with 0–2 $R^7$,
H, nitro, $N(R^{11})R^{12}$, $OC(=O)R^{10}$, $OR^{10}$, $OC(=O)NR^{10}R^{11}$, $NR^{10}C(=O)R^{10}$, $NR^{10}C(=O)OR^{21}$, $NR^{10}C(=O)NR^{10}R^{11}$, $NR^{10}SO_2NR^{10}R^{11}$, $NR^{10}SO_2R^{21}$, hydroxy, $OR^{22}$, —$N(R^{10})R^{11}$, —$N(R^{16})R^{17}$, aryl($C_0$–$C_6$ alkyl)carbonyl, aryl ($C_1$–$C_6$ alkyl), heteroaryl($C_1$–$C_6$ alkyl), $CONR^{18a}R^{20}$, $SO_2R^{18a}$, and $SO_2NR^{18a}R^{20}$,
providing that any of the above alkyl, cycloalkyl, aryl or heteroaryl groups may be unsubstituted or substituted independently with 1–2 $R^7$;

$R^{10}$ is selected from:
H, $CF_3$, $C_3$–$C_6$ alkenyl, $C_3$–$C_{11}$ cycloalkyl, aryl, ($C_3$–$C_{11}$ cycloalkyl)methyl, aryl($C_1$–$C_4$ alkyl), and $C_1$–$C_{10}$ alkyl substituted with 0–2 $R^6$;

$R^{11}$ is selected from:
H, hydroxy, $C_1$–$C_8$ alkyl, $C_3$–$C_6$ alkenyl, $C_3$–$C_{11}$ cycloalkyl, ($C_3$–$C_{11}$ cycloalkyl)methyl, $C_1$–$C_6$ alkoxy, benzyloxy, aryl, heteroaryl, heteroaryl ($C_1$–$C_4$ alkyl)-, aryl($C_1$–$C_4$ alkyl), adamantylmethyl, and $C_1$–$C_{10}$ alkyl substituted with 0–2 $R^4$;

$R^{12}$ is selected from:
H, $C_1$–$C_6$ alkyl, triphenylmethyl, methoxymethyl, methoxyphenyldiphenylmethyl, trimethylsilylethoxymethyl, ($C_1$–$C_6$ alkyl)carbonyl, ($C_1$–$C_6$ alkoxy)carbonyl, ($C_1$–$C_6$ alkyl)aminocarbonyl, $C_3$–$C_6$ alkenyl, $C_3$–$C_7$ cycloalkyl, $C_3$–$C_7$ cycloalkyl($C_1$–$C_4$ alkyl)-, aryl, heteroaryl ($C_1$–$C_6$ alkyl)carbonyl, heteroarylcarbonyl, aryl ($C_1$–$C_6$ alkyl)-, ($C_1$–$C_6$ alkyl)carbonyl, arylcarbonyl, $C_1$–$C_6$ alkylsulfonyl, arylsulfonyl, aryl($C_1$–$C_6$ alkyl)sulfonyl, heteroarylsulfonyl, heteroaryl($C_1$–$C_6$ alkyl)sulfonyl, aryloxycarbonyl, and aryl($C_1$–$C_6$ alkoxy)carbonyl, wherein said aryl groups are substituted with 0–2 substituents selected from the group consisting of $C_1$–$C_4$ alkyl, $C_1$–$C_4$ alkoxy, halo, $CF_3$, and nitro;

$R^{16}$ is selected from:
—C(=O)$OR^{18a}$, —C(=O)$R^{18b}$, —C(=O)N($R^{18b}$)$_2$, —$SO_2R^{18a}$, and —$SO_2$N($R^{18b}$)$_2$;

$R^{17}$ is selected from:
H, $C_1$–$C_6$ alkyl, $C_3$–$C_7$ cycloalkyl, $C_3$–$C_7$ cycloalkyl ($C_1$–$C_4$ alkyl)-, aryl, aryl($C_1$–$C_6$ alkyl)-, and heteroaryl($C_1$–$C_6$ alkyl);

$R^{18a}$ is selected from:
$C_1$–$C_8$ alkyl, $C_3$–$C_{11}$ cycloalkyl,
aryl($C_1$–$C_6$ alkyl)-, said aryl substituted with 0–4 $R^{19}$,
heteroaryl($C_1$–$C_6$ alkyl)-, said heteroaryl substituted with 0–4 $R^{19}$,
($C_1$–$C_6$ alkyl)heteroaryl, said heteroaryl substituted with 0–4 $R^{19}$,
heteroaryl substituted with 0–4 $R^{19}$,
phenyl substituted with 0–4 $R^{19}$, and
naphthyl substituted with 0–4 $R^{19}$;

$R^{18b}$ is H or $R^{18a}$;

$R^{19}$ is selected from:
H, halogen, $CF_3$, $CO_2H$, CN, $NO_2$, —$NR^{10}R^{12}$, $OCF_3$, $C_1$–$C_8$ alkyl, $C_2$–$C_6$ alkenyl, $C_2$–$C_6$ alkynyl, $C_3$–$C_{11}$ cycloalkyl, $C_3$–$C_7$ cycloalkyl($C_1$–$C_4$ alkyl)-, aryl ($C_1$–$C_6$ alkyl)-, $C_1$–$C_6$ alkoxy, $C_1$–$C_4$ alkoxycarbonyl, aryl, aryl-O—, aryl-$SO_2$—, heteroaryl, and heteroaryl-$SO_2$—, wherein said aryl and heteroaryl groups are substituted with 0–4 groups selected from hydrogen, halogen, $CF_3$, $C_1$–$C_3$ alkyl, and $C_1$–$C_3$ alkoxy;

$R^{20}$ is selected from:
hydroxy, $C_1$–$C_{10}$ alkyloxy, $C_3$–$C_{11}$ cycloalkyloxy, aryloxy, aryl($C_1$–$C_4$ alkyl)oxy,
$C_2$–$C_{10}$ alkylcarbonyloxy($C_1$–$C_2$ alkyl)oxy-,
$C_2$–$C_{10}$ alkoxycarbonyloxy($C_1$–$C_2$ alkyl)oxy-,
$C_2$–$C_{10}$ alkoxycarbonyl($C_1$–$C_2$ alkyl)oxy-,
$C_3$–$C_{10}$ cycloalkylcarbonyloxy($C_1$–$C_2$ alkyl)oxy-,
$C_3$–$C_{10}$ cycloalkoxycarbonyloxy($C_1$–$C_2$ alkyl)oxy-,
$C_3$–$C_{10}$ cycloalkoxycarbonyl($C_1$–$C_2$ alkyl)oxy-,
aryloxycarbonyl($C_1$–$C_2$ alkyl)oxy-,
aryloxycarbonyloxy($C_1$–$C_2$ alkyl)oxy-,
arylcarbonyloxy($C_1$–$C_2$ alkyl)oxy-,
$C_1$–$C_5$ alkoxy($C_1$–$C_5$ alkyl)carbonyloxy($C_1$–$C_2$ alkyl)oxy-,
(5-($C_1$–$C_5$ alkyl)-1,3-dioxa-cyclopenten-2-one-yl)methyloxy,
(5-aryl-1,3-dioxa-cyclopenten-2-one-yl)methyloxy, and
($R^{10}$)($R^{11}$)N—($C_1$–$C_{10}$ alkoxy)-;

$R^{21}$ is selected from:
$C_1$–$C_8$ alkyl, $C_2$–$C_6$ alkenyl, $C_3$–$C_{11}$ cycloalkyl, ($C_3$–$C_{11}$ cycloalkyl)methyl, aryl, aryl($C_1$–$C_4$ alkyl)-, and $C_1$–$C_{10}$ alkyl substituted with 0–2 $R^7$;

$R^{22}$ is selected from:
—C(=O)—$R^{18b}$, —C(=O)N($R^{18b}$)$_2$, —C(=O)$NHSO_2R^{18a}$, —C(=O)NHC(=O)$R^{18b}$, —C(=O)NHC(=O)$OR^{18a}$, and —C(=O)$NHSO_2NHR^{18b}$;

m is 0–2;
n is 0–4; and
p is 0–2;

with the following provisos:
(1) n and m are chosen such that the number of atoms connecting $R^1$ and —$COR^{20}$ in Formula (IV) is in the range of 8–14,
(2) when $R^{10}$ is hydrogen, $C_1$–$C_4$ alkyl, or phenyl ($C_1$–$C_4$ alkyl) and all $R^{19}$ groups are H, G is N,
(3) when G is $CR^{19}$, at least one $R^{19}$ group cannot be H.

[2c] More preferred compounds in the second embodiment are compounds of Formula IV:

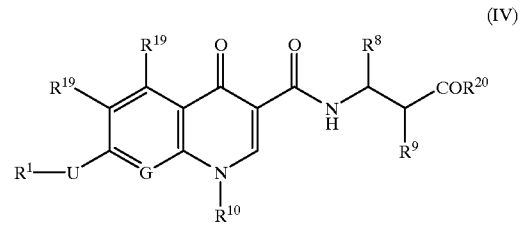

(IV)

including stereoisomeric forms thereof, or mixtures of stereoisomeric forms thereof, or pharmaceutically acceptable salt or prodrug forms thereof wherein:

$R^1$ is selected from:

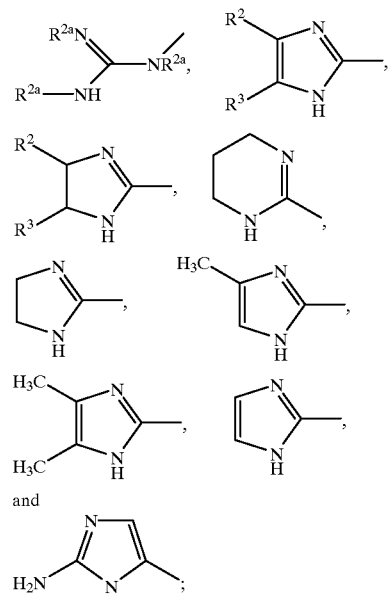

$R^2$ and $R^3$ are independently selected from:
H, $C_1$–$C_4$ alkoxy, $NR^{11}R^{12}$, halogen, $NO_2$, CN, $CF_3$, $C_1$–$C_6$ alkyl, $C_3$–$C_6$ alkenyl, $C_3$–$C_7$ cycloalkyl, $C_3$–$C_7$ cycloalkyl($C_1$–$C_4$ alkyl), aryl($C_1$–$C_6$ alkyl)-, ($C_1$–$C_6$ alkyl)carbonyl, ($C_1$–$C_6$ alkoxy)carbonyl, arylcarbonyl, and aryl substituted with 0–4 $R^7$,
alternatively, when $R^2$ and $R^3$ are substituents on adjacent atoms, they can be taken together with the carbon atoms to which they are attached to form a 5–7 membered carbocyclic or 5–7 membered heterocyclic aromatic or nonaromatic ring system, said carbocyclic or heterocyclic ring being substituted with 0–2 groups selected from $C_1$–$C_4$ alkyl, $C_1$–$C_4$ alkoxy, halo, cyano, amino, $CF_3$ and $NO_2$;

$R^{2a}$ is selected from:
  H, $C_1$–$C_{10}$ alkyl, $C_2$–$C_6$ alkenyl, $C_3$–$C_{11}$ cycloalkyl, $C_3$–$C_7$ cycloalkyl($C_1$–$C_4$ alkyl), aryl, aryl($C_1$–$C_4$ alkyl)-, ($C_2$–$C_7$ alkyl)carbonyl, arylcarbonyl, ($C_2$–$C_{10}$ alkoxy)carbonyl, $C_3$–$C_7$ cycloalkoxycarbonyl, $C_7$–$C_{11}$ bicycloalkoxycarbonyl, aryloxycarbonyl, aryl($C_1$–$C_{10}$ alkoxy)carbonyl, $C_1$–$C_6$ alkylcarbonyloxy($C_1$–$C_4$ alkoxy)carbonyl, arylcarbonyloxy($C_1$–$C_4$ alkoxy)carbonyl, and $C_3$–$C_7$ cycloalkylcarbonyloxy ($C_1$–$C_4$ alkoxy)carbonyl;

$R^4$ is selected from:
  H, $C_1$–$C_4$ alkyl, $C_3$–$C_7$ cycloalkyl, $C_3$–$C_7$ cycloalkyl($C_1$–$C_4$ alkyl)-, aryl, heteroaryl, aryl($C_1$–$C_4$ alkyl)-, and heteroaryl($C_1$–$C_4$ alkyl)-, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$, $R^6$ is selected from:
  H, $C_1$–$C_4$ alkyl, hydroxy, $C_1$–$C_4$ alkoxy, nitro, $C_1$–$C_4$ alkylcarbonyl, $-N(R^{11})R^{12}$, cyano, halo, $CF_3$, CHO, $CO_2R^{18b}$, $C(=O)R^{18b}$, $CONR^{17}R^{18b}$, $OC(=O)R^{10}$, $OR^{10}$, $OC(=O)NR^{10}R^{11}$, $NR^{10}C(=O)R^{10}$, $NR^{10}C(=O)OR^{21}$, $NR^{10}C(=O)NR^{10}R^{11}$, $NR^{10}SO_2NR^{10}R^{11}$, $NR^{10}SO_2R^{21}$, $S(O)_pR^{11}$, $SO_2NR^{10}R^{11}$,
  aryl substituted with 0–3 groups selected from halogen, $C_1$–$C_4$ alkoxy, $C_1$–$C_4$ alkyl, $CF_3$, $S(O)_m$Me, and $-NMe_2$,
  aryl($C_1$–$C_4$ alkyl)-, said aryl being substituted with 0–3 groups selected from halogen, $C_1$–$C_4$ alkoxy, $C_1$–$C_4$ alkyl, $CF_3$, $S(O)_p$Me, and $-NMe_2$, and
  a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$;

$R^7$ is selected from:
  H, hydroxy, $C_1$–$C_4$ alkyl, $C_1$–$C_4$ alkoxy, aryl, aryl($C_1$–$C_4$ alkyl)-, ($C_1$–$C_4$ alkyl)carbonyl, $CO_2R^{18a}$, $SO_2R^{11}$, $SO_2NR^{10}R^{11}$, $OR^{10}$, and $N(R^{11})R^{12}$;

U is selected from:
  $-(CH_2)_n-$, $-NH(CH_2)_n-$, $-N(R^{10})C(=O)-$, and $-NHC(=O)(CH_2)_n$;

G is N or $CR^{19}$;

$R^8$ is H;

$R^9$ is selected from:
  H, nitro, $N(R^{11})R^{12}$, $OC(=O)R^{10}$, $OR^{10}$, $OC(=O)NR^{10}R^{11}$, $NR^{10}C(=O)R^{10}$, $NR^{10}C(=O)OR^{21}$, $NR^{10}C(=O)NR^{10}R^{11}$, $NR^{10}SO_2NR^{10}R^{11}$, $NR^{10}SO_2R^{21}$, hydroxy, $OR^{22}$, $-N(R^{10})R^{11}$, $-N(R^{16})R^{17}$, aryl($C_0$–$C_4$ alkyl)carbonyl, aryl($C_1$–$C_4$ alkyl), heteroaryl($C_1$–$C_4$ alkyl), $CONR^{18a}R^{20}$, $SO_2R^{18a}$, and $SO_2NR^{18a}R^{20}$,
  providing that any of the above alkyl, cycloalkyl, aryl or heteroaryl groups may be unsubstituted or substituted independently with 1–2 $R^7$;

$R^{10}$ is selected from:
  H, $CF_3$, $C_3$–$C_6$ alkenyl, $C_3$–$C_6$ cycloalkyl, aryl, ($C_3$–$C_6$ cycloalkyl)methyl, aryl($C_1$–$C_4$ alkyl), and $C_1$–$C_4$ alkyl substituted with 0–2 $R^6$;

$R^{11}$ is selected from:
  H, hydroxy, $C_1$–$C_4$ alkyl, $C_3$–$C_6$ alkenyl, $C_3$–$C_6$ cycloalkyl, ($C_3$–$C_6$ cycloalkyl)methyl, $C_1$–$C_4$ alkoxy, benzyloxy, aryl, heteroaryl, heteroaryl ($C_1$–$C_4$ alkyl)-, aryl($C_1$–$C_4$ alkyl), adamantylmethyl, and $C_1$–$C_4$ alkyl substituted with 0–2 $R^4$;

$R^{12}$ is selected from:
  H, $C_1$–$C_4$ alkyl, ($C_1$–$C_4$ alkyl)carbonyl, ($C_1$–$C_4$ alkoxy)carbonyl, phenyl($C_1$–$C_4$ alkyl)-, phenylsulfonyl, phenyloxycarbonyl, and phenyl ($C_1$–$C_4$ alkoxy)carbonyl, wherein said phenyl groups are substituted with 0–2 substituents selected from the group consisting of $C_1$–$C_4$ alkyl, $C_1$–$C_4$ alkoxy, halo, $CF_3$, and nitro;

$R^{16}$ is selected from:
  $-C(=O)OR^{18a}$, $-C(=O)R^{18b}$, $-C(=O)N(R^{18b})_2$, $-SO_2R^{18a}$, and $-SO_2N(R^{18b})_2$;

$R^{17}$ is selected from:
  H, $C_1$–$C_4$ alkyl, $C_3$–$C_6$ cycloalkyl, $C_3$–$C_6$ cycloalkyl ($C_1$–$C_4$ alkyl)-, aryl, aryl($C_1$–$C_6$ alkyl)-, and heteroaryl($C_1$–$C_6$ alkyl);

$R^{18a}$ is selected from:
  $C_1$–$C_4$ alkyl, $C_3$–$C_6$ cycloalkyl,
  aryl($C_1$–$C_4$ alkyl)-, said aryl substituted with 0–4 $R^{19}$,
  heteroaryl($C_1$–$C_4$ alkyl)-, said heteroaryl substituted with 0–4 $R^{19}$,
  ($C_1$–$C_4$ alkyl)heteroaryl, said heteroaryl substituted with 0–4 $R^{19}$,
  heteroaryl substituted with 0–4 $R^{19}$,
  phenyl substituted with 0–4 $R^{19}$, and
  naphthyl substituted with 0–4 $R^{19}$;

$R^{18b}$ is H or $R^{18a}$;

$R^{19}$ is selected from:
  H, halogen, $CF_3$, $CO_2H$, CN, $NO_2$, $-NR^{11}R^{12}$, $OCF_3$, $C_1$–$C_6$ alkyl, $C_2$–$C_6$ alkenyl, $C_2$–$C_6$ alkynyl, $C_3$–$C_6$ cycloalkyl, $C_3$–$C_6$ cycloalkyl($C_1$–$C_4$ alkyl)-, aryl ($C_1$–$C_4$ alkyl)-, $C_1$–$C_6$ alkoxy, $C_1$–$C_4$ alkoxycarbonyl, aryl, aryl-O—, aryl-$SO_2$—, heteroaryl, and heteroaryl-$SO_2$—, wherein said aryl and heteroaryl groups are substituted with 0–4 groups selected from hydrogen, halogen, $CF_3$, $C_1$–$C_3$ alkyl, and $C_1$–$C_3$ alkoxy;

$R^{20}$ is selected from:
  hydroxy, $C_1$–$C_6$ alkyloxy, $C_3$–$C_6$ cycloalkyloxy, aryloxy,
  aryl($C_1$–$C_4$ alkyl)oxy,
  $C_2$–$C_{10}$ alkylcarbonyloxy($C_1$–$C_2$ alkyl)oxy-,
  $C_2$–$C_{10}$ alkoxycarbonyloxy($C_1$–$C_2$ alkyl)oxy-,
  $C_2$–$C_{10}$ alkoxycarbonyl($C_1$–$C_2$ alkyl)oxy-,
  $C_3$–$C_{10}$ cycloalkylcarbonyloxy($C_1$–$C_2$ alkyl)oxy-,
  $C_3$–$C_{10}$ cycloalkoxycarbonyloxy($C_1$–$C_2$ alkyl)oxy-,
  $C_3$–$C_{10}$ cycloalkoxycarbonyl($C_1$–$C_2$ alkyl)oxy-,
  aryloxycarbonyl($C_1$–$C_2$ alkyl)oxy-,
  aryloxycarbonyloxy($C_1$–$C_2$ alkyl)oxy-,
  arylcarbonyloxy($C_1$–$C_2$ alkyl)oxy-,
  $C_1$–$C_5$ alkoxy($C_1$–$C_5$ alkyl)carbonyloxy($C_1$–$C_2$ alkyl) oxy-,
  (5-($C_1$–$C_5$ alkyl)-1,3-dioxa-cyclopenten-2-one-yl) methyloxy,
  (5-aryl-1,3-dioxa-cyclopenten-2-one-yl)methyloxy, and
  $(R^{10})(R^{11})N-(C_1$–$C_{10}$ alkoxy)-;

$R^{21}$ is selected from:
  $C_1$–$C_4$ alkyl, $C_2$–$C_6$ alkenyl, $C_3$–$C_6$ cycloalkyl, ($C_3$–$C_6$ cycloalkyl)methyl, aryl, aryl($C_1$–$C_4$ alkyl)-, and $C_1$–$C_{10}$ alkyl substituted with 0–2 $R^7$;

$R^{22}$ is selected from:
  $-C(=O)-R^{18b}$, $-C(=O)N(R^{18b})_2$, $-C(=O)NHSO_2R^{18a}$, $-C(=O)NHC(=O)R^{18b}$, $-C(=O)NHC(=O)OR^{18a}$, and $-C(=O)NHSO_2NHR^{18b}$;

m is 0–2;

n is 0–4; and p is 0–2;

with the following provisos:
  (1) n and m are chosen such that the number of atoms connecting $R^1$ and —$COR^{20}$ in Formula (IV) is in the range of 8–14,
  (2) when $R^{10}$ is hydrogen, $C_1$–$C_4$ alkyl, or phenyl ($C_1$–$C_4$ alkyl) and all $R^{19}$ groups are H, G is N,
  (3) when G is $CR^{19}$, at least one $R^{19}$ group cannot be H.

[2d] Specifically preferred compounds of the above invention are compounds of Formula IV including enantiomeric or diastereomeric forms thereof, or mixtures of enantiomeric or diastereomeric forms thereof, or pharmaceutically acceptable salt or prodrug forms thereof selected from the group consisting of:

3-[7-[(imidazolin-2-ylamino)methyl]-1-methyl-6,8-difluoroquinoline-4-one-3-ylcarbonylamino]-2-(3,5-dimethylisoxazol-4-ylsulfonylamino)propionic acid, 3-[7-[(imidazolin-2-ylamino)methyl]-1-methyl-6,8-difluoroquinoline-4-one-3-ylcarbonylamino]-2-(benzyloxycarbonylamino)propionic acid, 3-[7-[(imidazolin-2-ylamino)methyl]-1-methyl-6,8-difluoroquinoline-4-one-3-ylcarbonylamino]-2-(n-butyloxycarbonylamino)propionic acid, 3-[7-[(imidazolin-2-ylamino)methyl]-1-methyl-6,8-difluoroquinoline-4-one-3-ylcarbonylamino]-2-(n-butylsulfonylamino)propionic acid, 3-[7-[(tetrahydropyrimid-2-ylamino)methyl]-1-methyl-6,8-difluoroquinoline-4-one-3-ylcarbonylamino]-2-(benzyloxycarbonylamino)propionic acid, 3-[7-[(tetrahydropyrimid-2-ylamino)methyl]-1-methyl-6,8-difluoroquinoline-4-one-3-ylcarbonylamino]-2-(n-butyloxycarbonylamino)propionic acid, 3-[7-[(tetrahydropyrimid-2-ylamino)methyl]-1-methyl-6,8-difluoroquinoline-4-one-3-ylcarbonylamino]-2-(phenylsulfonylamino)propionic acid, 3-[7-[(tetrahydropyrimid-2-ylamino)methyl]-1-methyl-6,8-difluoroquinoline-4-one-3-ylcarbonylamino]-2-(n-butylsulfonyl)aminopropionic acid, 3-[7-[(2-aminothiazol-4-yl)methyl]-1-methyl-6,8-difluoroquinoline-4-one-3-ylcarbonylamino]-2-(benzyloxycarbonylamino)propionic acid, 3-[7-[(imidazolin-2-ylamino)methyl]-1-methyl-6,8-difluoroquinoline-4-one-3-ylcarbonylamino]-2-((2,4,6-trimethylphenyl)sulfonylamino)propionic acid, 3-[7-[(tetrahydropyrimid-2-ylamino)methyl]-1-methyl-6,8-difluoroquinoline-4-one-3-ylcarbonylamino]-2-((2,4,6-trimethylphenyl)sulfonylamino)propionic acid, 3-[7-[(imidazol-2-ylamino)methyl]-1-methyl-6,8-difluoroquinoline-4-one-3-ylcarbonylamino]-2-(3,5-dimethylisoxazol-4-ylsulfonylamino)propionic acid, 3-[7-[(imidazol-2-ylamino)methyl]-1-methyl-6,8-difluoroquinoline-4-one-3-ylcarbonylamino]-2-(benzyloxycarbonylamino)propionic acid, 3-[7-[(imidazol-2-ylamino)methyl]-1-methyl-6,8-difluoroquinoline-4-one-3-ylcarbonylamino]-2-((2,4,6-trimethylphenyl)sulfonylamino)propionic acid, 3-[7-[(imidazol-2-ylamino)methyl]-1-methyl-6,8-difluoroquinoline-4-one-3-ylcarbonylamino]-2-((4-biphenyl)sulfonylamino)propionic acid, 3-[7-[(imidazol-2-ylamino)methyl]-1-methyl-6,8-difluoroquinoline-4-one-3-ylcarbonylamino]-2-(1-naphthylsulfonylamino)propionic acid, 3-[7-[(benzimidazol-2-ylamino)methyl]-1-methyl-6,8-difluoroquinoline-4-one-3-ylcarbonylamino]-2-((2,4,6-trimethylphenyl)sulfonylamino)propionic acid, 3-[7-[(4-methylimidazol-2-ylamino)methyl]-1-methyl-6,8-difluoroquinoline-4-one-3-ylcarbonylamino]-2-((2,4,6-trimethylphenyl)sulfonylamino)propionic acid, 3-[7-[(4,5-dimethylimidazol-2-ylamino)methyl]-1-methyl-6,8-difluoroquinoline-4-one-3-ylcarbonylamino]-2-((2,4,6-trimethylphenyl)sulfonylamino)propionic acid, 3-[7-[(4,5,6,7-tetrahydrobenzimidazol-2-ylamino)methyl]-1-methyl-6,8-difluoroquinoline-4-one-3-ylcarbonylamino]-2-((2,4,6-trimethylphenyl)sulfonylamino)propionic acid, 3-[7-[(pyridin-2-ylamino)methyl]-1-methyl-6,8-difluoroquinoline-4-one-3-ylcarbonylamino]-2-((2,4,6-trimethylphenyl)sulfonylamino)propionic acid, 3-[7-(2-aminopyridin-6-yl)-1-methyl-6,8-difluoroquinoline-4-one-3-ylcarbonylamino]-2-((2,4,6-trimethylphenyl)sulfonylamino)propionic acid, 3-[7-[(7-azabenzimidazol-2-yl)methyl]-1-methyl-6,8-difluoroquinoline-4-one-3-ylcarbonylamino]-2-((2,4,6-trimethylphenyl)sulfonylamino)propionic acid, 3-[7-[(benzimidazol-2-ylamino)methyl]-1-(2-phenylethyl)-6,8-difluoroquinoline-4-one-3-ylcarbonylamino]propionic acid, 3-[7-[(pyridin-2-ylamino)methyl]-1-(2-phenylethyl)-6,8-difluoroquinoline-4-one-3-ylcarbonylamino]propionic acid, 3-[7-[(imidazolin-2-ylamino)methyl]-1-(2-phenylethyl)-6,8-difluoroquinoline-4-one-3-ylcarbonylamino]propionic acid, 3-[7-[(imidazol-2-ylamino)methyl]-1-(2-phenylethyl)-6,8-difluoroquinoline-4-one-3-ylcarbonylamino]propionic acid, 3-[7-[(imidazolin-2-ylamino)methyl]-1-(2-phenylethyl)-6,8-difluoroquinoline-4-one-3-ylcarbonylamino]-2-(benzyloxycarbonylamino)propionic acid, 3-[7-[(imidazolin-2-ylamino)methyl]-1-(2-phenylethyl)-6,8-difluoroquinoline-4-one-3-ylcarbonylamino]-2-(n-butyloxycarbonylamino)propionic acid, 3-[7-[(imidazolin-2-ylamino)methyl]-1-(2-phenylethyl)-6,8-difluoroquinoline-4-one-3-ylcarbonylamino]-2-(phenylsulfonylamino)propionic acid, 3-[7-[(imidazolin-2-ylamino)methyl]-1-(2-phenylethyl)-6,8-difluoroquinoline-4-one-3-ylcarbonylamino]-2-(n-butylsulfonylamino)propionic acid, 3-[7-[(tetrahydropyrimid-2-ylamino)methyl]-1-(2-phenylethyl)-6,8-difluoroquinoline-4-one-3-ylcarbonylamino]-2-(benzyloxycarbonylamino)propionic acid, 3-[7-[(tetrahydropyrimid-2-ylamino)methyl]-1-(2-phenylethyl)-6,8-difluoroquinoline-4-one-3-ylcarbonylamino]-2-(n-butyloxycarbonylamino)propionic acid, 3-[7-[(tetrahydropyrimid-2-ylamino)methyl]-1-(2-phenylethyl)-6,8-difluoroquinoline-4-one-3-ylcarbonylamino]-2-(phenylsulfonylamino)propionic acid, 3-[7-[(tetrahydropyrimid-2-ylamino)methyl]-1-(2-phenylethyl)-6,8-difluoroquinoline-4-one-3-ylcarbonylamino]-2-(n-butylsulfonyl)aminopropionic acid, 3-[7-[(2-aminothiazol-4-yl)methyl]-1-(2-phenylethyl)-6,8-difluoroquinoline-4-one-3-ylcarbonylamino]-2-(phenylsulfonylamino)propionic acid, 3-[7-[(2-aminothiazol-4-yl)methyl]-1-(2-phenylethyl)-6,8-difluoroquinoline-4-one-3-ylcarbonylamino]-2-(benzyloxycarbonylamino)propionic acid, 3-[7-[(imidazolin-2-ylamino)methyl]-1-(2-phenylethyl)-6,8-difluoroquinoline-4-one-3-ylcarbonylamino]-2-((2,4,6-trimethylphenyl)sulfonylamino)propionic acid, 3-[7-[(tetrahydropyrimid-2-ylamino)methyl]-1-(2-phenylethyl)-6,8-difluoroquinoline-4-one-3-ylcarbonylamino]-2-((2,4,6-trimethylphenyl)sulfonylamino)propionic acid, 3-[7-[(imidazol-2-ylamino)methyl]-1-(2-phenylethyl)-6,8-difluoroquinoline-4-one-3-ylcarbonylamino]-2-(benzyloxycarbonylamino)propionic acid, 3-[7-[(imidazol-2-ylamino)methyl]-1-(2-phenylethyl)-6,8-difluoroquinoline-4-one-3-ylcarbonylamino]-2-(phenylsulfonylamino)propionic acid, 3-[7-[(imidazol-2-ylamino)methyl]-1-(2-phenylethyl)-6,8-difluoroquinoline-4-one-3-ylcarbonylamino]-2-((2,6-dichlorophenyl)sulfonylamino)propionic acid, 3-[7-[(imidazol-2-ylamino)methyl]-1-(2-phenylethyl)-6,8-difluoroquinoline-4-one-3-ylcarbonylamino]-2-((2,4,6-trimethylphenyl)sulfonylamino)propionic acid, 3-[7-[(imidazol-2-ylamino)methyl]-1-(2-phenylethyl)-6,8-difluoroquinoline-4-one-3-ylcarbonylamino]-2-((4-biphenyl)sulfonylamino)propionic acid, 3-[7-[(benzimidazol-2-ylamino)methyl]-1-(2-phenylethyl)-6,8-difluoroquinoline-4-one-3-ylcarbonylamino]-2-((2,4,6-trimethylphenyl)sulfonylamino)propionic acid, 3-[7-[(4-methylimidazol-2-ylamino)methyl]-1-(2-phenylethyl)-6,8-difluoroquinoline-4-one-3-ylcarbonylamino]-2-((2,4,6-trimethylphenyl)sulfonylamino)propionic acid, 3-[7-[(4,5-dimethylimidazol-2-ylamino)methyl]-1-(2-phenylethyl)-6,8-difluoroquinoline-4-one-3-ylcarbonylamino]-2-((2,4,6-trimethylphenyl)sulfonylamino)propionic acid, 3-[7-[(4,5,6,7-tetrahydrobenzimidazol-2-ylamino)methyl]-1-(2-phenylethyl)-6,8-difluoroquinoline-4-one-3-ylcarbonylamino]-2-((2,4,6-trimethylphenyl)sulfonylamino)propionic acid, 3-[7-[(pyridin-2-ylamino)methyl]-1-(2-phenylethyl)-6,8-difluoroquinoline-4-one-3-ylcarbonylamino]-2-((2,4,6-trimethylphenyl)sulfonylamino)propionic acid, 3-[7-(2-aminopyridin-6-yl)-1-(2-phenylethyl)-6,8-difluoroquinoline-4-one-3-ylcarbonylamino]-2-((2,4,6-trimethylphenyl)sulfonylamino)propionic acid, 3-[7-[(7-azabenzimidazol-2-yl)methyl]-1-(2-phenylethyl)-6,8-difluoroquinoline-4-one-3-ylcarbonylamino]-2-((2,4,6-trimethylphenyl)sulfonylamino)propionic acid

[3a] In a third embodiment of the present invention are compounds of Formula II:

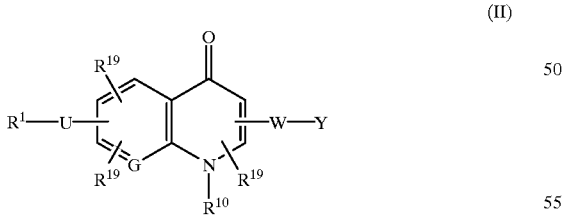

(II)

including stereoisomeric forms thereof, or mixtures of stereoisomeric forms thereof, or pharmaceutically acceptable salt or prodrug forms thereof wherein:

$R^1$ is selected from:

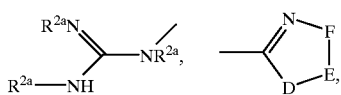

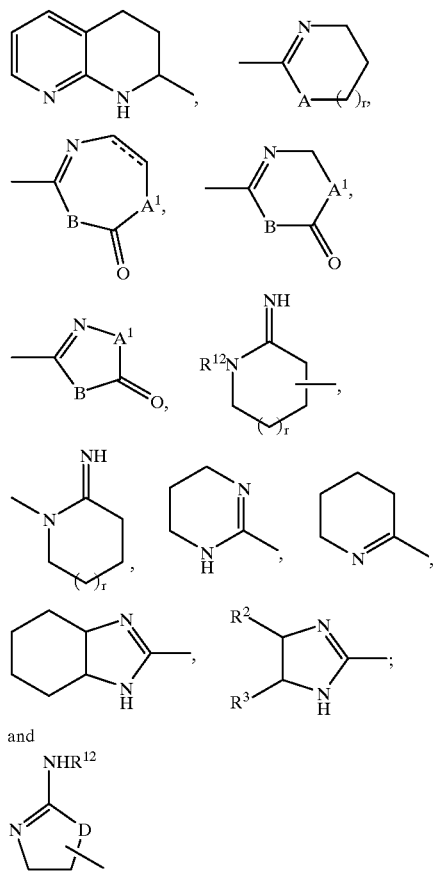

and

NHR$^{12}$

A is —CH$_2$— or —N(R$^{12}$)—;

A$^1$ and B are independently —CH$_2$— or —N(R$^{10}$)—;

D is —N(R$^{12}$)— or —S—;

E—F is —C(R$^2$)$_2$C(R$^3$)$_2$— or —CH(R$^2$)CH(R$^3$)—;

$R^2$ and $R^3$ are independently selected from:
H, $C_1$–$C_4$ alkoxy, NR$^{11}$R$^{12}$, halogen, NO$_2$, CN, CF$_3$, $C_1$–$C_6$ alkyl, $C_3$–$C_6$ alkenyl, $C_3$–$C_7$ cycloalkyl, $C_3$–$C_7$ cycloalkyl($C_1$–$C_4$ alkyl), aryl($C_1$–$C_6$ alkyl)-, ($C_1$–$C_6$ alkyl)carbonyl, ($C_1$–$C_6$ alkoxy)carbonyl, arylcarbonyl, and aryl substituted with 0–4 R$^7$, alternatively, when $R^2$ and $R^3$ are substituents on adjacent atoms, they can be taken together with the carbon atoms to which they are attached to form a 5–7 membered carbocyclic or 5–7 membered heterocyclic aromatic or nonaromatic ring system, said carbocyclic or heterocyclic ring being substituted with 0–2 groups selected from $C_1$–$C_4$ alkyl, $C_1$–$C_4$ alkoxy, halo, cyano, amino, CF$_3$ and NO$_2$;

$R^{2a}$ is selected from:
H, $C_1$–$C_{10}$ alkyl, $C_2$–$C_6$ alkenyl, $C_3$–$C_{11}$ cycloalkyl, $C_3$–$C_7$ cycloalkyl($C_1$–$C_4$ alkyl), aryl, aryl($C_1$–$C_4$ alkyl)-, ($C_2$–$C_7$ alkyl)carbonyl, arylcarbonyl, ($C_2$–$C_{10}$ alkoxy)carbonyl, $C_3$–$C_7$ cycloalkoxycarbonyl, $C_7$–$C_{11}$ bicycloalkoxycarbonyl, aryloxycarbonyl, aryl ($C_1$–$C_{10}$ alkoxy)carbonyl, $C_1$–$C_6$ alkylcarbonyloxy ($C_1$–$C_4$ alkoxy)carbonyl, arylcarbonyloxy($C_1$–$C_4$ alkoxy)carbonyl, and $C_3$–$C_7$ cycloalkylcarbonyloxy ($C_1$–$C_4$ alkoxy)carbonyl;

$R^4$ is selected from:
H, $C_1$–$C_6$ alkyl, $C_3$–$C_7$ cycloalkyl, $C_3$–$C_7$ cycloalkyl ($C_1$–$C_4$ alkyl)-, aryl, heteroaryl, aryl($C_1$–$C_6$ alkyl)-, and heteroaryl($C_1$–$C_6$ alkyl)-, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$, $R^6$ is selected from:
H, $C_1$–$C_{10}$ alkyl, hydroxy, $C_1$–$C_{10}$ alkoxy, nitro, $C_1$–$C_{10}$ alkylcarbonyl, —N($R^{11}$)$R^{12}$, cyano, halo, $CF_3$, CHO, $CO_2R^{18b}$, C(=O)$R^{18b}$, CON$R^{17}R^{18b}$, OC(=O)$R^{10}$, O$R^{10}$, OC(=O)N$R^{10}R^{11}$, N$R^{10}$C(=O)$R^{10}$, N$R^{10}$C(=O)O$R^{21}$, N$R^{10}$C(=O)N$R^{10}R^{11}$, N$R^{10}SO_2$N$R^{10}R^{11}$, N$R^{10}SO_2R^{21}$, S(O)$_pR^{11}$, $SO_2$N$R^{10}R^{11}$, aryl substituted with 0–3 groups selected from halogen, $C_1$–$C_6$ alkoxy, $C_1$–$C_6$ alkyl, $CF_3$, S(O)$_m$Me, and —N$Me_2$, aryl($C_1$–$C_4$ alkyl)-, said aryl being substituted with 0–3 groups selected from halogen, $C_1$–$C_6$ alkoxy, $C_1$–$C_6$ alkyl, $CF_3$, S(O)$_p$Me, and —N$Me_2$, and a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$;

$R^7$ is selected from:
H, hydroxy, $C_1$–$C_4$ alkyl, $C_1$–$C_4$ alkoxy, aryl, aryl ($C_1$–$C_4$ alkyl)-, ($C_1$–$C_4$ alkyl)carbonyl, $CO_2R^{18a}$, $SO_2R^{11}$, $SO_2$N$R^{10}R^{11}$, O$R^{10}$, and N($R^{11}$)$R^{12}$;

U is selected from:
—($CH_2$)$_n$—, —($CH_2$)$_n$O($CH_2$)$_m$—, —($CH_2$)$_n$N($R^{12}$)($CH_2$)$_m$—, —NH($CH_2$)$_n$—, —($CH_2$)$_n$C(=O)($CH_2$)$_m$—, —($CH_2$)$_n$S(O)$_p$($CH_2$)$_m$—, —($CH_2$)$_n$NHNH($CH_2$)$_m$—, —N($R^{10}$)C(=O)—, —NHC(=O)($CH_2$)$_n$—, —C(=O)N($R^{10}$)—, and —N($R^{10}$)S(O)$_p$—;

G is N or $CR^{19}$;

W is —C(=O)—N($R^{10}$)—($C_1$–$C_3$ alkylene)-, in which the alkylene group is substituted by $R^8$ and by $R^9$:

$R^8$ and $R^9$ are independently selected from:
H, $CO_2R^{18b}$, C(=O)$R^{18b}$, CON$R^{17}R^{18b}$,
$C_1$–$C_{10}$ alkyl substituted with 0–1 $R^6$,
$C_2$–$C_{10}$ alkenyl substituted with 0–1 $R^6$,
$C_2$–$C_{10}$ alkynyl substituted with 0–1 $R^6$,
$C_3$–$C_8$ cycloalkyl substituted with 0–1 $R^6$,
$C_5$–$C_6$ cycloalkenyl substituted with 0–1 $R^6$,
($C_1$–$C_{10}$ alkyl)carbonyl,
$C_3$–$C_{10}$ cycloalkyl($C_1$–$C_4$ alkyl)-,
phenyl substituted with 0–3 $R^6$,
naphthyl substituted with 0–3 $R^6$,
a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$,
$C_1$–$C_{10}$ alkoxy substituted with 0–2 $R^7$,
hydroxy, nitro, —N($R^{10}$)$R^{11}$, —N($R^{16}$)$R^{17}$, aryl($C_0$–$C_6$ alkyl)carbonyl, aryl($C_3$–$C_6$ alkyl), heteroaryl($C_1$–$C_6$ alkyl), CON$R^{18a}R^{20}$, $SO_2R^{18a}$, and $SO_2$N$R^{18a}R^{20}$,
providing that any of the above alkyl, cycloalkyl, aryl or heteroaryl groups may be unsubstituted or substituted independently with 1–2 $R^7$;

$R^{10}$ is selected from:
H, $CF_3$, $C_3$–$C_6$ alkenyl, $C_3$–$C_{11}$ cycloalkyl, aryl, ($C_3$–$C_{11}$ cycloalkyl)methyl, aryl($C_1$–$C_4$ alkyl), and $C_1$–$C_{10}$ alkyl substituted with 0–2 $R^6$;

$R^{11}$ is selected from:
H, hydroxy, $C_1$–$C_8$ alkyl, $C_3$–$C_6$ alkenyl, $C_3$–$C_{11}$ cycloalkyl, ($C_3$–$C_{11}$ cycloalkyl)methyl, $C_1$–$C_6$ alkoxy, benzyloxy, aryl, heteroaryl, heteroaryl ($C_1$–$C_4$ alkyl)-, aryl($C_1$–$C_4$ alkyl), adamantylmethyl, and $C_1$–$C_{10}$ alkyl substituted with 0–2 $R^4$;

alternatively, when $R^{10}$ and $R^{11}$ are both substituents on the same nitrogen atom (as in —N$R^{10}R^{11}$) they may be taken together with the nitrogen atom to which they are attached to form a heterocycle selected from:
3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl, and 1-piperazinyl;

said heterocycle being substituted with 0–3 groups selected from: $C_1$–$C_6$ alkyl, aryl, heteroaryl, aryl ($C_1$–$C_4$ alkyl)-, ($C_1$–$C_6$ alkyl)carbonyl, ($C_3$–$C_7$ cycloalkyl)carbonyl, ($C_1$–$C_6$ alkoxy)carbonyl, aryl($C_1$–$C_4$ alkoxy)carbonyl, $C_1$–$C_6$ alkylsulfonyl, and arylsulfonyl;

$R^{12}$ is selected from:
H, $C_1$–$C_6$ alkyl, triphenylmethyl, methoxymethyl, methoxyphenyldiphenylmethyl, trimethylsilylethoxymethyl, ($C_1$–$C_6$ alkyl)carbonyl, ($C_1$–$C_6$ alkoxy)carbonyl, ($C_1$–$C_6$ alkyl) aminocarbonyl, $C_3$–$C_6$ alkenyl, $C_3$–$C_7$ cycloalkyl, $C_3$–$C_7$ cycloalkyl($C_1$–$C_4$ alkyl)-, aryl, heteroaryl ($C_1$–$C_6$ alkyl)carbonyl, heteroarylcarbonyl, aryl ($C_1$–$C_6$ alkyl)-, ($C_1$–$C_6$ alkyl)carbonyl, arylcarbonyl, $C_1$–$C_6$ alkylsulfonyl, arylsulfonyl, aryl($C_1$–$C_6$ alkyl) sulfonyl, heteroarylsulfonyl, heteroaryl($C_1$–$C_6$ alkyl)sulfonyl, aryloxycarbonyl, and aryl($C_1$–$C_6$ alkoxy)carbonyl, wherein said aryl groups are substituted with 0–2 substituents selected from the group consisting of $C_1$–$C_4$ alkyl, $C_1$–$C_4$ alkoxy, halo, $CF_3$, and nitro;

$R^{16}$ is selected from:
—C(=O)O$R^{18a}$, —C(=O)$R^{18b}$, —C(=O)N($R^{18b}$)$_2$, —C(=O)NH$SO_2R^{18a}$, —C(=O)NHC(=O)$R^{18b}$, —C(=O)NHC(=O)O$R^{18a}$, —C(=O)NH$SO_2$NH$R^{18b}$, —$SO_2R^{18a}$, —$SO_2$N($R^{18b}$)$_2$, and —$SO_2$NHC(=O)O$R^{18b}$;

$R^{17}$ is selected from:
H, $C_1$–$C_6$ alkyl, $C_3$–$C_7$ cycloalkyl, $C_3$–$C_7$ cycloalkyl ($C_1$–$C_4$ alkyl)-, aryl, aryl($C_1$–$C_6$ alkyl)-, and heteroaryl($C_1$–$C_6$ alkyl);

$R^{18a}$ is selected from:
$C_1$–$C_8$ alkyl, $C_3$–$C_{11}$ cycloalkyl,
aryl($C_1$–$C_6$ alkyl)-, said aryl substituted with 0–4 $R^{19}$,
heteroaryl($C_1$–$C_6$ alkyl)-, said heteroaryl substituted with 0–4 $R^{19}$,
($C_1$–$C_6$ alkyl)heteroaryl, said heteroaryl substituted with 0–4 $R^{19}$,
heteroaryl substituted with 0–4 $R^{19}$,
phenyl substituted with 0–4 $R^{19}$, and
naphthyl substituted with 0–4 $R^{19}$;

$R^{18b}$ is H or $R^{18a}$;

$R^{19}$ is selected from:
H, halogen, $CF_3$, $CO_2$H, CN, $NO_2$, —N$R^{11}R^{12}$, $OCF_3$, $C_1$–$C_8$ alkyl, $C_2$–$C_6$ alkenyl, $C_2$–$C_6$ alkynyl, $C_3$–$C_{11}$ cycloalkyl, $C_3$–$C_7$ cycloalkyl($C_1$–$C_4$ alkyl)-, aryl ($C_1$–$C_6$ alkyl)-, $C_1$–$C_6$ alkoxy, $C_1$–$C_4$ alkoxycarbonyl, aryl, aryl-O—, aryl-$SO_2$—, heteroaryl, and heteroaryl-$SO_2$—, wherein said aryl and heteroaryl groups are substituted with 0–4 groups selected from hydrogen, halogen, $CF_3$, $C_1$–$C_3$ alkyl, and $C_1$–$C_3$ alkoxy;

$R^{20}$ is selected from:
  hydroxy, $C_1$–$C_{10}$ alkyloxy, $C_3$–$C_{11}$ cycloalkyloxy, aryloxy, aryl($C_1$–$C_4$ alkyl)oxy,
  $C_2$–$C_{10}$ alkylcarbonyloxy($C_1$–$C_2$ alkyl)oxy-,
  $C_2$–$C_{10}$ alkoxycarbonyloxy($C_1$–$C_2$ alkyl)oxy-,
  $C_2$–$C_{10}$ alkoxycarbonyl($C_1$–$C_2$ alkyl)oxy-,
  $C_3$–$C_{10}$ cycloalkylcarbonyloxy($C_1$–$C_2$ alkyl)oxy-,
  $C_3$–$C_{10}$ cycloalkoxycarbonyloxy($C_1$–$C_2$ alkyl)oxy-,
  $C_3$–$C_{10}$ cycloalkoxycarbonyl($C_1$–$C_2$ alkyl)oxy-,
  aryloxycarbonyl($C_1$–$C_2$ alkyl)oxy-,
  aryloxycarbonyloxy($C_1$–$C_2$ alkyl)oxy-,
  arylcarbonyloxy($C_1$–$C_2$ alkyl)oxy-,
  $C_1$–$C_5$ alkoxy($C_1$–$C_5$ alkyl)carbonyloxy($C_1$–$C_2$ alkyl)oxy-,
  (5-($C_1$–$C_5$ alkyl)-1,3-dioxa-cyclopenten-2-one-yl)methyloxy,
  (5-aryl-1,3-dioxa-cyclopenten-2-one-yl)methyloxy, and
  $(R^{10})(R^{11})N$—($C_1$–$C_{10}$ alkoxy)-;
$R^{21}$ is selected from:
  $C_1$–$C_8$ alkyl, $C_2$–$C_6$ alkenyl, $C_3$–$C_{11}$ cycloalkyl, ($C_3$–$C_{11}$ cycloalkyl)methyl, aryl, aryl($C_1$–$C_4$ alkyl)-, and $C_1$–$C_{10}$ alkyl substituted with 0–2 $R^7$;
$R^{22}$ is selected from:
  —C(=O)—$R^{18b}$, —C(=O)N($R^{18b}$)$_2$, —C(=O)NHSO$_2$$R^{18a}$, —C(=O)NHC(=O)$R^{18b}$, —C(=O)NHC(=O)OR$^{18a}$, and —C(=O)NHSO$_2$NHR$^{18b}$;
Y is selected from:
  —COR$^{20}$, —SO$_3$H, —PO$_3$H, —CONHNHSO$_2$CF$_3$, —CONHSO$_2$R$^{18a}$, —CONHSO$_2$NHR$^{18b}$, —NHCOCF$_3$, —NHCONHSO$_2$R$^{18a}$, —NHSO$_2$R$^{18a}$, —OPO$_3$H$_2$, —OSO$_3$H, —PO$_3$H$_2$, —SO$_2$NHCOR$^{18a}$, —SO$_2$NHCO$_2$R$^{18a}$, m is 0–2;
n is 0–4;
p is 0–2; and
r is 0–2;
with the proviso that n, and m are chosen such that the number of atoms connecting $R^1$ and Y is in the range of 8–14.

[3b] Preferred compounds of the third embodiment are those of Formula IV:

(IV)

including stereoisomeric forms thereof, or mixtures of stereoisomeric forms thereof, or pharmaceutically acceptable salt or prodrug forms thereof wherein:

$R^1$ is selected from:

A is —CH$_2$— or —N($R^{12}$)—;
$A^1$ and B are independently —CH$_2$— or —N($R^{10}$)—;
D is —N($R^{12}$)— or —S—;
E—F is —C($R^2$)$_2$C($R^3$)$_2$— or —CH($R^2$)CH($R^3$)—;
$R^2$ and $R^3$ are independently selected from:
  H, $C_1$–$C_4$ alkoxy, NR$^{11}$R$^{12}$, halogen, NO$_2$, CN, CF$_3$, $C_1$–$C_6$ alkyl, $C_3$–$C_6$ alkenyl, $C_3$–$C_7$ cycloalkyl, $C_3$–$C_7$ cycloalkyl($C_1$–$C_4$ alkyl), aryl($C_1$–$C_6$ alkyl)-, ($C_1$–$C_6$ alkyl)carbonyl, ($C_1$–$C_6$ alkoxy)carbonyl, arylcarbonyl, and aryl substituted with 0–4 $R^7$,
  alternatively, when $R^2$ and $R^3$ are substituents on adjacent atoms, they can be taken together with the carbon atoms to which they are attached to form a 5–7 membered carbocyclic or 5–7 membered heterocyclic aromatic or nonaromatic ring system, said carbocyclic or heterocyclic ring being substituted with 0–2 groups selected from $C_1$–$C_4$ alkyl, $C_1$–$C_4$ alkoxy, halo, cyano, amino, CF$_3$ and NO$_2$;
$R^{2a}$ is selected from:
  H, $C_1$–$C_{10}$ alkyl, $C_2$–$C_6$ alkenyl, $C_3$–$C_{11}$ cycloalkyl, $C_3$–$C_7$ cycloalkyl($C_1$–$C_4$ alkyl), aryl, aryl($C_1$–$C_4$ alkyl)-, ($C_2$–$C_7$ alkyl)carbonyl, arylcarbonyl, ($C_2$–$C_{10}$ alkoxy)carbonyl, $C_3$–$C_7$ cycloalkoxycarbonyl, $C_7$–$C_{11}$ bicycloalkoxycarbonyl, aryloxycarbonyl, aryl ($C_1$–$C_{10}$ alkoxy)carbonyl, $C_1$–$C_6$ alkylcarbonyloxy ($C_1$–$C_4$ alkoxy)carbonyl, arylcarbonyloxy($C_1$–$C_4$ alkoxy)carbonyl, and $C_3$–$C_7$ cycloalkylcarbonyloxy ($C_1$–$C_4$ alkoxy)carbonyl;
$R^4$ is selected from:
  H, $C_1$–$C_6$ alkyl, $C_3$–$C_7$ cycloalkyl, $C_3$–$C_7$ cycloalkyl ($C_1$–$C_4$ alkyl)-, aryl, heteroaryl, aryl($C_1$–$C_6$ alkyl)-, and heteroaryl($C_1$–$C_6$ alkyl)-, wherein said aryl or heteroaryl groups are substituted with 0–2 substituents independently selected from the group consisting of $C_1$–$C_4$ alkyl, $C_1$–$C_4$ alkoxy, F, Cl, Br, CF$_3$, and NO$_2$, $R^6$ is selected from:
- H, $C_1$–$C_{10}$ alkyl, hydroxy, $C_1$–$C_{10}$ alkoxy, nitro, $C_1$–$C_{10}$ alkylcarbonyl, —N($R^{11}$)$R^{12}$, cyano, halo, $CF_3$, CHO, $CO_2R^{18b}$, C(=O)$R^{18b}$, $CONR^{17}R^{18b}$, OC(=O)$R^{10}$, $OR^{10}$, OC(=O)$NR^{10}R^{11}$, $NR^{10}$C(=O)$R^{10}$, $NR^{10}$C(=O)$OR^{21}$, $NR^{10}$C(=O)$NR^{10}R^{11}$, $NR^{10}SO_2NR^{10}R^{11}$, $NR^{10}SO_2R^{21}$, S(O)$_pR^{11}$, $SO_2NR^{10}R^{11}$,
- aryl substituted with 0–3 groups selected from halogen, $C_1$–$C_6$ alkoxy, $C_1$–$C_6$ alkyl, $CF_3$, S(O)$_m$Me, and —NMe$_2$,
- aryl($C_1$–$C_4$ alkyl)-, said aryl being substituted with 0–3 groups selected from halogen, $C_1$–$C_6$ alkoxy, $C_1$–$C_6$ alkyl, $CF_3$, S(O)$_p$Me, and —NMe$_2$,
- a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$;

$R^7$ is selected from:
- H, hydroxy, $C_1$–$C_4$ alkyl, $C_1$–$C_4$ alkoxy, aryl, aryl($C_1$–$C_4$ alkyl)-, ($C_1$–$C_4$ alkyl)carbonyl, $CO_2R^{18a}$, $SO_2R^{11}$, $SO_2NR^{10}R^{11}$, $OR^{10}$, and N($R^{11}$)$R^{12}$;

U is selected from:
- —(CH$_2$)$_n$—, —(CH$_2$)$_n$O(CH$_2$)$_m$—, —NH(CH$_2$)$_n$—, —N($R^{10}$)C(=O)—, —NHC(=O)(CH$_2$)$_n$—, and —C(=O)N($R^{10}$)—;

G is N or $CR^{19}$;

$R^8$ is selected from:
- H, $CO_2R^{18b}$, C(=O)$R^{18b}$, $CONR^{17}R^{18b}$,
- $C_1$–$C_{10}$ alkyl substituted with 0–1 $R^6$,
- $C_2$–$C_{10}$ alkenyl substituted with 0–1 $R^6$,
- $C_2$–$C_{10}$ alkynyl substituted with 0–1 $R^6$,
- $C_3$–$C_8$ cycloalkyl substituted with 0–1 $R^6$,
- $C_5$–$C_6$ cycloalkenyl substituted with 0–1 $R^6$,
- ($C_1$–$C_{10}$ alkyl)carbonyl,
- $C_3$–$C_{10}$ cycloalkyl($C_1$–$C_4$ alkyl)-,
- phenyl substituted with 0–3 $R^6$,
- naphthyl substituted with 0–3 $R^6$,
- a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$;

$R^9$ is selected from:
- $C_1$–$C_{10}$ alkyl substituted with 0–1 $R^6$,
- $C_1$–$C_{10}$ alkoxy substituted with 0–2 $R^7$,
- H, nitro, N($R^{11}$)$R^{12}$, OC(=O)$R^{10}$, $OR^{10}$, OC(=O)$NR^{10}R^{11}$, $NR^{10}$C(=O)$R^{10}$, $NR^{10}$C(=O)$OR^{21}$, $NR^{10}$C(=O)$NR^{10}R^{11}$, $NR^{10}SO_2NR^{10}R^{11}$, $NR^{10}SO_2R^{21}$, hydroxy, $OR^{22}$, —N($R^{10}$)$R^{11}$, —N($R^{16}$)$R^{17}$, aryl($C_0$–$C_6$ alkyl)carbonyl, aryl($C_1$–$C_6$ alkyl), heteroaryl($C_1$–$C_6$ alkyl), $CONR^{18a}R^{20}$, $SO_2R^{18a}$, and $SO_2NR^{18a}R^{20}$,
- providing that any of the above alkyl, cycloalkyl, aryl or heteroaryl groups may be unsubstituted or substituted independently with 1–2 $R^7$;

$R^{10}$ is selected from:
- H, $CF_3$, $C_3$–$C_6$ alkenyl, $C_3$–$C_{11}$ cycloalkyl, aryl, ($C_3$–$C_{11}$ cycloalkyl)methyl, aryl($C_1$–$C_4$ alkyl), and $C_1$–$C_{10}$ alkyl substituted with 0–2 $R^6$;

$R^{11}$ is selected from:
- H, hydroxy, $C_1$–$C_8$ alkyl, $C_3$–$C_6$ alkenyl, $C_3$–$C_{11}$ cycloalkyl, ($C_3$–$C_{11}$ cycloalkyl)methyl, $C_1$–$C_6$ alkoxy, benzyloxy, aryl, heteroaryl, heteroaryl($C_1$–$C_4$ alkyl)-, aryl($C_1$–$C_4$ alkyl), adamantylmethyl, and $C_1$–$C_{10}$ alkyl substituted with 0–2 $R^4$;

$R^{12}$ is selected from:
- H, $C_1$–$C_6$ alkyl, triphenylmethyl, methoxymethyl, methoxyphenyldiphenylmethyl, trimethylsilylethoxymethyl, ($C_1$–$C_6$ alkyl)carbonyl, ($C_1$–$C_6$ alkoxy)carbonyl, ($C_1$–$C_6$ alkyl)aminocarbonyl, $C_3$–$C_6$ alkenyl, $C_3$–$C_7$ cycloalkyl, $C_3$–$C_7$ cycloalkyl($C_1$–$C_4$ alkyl)-, aryl, heteroaryl ($C_1$–$C_6$ alkyl)carbonyl, heteroarylcarbonyl, aryl($C_1$–$C_6$ alkyl)-, ($C_1$–$C_6$ alkyl)carbonyl, arylcarbonyl, $C_1$–$C_6$ alkylsulfonyl, arylsulfonyl, aryl($C_1$–$C_6$ alkyl)sulfonyl, heteroarylsulfonyl, heteroaryl($C_1$–$C_6$ alkyl)sulfonyl, aryloxycarbonyl, and aryl($C_1$–$C_6$ alkoxy)carbonyl, wherein said aryl groups are substituted with 0–2 substituents selected from the group consisting of $C_1$–$C_4$ alkyl, $C_1$–$C_4$ alkoxy, halo, $CF_3$, and nitro;

$R^{17}$ is selected from:
- H, $C_1$–$C_6$ alkyl, $C_3$–$C_7$ cycloalkyl, $C_3$–$C_7$ cycloalkyl($C_1$–$C_4$ alkyl)-, aryl, aryl($C_1$–$C_6$ alkyl)-, and heteroaryl($C_1$–$C_6$ alkyl);

$R^{18a}$ is selected from:
- $C_1$–$C_8$ alkyl, $C_3$–$C_{11}$ cycloalkyl,
- aryl($C_1$–$C_6$ alkyl)-, said aryl substituted with 0–4 $R^{19}$,
- heteroaryl($C_1$–$C_6$ alkyl)-, said heteroaryl substituted with 0–4 $R^{19}$,
- ($C_1$–$C_6$ alkyl)heteroaryl, said heteroaryl substituted with 0–4 $R^{19}$,
- heteroaryl substituted with 0–4 $R^{19}$,
- phenyl substituted with 0–4 $R^{19}$, and
- naphthyl substituted with 0–4 $R^{19}$;

$R^{18b}$ is H or $R^{18a}$;

$R^{19}$ is selected from:
- H, halogen, $CF_3$, $CO_2H$, CN, $NO_2$, —$NR^{11}R^{12}$, $OCF_3$, $C_1$–$C_8$ alkyl, $C_2$–$C_6$ alkenyl, $C_2$–$C_6$ alkynyl, $C_3$–$C_{11}$ cycloalkyl, $C_3$–$C_7$ cycloalkyl ($C_1$–$C_4$ alkyl)-, aryl ($C_1$–$C_6$ alkyl)-, $C_1$–$C_6$ alkoxy, $C_1$–$C_4$ alkoxycarbonyl, aryl, aryl-O—, aryl-$SO_2$—, heteroaryl, and heteroaryl-$SO_2$—, wherein said aryl and heteroaryl groups are substituted with 0–4 groups selected from hydrogen, halogen, $CF_3$, $C_1$–$C_3$ alkyl, and $C_1$–$C_3$ alkoxy;

$R^{20}$ is selected from:
- hydroxy, $C_1$–$C_{10}$ alkyloxy, $C_3$–$C_{11}$ cycloalkyloxy, aryloxy, aryl($C_1$–$C_4$ alkyl)oxy,
- $C_2$–$C_{10}$ alkylcarbonyloxy($C_1$–$C_2$ alkyl)oxy-,
- $C_2$–$C_{10}$ alkoxycarbonyloxy($C_1$–$C_2$ alkyl)oxy-,
- $C_2$–$C_{10}$ alkoxycarbonyl($C_1$–$C_2$ alkyl)oxy-,
- $C_3$–$C_{10}$ cycloalkylcarbonyloxy($C_1$–$C_2$ alkyl)oxy-,
- $C_3$–$C_{10}$ cycloalkoxycarbonyloxy($C_1$–$C_2$ alkyl)oxy-,
- $C_3$–$C_{10}$ cycloalkoxycarbonyl($C_1$–$C_2$ alkyl)oxy-,
- aryloxycarbonyl($C_1$–$C_2$ alkyl)oxy-,
- aryloxycarbonyloxy($C_1$–$C_2$ alkyl)oxy-,
- arylcarbonyloxy($C_1$–$C_2$ alkyl)oxy-,
- $C_1$–$C_5$ alkoxy($C_1$–$C_5$ alkyl)carbonyloxy($C_1$–$C_2$ alkyl)oxy-,
- (5-($C_1$–$C_5$ alkyl)-1,3-dioxa-cyclopenten-2-one-yl)methyloxy,
- (5-aryl-1,3-dioxa-cyclopenten-2-one-yl)methyloxy, and
- ($R^{10}$)($R^{11}$)N—($C_1$–$C_{10}$ alkoxy)-;

$R^{21}$ is selected from:
- $C_1$–$C_8$ alkyl, $C_2$–$C_6$ alkenyl, $C_3$–$C_{11}$ cycloalkyl, ($C_3$–$C_{11}$ cycloalkyl)methyl, aryl, aryl($C_1$–$C_4$ alkyl)-, and $C_1$–$C_{10}$ alkyl substituted with 0–2 $R^7$;

$R^{22}$ is selected from:
- —C(=O)$R^{18b}$, —C(=O)N($R^{18b}$)$_2$, —C(=O)NHSO$_2R^{18a}$, —C(=O)NHC(=O)$R^{18b}$, and —C(=O)NHC(=O)$OR^{18a}$;

m is 0–2;

n is 0–4;

p is 0–2; and r is 0–2;

with the proviso that n and m are chosen such that the number of atoms connecting $R^1$ and $COR^{20}$ of Formula (IV) is in the range of 8–14.

[3c] Preferred compounds of the third embodiment are those of Formula IV:

(IV)

including stereoisomeric forms thereof, or mixtures of stereoisomeric forms thereof, or pharmaceutically acceptable salt or prodrug forms thereof wherein:

$R^1$ is selected from:

A is —$CH_2$— or —$N(R^{12})$—;

$A^1$ and B are independently —$CH_2$— or —$N(R^{10})$—;

D is —$N(R^{12})$— or —S—;

E—F is —$C(R^2)_2C(R^3)_2$— or —$CH(R^2)CH(R^3)_2$—;

$R^2$ and $R^3$ are independently selected from:
 H, $C_1$–$C_4$ alkoxy, $NR^{11}R^{12}$, halogen, $NO_2$, CN, $CF_3$, $C_1$–$C_6$ alkyl, $C_3$–$C_6$ alkenyl, $C_3$–$C_7$ cycloalkyl, $C_3$–$C_7$ cycloalkyl($C_1$–$C_4$ alkyl), aryl($C_1$–$C_6$ alkyl)-, ($C_1$–$C_6$ alkyl)carbonyl, ($C_1$–$C_6$ alkoxy)carbonyl, arylcarbonyl, and aryl substituted with 0–4 $R^7$,
 alternatively, when $R^2$ and $R^3$ are substituents on adjacent atoms, they can be taken together with the carbon atoms to which they are attached to form a 5–7 membered carbocyclic or 5–7 membered heterocyclic aromatic or nonaromatic ring system, said carbocyclic or heterocyclic ring being substituted with 0–2 groups selected from $C_1$–$C_4$ alkyl, $C_1$–$C_4$ alkoxy, halo, cyano, amino, $CF_3$ and $NO_2$;

$R^{2a}$ is selected from:
 H, $C_1$–$C_{10}$ alkyl, $C_2$–$C_6$ alkenyl, $C_3$–$C_{11}$ cycloalkyl, $C_3$–$C_7$ cycloalkyl($C_1$–$C_4$ alkyl), aryl, aryl($C_1$–$C_4$ alkyl)-, ($C_2$–$C_7$ alkyl)carbonyl, arylcarbonyl, ($C_2$–$C_{10}$ alkoxy)carbonyl, $C_3$–$C_7$ cycloalkoxycarbonyl, $C_7$–$C_{11}$ bicycloalkoxycarbonyl, aryloxycarbonyl, aryl ($C_1$–$C_{10}$ alkoxy)carbonyl, $C_1$–$C_6$ alkylcarbonyloxy ($C_1$–$C_4$ alkoxy)carbonyl, arylcarbonyloxy($C_1$–$C_4$ alkoxy)carbonyl, and $C_3$–$C_7$ cycloalkylcarbonyloxy ($C_1$–$C_4$ alkoxy)carbonyl;

$R^4$ is selected from:
 H, $C_1$–$C_6$ alkyl, $C_3$–$C_7$ cycloalkyl, $C_3$–$C_7$ cycloalkyl ($C_1$–$C_4$ alkyl)-, aryl, heteroaryl, aryl($C_1$–$C_6$ alkyl)-, and heteroaryl($C_1$–$C_6$ alkyl)-, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$, $R^6$ is selected from:
 H, $C_1$–$C_{10}$ alkyl, hydroxy, $C_1$–$C_{10}$ alkoxy, nitro, $C_1$–$C_{10}$ alkylcarbonyl, —$N(R^{11})R^{12}$, cyano, halo, $CF_3$, CHO, $CO_2R^{18b}$, $C(=O)R^{18b}$, $CONR^{17}R^{18b}$, $OC(=O)R^{10}$, $OR^{10}$, $OC(=O)NR^{10}R^{11}$, $NR^{10}C(=O)R^{10}$, $N^{10}C(=O)OR^{21}$, $NR^{10}C(=O)NR^{10}R^{11}$, $NR^{10}SO_2NR^{10}R^{11}$, $NR^{10}SO_2R^{21}$, $S(O)_pR^{11}$, $SO_2NR^{10}R^{11}$,
 aryl substituted with 0–3 groups selected from halogen, $C_1$–$C_6$ alkoxy, $C_1$–$C_6$ alkyl, $CF_3$, $S(O)_m$Me, and —$NMe_2$, aryl($C_1$–$C_4$ alkyl)-, said aryl being substituted with 0–3 groups selected from halogen, $C_1$–$C_6$ alkoxy, $C_1$–$C_6$ alkyl, $CF_3$, $S(O)_p$Me, and —$NMe_2$, and
 a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$;

$R^7$ is selected from:
 H, hydroxy, $C_1$–$C_4$ alkyl, $C_1$–$C_4$ alkoxy, aryl, aryl ($C_1$–$C_4$ alkyl)-, ($C_1$–$C_4$ alkyl)carbonyl, $CO_2R^{18a}$, $SO_2R^{11}$, $SO_2NR^{10}R^{11}$, $OR^{10}$, and $N(R^{11})R^{12}$;

U is selected from:
 —$(CH_2)_n$—, —$(CH_2)_nO(CH_2)_m$—, —$NH(CH_2)_n$—, —$N(R^{10})C(=O)$—, —$NHC(=O)(CH_2)_n$—, and —$C(=O)N(R^{10})$—;

G is N or $CR^{19}$;

$R^8$ is H;

$R^9$ is selected from:
 H, nitro, $N(R^{11})R^{12}$, $OC(=O)R^{10}$, $OR^{10}$, $OC(=O)NR^{10}R^{11}$, $NR^{10}C(=O)R^{10}$, $NR^{10}C(=O)OR^{21}$, $NR^{10}C(=O)NR^{10}R^{11}$, $NR^{10}SO_2NR^{10}R^{11}$, $NR^{10}SO_2R^{21}$, hydroxy, $OR^{22}$, —$N(R^{10})R^{11}$, —$N(R^{16})R^{17}$, aryl($C_0$–$C_6$ alkyl)carbonyl, aryl ($C_1$–$C_6$ alkyl), heteroaryl($C_1$–$C_6$ alkyl), $CONR^{18a}R^{20}$, $SO_2R^{18a}$, and $SO_2NR^{18a}R^{20}$,
 providing that any of the above alkyl, cycloalkyl, aryl or heteroaryl groups may be unsubstituted or substituted independently with 1–2 $R^7$;

$R^{10}$ is selected from:
 H, $CF_3$, $C_3$–$C_6$ alkenyl, $C_3$–$C_{11}$ cycloalkyl, aryl, ($C_3$–$C_{11}$ cycloalkyl)methyl, aryl($C_1$–$C_4$ alkyl), and $C_1$–$C_{10}$ alkyl substituted with 0–2 $R^6$;

$R^{11}$ is selected from:
 H, hydroxy, $C_1$–$C_8$ alkyl, $C_3$–$C_6$ alkenyl, $C_3$–$C_{11}$ cycloalkyl, ($C_3$–$C_{11}$ cycloalkyl)methyl, $C_1$–$C_6$ alkoxy, benzyloxy, aryl, heteroaryl, heteroaryl ($C_1$–$C_4$ alkyl)-, aryl($C_1$–$C_4$ alkyl), adamantylmethyl, and $C_1$–$C_{10}$ alkyl substituted with 0–2 $R^4$;

$R^{12}$ is selected from:
 H, $C_1$–$C_4$ alkyl, ($C_1$–$C_4$ alkyl)carbonyl, ($C_1$–$C_4$ alkoxy)carbonyl, phenyl($C_1$–$C_4$ alkyl)-, phenylsulfonyl, phenyloxycarbonyl, and phenyl ($C_1$–$C_4$ alkoxy)carbonyl, wherein said phenyl groups are substituted with 0–2 substituents selected from the group consisting of $C_1$–$C_4$ alkyl, $C_1$–$C_4$ alkoxy, halo, $CF_3$, and nitro;

$R^{17}$ is selected from:
  H, $C_1-C_6$ alkyl, $C_3-C_7$ cycloalkyl, $C_3-C_7$ cycloalkyl($C_1-C_4$ alkyl)-, aryl, aryl($C_1-C_6$ alkyl)-, and heteroaryl($C_1-C_6$ alkyl);

$R^{18a}$ is selected from:
  $C_1-C_8$ alkyl, $C_3-C_{11}$ cycloalkyl,
  aryl($C_1-C_6$ alkyl)-, said aryl substituted with 0–4 $R^{19}$,
  heteroaryl($C_1-C_6$ alkyl)-, said heteroaryl substituted with 0–4 $R^{19}$,
  ($C_1-C_6$ alkyl)heteroaryl, said heteroaryl substituted with 0–4 $R^{19}$,
  heteroaryl substituted with 0–4 $R^{19}$,
  phenyl substituted with 0–4 $R^{19}$, and
  naphthyl substituted with 0–4 $R^{19}$;

$R^{18b}$ is H or $R^{18a}$;

$R^{19}$ is selected from:
  H, halogen, $CF_3$, $CO_2H$, CN, $NO_2$, —$NR^{11}R^{12}$, $OCF_3$, $C_1-C_8$ alkyl, $C_2-C_6$ alkenyl, $C_2-C_6$ alkynyl, $C_3-C_{11}$ cycloalkyl, $C_3-C_7$ cycloalkyl($C_1-C_4$ alkyl)-, aryl($C_1-C_6$ alkyl)-, $C_1-C_6$ alkoxy, $C_1-C_4$ alkoxycarbonyl, aryl, aryl-O—, aryl-$SO_2$—, heteroaryl, and heteroaryl-$SO_2$—, wherein said aryl and heteroaryl groups are substituted with 0–4 groups selected from hydrogen, halogen, $CF_3$, $C_1-C_3$ alkyl, and $C_1-C_3$ alkoxy;

$R^{20}$ is selected from:
  hydroxy, $C_1-C_{10}$ alkyloxy, $C_3-C_{11}$ cycloalkyloxy, aryloxy, aryl($C_1-C_4$ alkyl)oxy,
  $C_2-C_{10}$ alkylcarbonyloxy($C_1-C_2$ alkyl)oxy-,
  $C_2-C_{10}$ alkoxycarbonyloxy($C_1-C_2$ alkyl)oxy-,
  $C_2-C_{10}$ alkoxycarbonyl($C_1-C_2$ alkyl)oxy-,
  $C_3-C_{10}$ cycloalkylcarbonyloxy($C_1-C_2$ alkyl)oxy-,
  $C_3-C_{10}$ cycloalkoxycarbonyloxy($C_1-C_2$ alkyl)oxy-,
  $C_3-C_{10}$ cycloalkoxycarbonyl($C_1-C_2$ alkyl)oxy-,
  aryloxycarbonyl($C_1-C_2$ alkyl)oxy-,
  aryloxycarbonyloxy($C_1-C_2$ alkyl)oxy-,
  arylcarbonyloxy($C_1-C_2$ alkyl)oxy-,
  $C_1-C_5$ alkoxy($C_1-C_5$ alkyl)carbonyloxy($C_1-C_2$ alkyl)oxy-,
  (5-($C_1-C_5$ alkyl)-1,3-dioxa-cyclopenten-2-one-yl)methyloxy,
  (5-aryl-1,3-dioxa-cyclopenten-2-one-yl)methyloxy, and
  $(R^{10})(R^{11})N$—($C_1-C_{10}$ alkoxy)-;

$R^{21}$ is selected from:
  $C_1-C_8$ alkyl, $C_2-C_6$ alkenyl, $C_3-C_{11}$ cycloalkyl, ($C_3-C_{11}$ cycloalkyl)methyl, aryl, aryl($C_1-C_4$ alkyl)-, and $C_1-C_{10}$ alkyl substituted with 0–2 $R^7$;

$R^{22}$ is selected from:
  —$C(=O)R^{18b}$, —$C(=O)N(R^{18b})_2$, —$C(=O)NHSO_2R^{18a}$, —$C(=O)NHC(=O)R^{18b}$, and —$C(=O)NHC(=O)OR^{18a}$;

m is 0–2;
n is 0–4;
p is 0–2; and
r is 0–2;

with the proviso that n and m are chosen such that the number of atoms connecting $R^1$ and $COR^{20}$ of Formula (iv) is in the range of 8–14.

[3d] Specifically preferred compounds of the above invention are compounds of Formula IV including enantiomeric or diastereomeric forms thereof, or mixtures of enantiomeric or diastereomeric forms thereof, or pharmaceutically acceptable salt or prodrug forms thereof selected from the group consisting of:

3-[7-[(imidazolin-2-ylamino)methyl]-1-methylquinoline-4-one-3-ylcarbonylamino]-2-(3,5-dimethylisoxazol-4-ylsulfonylamino)propionic acid, 3-[7-[(imidazolin-2-ylamino)methyl]-1-methylquinoline-4-one-3-ylcarbonylamino]-2-(benzyloxycarbonylamino)propionic acid, 3-[7-[(imidazolin-2-ylamino)methyl]-1-methylquinoline-4-one-3-ylcarbonylamino]-2-(n-butyloxycarbonylamino)propionic acid, 3-[7-[(imidazolin-2-ylamino)methyl]-1-methylquinoline-4-one-3-ylcarbonylamino]-2-(n-butylsulfonylamino)propionic acid, 3-[7-[(imidazolin-2-ylamino)methyl]-1-methylquinoline-4-one-3-ylcarbonylamino]-2-((2,4,6-trimethylphenyl)sulfonylamino)propionic acid, 3-[7-[(imidazolin-2-ylamino)methyl]-1-(2-phenylethyl)quinoline-4-one-3-ylcarbonylamino]-2-(benzyloxycarbonylamino)propionic acid, 3-[7-[(imidazolin-2-ylamino)methyl]-1-(2-phenylethyl)quinoline-4-one-3-ylcarbonylamino]-2-(n-butyloxycarbonyl-amino)propionic acid, 3-[7-[(imidazolin-2-ylamino)methyl]-1-(2-phenylethyl)quinoline-4-one-3-ylcarbonylamino]-2-(phenylsulfonylamino)propionic acid, 3-[7-[(imidazolin-2-ylamino)methyl]-1-(2-phenylethyl)quinoline-4-one-3-ylcarbonylamino]-2-(n-butylsulfonylamino)propionic acid, 3-[7-[(imidazolin-2-ylamino)methyl]-1-(2-phenylethyl)quinoline-4-one-3-ylcarbonylamino]-2-((2,4,6-trimethylphenyl)sulfonylamino)propionic acid, 3-[7-[(tetrahydropyrimid-2-ylamino)methyl]-1-methylquinoline-4-one-3-ylcarbonylamino]-2-(benzyloxycarbonylamino)propionic acid, 3-[7-[(tetrahydropyrimid-2-ylamino)methyl]-1(2-phenylethyl)quinoline-4-one-3-ylcarbonylamino]-2-(n-butyloxycarbonylamino)propionic acid, 3-[7-[(tetrahydropyrimid-2-ylamino)methyl]-1-(2-phenylethyl)quinoline-4-one-3-ylcarbonylamino]-2-(phenylsulfonylamino)propionic acid, 3-[7-[(tetrahydropyrimid-2-ylamino)methyl]-1-methylquinoline-4-one-3-ylcarbonylamino]-2-(n-butylsulfonyl)aminopropionic acid, 3-[7-[(tetrahydropyrimid-2-ylamino)methyl]-1-methylquinoline-4-one-3-ylcarbonylamino]-2-((2,4,6-trimethylphenyl)sulfonylamino)propionic acid, 3-[7-[(tetrahydropyrimid-2-ylamino)methyl]-1-(2-phenylethyl)quinoline-4-one-3-ylcarbonylamino]-2-(benzyloxycarbonylamino)propionic acid, 3-[7-[(tetrahydropyrimid-2-ylamino)methyl]-1-(2-phenylethyl)quinoline-4-one-3-ylcarbonylamino]-2-(n-butyloxycarbonylamino)propionic acid, 3-[7-[(tetrahydropyrimid-2-ylamino)methyl]-1-(2-phenylethyl)quinoline-4-one-3-ylcarbonylamino]-2-(phenylsulfonylamino)propionic acid, 3-[7-[(tetrahydropyrimid-2-ylamino)methyl]-1-(2-phenylethyl)quinoline-4-one-3-ylcarbonylamino]-2-(n-butylsulfonylamino)propionic acid, 3-[7-[(tetrahydropyrimid-2-ylamino)methyl]-1-(2-phenylethyl)quinoline-4-one-3-ylcarbonylamino]-2-((2,4,6-trimethylphenyl)sulfonylamino)propionic acid 3-[7-[(imidazolin-2-ylamino)methyl]-1-methyl-6,8-difluoroquinoline-4-one-3-ylcarbonylamino]-2-(benzyloxycarbonylamino)propionic acid, 3-[7-[(imidazolin-2-ylamino)methyl]-1-methyl-6,8-difluoroquinoline-4-one-3-ylcarbonylamino]-2-(n-butyloxycarbonylamino)propionic acid, 3-[7-[(imidazolin-2-ylamino)methyl]-1-methyl-6,8-difluoroquinoline-4-one-3-ylcarbonylamino]-2-(n-butylsulfonylamino)propionic acid, 3-[7-[(imidazolin-2-ylamino)methyl]-1-methyl-6,8-difluoroquinoline-4-one-3-ylcarbonylamino]-2-((2,4,6-trimethylphenyl)sulfonylamino)propionic acid, 3-[7-[(imidazolin-2-ylamino)methyl]-1-(2-phenylethyl)-6,8-difluoroquinoline-4-one-3-ylcarbonylamino]-2-(benzyloxycarbonylamino)propionic acid, 3-[7-[(imidazolin-2-ylamino)methyl]-1-(2-phenylethyl)-6,8-difluoroquinoline-4-one-3-ylcarbonylamino]-2-(n-butyloxycarbonylamino)propionic acid, 3-[7-[(imidazolin-2-ylamino)methyl]-1-(2-phenylethyl)-6,8-difluoroquinoline-4-one-3-ylcarbonylamino]-2-(phenylsulfonylamino)propionic acid, 3-[7-[(imidazolin-2-ylamino)methyl]-1-(2-phenylethyl)-6,8-difluoroquinoline-4-one-3-ylcarbonylamino]-2-(n-butylsulfonylamino)propionic acid, 3-[7-[(imidazolin-2-ylamino)methyl]-1-(2-phenylethyl)-6,8-difluoroquinoline-4-one-3-ylcarbonylamino]-2-((2,4,6-trimethylphenyl)sulfonylamino)propionic acid, 3-[7-[(tetrahydropyrimid-2-ylamino)methyl]-1-methyl-6,8-difluoroquinoline-4-one-3-ylcarbonylamino]-2-(benzyloxycarbonylamino)propionic acid, 3-[7-[(tetrahydropyrimid-2-ylamino)methyl]-1-(2-phenylethyl)-6,8-difluoroquinoline-4-one-3-ylcarbonylamino]-2-(n-butyloxycarbonylamino) propionic acid, 3-[7-[(tetrahydropyrimid-2-ylamino)methyl]-1-(2-phenylethyl)-6,8-difluoroquinoline-4-one-3-ylcarbonylamino]-2-(phenylsulfonylamino)propionic acid, 3-[7-[(tetrahydropyrimid-2-ylamino)methyl]-1-methylquinoline-4-one-3-ylcarbonylamino]-2-(n-butylsulfonyl)aminopropionic acid, 3-[7-[(tetrahydropyrimid-2-ylamino)methyl]-1-methyl-6,8-difluoroquinoline-4-one-3-ylcarbonylamino]-2-((2,4,6-trimethylphenyl)sulfonylamino)propionic acid, 3-[7-[(tetrahydropyrimid-2-ylamino)methyl]-1-(2-phenylethyl)-6,8-difluoroquinoline-4-one-3-ylcarbonylamino]-2-(benzyloxycarbonylamino)propionic acid, 3-[7-[(tetrahydropyrimid-2-ylamino)methyl]-1-(2-phenylethyl)-6,8-difluoroquinoline-4-one-3-ylcarbonylamino]-2-(n-butyloxycarbonylamino) propionic acid, 3-[7-[(tetrahydropyrimid-2-ylamino)methyl]-1-(2-phenylethyl)-6,8-difluoroquinoline-4-one-3-ylcarbonylamino]-2-(phenylsulfonylamino)propionic acid, 3-[7-[(tetrahydropyrimid-2-ylamino)methyl]-1-(2-phenylethyl)-6,8-difluoroquinoline-4-one-3-ylcarbonylamino]-2-(n-butylsulfonylamino)propionic acid, 3-[7-[(tetrahydropyrimid-2-ylamino)methyl]-1-(2-phenylethyl)-6,8-difluoroquinoline-4-one-3-ylcarbonylamino]-2-((2,4,6-trimethylphenyl)sulfonylamino)propionic acid

[4a] In a fourth embodiment of the present invention are preferred compounds of Formula II:

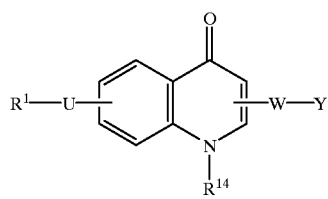

including stereoisomeric forms thereof, or mixtures of stereoisomeric forms thereof, or pharmaceutically acceptable salt or prodrug forms thereof wherein:

$R^1$ is selected from:

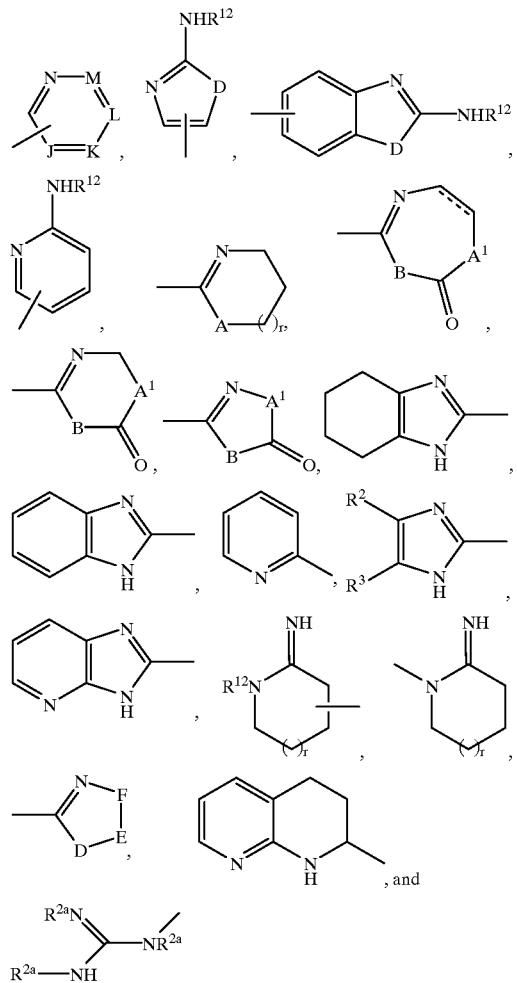

A is —$CH_2$— or —N($R^{12}$)—;
$A^1$ and B are independently —$CH_2$— or —N($R^{10}$)—;
D is —N($R^{12}$)— or —S—;
E—F is —C($R^2$)=C($R^3$)— or —C($R^2$)$_2$C($R^3$)$_2$—;
J is —C($R^2$)— or —N—;
K, L and M are independently —C($R^2$)— or —C($R^3$)—;
$R^2$ and $R^3$ are independently selected from:
  H, $C_1$–$C_4$ alkoxy, N$R^{11}R^{12}$, halogen, $NO_2$, CN, $CF_3$, $C_1$–$C_6$ alkyl, $C_3$–$C_6$ alkenyl, $C_3$–$C_7$ cycloalkyl, $C_3$–$C_7$ cycloalkyl($C_1$–$C_4$ alkyl), aryl($C_1$–$C_6$ alkyl)-, ($C_1$–$C_6$ alkyl)carbonyl, ($C_1$–$C_6$ alkoxy)carbonyl, arylcarbonyl, and aryl substituted with 0–4 $R^7$, alternatively, when $R^2$ and $R^3$ are substituents on adjacent atoms, they can be taken together with the carbon atoms to which they are attached to form a 5–7 membered carbocyclic or 5–7 membered heterocyclic aromatic or nonaromatic ring system, said carbocyclic or heterocyclic ring being substituted with 0–2 groups selected from $C_1$–$C_4$ alkyl, $C_1$–$C_4$ alkoxy, halo, cyano, amino, $CF_3$ and $NO_2$;

$R^{2a}$ is selected from:
H, $C_1$–$C_{10}$ alkyl, $C_2$–$C_6$ alkenyl, $C_3$–$C_{11}$ cycloalkyl, $C_3$–$C_7$ cycloalkyl($C_1$–$C_4$ alkyl), aryl, aryl($C_1$–$C_4$ alkyl)-, ($C_2$–$C_7$ alkyl)carbonyl, arylcarbonyl, ($C_2$–$C_{10}$ alkoxy)carbonyl, $C_3$–$C_7$ cycloalkoxycarbonyl, $C_7$–$C_{11}$ bicycloalkoxycarbonyl, aryloxycarbonyl, aryl($C_1$–$C_{10}$ alkoxy)carbonyl, $C_1$–$C_6$ alkylcarbonyloxy ($C_1$–$C_4$ alkoxy)carbonyl, arylcarbonyloxy($C_1$–$C_4$ alkoxy)carbonyl, and $C_3$–$C_7$ cycloalkylcarbonyloxy ($C_1$–$C_4$ alkoxy)carbonyl;

$R^4$ is selected from:
H, $C_1$–$C_6$ alkyl, $C_3$–$C_7$ cycloalkyl, $C_3$–$C_7$ cycloalkyl($C_1$–$C_4$ alkyl)-, aryl, heteroaryl, aryl($C_1$–$C_6$ alkyl)-, and heteroaryl($C_1$–$C_6$ alkyl)-, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$, $R^6$ is selected from:
H, $C_1$–$C_{10}$ alkyl, hydroxy, $C_1$–$C_{10}$ alkoxy, nitro, $C_1$–$C_{10}$ alkylcarbonyl, —$N(R^{11})R^{12}$, cyano, halo, $CF_3$, CHO, $CO_2R^{18b}$, $C(=O)R^{18b}$, $CONR^{17}R^{18b}$, $OC(=O)R^{10}$, $OR^{10}$, $OC(=O)NR^{10}R^{11}$, $NR^{10}C(=O)R^{10}$, $NR^{10}C(=O)OR^{21}$, $NR^{10}C(=O)NR^{10}R^{11}$, $NR^{10}SO_2NR^{10}R^{11}$, $NR^{10}SO_2R^{21}$, $S(O)_pR^{11}$, $SO_2NR^{10}R^{11}$,
aryl substituted with 0–3 groups selected from halogen, $C_1$–$C_6$ alkoxy, $C_1$–$C_6$ alkyl, $CF_3$, $S(O)_m$Me, and —$NMe_2$,
aryl($C_1$–$C_4$ alkyl)-, said aryl being substituted with 0–3 groups selected from halogen, $C_1$–$C_6$ alkoxy, $C_1$–$C_6$ alkyl, $CF_3$, $S(O)_p$Me, and —$NMe_2$,
a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$;

$R^7$ is selected from:
H, hydroxy, $C_1$–$C_4$ alkyl, $C_1$–$C_4$ alkoxy, aryl, aryl($C_1$–$C_4$ alkyl)-, ($C_1$–$C_4$ alkyl)carbonyl, $CO_2R^{18a}$, $SO_2R^{11}$, $SO_2NR^{10}R^{11}$, $OR^{10}$, and $N(R^{11})R^{12}$;

U is selected from:
—$(CH_2)_n$—, —$(CH_2)_nO(CH_2)_m$—, —$(CH_2)_nN(R^{12})(CH_2)_m$—, —$NH(CH_2)_n$—, —$N(R^{10})C(=O)$—, —$NHC(=O)(CH_2)_n$—, —$C(=O)N(R^{10})$—, and —$N(R^{10})S(O)_p$—;

G is N or $CR^{19}$;

W is —$C(=O)$—$N(R^{10})$—$(C_1$–$C_3$ alkylene)-, in which the alkylene group is substituted by $R^8$ and by $R^9$:

$R^8$ is selected from:
H, $C_1$–$C_4$ alkyl, hydroxy, $C_1$–$C_4$ alkoxy, halo, $CF_3$, $CO_2H$, $NR^{10}SO_2R^{21}$, pyridyl, —$N(R^{16})R^{17}$,
phenyl substituted with 0–3 groups selected from halogen, $C_1$–$C_4$ alkoxy, $C_1$–$C_4$ alkyl, $CF_3$, $S(O)_m$Me, and —$NMe_2$;
phenyl($C_1$–$C_4$ alkyl), said phenyl being substituted with 0–3 groups selected from halogen, $C_1$–$C_4$ alkoxy, $C_1$–$C_4$ alkyl, $CF_3$, $S(O)_p$Me, and —$NMe_2$, and carboxy($C_1$–$C_3$ alkyl)-;

$R^9$ is selected from:
H, $CO_2R^{18b}$, $C(=O)R^{18b}$, $CONR^{17}R^{18b}$,
$C_1$–$C_6$ alkyl substituted with 0–1 $R^6$,
$C_2$–$C_4$ alkenyl substituted with 0–1 $R^6$,
$C_2$–$C_4$ alkynyl substituted with 0–1 $R^6$,
$C_3$–$C_8$ cycloalkyl substituted with 0–1 $R^6$,
$C_5$–$C_6$ cycloalkenyl substituted with 0–1 $R^6$,
($C_1$–$C_4$ alkyl)carbonyl,
$C_3$–$C_{10}$ cycloalkyl($C_1$–$C_4$ alkyl)-,
phenyl substituted with 0–3 $R^6$,
naphthyl substituted with 0–3 $R^6$,
a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$,
$C_1$–$C_4$ alkoxy substituted with 0–2 $R^7$,
hydroxy, $CO_2H$, nitro, —$N(R^{10})R^{11}$, —$N(R^{16})R^{17}$, phenyl($C_0$–$C_4$ alkyl)carbonyl, phenyl($C_1$–$C_4$ alkyl)-, heteroaryl($C_1$–$C_6$ alkyl)-, $CONR^{18a}R^{20}$, $SO_2R^{18a}$, and $SO_2NR^{18a}R^{20}$,
providing that any of the above alkyl, cycloalkyl, phenyl or heteroaryl groups may be unsubstituted or substituted independently with 1–2 $R^7$;

$R^{10}$ is selected from:
H, $CF_3$, $C_3$–$C_6$ alkenyl, $C_3$–$C_{11}$ cycloalkyl, phenyl, ($C_3$–$C_{11}$ cycloalkyl)methyl, phenyl($C_1$–$C_4$ alkyl), and $C_1$–$C_{10}$ alkyl substituted with 0–2 $R^6$;

$R^{11}$ is selected from:
H, hydroxy, $C_1$–$C_8$ alkyl, $C_3$–$C_6$ alkenyl, $C_3$–$C_{11}$ cycloalkyl, ($C_3$–$C_{11}$ cycloalkyl)methyl, $C_1$–$C_6$ alkoxy, benzyloxy, aryl, heteroaryl, heteroaryl($C_1$–$C_4$ alkyl)-, aryl($C_1$–$C_4$ alkyl), adamantylmethyl, and $C_1$–$C_{10}$ alkyl substituted with 0–2 $R^4$;
alternatively, when $R^{10}$ and $R^{11}$ are both substituents on the same nitrogen atom (as in —$NR^{10}R^{11}$) they may be taken together with the nitrogen atom to which they are attached to form a heterocycle selected from:
3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl, and 1-piperazinyl;
said heterocycle being substituted with 0–3 groups selected from: $C_1$–$C_6$ alkyl, aryl, heteroaryl, aryl($C_1$–$C_4$ alkyl)-, ($C_1$–$C_6$ alkyl)carbonyl, ($C_3$–$C_7$ cycloalkyl)carbonyl, ($C_1$–$C_6$ alkoxy)carbonyl, aryl($C_1$–$C_4$ alkoxy)carbonyl, $C_1$–$C_6$ alkylsulfonyl, and arylsulfonyl;

$R^{12}$ is selected from:
H, $C_1$–$C_6$ alkyl, triphenylmethyl, methoxymethyl, methoxyphenyldiphenylmethyl, trimethylsilylethoxymethyl, ($C_1$–$C_6$ alkyl)carbonyl, ($C_1$–$C_6$ alkoxy)carbonyl, ($C_1$–$C_6$ alkyl)aminocarbonyl, $C_3$–$C_6$ alkenyl, $C_3$–$C_7$ cycloalkyl, $C_3$–$C_7$ cycloalkyl($C_1$–$C_4$ alkyl)-, aryl, heteroaryl ($C_1$–$C_6$ alkyl)carbonyl, heteroarylcarbonyl, aryl ($C_1$–$C_6$ alkyl)-, ($C_1$–$C_6$ alkyl)carbonyl, arylcarbonyl, $C_1$–$C_6$ alkylsulfonyl, arylsulfonyl, aryl($C_1$–$C_6$ alkyl)sulfonyl, heteroarylsulfonyl, heteroaryl($C_1$–$C_6$ alkyl)sulfonyl, aryloxycarbonyl, and aryl($C_1$–$C_6$ alkoxy)carbonyl, wherein said aryl groups are substituted with 0–2 substituents selected from the group consisting of $C_1$–$C_4$ alkyl, $C_1$–$C_4$ alkoxy, halo, $CF_3$, and nitro;

$R^{14}$ is selected from:
H, $C_1$-$C_4$ alkyl, and phenyl($C_1$-$C_4$ alkyl);

$R^{16}$ is selected from:
—C(=O)OR$^{18a}$, —C(=O)R$^{18b}$, —C(=O)N(R$^{18b}$)$_2$, —C(=O)NHSO$_2$R$^{18a}$, —C(=O)NHC(=O)R$^{18b}$, —C(=O)NHC(=O)OR$^{18a}$, —C(=O)NHSO$_2$NHR$^{18b}$, —SO$_2$R$^{18a}$, —SO$_2$N(R$^{18b}$)$_2$, and —SO$_2$NHC(=O)OR$^{18b}$;

$R^{17}$ is selected from:
H, $C_1$-$C_6$ alkyl, $C_3$-$C_7$ cycloalkyl, $C_3$-$C_7$ cycloalkyl($C_1$-$C_4$ alkyl)-, aryl, aryl($C_1$-$C_6$ alkyl)-, and heteroaryl($C_1$-$C_6$ alkyl);

$R^{18a}$ is selected from:
$C_1$-$C_6$ alkyl, aryl-, fluoro($C_3$-$C_6$ alkyl), aryl($C_1$-$C_4$ alkyl)-, di($C_1$-$C_4$ alkyl)amino($C_1$-$C_4$ alkyl), morpholino($C_1$-$C_4$ alkyl), piperidino($C_1$-$C_4$ alkyl), N—($C_1$-$C_4$ alkyl)piperidino($C_1$-$C_4$ alkyl), and phenyl substituted by one or two optional groups selected from $C_1$-$C_4$ alkyl, $C_1$-$C_4$ alkoxy, and halogen;

$R^{18b}$ is H or $R^{18a}$;

$R^{19}$ is selected from:
H, halogen, $CF_3$, $CO_2H$, CN, $NO_2$, —NR$^{11}$R$^{12}$, $OCF_3$, $C_1$-$C_8$ alkyl, $C_2$-$C_6$ alkenyl, $C_2$-$C_6$ alkynyl, $C_3$-$C_{11}$ cycloalkyl, $C_3$-$C_7$ cycloalkyl($C_1$-$C_4$ alkyl)-, aryl($C_1$-$C_6$ alkyl)-, $C_1$-$C_6$ alkoxy, $C_1$-$C_4$ alkoxycarbonyl, aryl, aryl-O—, aryl-SO$_2$—, heteroaryl, and heteroaryl-SO$_2$—, wherein said aryl and heteroaryl groups are substituted with 0–4 groups selected from hydrogen, halogen, $CF_3$, $C_1$-$C_3$ alkyl, and $C_1$-$C_3$ alkoxy;

$R^{20}$ is selected from:
hydroxy, $C_1$-$C_{10}$ alkyloxy, $C_3$-$C_{11}$ cycloalkyloxy, aryloxy, aryl($C_1$-$C_4$ alkyl)oxy,
$C_2$-$C_{10}$ alkylcarbonyloxy($C_1$-$C_2$ alkyl)oxy-,
$C_2$-$C_{10}$ alkoxycarbonyloxy($C_1$-$C_2$ alkyl)oxy-,
$C_2$-$C_{10}$ alkoxycarbonyl($C_1$-$C_2$ alkyl)oxy-,
$C_3$-$C_{10}$ cycloalkylcarbonyloxy($C_1$-$C_2$ alkyl)oxy-,
$C_3$-$C_{10}$ cycloalkoxycarbonyloxy($C_1$-$C_2$ alkyl)oxy-,
$C_3$-$C_{10}$ cycloalkoxycarbonyl($C_1$-$C_2$ alkyl)oxy-,
aryloxycarbonyl($C_1$-$C_2$ alkyl)oxy-,
aryloxycarbonyloxy($C_1$-$C_2$ alkyl)oxy-,
arylcarbonyloxy($C_1$-$C_2$ alkyl)oxy-,
$C_1$-$C_5$ alkoxy($C_1$-$C_5$ alkyl)carbonyloxy($C_1$-$C_2$ alkyl)oxy-,
(5-($C_1$-$C_5$ alkyl)-1,3-dioxa-cyclopenten-2-one-yl)methyloxy,
(5-aryl-1,3-dioxa-cyclopenten-2-one-yl)methyloxy, and
(R$^{10}$)(R$^{11}$)N—($C_1$-$C_{10}$ alkoxy)-;

$R^{21}$ is selected from:
$C_1$-$C_8$ alkyl, $C_2$-$C_6$ alkenyl, $C_3$-$C_{11}$ cycloalkyl, ($C_3$-$C_{11}$ cycloalkyl)methyl, aryl, aryl($C_1$-$C_4$ alkyl)-, and $C_1$-$C_{10}$ alkyl substituted with 0–2 $R^7$;

Y is selected from:
—COR$^{20}$, —CONHNHSO$_2$CF$_3$, —CONHSO$_2$R$^{18a}$, —CONHSO$_2$NHR$^{18b}$, —NHCOCF$_3$, and —NHSO$_2$R$^{18a}$;

m is 0–2;

n is 0–4;

p is 0–2;

r is 0–2;

with the proviso that n and m are chosen such that the number of atoms connecting $R^1$ and Y is in the range of 8–14.

[4b] Preferred compounds of the fourth embodiment of the present invention are those of Formula III:

(III)

including stereoisomeric forms thereof, or mixtures of stereoisomeric forms thereof, or pharmaceutically acceptable salt or prodrug forms thereof wherein:

$R^1$ is selected from:

A is —CH$_2$— or —N(R$^{12}$)—;

$A^1$ and B are independently —CH$_2$— or —N(R$^{10}$)—;

D is —N(R$^{12}$)— or —S—;

E—F is —C(R$^2$)=C(R$^3$)— or —C(R$^2$)$_2$C(R$^3$)$_2$—;

$R^2$ and $R^3$ are independently selected from:
H, $C_1$-$C_4$ alkoxy, NR$^{11}$R$^{12}$, halogen, $NO_2$, CN, $CF_3$, $C_1$-$C_6$ alkyl, $C_3$-$C_6$ alkenyl, $C_3$-$C_7$ cycloalkyl, $C_3$-$C_7$ cycloalkyl($C_1$-$C_4$ alkyl), aryl($C_1$-$C_6$ alkyl)-, ($C_1$-$C_6$ alkyl)carbonyl, ($C_1$-$C_6$ alkoxy)carbonyl, arylcarbonyl, and aryl substituted with 0–4 $R^7$, alternatively, when $R^2$ and $R^3$ are substituents on adjacent atoms, they can be taken together with the carbon atoms to which they are attached to form a 5–7 membered carbocyclic or 5–7 membered heterocyclic aromatic or nonaromatic ring system, said carbocyclic or heterocyclic ring being substituted with 0–2 groups selected from $C_1$–$C_4$ alkyl, $C_1$–$C_4$ alkoxy, halo, cyano, amino, $CF_3$ and $NO_2$;

$R^{2a}$ is selected from:
H, $C_1$–$C_{10}$ alkyl, $C_2$–$C_6$ alkenyl, $C_3$–$C_{11}$ cycloalkyl, $C_3$–$C_7$ cycloalkyl($C_1$–$C_4$ alkyl), aryl, aryl($C_1$–$C_4$ alkyl)-, ($C_2$–$C_7$ alkyl)carbonyl, arylcarbonyl, ($C_2$–$C_{10}$ alkoxy)carbonyl, $C_3$–$C_7$ cycloalkoxycarbonyl, $C_7$–$C_{11}$ bicycloalkoxycarbonyl, aryloxycarbonyl, aryl($C_1$–$C_{10}$ alkoxy)carbonyl, $C_1$–$C_6$ alkylcarbonyloxy($C_1$–$C_4$ alkoxy)carbonyl, arylcarbonyloxy($C_1$–$C_4$ alkoxy)carbonyl, and $C_3$–$C_7$ cycloalkylcarbonyloxy($C_1$–$C_4$ alkoxy)carbonyl;

$R^4$ is selected from:
H, $C_1$–$C_6$ alkyl, $C_3$–$C_7$ cycloalkyl, $C_3$–$C_7$ cycloalkyl($C_1$–$C_4$ alkyl)-, aryl, heteroaryl, aryl($C_1$–$C_6$ alkyl)-, and heteroaryl($C_1$–$C_6$ alkyl)-, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$, $R^6$ is selected from:
H, $C_1$–$C_{10}$ alkyl, hydroxy, $C_1$–$C_{10}$ alkoxy, nitro, $C_1$–$C_{10}$ alkylcarbonyl, —$N(R^{11})R^{12}$, cyano, halo, $CF_3$, CHO, $CO_2R^{18b}$, C(=O)$R^{18b}$, CONR$^{17}R^{18b}$, OC(=O)$R^{10}$, $OR^{10}$, OC(=O)NR$^{10}R^{11}$, NR$^{10}$C(=O)$R^{10}$, NR$^{10}$C(=O)$OR^{21}$, NR$^{10}$C(=O)NR$^{10}R^{11}$, NR$^{10}SO_2NR^{10}R^{11}$, NR$^{10}SO_2R^{21}$, S(O)$_p R^{11}$, $SO_2NR^{10}R^{11}$,
aryl substituted with 0–3 groups selected from halogen, $C_1$–$C_6$ alkoxy, $C_1$–$C_6$ alkyl, $CF_3$, S(O)$_m$Me, and —NMe$_2$,
aryl($C_1$–$C_4$ alkyl)-, said aryl being substituted with 0–3 groups selected from halogen, $C_1$–$C_6$ alkoxy, $C_1$–$C_6$ alkyl, $CF_3$, S(O)$_p$Me, and —NMe$_2$, and
a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$;

$R^7$ is selected from:
H, hydroxy, $C_1$–$C_4$ alkyl, $C_1$–$C_4$ alkoxy, aryl, aryl($C_1$–$C_4$ alkyl)-, ($C_1$–$C_4$ alkyl)carbonyl, $CO_2R^{18a}$, $SO_2R^{11}$, $SO_2NR^{10}R^{11}$, $OR^{10}$, and $N(R^{11})R^{12}$;

U is selected from:
—(CH$_2$)$_n$—, —(CH$_2$)$_n$O(CH$_2$)$_m$—, —(CH$_2$)$_n$N(R$^{12}$)(CH$_2$)$_m$—, —NH(CH$_2$)$_n$—, —N(R$^{10}$)C(=O)—, and —NHC(=O)(CH$_2$)$_n$—;

G is N or CR$^{19}$;

$R^8$ is H;

$R^9$ is selected from:
H, $CO_2R^{18b}$, C(=O)$R^{18b}$, CONR$^{17}R^{18b}$,
$C_1$–$C_6$ alkyl substituted with 0–1 $R^6$,
$C_2$–$C_4$ alkenyl substituted with 0–1 $R^6$,
$C_2$–$C_4$ alkynyl substituted with 0–1 $R^6$,
$C_3$–$C_8$ cycloalkyl substituted with 0–1 $R^6$,
$C_5$–$C_6$ cycloalkenyl substituted with 0–1 $R^6$,
($C_1$–$C_4$ alkyl)carbonyl,
$C_3$–$C_{10}$ cycloalkyl($C_1$–$C_4$ alkyl)-,
phenyl substituted with 0–3 $R^6$,
naphthyl substituted with 0–3 $R^6$,
a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$, $C_1$–$C_4$ alkoxy substituted with 0–2 $R^7$,
hydroxy, $CO_2H$, nitro, —$N(R^{10})R^{11}$, —$N(R^{16})R^{17}$, phenyl($C_0$–$C_4$ alkyl)carbonyl, phenyl($C_1$–$C_4$ alkyl)-, heteroaryl($C_1$–$C_6$ alkyl)-, CONR$^{18a}R^{20}$, $SO_2R^{18a}$, and $SO_2NR^{18a}R^{20}$, providing that any of the above alkyl, cycloalkyl, phenyl or heteroaryl groups may be unsubstituted or substituted independently with 1–2 $R^7$;

$R^{10}$ is selected from:
H, $CF_3$, $C_3$–$C_6$ alkenyl, $C_3$–$C_{11}$ cycloalkyl, phenyl, ($C_3$–$C_{11}$ cycloalkyl)methyl, phenyl($C_1$–$C_4$ alkyl), and $C_1$–$C_{10}$ alkyl substituted with 0–2 $R^6$;

$R^{11}$ is selected from:
H, hydroxy, $C_1$–$C_8$ alkyl, $C_3$–$C_6$ alkenyl, $C_3$–$C_{11}$ cycloalkyl, ($C_3$–$C_{11}$ cycloalkyl)methyl, $C_1$–$C_6$ alkoxy, benzyloxy, aryl, heteroaryl, heteroaryl($C_1$–$C_4$ alkyl)-, aryl($C_1$–$C_4$ alkyl), adamantylmethyl, and $C_1$–$C_{10}$ alkyl substituted with 0–2 $R^4$;

alternatively, when $R^{10}$ and $R^{11}$ are both substituents on the same nitrogen atom (as in —NR$^{10}R^{11}$) they may be taken together with the nitrogen atom to which they are attached to form a heterocycle selected from:
3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl, and 1-piperazinyl;

said heterocycle being substituted with 0–3 groups selected from: $C_1$–$C_6$ alkyl, aryl, heteroaryl, aryl($C_1$–$C_4$ alkyl)-, ($C_1$–$C_6$ alkyl)carbonyl, ($C_3$–$C_7$ cycloalkyl)carbonyl, ($C_1$–$C_6$ alkoxy)carbonyl, aryl($C_1$–$C_4$ alkoxy)carbonyl, $C_1$–$C_6$ alkylsulfonyl, and arylsulfonyl;

$R^{12}$ is selected from:
H, $C_1$–$C_6$ alkyl, triphenylmethyl, methoxymethyl, methoxyphenyldiphenylmethyl, trimethylsilylethoxymethyl, ($C_1$–$C_6$ alkyl)carbonyl, ($C_1$–$C_6$ alkoxy)carbonyl, ($C_1$–$C_6$ alkyl)aminocarbonyl, $C_3$–$C_6$ alkenyl, $C_3$–$C_7$ cycloalkyl, $C_3$–$C_7$ cycloalkyl($C_1$–$C_4$ alkyl)-, aryl, heteroaryl ($C_1$–$C_6$ alkyl)carbonyl, heteroarylcarbonyl, aryl($C_1$–$C_6$ alkyl)-, ($C_1$–$C_6$ alkyl)carbonyl, arylcarbonyl, $C_1$–$C_6$ alkylsulfonyl, arylsulfonyl, aryl($C_1$–$C_6$ alkyl)sulfonyl, heteroarylsulfonyl, heteroaryl($C_1$–$C_6$ alkyl)sulfonyl, aryloxycarbonyl, and aryl($C_1$–$C_6$ alkoxy)carbonyl, wherein said aryl groups are substituted with 0–2 substituents selected from the group consisting of $C_1$–$C_4$ alkyl, $C_1$–$C_4$ alkoxy, halo, $CF_3$, and nitro;

$R^{14}$ is selected from H, $CH_3$, benzyl and phenylethyl;

$R^{16}$ is selected from:
—C(=O)O$R^{18a}$, —C(=O)$R^{18b}$, —C(=O)N(R$^{18b}$)$_2$, —C(=O)NHSO$_2R^{18a}$, —C(=O)NHC(=O)$R^{18b}$, —C(=O)NHC(=O)O$R^{18a}$, —C(=O)NHSO$_2$NHR$^{18b}$, —SO$_2R^{18a}$, —SO$_2$N(R$^{18b}$)$_2$, and —SO$_2$NHC(=O)O$R^{18b}$;

$R^{17}$ is selected from:
H, $C_1$–$C_6$ alkyl, $C_3$–$C_7$ cycloalkyl, $C_3$–$C_7$ cycloalkyl($C_1$–$C_4$ alkyl)-, aryl, aryl($C_1$–$C_6$ alkyl)-, and heteroaryl($C_1$–$C_6$ alkyl);

$R^{18a}$ is selected from:
$C_1$–$C_6$ alkyl, aryl-, fluoro($C_3$–$C_6$ alkyl), aryl($C_1$–$C_4$ alkyl)-, di($C_1$–$C_4$ alkyl)amino($C_1$–$C_4$ alkyl), morpholino($C_1$–$C_4$ alkyl), piperidino($C_1$–$C_4$ alkyl), N—(C$_1$–C$_4$ alkyl)piperidino(C$_1$–C$_4$ alkyl), and phenyl substituted by one or two optional groups selected from C$_1$–C$_4$ alkyl, C$_1$–C$_4$ alkoxy, and halogen;

R$^{18b}$ is H or R$^{18a}$;

R$^{19}$ is selected from:
H, halogen, CF$_3$, CO$_2$H, CN, NO$_2$, —NR$^{11}$R$^{12}$, OCF$_3$, C$_1$–C$_8$ alkyl, C$_2$–C$_6$ alkenyl, C$_2$–C$_6$ alkynyl, C$_3$–C$_{11}$ cycloalkyl, C$_3$–C$_7$ cycloalkyl(C$_1$–C$_4$ alkyl)-, aryl (C$_1$–C$_6$ alkyl)-, C$_1$–C$_6$ alkoxy, C$_1$–C$_4$ alkoxycarbonyl, aryl, aryl-O—, aryl-SO$_2$—, heteroaryl, and heteroaryl-SO$_2$—, wherein said aryl and heteroaryl groups are substituted with 0–4 groups selected from hydrogen, halogen, CF$_3$, C$_1$–C$_3$ alkyl, and C$_1$–C$_3$ alkoxy;

R$^{20}$ is selected from:
hydroxy, C$_1$–C$_{10}$ alkyloxy, C$_3$–C$_{11}$ cycloalkyloxy, aryloxy, aryl(C$_1$–C$_4$ alkyl)oxy,
C$_2$–C$_{10}$ alkylcarbonyloxy(C$_1$–C$_2$ alkyl)oxy-,
C$_2$–C$_{10}$ alkoxycarbonyloxy(C$_1$–C$_2$ alkyl)oxy-,
C$_2$–C$_{10}$ alkoxycarbonyl(C$_1$–C$_2$ alkyl)oxy-,
C$_3$–C$_{10}$ cycloalkylcarbonyloxy(C$_1$–C$_2$ alkyl)oxy-,
C$_3$–C$_{10}$ cycloalkoxycarbonyloxy(C$_1$–C$_2$ alkyl)oxy-,
C$_3$–C$_{10}$ cycloalkoxycarbonyl(C$_1$–C$_2$ alkyl)oxy-,
aryloxycarbonyl(C$_1$–C$_2$ alkyl)oxy-,
aryloxycarbonyloxy(C$_1$–C$_2$ alkyl)oxy-,
arylcarbonyloxy(C$_1$–C$_2$ alkyl)oxy-,
C$_1$–C$_5$ alkoxy(C$_1$–C$_5$ alkyl)carbonyloxy(C$_1$–C$_2$ alkyl)oxy-,
(5-(C$_1$–C$_5$ alkyl)-1,3-dioxa-cyclopenten-2-one-yl)methyloxy,
(5-aryl-1,3-dioxa-cyclopenten-2-one-yl)methyloxy, and
(R$^{10}$)(R$^{11}$)N—(C$_1$–C$_{10}$ alkoxy)-;

R$^{21}$ is selected from:
C$_1$–C$_8$ alkyl, C$_2$–C$_6$ alkenyl, C$_3$–C$_{11}$ cycloalkyl, (C$_3$–C$_{11}$ cycloalkyl)methyl, aryl, aryl(C$_1$–C$_4$ alkyl)-, and C$_1$–C$_{10}$ alkyl substituted with 0–2 R$^7$;

m is 0–2;
n is 0–4;
p is 0–2; and
r is 0–2;

with the following provisos:
(1) n and m are chosen such that the number of atoms connecting R$^1$ and COR$^{20}$ of Formula (III) is in the range of 8–14; and
(2) one of the groups R$^8$ or R$^9$ must be hydrogen.

[4c] More preferred compounds of the fourth embodiment of the present invention are those of Formula III:

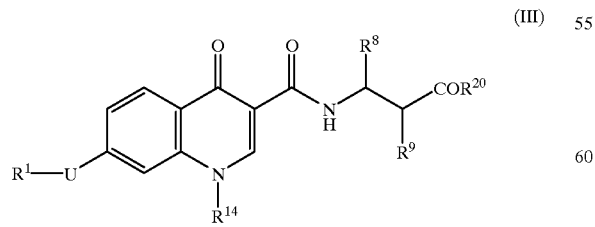

(III)

including stereoisomeric forms thereof, or mixtures of stereoisomeric forms thereof, or pharmaceutically acceptable salt or prodrug forms thereof wherein:

R$^1$ is selected from:

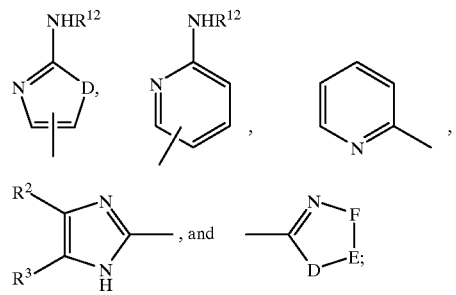

A is —CH$_2$— or —N(R$^{12}$)—;
A$^1$ and B are independently —CH$_2$— or —N(R$^{10}$)—;
D is —N(R$^{12}$)— or —S—;
E—F is 13 C(R$^2$)═C(R$^3$)— or —C(R$^2$)$_2$C(R$^3$)$_2$—;
R$^2$ and R$^3$ are independently selected from:
H, C$_1$–C$_4$ alkoxy, NR$^{11}$R$^{12}$, halogen, NO$_2$, CN, CF$_3$, C$_1$–C$_6$ alkyl, C$_3$–C$_6$ alkenyl, C$_3$–C$_7$ cycloalkyl, C$_3$–C$_7$ cycloalkyl(C$_1$–C$_4$ alkyl), aryl(C$_1$–C$_6$ alkyl)-, (C$_1$–C$_6$ alkyl)carbonyl, (C$_1$–C$_6$ alkoxy)carbonyl, arylcarbonyl, and aryl substituted with 0–4 R$^7$,
alternatively, when R$^2$ and R$^3$ are substituents on adjacent atoms, they can be taken together with the carbon atoms to which they are attached to form a 5–7 membered carbocyclic or 5–7 membered heterocyclic aromatic or nonaromatic ring system, said carbocyclic or heterocyclic ring being substituted with 0–2 groups selected from C$_1$–C$_4$ alkyl, C$_1$–C$_4$ alkoxy, halo, cyano, amino, CF$_3$ and NO$_2$;

R$^4$ is selected from:
H, C$_1$–C$_6$ alkyl, C$_3$–C$_7$ cycloalkyl, C$_3$–C$_7$ cycloalkyl(C$_1$–C$_4$ alkyl)-, aryl, heteroaryl, aryl(C$_1$–C$_6$ alkyl)-, and heteroaryl(C$_1$–C$_6$ alkyl)-, wherein said aryl or heteroaryl groups are substituted with 0–2 substituents independently selected from the group consisting of C$_1$–C$_4$ alkyl, C$_1$–C$_4$ alkoxy, F, Cl, Br, CF$_3$, and NO$_2$, R$^6$ is selected from:
H, C$_1$–C$_{10}$ alkyl, hydroxy, C$_1$–C$_{10}$ alkoxy, nitro, C$_1$–C$_{10}$ alkylcarbonyl, —N(R$^{11}$)R$^{12}$, cyano, halo, CF$_3$, CHO, CO$_2$R$^{18b}$, C(═O)R$^{18b}$, CONR$^{17}$R$^{18b}$, OC(═O)R$^{10}$, OR$^{10}$, OC(═O)NR$^{10}$R$^{11}$, NR$^{10}$C(═O)R$^{10}$, NR$^{10}$C(═O)OR$^{21}$, N$^{10}$C(═O)NR$^{10}$R$^{11}$, NR$^{10}$SO$_2$NR$^{10}$R$^{11}$, NR$^{10}$SO$_2$R$^{21}$, S(O)$_p$R$^{11}$, SO$_2$NR$^{10}$R$^{11}$,
aryl substituted with 0–3 groups selected from halogen, C$_1$–C$_6$ alkoxy, C$_1$–C$_6$ alkyl, CF$_3$, S(O)$_m$Me, and —NMe$_2$,
aryl(C$_1$–C$_4$ alkyl)-, said aryl being substituted with 0–3 groups selected from halogen, C$_1$–C$_6$ alkoxy, C$_1$–C$_6$ alkyl, CF$_3$, S(O)$_p$Me, and —NMe$_2$, and
a 5–10 membered heterocyclic ring containing 1–3 N, O, or S heteroatoms, wherein said heterocyclic ring may be saturated, partially saturated, or fully unsaturated, said heterocyclic ring being substituted with 0–2 R$^7$;

R$^7$ is selected from:
H, hydroxy, C$_1$–C$_4$ alkyl, C$_1$–C$_4$ alkoxy, aryl, aryl(C$_1$–C$_4$ alkyl)-, (C$_1$–C$_4$ alkyl)carbonyl, CO$_2$R$^{18a}$, SO$_2$R$^{11}$, SO$_2$NR$^{10}$R$^{11}$, OR$^{10}$, and N(R$^{11}$)R$^{12}$;

U is selected from:
—(CH$_2$)$_n$—, —NH(CH$_2$)$_n$—, —N(R$^{10}$)C(═O)—, and —NHC(═O)(CH$_2$)$_n$—;

G is N or $CR^{19}$;

$R^8$ is H;

$R^9$ is selected from:
  H, hydroxy, $CO_2H$, nitro, $-N(R^{10})R^{11}$, $-N(R^{16})R^{17}$, phenyl($C_0$–$C_4$ alkyl)carbonyl, phenyl($C_1$–$C_4$ alkyl)-, heteroaryl($C_1$–$C_6$ alkyl)-, $CONR^{18a}R^{20}$, $SO_2R^{18a}$, and $SO_2NR^{18a}R^{20}$,
  providing that any of the above phenyl or heteroaryl groups may be unsubstituted or substituted independently with 1–2 $R^7$;

$R^{10}$ is selected from:
  H, $CF_3$, $C_3$–$C_6$ alkenyl, $C_3$–$C_{11}$ cycloalkyl, phenyl, ($C_3$–$C_{11}$ cycloalkyl)methyl, phenyl($C_1$–$C_4$ alkyl), and $C_1$–$C_{10}$ alkyl substituted with 0–2 $R^6$;

$R^{11}$ is selected from:
  H, hydroxy, $C_1$–$C_8$ alkyl, $C_3$–$C_6$ alkenyl, $C_3$–$C_{11}$ cycloalkyl, ($C_3$–$C_{11}$ cycloalkyl)methyl, $C_1$–$C_6$ alkoxy, benzyloxy, aryl, heteroaryl, heteroaryl ($C_1$–$C_4$ alkyl)-, aryl($C_1$–$C_4$ alkyl), adamantylmethyl, and $C_1$–$C_{10}$ alkyl substituted with 0–2 $R^4$;
  alternatively, when $R^{10}$ and $R^{11}$ are both substituents on the same nitrogen atom (as in $-NR^{10}R^{11}$) they may be taken together with the nitrogen atom to which they are attached to form a heterocycle selected from:
  3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl, and 1-piperazinyl;
  said heterocycle being substituted with 0–3 groups selected from: $C_1$–$C_6$ alkyl, aryl, heteroaryl, aryl ($C_1$–$C_4$ alkyl)-, ($C_1$–$C_6$ alkyl)carbonyl, ($C_3$–$C_7$ cycloalkyl)carbonyl, ($C_1$–$C_6$ alkoxy)carbonyl, aryl($C_1$–$C_4$ alkoxy)carbonyl, $C_1$–$C_6$ alkylsulfonyl, and arylsulfonyl;

$R^{12}$ is selected from:
  H, $C_1$–$C_4$ alkyl, ($C_1$–$C_4$ alkyl)carbonyl, ($C_1$–$C_4$ alkoxy)carbonyl, phenyl($C_1$–$C_4$ alkyl)-, phenylsulfonyl, phenyloxycarbonyl, and phenyl ($C_1$–$C_4$ alkoxy)carbonyl, wherein said phenyl groups are substituted with 0–2 substituents selected from the group consisting of $C_1$–$C_4$ alkyl, $C_1$–$C_4$ alkoxy, halo, $CF_3$, and nitro;

$R^{14}$ is selected from H, $CF_3$, $CH_3$, and benzyl;

$R^{16}$ is selected from:
  $-C(=O)OR^{18a}$, $-C(=O)R^{18b}$, $-C(=O)N(R^{18b})_2$, $-C(=O)NHSO_2R^{18a}$, $-C(=O)NHC(=O)R^{18b}$, $-C(=O)NHC(=O)OR^{18a}$, $-C(=O)NHSO_2NHR^{18b}$, $-SO_2R^{18a}$, $-SO_2N(R^{18b})_2$, and $-SO_2NHC(=O)OR^{18b}$;

$R^{17}$ is selected from:
  H, $C_1$–$C_6$ alkyl, $C_3$–$C_7$ cycloalkyl, $C_3$–$C_7$ cycloalkyl ($C_1$–$C_4$ alkyl)-, aryl, aryl($C_1$–$C_6$ alkyl)-, and heteroaryl($C_1$–$C_6$ alkyl);

$R^{18a}$ is selected from:
  $C_1$–$C_6$ alkyl, aryl, fluoro($C_3$–$C_6$ alkyl), aryl($C_1$–$C_4$ alkyl-, di($C_1$–$C_4$ alkyl)amino($C_1$–$C_4$ alkyl), morpholino($C_1$–$C_4$ alkyl), piperidino($C_1$–$C_4$ alkyl), N—($C_1$–$C_4$ alkyl)piperidino($C_1$–$C_4$ alkyl), and phenyl substituted by one or two optional groups selected from $C_1$–$C_4$ alkyl, $C_1$–$C_4$ alkoxy, and halogen;

$R^{18b}$ is H or $R^{18a}$;

$R^{19}$ is selected from:
  H, halogen, $CF_3$, $CO_2H$, CN, $NO_2$, $-NR^{11}R^{12}$, $OCF_3$, $C_1$–$C_8$ alkyl, $C_2$–$C_6$ alkenyl, $C_2$–$C_6$ alkynyl, $C_3$–$C_{11}$ cycloalkyl, $C_3$–$C_7$ cycloalkyl($C_1$–$C_4$ alkyl)-, aryl ($C_1$–$C_6$ alkyl)-, $C_1$–$C_6$ alkoxy, $C_1$–$C_4$ alkoxycarbonyl, aryl, aryl-O—, aryl-$SO_2$—, heteroaryl, and heteroaryl-$SO_2$—, wherein said aryl and heteroaryl groups are substituted with 0–4 groups selected from hydrogen, halogen, $CF_3$, $C_1$–$C_3$ alkyl, and $C_1$–$C_3$ alkoxy;

$R^{20}$ is selected from:
  hydroxy, $C_1$–$C_{10}$ alkyloxy, $C_3$–$C_{11}$ cycloalkyloxy, aryloxy, aryl($C_1$–$C_4$ alkyl)oxy,
  $C_2$–$C_{10}$ alkylcarbonyloxy($C_1$–$C_2$ alkyl)oxy-,
  $C_2$–$C_{10}$ alkoxycarbonyloxy($C_1$–$C_2$ alkyl)oxy-,
  $C_2$–$C_{10}$ alkoxycarbonyl($C_1$–$C_2$ alkyl)oxy-,
  $C_3$–$C_{10}$ cycloalkylcarbonyloxy($C_1$–$C_2$ alkyl)oxy-,
  $C_3$–$C_{10}$ cycloalkoxycarbonyloxy($C_1$–$C_2$ alkyl)oxy-,
  $C_3$–$C_{10}$ cycloalkoxycarbonyl($C_1$–$C_2$ alkyl)oxy-,
  aryloxycarbonyl($C_1$–$C_2$ alkyl)oxy-,
  aryloxycarbonyloxy($C_1$–$C_2$ alkyl)oxy-,
  arylcarbonyloxy($C_1$–$C_2$ alkyl)oxy-,
  $C_1$–$C_5$ alkoxy($C_1$–$C_5$ alkyl)carbonyloxy($C_1$–$C_2$ alkyl)oxy-,
  (5-($C_1$–$C_5$ alkyl)-1,3-dioxa-cyclopenten-2-one-yl)methyloxy,
  (5-aryl-1,3-dioxa-cyclopenten-2-one-yl)methyloxy, and
  $(R^{10})(R^{11})N-(C_1-C_{10}$ alkoxy)-;

$R^{21}$ is selected from:
  $C_1$–$C_8$ alkyl, $C_2$–$C_6$ alkenyl, $C_3$–$C_{11}$ cycloalkyl, ($C_3$–$C_{11}$ cycloalkyl)methyl, aryl, aryl($C_1$–$C_4$ alkyl)-, and $C_1$–$C_{10}$ alkyl substituted with 0–2 $R^7$;

m is 0–2;

n is 0–4;

p is 0–2; and r is 0–2;

with the following provisos:
  (1) n and m are chosen such that the number of atoms connecting $R^1$ and $COR^{20}$ of Formula (III) is in the range of 8–14; and
  (2) one of the groups $R^8$ or $R^9$ must be hydrogen.

[4d] Further preferred compounds of the fourth embodiment of the present invention are those of Formula III:

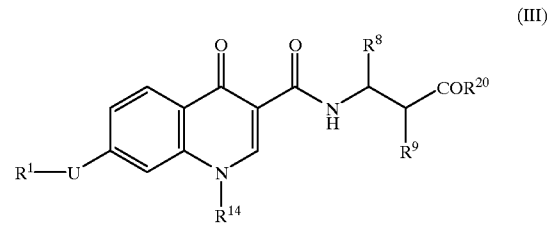

(III)

including stereoisomeric forms thereof, or mixtures of stereoisomeric forms thereof, or pharmaceutically acceptable salt or prodrug forms thereof wherein:

$R^1$ is selected from:

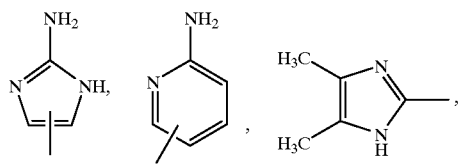

-continued

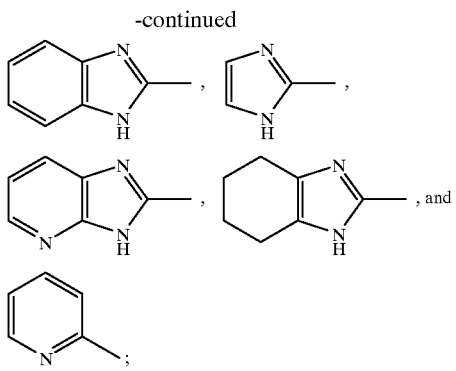

$R^4$ is selected from:
H, $C_1$–$C_6$ alkyl, $C_3$–$C_7$ cycloalkyl, $C_3$–$C_7$ cycloalkyl ($C_1$–$C_4$ alkyl)-, aryl, heteroaryl, aryl($C_1$–$C_6$ alkyl)-, and heteroaryl($C_1$–$C_6$ alkyl)-, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$, $R^6$ is selected from:
H, $C_1$–$C_{10}$ alkyl, hydroxy, $C_1$–$C_{10}$ alkoxy, nitro, $C_1$–$C_{10}$ alkylcarbonyl, —$N(R^{11})R^{12}$, cyano, halo, $CF_3$, CHO, $CO_2R^{18b}$, $C(=O)R^{18b}$, $CONR^{17}R^{18b}$, $OC(=O)R^{10}$, $OR^{10}$, $OC(=O)NR^{10}R^{11}$, $NR^{10}C(=O)R^{10}$, $NR^{10}C(=O)OR^{21}$, $NR^{10}C(=O)NR^{10}R^{11}$, $NR^{10}SO_2NR^{10}R^{11}$, $NR^{10}SO_2R^{21}$, $S(O)_pR^{11}$, $SO_2NR^{10}R^{11}$,
aryl substituted with 0–3 groups selected from halogen, $C_1$–$C_6$ alkoxy, $C_1$–$C_6$ alkyl, $CF_3$, $S(O)_mMe$, and —$NMe_2$,
aryl($C_1$–$C_4$ alkyl)-, said aryl being substituted with 0–3 groups selected from halogen, $C_1$–$C_6$ alkoxy, $C_1$–$C_6$ alkyl, $CF_3$, $S(O)_pMe$, and —$NMe_2$, and
a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$;

$R^7$ is selected from:
H, hydroxy, $C_1$–$C_4$ alkyl, $C_1$–$C_4$ alkoxy, aryl, aryl($C_1$–$C_4$ alkyl)-, ($C_1$–$C_4$ alkyl)carbonyl, $CO_2R^{18a}$, $SO_2R^{11}$, $SO_2NR^{10}R^{11}$, $OR^{10}$, and $N(R^{11})R^{12}$;

U is selected from:
—$(CH_2)_n$—, —$NH(CH_2)_n$—, —$N(R^{10})C(=O)$—, and —$NHC(=O)(CH_2)_n$—;

G is N or $CR^{19}$;
$R^8$ is H;
$R^9$ is selected from:
H, hydroxy, $CO_2H$, —$N(R^{10})R^{11}$, —$N(R^{16})R^{17}$, phenyl($C_0$–$C_4$ alkyl)carbonyl, phenyl($C_1$–$C_4$ alkyl)-, heteroaryl($C_1$–$C_6$ alkyl)-, $CONR^{18a}R^{20}$, $SO_2R^{18a}$, and $SO_2NR^{18a}R^{20}$,
providing that any of the above phenyl or heteroaryl groups may be unsubstituted or substituted independently with 1–2 $R^7$;

$R^{10}$ is selected from:
H, $CF_3$, $C_3$–$C_6$ alkenyl, $C_3$–$C_{11}$ cycloalkyl, phenyl, ($C_3$–$C_{11}$ cycloalkyl)methyl, phenyl($C_1$–$C_4$ alkyl), and $C_1$–$C_{10}$ alkyl substituted with 0–2 $R^6$;

$R^{11}$ is selected from:
H, hydroxy, $C_1$–$C_8$ alkyl, $C_3$–$C_6$ alkenyl, $C_3$–$C_{11}$ cycloalkyl, ($C_3$–$C_{11}$ cycloalkyl)methyl, $C_1$–$C_6$ alkoxy, benzyloxy, aryl, heteroaryl, heteroaryl ($C_1$–$C_4$ alkyl)-, aryl($C_1$–$C_4$ alkyl), adamantylmethyl, and $C_1$–$C_{10}$ alkyl substituted with 0–2 $R^4$;

alternatively, when $R^{10}$ and $R^{11}$ are both substituents on the same nitrogen atom (as in —$NR^{10}R^{11}$) they may be taken together with the nitrogen atom to which they are attached to form a heterocycle selected from:
3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl, and 1-piperazinyl;
said heterocycle being substituted with 0–3 groups selected from: $C_1$–$C_6$ alkyl, aryl, heteroaryl, aryl ($C_1$–$C_4$ alkyl)-, ($C_1$–$C_6$ alkyl)carbonyl, ($C_3$–$C_7$ cycloalkyl)carbonyl, ($C_1$–$C_6$ alkoxy)carbonyl, aryl($C_1$–$C_4$ alkoxy)carbonyl, $C_1$–$C_6$ alkylsulfonyl, and arylsulfonyl;

$R^{12}$ is selected from:
H, $C_1$–$C_4$ alkyl, ($C_1$–$C_4$ alkyl)carbonyl, ($C_1$–$C_4$ alkoxy)carbonyl, phenyl($C_1$–$C_4$ alkyl)-, phenylsulfonyl, phenyloxycarbonyl, and phenyl ($C_1$–$C_4$ alkoxy)carbonyl, wherein said phenyl groups are substituted with 0–2 substituents selected from the group consisting of $C_1$–$C_4$ alkyl, $C_1$–$C_4$ alkoxy, halo, $CF_3$, and nitro;

$R^{14}$ is selected from H, $CF_3$, $CH_3$, and benzyl;
$R^{16}$ is selected from:
—$C(=O)OR^{18a}$, —$C(=O)R^{18b}$, —$C(=O)N(R^{18b})_2$, —$C(=O)NHSO_2R^{18a}$, —$C(=O)NHC(=O)R^{18b}$, —$C(=O)NHC(=O)OR^{18a}$, —$C(=O)NHSO_2NHR^{18b}$, —$SO_2R^{18a}$, —$SO_2N(R^{18b})_2$, and —$SO_2NHC(=O)OR^{18b}$;

$R^{17}$ is selected from:
H, $C_1$–$C_6$ alkyl, $C_3$–$C_7$ cycloalkyl, $C_3$–$C_7$ cycloalkyl ($C_1$–$C_4$ alkyl)-, aryl, aryl($C_1$–$C_6$ alkyl)-, and heteroaryl($C_1$–$C_6$ alkyl);

$R^{18a}$ is selected from:
$C_1$–$C_6$ alkyl, aryl-, fluoro($C_3$–$C_6$ alkyl), aryl($C_1$–$C_4$ alkyl-, di($C_1$–$C_4$ alkyl)amino($C_1$–$C_4$ alkyl), morpholino($C_1$–$C_4$ alkyl), piperidino($C_1$–$C_4$ alkyl), N—($C_1$–$C_4$ alkyl)piperidino($C_1$–$C_4$ alkyl), and phenyl substituted by one or two optional groups selected from $C_1$–$C_4$ alkyl, $C_1$–$C_4$ alkoxy, and halogen;

$R^{18b}$ is H or $R^{18a}$;
$R^{19}$ is selected from:
H, halogen, $CF_3$, $CO_2H$, CN, $NO_2$, —$NR^{11}R^{12}$, $OCF_3$, $C_1$–$C_8$ alkyl, $C_2$–$C_6$ alkenyl, $C_2$–$C_6$ alkynyl, $C_3$–$C_{11}$ cycloalkyl, $C_3$–$C_7$ cycloalkyl($C_1$–$C_4$ alkyl)-, aryl ($C_1$–$C_6$ alkyl)-, $C_1$–$C_6$ alkoxy, $C_1$–$C_4$ alkoxycarbonyl, aryl, aryl-O—, aryl-$SO_2$—, heteroaryl, and heteroaryl-$SO_2$—, wherein said aryl and heteroaryl groups are substituted with 0–4 groups selected from hydrogen, halogen, $CF_3$, $C_1$–$C_3$ alkyl, and $C_1$–$C_3$ alkoxy;

$R^{20}$ is selected from:
hydroxy, $C_1$–$C_{10}$ alkyloxy, $C_3$–$C_{11}$ cycloalkyloxy, aryloxy, aryl($C_1$–$C_4$ alkyl)oxy,
$C_2$–$C_{10}$ alkylcarbonyloxy($C_1$–$C_2$ alkyl)oxy-,
$C_2$–$C_{10}$ alkoxycarbonyloxy($C_1$–$C_2$ alkyl)oxy-,
$C_2$–$C_{10}$ alkoxycarbonyl($C_1$–$C_2$ alkyl)oxy-,
$C_3$–$C_{10}$ cycloalkylcarbonyloxy($C_1$–$C_2$ alkyl)oxy-,
$C_3$–$C_{10}$ cycloalkoxycarbonyloxy($C_1$–$C_2$ alkyl)oxy-,
$C_3$–$C_{10}$ cycloalkoxycarbonyl($C_1$–$C_2$ alkyl)oxy-,
aryloxycarbonyl($C_1$–$C_2$ alkyl)oxy-, aryloxycarbonyloxy($C_1$–$C_2$ alkyl)oxy-,
arylcarbonyloxy($C_1$–$C_2$ alkyl)oxy-,
$C_1$–$C_5$ alkoxy($C_1$–$C_5$ alkyl)carbonyloxy($C_1$–$C_2$ alkyl)oxy-,
(5-($C_1$–$C_5$ alkyl)-1,3-dioxa-cyclopenten-2-one-yl)methyloxy,
(5-aryl-1,3-dioxa-cyclopenten-2-one-yl)methyloxy, and
$(R^{10})(R^{11})N$—($C_1$–$C_{10}$ alkoxy)-;

$R^{21}$ is selected from:
$C_1$–$C_8$ alkyl, $C_2$–$C_6$ alkenyl, $C_3$–$C_{11}$ cycloalkyl, ($C_3$–$C_{11}$ cycloalkyl)methyl, aryl, aryl($C_1$–$C_4$ alkyl)-, and $C_1$–$C_{10}$ alkyl substituted with 0–2 $R^7$;

m is 0–2;
n is 0–4;
p is 0–2; and
r is 0–2;

with the following provisos:
(1) n and m are chosen such that the number of atoms connecting $R^1$ and $COR^{20}$ in Formula (III) is in the range of 8–14; and
(2) one of the groups $R^8$ or $R^9$ must be hydrogen.

[4e] Specifically preferred compounds of the above invention are compounds of Formula III including enantiomeric or diastereomeric forms thereof, or mixtures of enantiomeric or diastereomeric forms thereof, or pharmaceutically acceptable salt or prodrug forms thereof selected from the group consisting of:

3-[7-[(imidazol-2-ylamino)methyl]-1-cyclopropylylquinoline-4-one-3-ylcarbonylamino]-2-((2,4,6-trimethylphenyl)sulfonylamino)propionic acid, 3-[7-[(imidazol-2-ylamino)methyl]-1-cyclopentylquinoline-4-one-3-ylcarbonylamino]-2-((4-phenylbenzene)sulfonylamino)propionic acid, 3-[7-[(benzimidazol-2-ylamino)methyl]-1-methylquinoline-4-one-3-ylcarbonylamino]-2-((2,4,6-trimethylphenyl)sulfonylamino)propionic acid, 3-[7-[(4,5-dimethylimidazol-2-ylamino)methyl]-1-trifluoromethylquinoline-4-one-3-ylcarbonylamino]-2-((2,6-dichlorophenyl)sulfonylamino)propionic acid, 3-[7-(2-aminopyridin-6-yl)-1-phenylquinoline-4-one-3-ylcarbonylamino]-2-((2,4,6-trimethylphenyl)sulfonylamino)propionic acid, 3-[7-[(7-azabenzimidazol-2-yl)methyl]-1-cyclohexylquinoline-4-one-3-ylcarbonylamino]-2-((2,4,6-trimethylphenyl)sulfonylamino)propionic acid, 3-[7-[(imidazol-2-ylamino)methyl]-1-cyclopropylquinoline-4-one-3-ylcarbon-ylamino]-2-((2,2-dichloro-4-phenylbenzene)sulfonylamino)propionic acid, In a fifth embodiment the present invention provides for a method for the treatment of cancer metastasis, diabetic retinopathy, neovascular glaucoma, thrombosis, restenosis, osteoporosis, or macular degeneration which comprises administering to a host in need of such treatment a therapeutically effective amount of a compound of Formula (I) or Formula (II).

In a sixth embodiment the present invention provides for a pharmaceutical composition comprising a pharmaceutically acceptable carrier and a compound of Formula (I) or Formula (II).

In the present invention it has been discovered that the compounds of Formulae I–IV above are useful as inhibitors of cell-matrix and cell-cell adhesion processes. The present invention includes novel compounds of Formulae I–IV and methods for using such compounds for the prevention or treatment of diseases resulting from abnormal cell adhesion to the extracellular matrix which comprises administering to a host in need of such treatment a therapeutically effective amount of such compound of Formulae I–IV.

In the present invention it has also been discovered that the compounds of Formulae I–IV above are useful as inhibitors of $\alpha_v\beta_3$. The compounds of the present invention inhibit the binding of vitronectin to $\alpha_v\beta_3$ and inhibit cell adhesion.

The present invention also provides pharmaceutical compositions comprising a compound of Formulae I–IV and a pharmaceutically acceptable carrier.

The compounds of Formulae I–IV of the present invention are useful for the treatment (including prevention) of angiogenic disorders. The term "angiogenic disorders" as used herein includes conditions involving abnormal neovascularization, such as tumor metastasis and ocular neovascularization, including, for example, diabetic retinopathy, neovascular glaucoma, age-related macular degeneration, and retinal vein occlusion, comprising administering to a mammal in need of such treatment a therapeutically effective amount of a compound of Formulae I–IV described above.

The compounds of Formulae I–IV of the present invention ay be useful for the treatment or prevention of other diseases which involve cell adhesion processes, including, but not limited to, inflammation, bone degradation, thromboembolic disorders, restenosis, rheumatoid arthritis, asthma, allergies, adult respiratory distress syndrome, graft versus host disease, organ transplantation rejection, septic shock, psoriasis, eczema, contact dermatitis, osteoporosis, osteoarthritis, atherosclerosis, inflammatory bowel disease and other autoimmune diseases. The compounds of Formulae IV of the present invention may also be useful for wound healing.

The term "thromboembolic disorders" as used herein includes conditions involving platelet activation and aggregation, such as arterial or venous cardiovascular or cerebrovascular thromboembolic disorders, including, for example, thrombosis, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, myocardial infarction, cerebral embolism, kidney embolisms, pulmonary embolisms, or such disorders associated with diabetes, comprising administering to a mammal in need of such treatment a therapeutically effective amount of a compound of Formulae I–IV described above.

The compounds of the present invention may be used for other ex vivo applications to prevent cellular adhesion in biological samples.

The compounds of the present invention can also be administered in combination with one or more additional therapeutic agents selected from: anti-coagulant or coagulation inhibitory agents, such as heparin or warfarin; anti-platelet or platelet inhibitory agents, such as aspirin, piroxicam, ticlopidine, or clopidogrel; factor Xa inhibitors; thrombin inhibitors such as boropeptides, hirudin or argatroban; or thrombolytic or fibrinolytic agents, such as plasminogen activators, anistreplase, urokinase, or streptokinase.

The compounds of Formulae I–IV of the present invention can be administered in combination with one or more of the foregoing additional therapeutic agents, thereby to reduce the doses of each drug required to achieve the desired therapeutic effect. Thus, the combination treatment of the present invention permits the use of lower doses of each component, with reduced adverse, toxic effects of each component. A lower dosage minimizes the potential of side effects of the compounds, thereby providing an increased margin of safety relative to the margin of safety for each component when used as a single agent. Such combination therapies may be employed to achieve synergistic or additive therapeutic effects for the treatment of thromboembolic disorders.

By "therapeutically effective amount" it is meant an amount of a compound of Formulae I–IV that when administered alone or in combination with an additional therapeutic agent to a cell or mammal is effective to prevent or ameliorate the thromboembolic disease condition or the progression of the disease.

By "administered in combination" or "combination therapy" it is meant that the compound of Formulae I–IV and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The term anti-coagulant agents (or coagulation inhibitory agents), as used herein, denotes agents that inhibit blood coagulation. Such agents include warfarin (available as COUMADIN™) and heparin.

The term anti-platelet agents (or platelet inhibitory agents), as used herein, denotes agents that inhibit platelet function such as by inhibiting the aggregation, adhesion or granular secretion of platelets. Such agents include the various known non-steroidal anti-inflammatory rugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), and piroxicam. Piroxicam is commercially available from Pfizer, Inc. (New York, N.Y.), as Feldane®. Other suitable anti-platelet agents include ticlopidine and clopidogrel, including pharmaceutically acceptable salts or prodrugs thereof. Ticlopidine and clopidogrel are also preferred compounds since they are known to be gentle on the gastro-intestinal tract in use. Still other suitable platelet inhibitory agents include thromboxane-A2-receptor antagonists and thromboxane-A2-synthetase inhibitors, as well as pharmaceutically acceptable salts or prodrugs thereof.

The phrase thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. Such inhibitors include boroarginine derivatives and boropeptides, hirudin and argatroban, including pharmaceutically acceptable salts and prodrugs thereof. Boroarginine derivatives and boropeptides include N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. Boropeptide thrombin inhibitors include compounds described in Kettner et al., U.S. Pat. No. 5,187,157 and European Patent Application Publication Number 293 881 A2, the disclosures of which are hereby incorporated herein by reference. Other suitable boroarginine derivatives and boropeptide thrombin inhibitors include those disclosed in PCT Application Publication Number 92/07869 and European Patent Application Publication Number 471 651 A2, the disclosures of which are hereby incorporated herein by reference, in their entirety.

The phrase thrombolytics (or fibrinolytic) agents (or thrombolytics or fibrinolytics), as used herein, denotes agents that lyse blood clots (thrombi). Such agents include tissue plasminogen activator, anistreplase, urokinase or streptokinase, including pharmaceutically acceptable salts or prodrugs thereof. Tissue plasminogen activator (tPA) is commercially available from Genentech Inc., South San Francisco, Calif. The term anistreplase, as used herein, refers to anisoylated plasminogen streptokinase activator complex, as described, for example, in European Patent Application No. 028,489, the disclosures of which are hereby incorporated herein by reference herein, in their entirety. Anistreplase is commercially available as Eminase®. The term urokinase, as used herein, is intended to denote both dual and single chain urokinase, the latter also being referred to herein as pro-urokinase.

Administration of the compounds of Formulae I–IV of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

The compounds of the present invention are also useful as standard or reference compounds, for example as a quality standard or control, in tests or assays involving the binding of vitronectin or fibrinogen to $\alpha_v\beta_3$ Such compounds may be provided in a commercial kit, for example, for use in pharmaceutical research involving $\alpha_v\beta_3$. The compounds of the present invention may also be used in diagnostic assays involving $\alpha_v\beta_3$.

The compounds herein described may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention that contain asymmetrically substituted carbon atoms may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

When any variable (for example but not limited to, $R^2$, $R^4$, $R^6$, $R^7$, $R^8$, $R^{12}$, and $R^{14}$, n, etc.) occurs more than one time in any constituent or in any formula, its definition on each occurrence is independent of its definition at every other occurrence. Thus, for example, if a group is shown to be substituted with 0–2 $R^4$, then said group may optionally be substituted with up to two $R^4$ and $R^4$ at each occurrence is selected independently from the defined list of possible $R^4$. Also, by way of example, for the group —N($R^{5a}$)$_2$, each of the two $R^{5a}$ substituents on N is independently selected from the defined list of possible $R^{5a}$. Similarly, by way of example, for the group —C($R^7$)$_2$—, each of the two $R^7$ substituents on C is independently selected from the defined list of possible $R^7$.

When a bond to a substituent is shown to cross the bond connecting two atoms in a ring, then such substituent may be bonded to any atom on the ring. When a bond joining a substituent to another group is not specifically shown or the atom in such other group to which the bond joins is not specifically shown, then such substituent may form a bond with any atom on such other group.

When a substituent is listed without indicating the tom via which such substituent is bonded to the rest of the compound of Formulae I–IV, then such substituent may be bonded via any atom in such substituent. For example, when the substituent is piperazinyl, piperidinyl, or tetrazolyl, unless specified otherwise, said piperazinyl, piperidinyl, tetrazolyl group may be bonded to the rest of the compound of Formulae I–IV via any atom in such piperazinyl, piperidinyl, tetrazolyl group.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted", as used herein, means that any one or more hydrogen on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

As used herein, "alkyl" is intended to include both branched and straight-chain saturated aliphatic hydrocarbon groups having the specified number of carbon atoms (for example, "$C_1$–$C_{10}$" denotes alkyl having 1 to 10 carbon atoms); "haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)); "alkoxy" represents an alkyl group of indicated number of carbon atoms attached through an oxygen bridge; "cycloalkyl" is intended to include saturated ring groups, including mono-, bi-, or polycyclic ring systems, such as cyclopropyl, cyclobutyl, cyclopentyl, cyclohexyl, cycloheptyl, cyclooctyl, and adamantyl; and "biycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl and the like; and "alkynyl" is intended to include hydrocarbon chains of either a straight or branched configuration and one or more triple carbon-carbon bonds which may occur in any stable point along the chain, such as ethynyl, propynyl and the like.

The terms "alkylene", "alkenylene", "phenylene", and the like, refer to alkyl, alkenyl, and phenyl groups, respectively, which are connected by two bonds to the rest of the structure of Formulae I–IV. Such "alkylene", "alkenylene", "phenylene", and the like, may alternatively and equivalently be denoted herein as "-(alkyl)-", "-(alkenyl)-" and "-(phenyl)-", and the like.

"Halo" or "halogen" as used herein refers to fluoro, chloro, bromo and iodo; and "counterion" is used to represent a small, negatively charged species such as chloride, bromide, hydroxide, acetate, sulfate and the like.

As used herein, "aryl" or "aromatic residue" is intended to mean phenyl or naphthyl optionally substituted with 1–3 $R^{19}$; the term "arylalkyl" represents an aryl group attached through an alkyl bridge.

As used herein, "carbocycle" or "carbocyclic residue" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" or "heterocyclic" is intended to mean a stable 5- to 7-membered monocyclic or bicyclic or 7- to 10-membered bicyclic heterocyclic ring which may be saturated, partially unsaturated, or aromatic, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl (pyridinyl), pyrimidinyl, furanyl(furyl), thiazolyl, thienyl, pyrrolyl, pyrazolyl, imidazolyl, tetrazolyl, benzofuranyl, benzothiophenyl, indolyl, indolenyl, isoxazolinyl, isoxazolyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathiinyl, 2H-pyrrolyl, pyrrolyl, imidazolyl, pyrazolyl, isothiazolyl, isoxazolinyl, isoxazolyl, oxazolyl, pyridinyl, pyrazinyl, pyrimidinyl, pyridazinyl, indolizinyl, isoindolyl, 3H-indolyl, indolyl, 1H-indazolyl, purinyl, 4H-quinolizinyl, isoquinolinyl, quinolinyl, phthalazinyl, naphthyridinyl, quinoxalinyl, quinazolinyl, cinnolinyl, pteridinyl, 4aH-carbazole, carbazole, β-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, pyrrolidinyl, pyrrolinyl, imidazolidinyl, imidazolinyl, pyrazolidinyl, pyrazolinyl, piperidinyl, piperazinyl, indolinyl, isoindolinyl, quinuclidinyl, morpholinyl or oxazolidinyl. Also included are fused ring and spiro compounds containing, for example, the above heterocycles.

At used herein, the term "heteroaryl" refers to aromatic heterocyclic groups. Such heteroaryl groups are preferably 5–6 membered monocylic groups or 8–10 membered fused bicyclic groups. Examples of such heteroaryl groups include, but are not limited to pyridyl(pyridinyl), pyrimidinyl, furanyl(furyl), thiazolyl, thienyl, pyrrolyl, pyrazolyl, imidazolyl, indolyl, isoxazolyl, oxazolyl, pyrazinyl, pyrimidinyl, pyridazinyl, benzofuranyl, benzothienyl, benzimidazolyl, quinolinyl, or isoquinolinyl.

As used herein, "pharmaceutically acceptable salts" refer to derivatives of the disclosed compounds wherein the parent compound of Formulae I–IV is modified by making acid or base salts of the compound of Formulae I–IV. Examples of pharmaceutically acceptable salts include, but are not limited to, mineral or organic acid salts of basic residues such as amines; alkali or organic salts of acidic residues such as carboxylic acids; and the like.

"Prodrugs" are considered to be any covalently bonded carriers which release the active parent drug according to Formulae I–IV in vivo when such prodrug is administered to a mammalian subject. Prodrugs of the compounds of Formulae I–IV are prepared by modifying functional groups present in the compounds in such a way that the modifications are cleaved, either in routine manipulation or in vivo, to the parent compounds. Prodrugs include compounds of Formulae I–IV wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of Formulae I–IV, and the like. Examples of representative carboxyl and amino prodrugs are included under the definition of $R^2$, $R^3$, and Y.

The pharmaceutically acceptable salts of the compounds of Formulae I–IV include the conventional non-toxic salts or the quaternary ammonium salts of the compounds of Formulae I–IV formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formulae I–IV which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formulae I–IV with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammoinum hydroxide and the like.

As discussed above, pharmaceutically acceptable salts of the compounds of the invention can be prepared by reacting the free acid or base forms of these compounds with a stoichiometric amount of the appropriate base or acid, respectively, in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

The disclosures of all of the references cited herein are hereby incorporated herein by reference in their entirety.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereof as appreciated by those skilled in the art. Preferred methods include, but are not limited to, those described below. All literature cited herein is incorporated in its entirety by reference.

Compounds of Formulae I–IV can be conveniently prepared by cyclization of aniline derived aminomethylenemalonates (Gould-Jacobs reaction, for a review of quinolone synthesis, see Radl, S.; Bouzard, D. Recent Advances in the Synthesis of Antibacterial Quinolones. *Heterocycles* 1992, 34:2143–2177).

Scheme I illustrates a synthetic sequence which will provide the quinolones of this invention. Reaction of a 3-Bromoaniline with diethyl ethoxymethylenemalonate (Albrect, R. *Prog. Drug Res.* 1977, 21:9) results in a vinylogous amide which is cyclized in diphenyl ether at reflux to afford the 7-bromoquinolone. After $N^1$-alkylation, the bromide is converted to an olefin via Stille coupling to a vinyltin species or Heck olefination using styrene. Ozonolysis of the olefin provides the aldehyde.

Reductive amination of the intermediate aldehyde (for suitable methods see, Abdel-Magid, A. F.; Maryanoff, C. A.; Carson, K. G. *Tetrahedron Lett.* 1990, 31:5595–5598, and references contained therein) with a variety of heteroaryl amines, which may additionally contain suitable protecting groups, provides the substituted amines. Alternatively, depending on the nature of the heterocyclic amine, the reductive amination can be carried out in a two step procedure, wherein initial formation of an imine is carried out by treatment of the aldehyde with the desired amine in the presence of a dehydrating agent such as magnesium sulfate, sodium sulfate, or molecular sieves, in a suitable solvent such as carbon tetrachloride, methylene chloride, benzene or toluene (for example see, Modern Synthetic Reactions 2nd ed. House, H. O., Benjamin/Cummings Publishing Co., Menlo Park, Calif., 1972.). The imine is subsequently reduced using one of a variety of reducing agents such as sodium borohydride, sodium cyanoborohydride, or sodium triacetoxyborohydride, in a suitable solvent such as methanol, ethanol, tetrahydrofuran, dioxane or 1,2-dichloroethane, to provide the desired amine. Subsequent saponification of the ester using conventional methods known to one skilled in the art of organic synthesis gives the desired acids. In the case of tert-butyl esters the acid may be produced either by the action of trifluoroacetic acid with or without an inert solvent such as methylene chloride, or by the action of anhydrous HCl in a solvent such as ether or dioxane. Coupling of the resulting acids to appropriately substituted α- or β-amino esters affords an intermediate which can be deprotected to give compounds of Formulae I–IV. The coupling is carried out using any of the many methods for the formation of amide bonds known to one skilled in the art of organic synthesis. These methods include but are not limited to conversion of the acid to the corresponding acid chloride, or use of standard coupling procedures such as the azide method, mixed carbonic acid anhydride(isobutyl chloroformate) method, carbodiimide (dicyclohexylcarbodiimide, diisopropylcarbodiimide, or water-soluble carbodiimides) method, active ester (p-nitrophenyl ester, N-hydroxysuccinic imido ester) method, carbonyldiimidazole method, phosphorus reagents such as BOP-Cl. Some of these methods (especially the carbodiimide) can be enhanced by the addition of 1-hydroxybenzotriazole. Global deprotection of the remaining protecting groups may be accomplished by methods known to one skilled in the art (for example see, Protective Groups in Organic Synthesis 2nd,ed. Greene, T. W., and Wuts, P. G. M., John Wiley & Sons, Inc. New York, 1991.).

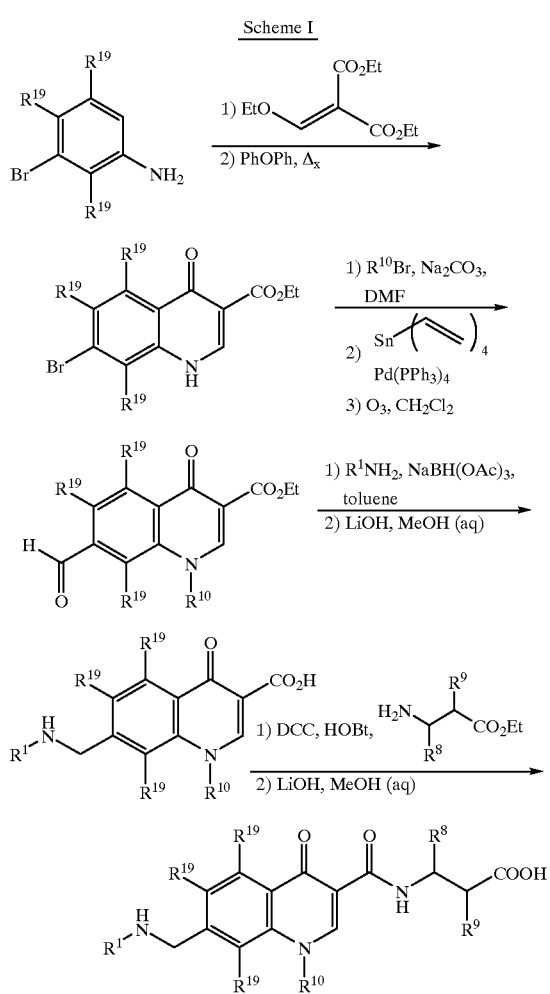

Scheme I

The compounds of the present invention wherein Y is an oxyalkoxy group, e.g. alkoxycarbonyloxyalkoxy, may be prepared by reacting a suitably protected carboxylic acid of Formulae I–IV with an e.g. an alkoxycarbonyloxyalkyl chloride in the presence of an iodide source, such as tetrabutylammonium iodide or potassium iodide, and an acid scavenger, such as triethylamine or potassium carbonate, using procedures known to those skilled in the art.

As an alternative to the quinolone synthesis outlined above, the quinolone nucleus may be formed using the route illustrated in Scheme II. Similar methodology for the preparation of quinolones was first described in German patent application DE3142854. Starting from a 4-bromo-3-fluorobenzoyl chloride, condensation with malonic acid monoethyl ester monopotassium salt gives a benzoyl acetate that is subsequently reacted with triethyl orthoformate. The resulting ethoxymethylene derivative is reacted with a primary amine and cyclized to the quinolone.

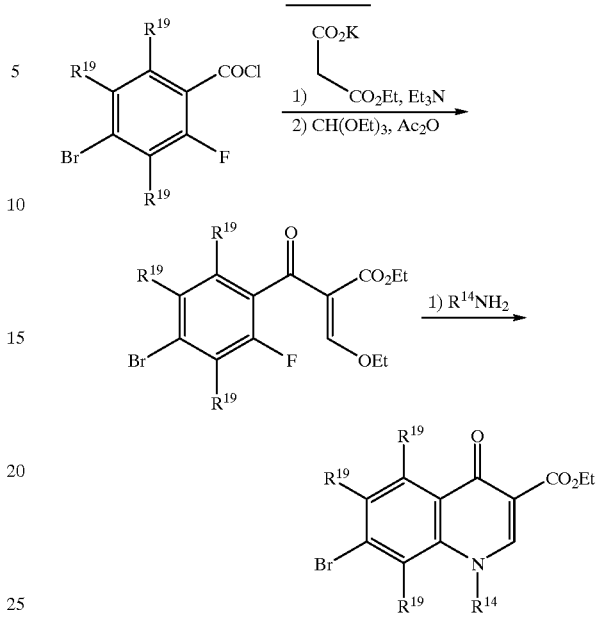

Scheme II

The appropriately substituted racemic β-amino acids may be purchased commercially or, as is shown in Scheme III, Method 1, prepared from the appropriate aldehyde, malonic acid and ammonium acetate according to the procedure of Johnson and Livak, *J. Am. Chem. Soc.* 1936, 58, 299. Racemic β-substituted-β-amino esters may be prepared through the reaction of dialkylcuprates or alkyllithiums with 4-benzoyloxy-2-azetidinone followed by treatment with anhydrous ethanol (Scheme III, Method 2) or by reductive amination of β-keto esters as is described in published PCT patent application WO9316038 (see also Rico et al., J. Org. Chem. 1993, 58, 7948–51). Enantiomerically pure β-substituted-β-amino acids can be obtained through the optical resolution of the racemic mixture or can be prepared using numerous methods, including: Arndt-Eistert homologation of the corresponding α-amino acids as shown in Scheme III, Method 3 (see Meier, and Zeller, *Angew. Chem. Int. Ed. Engl.* 1975, 14, 32; Rodriguez, et al. *Tetrahedron Lett.* 1990, 31, 5153; Greenlee, *J. Med. Chem.* 1985, 28, 434 and references cited within); and through an enantioselective hydrogenation of a dehydroamino acid as is shown in Scheme III, Method 4 (see Asymmetric Synthesis, Vol. 5, (Morrison, ed.) Academic Press, New York, 1985). A comprehensive treatise on the preparation of β-amino acid derivatives may be found in published PCT patent application WO 9307867, the disclosure of which is hereby incorporated by reference.

Scheme III

Method 1

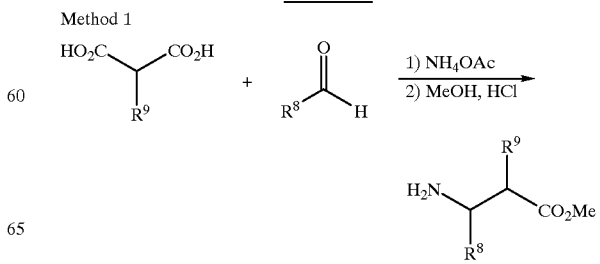

Method 2

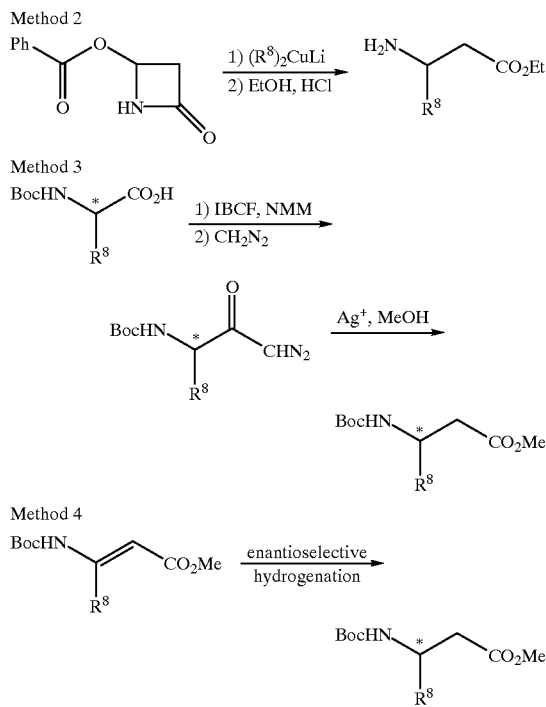

Method 3

Method 4

The synthesis of $N^2$-substituted diaminopropionic acid derivatives can be carried out via Hoffman rearrangement of a wide variety of asparagine derivatives as described in Waki, M., et al., Synthesis, 266–268, (1981).

A convenient preparation of suitably protected 2-aminoimidazoles is outlined in Scheme IV.

Scheme IV

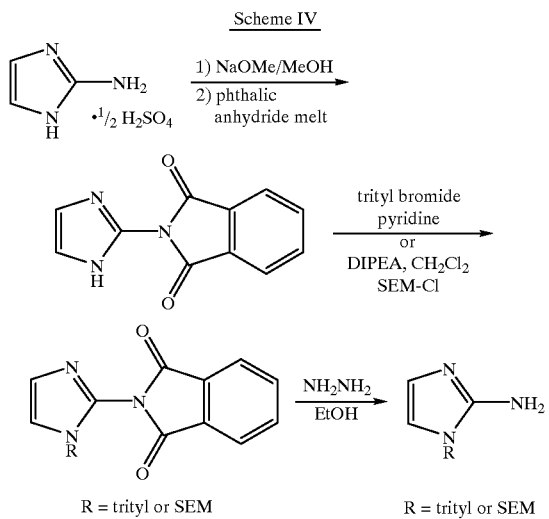

R = trityl or SEM

Additional compounds of Formulae I–IV where $R^9$ is $N(R^{16})R^{17}$ can be prepared from the compounds of Scheme I, wherein $R^{16}$ is Cbz (benzyloxycarbonyl), is shown in Scheme V. Selective removal of the Cbz group may be accomplished by hydrogenation using palladium on carbon in a suitable solvent such as methanol or ethanol.

The resulting amines can be converted to additional compound of Formulae I–IV by treatment with a wide variety of reagents, for example, acyl halides, chloroformates, isocyanates, sulfonylchlorides, chlorosulfonamides, and sulfonylisocyanates, etc. using standard methods.

Scheme V

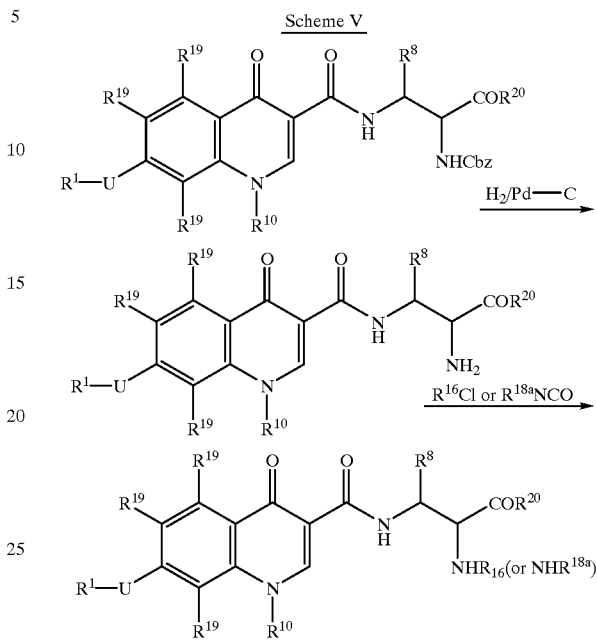

Scheme VI illustrates a synthetic sequence which will provide the naphthyridines of this invention. Reaction of 2,4-dichloronicotinic acid with phosphorus pentachloride provides the acid chloride which reacts with ethyl malonate giving nicotinyl acetate. Reaction of nicotinyl acetate with ethyl orthoformate provides ethoxyethylene malonate, which then reacts with the desired amine, resulting in intermediate which can be cyclized in the presence of a base such as sodium hydride or potassium carbonate to yield the desired 6-chloronaphthyridine. (J. Med. Chem. 1992, 35, 518–525). Coupling of the desired 6-chloronaphthyridine with tributylvinyltin provides an olefin, 6-vinylnaphthyridine, (J. Heterocyclic chem. 1991, 28, 191) upon which further synthetic transformation as in Scheme I affords the naphthyridines of this invention.

Scheme VI

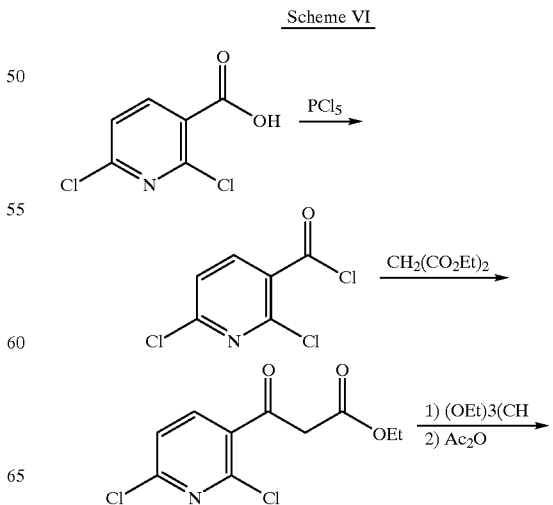

-continued

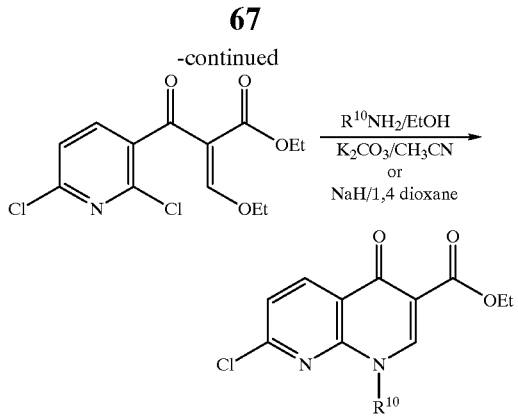

The detailed processes for preparing the compounds of Formulae I–IV are illustrated by the following Examples. It is, however, understood that this invention is not limited to the specific details of these examples. Proton nuclear magnetic resonance spectra ($^1$H NMR) were measured in chloroform-d (CDCl$_3$) unless otherwise specified, and reported in parts per million (ppm) downfield from tetramethylsilane (TMS). The coupling patterns are reported as follows: s, singlet; d, doublet; t, triplet; q, quartet; qt, quintet; m, multiplet.

EXAMPLE 1

1-Triphenylmethyl-2-aminoimidazole
Part A. 2-Phthalamidoimidazole

2-Aminoimidazole sulfate (2.64 g, 20 mmol) was dissolved in 200 mL of anhydrous methanol and cooled to −78° C. A 25% solution of sodium methoxide in methanol (4.57 mL, 20 mmol) was added dropwise. The reaction mixture was allowed to warm to room temperature and stirred for an additional 3 h. The solution was filtered and concentrated on the rotary evaporator to afford a brown oil (1.6 g, 96.4%); $^1$H NMR (300 MHz, DMSO-d$_6$) δ 5.0 (bs, 2H), 6.32, (s, 2H).

Phthalic anhydride (4.14 g, 29.2 mmol) and 2-aminoimidazole (2.32 g, 29.2 mmol) were heated to 170° C. for 15 min. The crude reaction mixture was purified using flash chromatography (gradient: chloroform:methanol= 95:5–80:20) to yield 4.66 g (75%) of a brown solid; $^1$H NMR (300 MHz, DMSO-d$_6$) δ 7.16 (bs, 2H), 7.94–8.06 (m, 4H), 12.35 (bs, 1H); MS (ESI) m/z 214.2 (M+H)$^+$.

Part B. 1-Triphenylmethyl-2-phthalamidoimidazole

The product of Ex. 1, Part A, (4.66 g, 21.9 mmol) was dissolved in 100 mL of anhydrous pyridine and triphenylmethyl chloride (9.15 g, 32.82 mmol) was added. The reaction mixture was heated at reflux for 24 h. Pyridine was removed and the residue was purified using flash chromatography (chloroform:methanol 5–10%) to yield the desired product (2.74 g, 27.5% yield); $^1$H NMR (300 MHz, CDCl$_3$) δ 6.80 (d, J=1.1 Hz, 1H), 7.06 (t, J=7.3 Hz, 3H), 7.17 (t, J=7.7 Hz, 7H), 7.28 (d, 6H, 7.64, s 4H); MS (NH$_3$-DCI) m/z 456 (M+H)$^+$.

Part C. 1-Triphenylmethyl-2-aminoimidazole

The product of Ex. 1, Part B, (2.60 g, 5.7 mmol) and hydrazine (1.83 g, 57 mmol) were heated at reflux in 250 mL of anhydrous ethanol for 1 hr. The reaction mixture was cooled and the solvent removed in vacuo. The solid residue was purified using flash chromatography (CHCl$_3$:MeOH= 10:1) to yield 1.8 g (97%) of the title compound as a yellow solid; $^1$H NMR (300 MHz, DMSO-d$_6$) δ 6.26 (d, J=1.8 Hz, 1H), 6.51 (d, J=1.8 Hz, 1H), 7.13 (d, J=7 Hz, 6H), 7.33–7.44 (m, 9H); MS (NH$_3$-DCI) m/z 326 (M+H)$^+$.

EXAMPLE 2

3-Carboxy-1-methyl-7-[(1-triphenylmethylimidazol-2-ylamino)methyl]quinolin-4-one
Part A. 7-Bromo-3-(ethoxycarbonyl)quinolin-4-one 3-Bromoaniline (50 g, 291 mmol) and diethyl ethoxymethylenemalonate (63 g, 291 mmol) were mixed together and allowed to stand at room temperature overnight. White crystals were filtered and recrystallized from a mixture of ethyl and petroleum ether (1:1). The product was then heated at reflux in diphenyl ether (700 mL) for 2 h. After cooling, the solid was filtered and washed several times with ether to give a colorless solid (59.6 g, 68%) which was the mixture of isomers (93:7) wherein the desired isomer was the major component; $^1$H NMR (300 MHz, DMSO-d$_6$) δ 8.59 (s, 1H), 8.06 (d, 1H, J=8.8 Hz), 7.82 (d, 1H, J=1.8 Hz), 7.55 (dd, 1H, J=8.8, 1.8 Hz ), 4.21 (q, 2H, J=7 Hz), 1.28 (t, 3H, J=7 Hz); MS (NH$_3$-CI) m/z 296 (M+H)$^+$.

Part B. 7-Bromo-3-ethoxycarbonyl-1-methylquinolin-4-one

The product of Ex. 2, Part A (20 g, 68 mmol) was suspended in DMF. Methyl iodide (48.1 g, 339 mmol) and potassium carbonate (23.4 g, 170 mmol) were added and reaction mixture was stirred at 60° C. overnight. The reaction mixture was poured over ice and the resulting precipitate that was filtered and washed with water to yield a white solid (18.96 g, 90%); $^1$H NMR (300 MHz, DMSO-d$_6$) δ 8.67 (s, 1H), 8.12 (d, J=8.8 Hz, 1 H), 7.97 (s, 1H), 7.66 (d, J=8.4 Hz, 1H), 4.23 (q, 2H), 1.28 (t, 3H); MS (NH$_3$-CI) m/z 312 (M+H)$^+$.

Part C. 7-Ethenyl-3-ethoxycarbonyl-1-methylquinolin-4-one

A solution of the product of Ex. 2, Part B (0.492 g, 1.59 mmol) in toluene was degassed and kept under nitrogen. Tributylvinyltin (0.506 g, 1.59 mmol) and tetrakis (triphenylphosphine)palladium(0)(37 mg, 0.032 mmol) were added and the reaction mixture heated at reflux for 3 h. After cooling, the product was filtered and washed with ether to give 301 mg (73%); $^1$H NMR (300 MHz, DMSO-d$_6$) δ 8.48 (d, 1H, J=8.4 Hz), 8.45 (s, 1H), 7.55 (dd, 1H, J=1.1, 8 Hz, 7.32 (d, 1H, J=1.5 Hz), 6.83 (dd, 1H, J=11 Hz, 17.6 Hz), 5.95 (d, 1H, J=17.6 Hz), 5.49 (d, 1H, J=11 Hz), 4.4 (q, 2H, J=7 Hz), 3.89 (s, 1H), 1.42 (t, 3H, J=7 Hz); MS (NH$_3$-CI) m/z 258 (M+H)$^+$.

Part D. 3-Ethoxycarbonyl-7-formyl-1-methylquinolin-4-one

The product of Ex. 2, Part C (150 mg, 0.58 mmol) and small crystal of Sudan Red was dissolved in 15 mL of dichloromethane and the reaction mixture was cooled to −78° C. Ozone was purged through the solution for about 5 min, until the color changed from bright red to light green. The reaction mixture was purged with nitrogen for 5 min, 0.9 mL of dimethyl sulfite was added, and the reaction mixture stirred at room temperature for 4 h. Solvent was removed and the crude product was purified on a silica gel column eluted with gradient of 2–5% MeOH/CHCl$_3$ to give a white solid (95 mg, 63%); $^1$H NMR (300 MHz, DMSO-d$_6$) δ 10.21 (s, 1H), 8.78 (s, 1H), 8.39 (d, 1H, J=8.1 Hz), 8.30 (d, 1H, J=2.6 Hz), 7.93 (d, 1H, J=9.2 Hz), 4.24 (q, 2H, J=7 Hz), 4.01 (s, 3H), 1.30 (t, 3H, J=7 Hz); MS (NH$_3$-CI) m/z 260 (M+H)$^+$.

Part E. 3-Ethoxycarboxy-1-methyl-7-[(1-triphenylmethylimidazol-2-ylamino)methyl]quinolin-4-one 1-Triphenylmethyl-2-aminoimidazole (0.201 g, 0.62 mmol) and the product of Ex. 2, Part D, (0.16 g, 0.62 mmol) were heated at reflux in toluene (25 mL). The progress of the reaction was monitored by $^1$H NMR. After 6 h, the mixture was cooled to room temperature and triacetoxyborohydride (0.52 g, 2.5 mmol) was added. The reaction mixture was stirred for 24 h. Water (100 mL) was added, the organic layer was separated and the water layer was extracted with ethyl acetate. The combined organic layers were concentrated and purified by flash chromatography (MeOH/CHCl$_3$) to yield the product as a colorless solid (0.22 g, 61%); $^1$H NMR (300

MHz, DMSO-d<sub>6</sub>) δ 8.63 (s, 1H), 7.98 (d, J=8.1 Hz, 1H), 7.41–7.32 (m, 10H), 7.14 (dd, J=6.6, 14.5 Hz, 6H), 6.73 (d, J=8.1 Hz, 1H), 6.50 (d, J=1.8 Hz, 1H), 6.29 (d, J=1.8 Hz, 1H), 4.32 (d, J=5.9 Hz, 2H), 4.21 (q, J=7.3 Hz, 2H), 4.02 (t, 1H), 3.79 (s, 3H), 1.28 (t, J=7.3 Hz, 3H); MS (NH$_3$-CI) m/z 569 (M+H)$^+$.

Part F. 3-Carboxy-1-methyl-7-[(1-triphenylmethylimidazol-2-ylamino)methyl]quinolin-4-one A mixture of the product of Ex. 2, Part E (200 mg, 0.35 mmol), and 0.5 M lithium hydroxide (2.1 mL, 1.0 mmol) in THF (10 mL) was stirred at room temperature for 3 h. Water (10 mL) was added, the volatiles were evaporated, and the aqueous solution acidified with HCl to pH 2. The resulting solution was extracted with CHCl$_3$ to give 160 mg of yellow solid. The crude acid was purified on a silica gel column eluted with 5–10% MeOH/CHCl$_3$ to give a white solid (113 mg, 59%); $^1$H NMR (300 MHz, DMSO-d$_6$) δ 9.0 (s, 1H), 8.11 (d, 1H, J=8 Hz), 7.56 (s, 1H), 7.31–7.2 (m, 9H), 7.13 (d, 6H, J=7 Hz), 6.87 (d, 1H, J=8.4 Hz), 6.9 (d, 1H, J=1.5 Hz), 6.30 (d, 1H, J=1.8 Hz), 4.39 (d, 2H, J=5.9 Hz), 4.18 (t, 1H), 3.98 (s, 3H); MS (ESI) m/z 541 (M+H)$^+$.

EXAMPLE 3 tert-Butyl 3-amino-(2S)-[N-(2,4,6-trimethylphenyl)sulfonylamino]propionate hydrochloride Part A. N-(2,4,6 trimethylphenyl)sulfonyl-L-asparagine L-Asparagine (20.0 g, 0.15 mol) was suspended in a mixture of tetrahydrofuran (130 mL) and water (250 mL). Triethylamine (49 g, 0.48 mol) was added followed by mesitylenesulfonyl chloride (49.7 g, 0.227 mol). The reaction mixture became slightly exothermic and the solids dissolved over a period of 0.5 h to yield a yellow solution. The reaction mixture was stirred for 3 h at room temperature, then washed with ether, and methylene chloride. The aqueous layer was separated, and acidified to ca. pH=1.5 with conc. HCl, during which time a thick precipitate formed. After 0.5 h, the product was filtered, washed with water, and dried to yield a white solid (34 g, 72%); mp: 193.5–195° C.; $^1$H NMR (DMSO-d$_6$) δ 2.24 (s, 3H), 2.28 (dd, 1H), 2.45 (dd, 1H), 2.55 (s, 6H), 3.98 (m, 1H), 6.88 (bs, 1H), 6.99 (s, 2H), 7.32 (bs, 1H), 7.82 (d, 2H), 12.58 (bs, 1H); Mass spectrum (ESI) m/z 315.2 (M+H)$^+$.

Part B. 3-Amino-(2S)-N-(2,4,6 trimethylphenyl)sulfonylaminopropionic acid

Sodium hydroxide (32 g, 0.80 mol), was dissolved in water (200 mL) and cooled in an ice bath. Bromine (19.2 g, 0.12 mol) was added dropwise over 5 min and the mixture allowed to stir for 15 min. The product of Ex.3, Part A, (31.44 g, 0.10 mol), was added in several portions over a period of ca. 10 min. during which time the yellow color faded. The reaction mixture was gently heated on a steam bath during which time the internal temperature rose to ca. 85° C. After 1 h, the reaction mixture was allowed to cool to room temperature then cooled in an ice bath. The reaction mixture was cautiously acidified to pH=6 with conc. HCl, during which time a solid formed and gas was evolved. The solid was filtered, washed with cold water, and allowed to dry overnight, to yield the product as a white solid (23.9 g, 83%); $^1$H NMR (300 MHz, DMSO-d$_6$) δ 2.26 (s, 3H), 2.59 (s, 6H), 2.80 (dd, 1H), 2.94 (dd, 1H), 3.07 (dd, 1H), 7.06 (s, 2H); Mass spectrum (ESI) m/z 287.2 (M+H)$^+$.

Part C. tert-Butyl 3-amino-(2S)-N-(2,4,6-trimethylphenyl)sulfonylaminopropionate The product of Ex.3, Part B, (11.45 g, 0.04 mol), was placed in a Parr bottle, and dissolved in dioxane (170 mL), and conc. sulfuric acid (11 mL) was added. The reaction mixture was cooled in a dry ice-acetone bath and ca. 185 mL of isobutylene was added. The bottle was sealed and agitated for 114 h. The bottle was de-pressurized, then purged with nitrogen for a brief time. The reaction mixture was poured into a rapidly stirred mixture of water (225 mL) containing sodium hydroxide (17 g) and ether (600 mL) which had been pre-cooled in an ice bath. The layers were separated. The aqueous layer was extracted with additional ether. The pH of the aqueous layer was carefully adjusted with conc. HCl to pH=11 and extracted four times with ether. The organic layers from the pH 11 adjusted extraction were combined, dried with anhydrous sodium sulfate, filtered, and evaporated to yield the product as a viscous oil which solidified (8.64 g, 63%); $^1$H NMR (300 MHz, CDCl$_3$) δ 1.28 (s, 9H), 2.28 (s, 3H), 2.67 (s, 6H), 2.93 (m, 2H), 3.69 (m, 1H), 6.95 (s, 2H).

EXAMPLE 4

3-[7-[(imidazol-2-ylamino)methyl]-1-methylquinoline-4-one-3-ylcarbonylamino]-(2S)-[N-(2,4,6-trimethylphenyl)sulfonylamino]propionic acid Part A. tert-Butyl 3-[7-[(imidazol-2-ylamino)methyl]-1-methylquinoline-4-one-3-ylcarbonylamino]-(2S)-[N-(2,4,6-trimethylphenyl)sulfonylamino]propionate To a solution of the compound of Ex. 2 (150 mg, 0.28 mmol), the compound of Ex. 3 (95 mg, 0.28 mmol), and 2-(1H-benzotriazol-1-yl)-1,1,3,3-tetramethyluronium tetrafluoroborate (TBTU, 90 mg, 0.28 mmol) in DMF (10 mL) was added triethylamine (0.1 mL, 0.72 mmol). The resulting mixture was stirred at room temperature overnight. Ethyl acetate was added (75 mL), and solution was washed with water (2×), saturated sodium bicarbonate, and brine. The organic layer was dried and the solvent evaporated in vacuo to yield a yellow solid (210 mg, 88%). $^1$H NMR (300 MHz, DMSO-d$_6$) δ 10.25 (t, 1H), 8.62 (s, 1H), 8.25 (d, 1H, J=8 Hz), 8.02 (s 1H), 7.29–7.3 (m, 9H), 7.17–7.20 (m, 6H), 6.9 (bs, 1H), 6.83 (s 2H), 6.75 (d, 1H), 6.70 (d, J=1.5 Hz, 1H), 6.45 (d, J=1.5 Hz, 1H), 6.2 (d, 1H), 4.44 (d J=5.9 Hz, 2H) 4.05 (m, 1H), 3.80 (s, 3H), 3.6–3.8 (m, 2H), 2.63 (s, 6H), 2.13 (s, 3H), 1.29 (s, 9H).

Part B. 3-[7-[(imidazol-2-ylamino)methyl]-1-methylquinoline-4-one-3-ylcarbonylamino]-(2S)-[N-(2,4,6-trimethylphenyl)sulfonylamino]propionic acid The compound of Ex. 4, Part A (210 mg, 0.243 mmol) was heated at reflux overnight in trifluoroacetic acid (5 mL). The solvent was evaporated in vacuo, 5 mL of water was added, and the pH was adjusted to 7. The crude product was purified using reverse phase HPLC, eluting with 20–100% acetonitrile/water. Fractions containing the product were pooled, concentrated in vacuo to remove acetonitrile, and lyophilized to give a white powder (70 mg, 42%); $^1$H NMR (300 MHz, DMSO-d$_6$) δ12.37(s, 2H), 9.95 (t, 1H), 8.70 (t, 1H), 8.63 (s, 1H), 8.33 (d, 1H, J=8.4 Hz), 8.10 (d, 1H, J=8.8 Hz), 7.82 (s, 1H), 7.55 (d, 1H, J=8 Hz), 7.01 (s, 2H), 6.61 (s, 2H), 4.69 (d, 2H, J=6.2 Hz), 3.99 (s, 3H), 3.9 (m, 1H), 3.7 (m, 2H), 2.47 (s, 6H), 1.76 (s, 3H); MS (ESI) m/z 567 (M+H)$^+$.

The examples listed in Table 1 were prepared in an analogous fashion to that described in Example 4.

TABLE 1

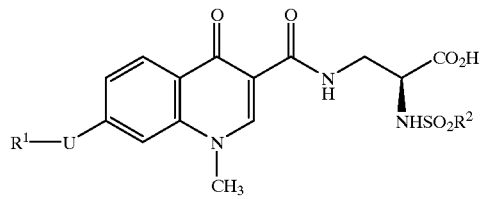

| Ex. | R¹ | U | R² | MS (M + H)⁺ |
|---|---|---|---|---|
| 5 | imidazol-2-yl | NHCH$_2$ | Ph(2,6-Cl$_2$) | 593 |
| 6 | imidazol-2-yl | NHCH$_2$ | Ph(2,6-Cl$_2$-4-Ph) | 669 |
| 7 | imidazol-2-yl | NHCH$_2$ | Ph(2,4,6-Me$_3$) | 567 |
| 8 | amino(imino)methyl | NHCH$_2$ | Ph(2,6-Cl$_2$) | 569 |
| 9 | amino(imino)methyl | NHCH$_2$ | Ph(2,4,6-Me$_3$) | 543 |
| 10 | imidazolin-2-yl | NHCH$_2$ | Ph(2,6-Cl$_2$) | 595 |
| 11 | tetrahydropyrimidin-2-yl | NHCH$_2$ | Ph(2,4,6-Me$_3$) | 583 |
| 12 | imidazolin-2-yl | NHCH$_2$ | Ph(2,4,6-Me$_3$) | 569 |
| 13 | imidazol-2-yl | NHCH$_2$ | Ph(2,6-Me$_2$-4-Ph) | 629 |
| 14 | imidazol-2-yl | NHCH$_2$ | isoxazol-4-yl(3,5-Me$_2$) | 544 |

Utility

The compounds of Formula I–IV of the present invention possess activity as antagonists of integrins such as, for example, the $\alpha_v\beta_3$ or vitronectin receptor, $\alpha_v\beta_5$ or $\alpha_5\beta_1$, and as such have utility in the treatment and diagnosis of cell adhesion, angiogenic disorders, inflammation, bone degradation, cancer metastases, diabetic retinopathy, thrombosis, restenosis, macular degeneration, and other conditions mediated by cell adhesion and/or cell migration and/or angiogenesis. The integrin antagonist activity of the compounds of the present invention is demonstrated using assays which measure the binding of a specific integrin to a native ligand, for example, using the ELISA assay described below for the binding of vitronectin to the $\alpha_v\beta_3$ receptor.

The compounds of the present invention possess selectivity for the $\alpha_v\beta_3$ receptor relative to the GPIIb/IIIa receptor as demonstrated by their reduced activity in standard assays of platelet aggregation, such as the platelet aggregation assay described below.

One of the major roles of integrins in vivo is to mediate cellular interactions with adjacent cells. Cell based adhesion assays can be used to mimic these interactions in vitro. A cell based assay is more representative of the in vivo situation than an ELISA since the receptor is maintained in membranes in the native state. The compounds of the present invention have activity in cell-based assays of adhesion, for example as demonstrated in using the cell adhesion assays described below.

The compounds of Formula I–IV of the present invention may be useful for the treatment or prevention of other diseases which involve cell adhesion processes, including, but not limited to, osteoporosis, rheumatoid arthritis, autoimmune disorders, bone degradation, rheumatoid arthritis, asthma, allergies, adult respiratory distress syndrome, graft versus host disease, organ transplantation, septic shock, psoriasis, eczema, contact dermatitis, osteoarthritis, atherosclerosis, metastasis, wound healing, inflammatory bowel disease and other angiogenic disorders.

The compounds of Formula I–IV have the ability to suppress/inhibit angiogenesis in vivo, for example, as demonstrated using animal models of ocular neovascularization.

The compounds provided by this invention are also useful as standards and reagents in determining the ability of a potential pharmaceutical to inhibit integrin-ligand binding. These may be provided in a commercial kit comprising a compound of this invention.

As used herein "µg" denotes microgram, "mg" denotes milligram, "g" denotes gram, "µL" denotes microliter, "mL" denotes milliliter, "L" denotes liter, "nM" denotes nanomolar, "µM" denotes micromolar, "mM" denotes millimolar, "M" denotes molar and "nm" denotes nanometer. "Sigma" stands for the Sigma-Aldrich Corp. of St. Louis, Mo.

The utility of the compounds of the present invention may be assessed by testing in one or more of the following assays as described in detail below: Purified $\alpha_v\beta_3$ (human placenta)—Vitronectin ELISA, $\alpha_v\beta_3$-Vitronectin Binding Assay, Human Aortic Smooth Muscle Cell Migration Assay, In Vivo Angiogenesis Model, Pig Restenosis Model, Mouse Retinopathy Model. A compound of the present invention is considered to be active if it has an IC$_{50}$ or K$_i$ value of less than about 10 µM for the inhibition of $\alpha_v\beta_3$-Vitronectin Binding Assay, with compounds preferably having K$_i$ values of less than about 0.1 µM. Tested compounds of the present invention are active in the $\alpha_v\beta_3$-Vitronectin Binding Assay.

Purified $\alpha_v\beta_3$ (human placenta)—Vitronectin ELISA

The $\alpha_v\beta_3$ receptor was isolated from human placental extracts prepared using octylglucoside. The extracts were passed over an affinity column composed of anti-$\alpha_v\beta_3$ monoclonal antibody (LM609) bound to Affigel. The column was subsequently washed extensively at pH 7 and pH 4.5 followed by elution at pH 3. The resulting sample was concentrated by wheat germ agglutinin chromatography to provide two bands by SDS gel electrophoresis which were confirmed as $\alpha_v\beta_3$ by western blotting.

Affinity purified protein was diluted at different levels and plated to 96 well plates. ELISA was performed using fixed concentration of biotinylated vitronectin (approximately 80 nM/well). This receptor preparation contains the $\alpha_v\beta_3$ with no detectable levels of $\alpha_v\beta_5$ according to the gel and according to effects of blocking antibodies for the $\alpha_v\beta_3$ or $\alpha_v\beta_5$ integrins in the ELISA.

A submaximal concentration of biotinylated vitronectin was selected based on a concentration response curve with fixed receptor concentration and variable concentrations of biotinylated vitronectin.

$\alpha_v\beta_3$-Vitronectin Binding Assay

The purified receptor is diluted with coating buffer (20 mM Tris HCl, 150 mM NaCl, 2.0 mM CaCl$_2$, 1.0 mM MgCl$_2$.6H$_2$O, 1.0 mM MnCl$_2$.4H$_2$O) and coated (100 µL/well) on Costar (3590) high capacity binding plates overnight at 4° C. The coating solution is discarded and the plates washed once with blocking/binding buffer (B/B buffer, 50 mM Tris HCl, 100 mM NaCl, 2.0 mM CaCl$_2$,1.0 mM MgCl$_2$.6H$_2$O,1.0 mM MnCl$_2$.4H$_2$O). Receptor is then blocked (200 µL/well) with 3.5% BSA in B/B buffer for 2 hours at room temperature. After washing once with 1.0% BSA in B/B buffer, biotinylated vitronectin (100 µL) and either inhibitor (11 µL) or B/B buffer w/1.0% BSA (11 µL)is added to each well. The plates are incubated 2 hours at room temperature. The plates are washed twice with B/B buffer and incubated 1 hour at room temperature with anti-biotin alkaline phosphatase (100 µL/well) in B/B buffer containing 1.0% BSA. The plates are washed twice with B/B buffer and alkaline phosphatase substrate (100 µL) is added. Color is developed at room temperature. Color development is stopped by addition of 2N NaOH (25 µL/well) and absorbance is read at 405 nm. The IC$_{50}$ is the concentration of test substance needed to block 50% of the vitronectin binding to the receptor.

Integrin Cell-Based Adhesion Assays

In the adhesion assays, a 96 well plate was coated with the ligand (i.e., fibrinogen) and incubated overnight at 4° C. The following day, the cells were harvested, washed and loaded with a fluorescent dye. Test compounds and cells were added together and then were immediately added to the coated plate. After incubation, loose cells are removed from the plate, and the plate (with adherent cells) is counted on a fluorometer. The ability of test compounds to inhibit cell adhesion by 50% is given by the $IC_{50}$ value and represents a measure of potency of inhibition of integrin mediated binding. Compounds were tested for their ability to block cell adhesion using assays specific for $\alpha_v\beta_3$, $\alpha_v\beta_5$ and $\alpha_5\beta_1$ integrin interactions.

Platelet Aggregation Assay

Venous blood was obtained from anesthetized mongrel dogs or from healthy human donors who were drug- and aspirin-free for at least two weeks prior to blood collection. Blood was collected into citrated Vacutainer tubes. The blood was centrifuged for 15 minutes at 150×g (850 RPM in a Sorvall RT6000 Tabletop Centrifuge with H-1000 B rotor) at room temperature, and platelet-rich plasma (PRP) was removed. The remaining blood was centrifuged for 15 minutes at 1500×g (26,780 RPM) at room temperature, and platelet-poor plasma (PPP) was removed. Samples were assayed on a PAP-4 Platelet Aggregation Profiler, using PPP as the blank (100% transmittance). 200 $\mu$L of PRP ($5 \times 10^8$ platelets/mL) were added to each micro test tube, and transmittance was set to 0%. 20 $\mu$L of ADP (10 $\mu$M) was added to each tube, and the aggregation profiles were plotted (% transmittance versus time). Test agent (20 $\mu$L) was added at different concentrations prior to the addition of the platelet agonist. Results are expressed as % inhibition of agonist-induced platelet aggregation.

Human Aortic Smooth Muscle Cell Migration Assay

A method for assessing $\alpha_v\beta_3$-mediated smooth muscle cell migration and agents which inhibit $\alpha_v\beta_3$-mediated smooth muscle cell migration is described in Liaw et al., *J. Clin. Invest.* (1995) 95: 713–724).

In Vivo Angiogenesis Model

A quantitative method for assessing angiogenesis and antiangiogenic agents is described in Passaniti et al., *Laboratory Investigation* (1992) 67: 519–528.

Pig Restenosis Model

A method for assessing restenosis and agents which inhibit restenosis is described in Schwartz et al., *J. Am. College of Cardiology* (1992) 19: 267–274.

Mouse Retinopathy Model

A method for assessing retinopathy and agents which inhibit retinopathy is described in Smith et al., *Invest. Ophthal. & Visual Science* (1994) 35: 101–111.

Dosage and Formulation

The compounds of this invention can be administered by any means that produces contact of the active agent with the agent's site of action, the $\alpha_v\beta_3$ integrin, in the body of a mammal. They can be administered by any conventional means available for use in conjunction with pharmaceuticals, either as individual therapeutic agents or in a combination of therapeutic agents, such as a antiplatelet agent such as aspirin, piroxicam, or ticlopidine which are agonist-specific, or an anti-coagulant such as warfarin or heparin, or a thrombin inhibitor such as a boropeptide, hirudin or argatroban, or a thrombolytic agent such as tissue plasminogen activator, anistreplase, urokinase or streptokinase, or combinations thereof. The compounds of the invention, or compounds of the invention in combination with other therapeutic agents, can be administered alone, but generally administered with a pharmaceutical carrier selected on the basis of the chosen route of administration and standard pharmaceutical practice.

The dosage of the novel compounds of this invention administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to 10 milligrams per kilogram of body weight.

Dosage forms (compositions suitable for administration) contain from about 0.1 milligram to about 100 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 10 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil is prepared and injected by means of a positive displacement pump into gelatin to form soft gelatin capsules containing 10 milligrams of the active ingredient. The capsules are washed and dried.

Tablets

A large number of tablets are prepared by conventional procedures so that the dosage unit was 10 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

The combination products of this invention, such as the novel $\alpha_v\beta_3$ antagonist compounds of this invention in combination with an anti-coagulant agent such as warfarin or heparin, or an anti-platelet agent such as aspirin, piroxicam or ticlopidine, or a thrombin inhibitor such as a boropeptide, hirudin or argatroban, or a thrombolytic agent such as tissue plasminogen activator, anistreplase, urokinase or streptokinase, or combinations thereof, can be in any dosage form, such as those described above, and can also be administered in various ways, as described above.

In a preferred embodiment, the combination products of the invention are formulated together, in a single dosage form (that is, combined together in one capsule, tablet, powder, or liquid, etc.). When the combination products are not formulated together in a single dosage form, the $\alpha_v\beta_3$ antagonist compounds of this invention and the anti-coagulant agent, anti-platelet agent, thrombin inhibitor, and/ or thrombolytic agent may be administered at the same time (that is, together), or in any order, for example the compounds of this invention are administered first, followed by administration of the anti-coagulant agent, anti-platelet agent, thrombin inhibitor, and/or thrombolytic agent. When not administered at the same time, preferably the administration of the compound of this invention and any anti-coagulant agent, anti-platelet agent, thrombin inhibitor, and/ or thrombolytic agent occurs less than about one hour apart, more preferably less than about 30 minutes apart, even more preferably less than about 15 minutes apart, and most preferably less than about 5 minutes apart. Preferably, administration of the combination products of the invention is oral. The terms oral agent, oral inhibitor, oral compound, or the like, as used herein, denote compounds which may be orally administered. Although it is preferable that the $\alpha_v\beta_3$ antagonist compounds of this invention and the anti-coagulant agent, anti-platelet agent, thrombin inhibitor, and/ or thrombolytic agent are both administered in the same fashion (that is, for example, both orally), if desired, they may each be administered in different fashions (that is, for example, one component of the combination product may be administered orally, and another component may be administered intravenously). The dosage of the combination products of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

As discussed above, where two or more of the foregoing therapeutic agents are combined or co-administered with the compounds of this invention, generally the amount of each component in a typical daily dosage and typical dosage form may be reduced relative to the usual dosage of the agent when administered alone, in view of the additive or synergistic effect which would be obtained as a result of addition of further agents in accordance with the present invention.

Particularly when provided as a single dosage form, the potential exists for a chemical interaction between the combined active ingredients (for example, a novel compound of this invention and an anti-coagulant such as warfarin or heparin, or a novel compound of this invention and an anti-platelet agent such as aspirin, piroxicam or ticlopidine, or a novel compound of this invention and a thrombin inhibitor such as a boropeptide, hirudin or argatroban, or a novel compound of this invention and a thrombolytic agent such as tissue plasminogen activator, anistreplase, urokinase or streptokinase, or combinations thereof). For this reason, the preferred dosage forms of the combination products of this invention are formulated such that although the active ingredients are combined in a single dosage form, the physical contact between the active ingredients is minimized (that is, reduced).

In order to minimize contact, one embodiment of this invention where the product is orally administered provides for a combination product wherein one active ingredient is enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time by the same manner, will be readily apparent to those skilled in the art, once armed with the present disclosure.

Pharmaceutical kits useful in, for example, the inhibition of thrombus formation, the prevention of blood clots, and/or the treatment of thromboembolic disorders, which comprise a therapeutically effective amount of a compound according to the method of the present invention along with a therapeutically effective amount of an anti-coagulant agent such as warfarin or heparin, or an anti-platelet agent such as aspirin, piroxicam or ticlopidine, or a thrombin inhibitor such as a boropeptide, hirudin or argatroban, or a thrombolytic agent such as tissue plasminogen activator, anistreplase, urokinase or streptokinase, or combinations thereof, in one or more sterile containers, are also within the ambit of the present invention. Sterilization of the container may be carried out using conventional sterilization methodology well known to those skilled in the art. The sterile containers of materials may comprise separate containers, or one or more multi-part containers, as exemplified by the UNIVIAL™ two-part container (available from Abbott Labs, Chicago, Ill.), as desired. The compounds according to the method of the invention and the anti-coagulant agent, anti-platelet agent, thrombin inhibitor, thrombolytic agent, and/or combinations thereof, may be separate, or combined into a single dosage form as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

What is claimed is:

1. A compound of Formula I:

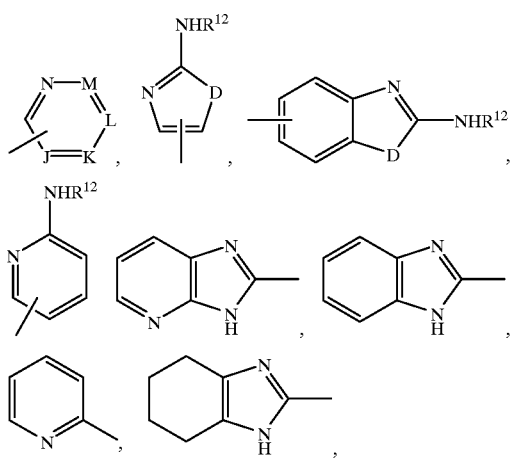

(I)

including stereoisomeric forms thereof, or mixtures of stereoisomeric forms thereof, or pharmaceutically acceptable salt forms thereof wherein:

$R^1$ is selected from:

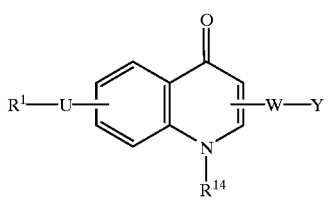

-continued

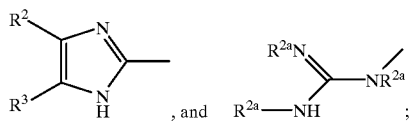

D is —N($R^{12}$)— or —S—;

J is —C($R^2$)— or —N—;

K, L and M are independently —C($R^2$)— or —C($R^3$)—;

$R^2$ and $R^3$ are independently selected from:
H, $C_1$–$C_4$ alkoxy, $NR^{11}R^{12}$, halogen, $NO_2$, CN, $CF_3$, $C_1$–$C_6$ alkyl, $C_3$–$C_6$ alkenyl, $C_3$–$C_7$ cycloalkyl, $C_3$–$C_7$ cycloalkyl($C_1$–$C_4$ alkyl), aryl($C_1$–$C_6$ alkyl)-, ($C_1$–$C_6$ alkyl)carbonyl, ($C_1$–$C_6$ alkoxy)carbonyl, arylcarbonyl, and aryl substituted with 0–4 $R^7$, alternatively, when $R^2$ and $R^3$ are substituents on adjacent atoms, they can be taken together with the carbon atoms to which they are attached to form a 5–7 membered carbocyclic or 5–7 membered heterocyclic aromatic or nonaromatic ring system, said carbocyclic or heterocyclic ring being substituted with 0–2 groups selected from $C_1$–$C_4$ alkyl, $C_1$–$C_4$ alkoxy, halo, cyano, amino, $CF_3$ and $NO_2$;

$R^{2a}$ is selected from:
H, $C_1$–$C_{10}$ alkyl, $C_2$–$C_6$ alkenyl, $C_3$–$C_{11}$ cycloalkyl, $C_3$–$C_7$ cycloalkyl($C_1$–$C_4$ alkyl), aryl, aryl($C_1$–$C_4$ alkyl)-, ($C_2$–$C_7$ alkyl)carbonyl, arylcarbonyl, ($C_2$–$C_{10}$ alkoxy)carbonyl, $C_3$–$C_7$ cycloalkoxycarbonyl, $C_7$–$C_{11}$ bicycloalkoxycarbonyl, aryloxycarbonyl, aryl ($C_1$–$C_{10}$ alkoxy)carbonyl, $C_1$–$C_6$ alkylcarbonyloxy ($C_1$–$C_4$ alkoxy)carbonyl, arylcarbonyloxy($C_1$–$C_4$ alkoxy)carbonyl, and $C_3$–$C_7$ cycloalkylcarbonyloxy ($C_1$–$C_4$ alkoxy)carbonyl;

$R^4$ is selected from:
H, $C_1$–$C_{10}$ alkyl, ($C_1$–$C_{10}$ alkyl)carbonyl, aryl, aryl ($C_1$–$C_4$ alkyl)-, $C_3$–$C_{11}$ cycloalkyl, and $C_3$–$C_{11}$ cycloalkyl($C_1$–$C_4$ alkyl)-;

U is selected from:
—$(CH_2)_n$—, —$(CH_2)_nO(CH_2)_m$—, —$(CH_2)_nN(R^{12})$($CH_2)_m$—, —N(H)($CH_2)_n$—, —$(CH_2)_nC(=O)$($CH_2)_m$—, —$(CH_2)_nS(O)_p(CH_2)_m$—, —$(CH_2)_nNHNH(CH_2)_m$—, —N($R^{10}$)C(=O)—, —NHC (=O)($CH_2)_n$—, —C(=O)N($R^{10}$)—, and —N($R^{10}$) S(O)$_p$—;

W is —C(=O)—N($R^{10}$)—($C_2$–$C_3$ alkylene)-, in which the alkylene group is substituted by $R^8$ and by $R^9$:

$R^8$ and $R^9$ are independently selected from:
H, $CO_2R^{18b}$, C(=O)$R^{18b}$, $CONR^{17}R^{18b}$,
hydroxy, $C_5$–$C_{10}$ alkoxy, nitro, —N($R^{10}$)$R^{11}$, —N($R^{16}$) $R^{17}$, aryl($C_0$–$C_6$ alkyl)carbonyl, aryl($C_3$–$C_6$ alkyl), heteroaryl($C_1$–$C_6$ alkyl), $CONR^{18a}R^{20}$, $SO_2R^{18a}$, $SO_2NR^{18a}R^{20}$,
$C_1$–$C_{10}$ alkyl substituted with 0–1 $R^6$,
$C_5$–$C_{10}$ alkenyl substituted with 0–1 $R^6$,
$C_5$–$C_{10}$ alkynyl substituted with 0–1 $R^6$,
$C_3$–$C_8$ cycloalkyl substituted with 0–1 $R^6$,
$C_5$–$C_6$ cycloalkenyl substituted with 0–1 $R^6$,
$C_1$–$C_{10}$ alkylcarbonyl,
$C_3$–$C_{10}$ cycloalkyl($C_1$–$C_4$ alkyl)-,
phenyl substituted with 1–3 $R^6$,
naphthyl substituted with 0–3 $R^6$,
a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$, and $C_5$–$C_{10}$ alkyl substituted with 0–3 $R^7$, providing that any of the above alkyl, cycloalkyl, aryl or heteroaryl groups may be unsubstituted or substituted independently with 1–2 $R^7$;

$R^6$ is selected from:

H, $C_1$–$C_{10}$ alkyl, hydroxy, $C_1$–$C_{10}$ alkoxy, nitro, $C_1$–$C_{10}$ alkylcarbonyl, —N($R^{11}$)$R^{12}$, cyano, halo, $CF_3$, CHO, $CO_2R^{18b}$, C(=O)$R^{18b}$, $CONR^{17}R^{18b}$, OC(=O)$R^{10}$, $OR^{10}$, OC(=O)$NR^{10}R^{11}$, $NR^{10}$C(=O)$R^{10}$, $NR^{10}$C(=O)$OR^{21}$, $NR^{10}$C(=O)$NR^{10}R^{11}$, $NR^{10}SO_2NR^{10}R^{11}$, $NR^{10}SO_2R^{21}$, S(O)$_pR^{11}$, $SO_2NR^{10}R^{11}$, aryl substituted with 0–3 groups selected from halogen, $C_1$–$C_6$ alkoxy, $C_1$–$C_6$ alkyl, $CF_3$, S(O)$_m$Me, and —$NMe_2$, aryl($C_1$–$C_4$ alkyl)-, said aryl being substituted with 0–3 groups selected from halogen, $C_1$–$C_6$ alkoxy, $C_1$–$C_6$ alkyl, $CF_3$, S(O)$_p$Me, and —$NMe_2$, and a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$;

$R^7$ is selected from:

H, hydroxy, $C_1$–$C_4$ alkyl, $C_1$–$C_4$ alkoxy, aryl, aryl($C_1$–$C_4$ alkyl)-, ($C_1$–$C_4$ alkyl)carbonyl, $CO_2R^{18a}$, $SO_2R^{11}$, $SO_2NR^{10}R^{11}$, $OR^{10}$, and N($R^{11}$)$R^{12}$;

$R^{10}$ is selected from:

H, $C_3$–$C_6$ alkenyl, $C_3$–$C_{11}$ cycloalkyl, aryl, ($C_3$–$C_{11}$ cycloalkyl)methyl, aryl($C_1$–$C_4$ alkyl), and $C_1$–$C_{10}$ alkyl substituted with 0–2 $R^6$;

$R^{11}$ is selected from:

H, hydroxy, $C_1$–$C_8$ alkyl, $C_3$–$C_6$ alkenyl, $C_3$–$C_{11}$ cycloalkyl, ($C_3$–$C_{11}$ cycloalkyl)methyl, $C_1$–$C_6$ alkoxy, benzyloxy, aryl, heteroaryl, heteroaryl($C_1$–$C_4$ alkyl)-, aryl($C_1$–$C_4$ alkyl), adamantylmethyl, and $C_1$–$C_{10}$ alkyl substituted with 0–2 $R^4$, alternatively, when $R^{10}$ and $R^{11}$ are both substituents on the same nitrogen atom (as in —$NR^{10}R^{11}$) they may be taken together with the nitrogen atom to which they are attached to form a heterocycle selected from:

3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl, and 1-piperazinyl;

said heterocycle being substituted with 0–3 groups selected from: $C_1$–$C_6$ alkyl, aryl, heteroaryl, aryl($C_1$–$C_4$ alkyl)-, ($C_1$–$C_6$ alkyl)carbonyl, ($C_3$–$C_7$ cycloalkyl)carbonyl, ($C_1$–$C_6$ alkoxy)carbonyl, aryl($C_1$–$C_4$ alkoxy)carbonyl, $C_1$–$C_6$ alkylsulfonyl, and arylsulfonyl;

$R^{12}$ is selected from:

H, $C_1$–$C_6$ alkyl, triphenylmethyl, methoxymethyl, methoxyphenyldiphenylmethyl, trimethylsilylethoxymethyl, ($C_1$–$C_6$ alkyl)carbonyl, ($C_1$–$C_6$ alkoxy)carbonyl, ($C_1$–$C_6$ alkyl)aminocarbonyl, $C_3$–$C_6$ alkenyl, $C_3$–$C_7$ cycloalkyl, $C_3$–$C_7$ cycloalkyl($C_1$–$C_4$ alkyl)-, aryl, heteroaryl ($C_1$–$C_6$ alkyl)carbonyl, heteroarylcarbonyl, aryl($C_1$–$C_6$ alkyl)-, ($C_1$–$C_6$ alkyl)carbonyl, arylcarbonyl, $C_1$–$C_6$ alkylsulfonyl, arylsulfonyl, aryl($C_1$–$C_6$ alkyl)sulfonyl, heteroarylsulfonyl, heteroaryl($C_1$–$C_6$ alkyl)sulfonyl, aryloxycarbonyl, and aryl($C_1$–$C_6$ alkoxy)carbonyl, wherein said aryl groups are substituted with 0–2 substituents selected from the group consisting of $C_1$–$C_4$ alkyl, $C_1$–$C_4$ alkoxy, halo, $CF_3$, and nitro;

$R^{14}$ is selected from H, $C_1$–$C_4$ alkyl, and phenyl($C_1$–$C_4$ alkyl);

$R^{16}$ is selected from:

—C(=O)$OR^{18a}$, —C(=O)$R^{18b}$, —C(=O)N($R^{18b}$)$_2$, —C(=O)$NHSO_2R^{18a}$, —C(=O)NHC(=O)$R^{18b}$, —C(=O)NHC(=O)$OR^{18a}$, —C(=O)$NHSO_2NHR^{18b}$, —$SO_2R^{18a}$, —$SO_2$N($R^{18b}$)$_2$, and —$SO_2$NHC(=O)$OR^{18b}$;

$R^{17}$ is selected from:

H, $C_1$–$C_6$ alkyl, $C_3$–$C_7$ cycloalkyl, $C_3$–$C_7$ cycloalkyl($C_1$–$C_4$ alkyl)-, aryl, aryl($C_1$–$C_6$ alkyl)-, and heteroaryl($C_1$–$C_6$ alkyl);

$R^{18a}$ is selected from:

$C_7$–$C_8$ alkyl, $C_3$–$C_{11}$ cycloalkyl, aryl($C_1$–$C_6$ alkyl)-, said aryl substituted with 0–4 $R^{19}$, heteroaryl($C_1$–$C_6$ alkyl)-, said heteroaryl substituted with 0–4 $R^{19}$, ($C_1$–$C_6$ alkyl)heteroaryl, said heteroaryl substituted with 0–4 $R^{19}$, heteroaryl substituted with 0–4 $R^{19}$, phenyl substituted with 3–4 $R^{19}$, and naphthyl substituted with 0–4 $R^{19}$;

$R^{18b}$ is H or $R^{18a}$;

$R^{19}$ is selected from:

H, halogen, $CF_3$, $CO_2H$, CN, $NO_2$, —$NR^{11}R^{12}$, $OCF_3$, $C_1$–$C_8$ alkyl, $C_2$–$C_6$ alkenyl, $C_2$–$C_6$ alkynyl, $C_3$–$C_{11}$ cycloalkyl, $C_3$–$C_7$ cycloalkyl($C_1$–$C_4$ alkyl)-, aryl ($C_1$–$C_6$ alkyl)-, $C_1$–$C_6$ alkoxy, $C_1$–$C_4$ alkoxycarbonyl, aryl, aryl-O—, aryl-$SO_2$—, heteroaryl, and heteroaryl-$SO_2$—, wherein said aryl and heteroaryl groups are substituted with 0–4 groups selected from hydrogen, halogen, $CF_3$, $C_1$–$C_3$ alkyl, and $C_1$–$C_3$ alkoxy;

$R^{20}$ is selected from:

hydroxy, $C_1$–$C_{10}$ alkyloxy, $C_3$–$C_{11}$ cycloalkyloxy, aryloxy, aryl($C_1$–$C_4$ alkyl)oxy, $C_2$–$C_{10}$ alkylcarbonyloxy($C_1$–$C_2$ alkyl)oxy-, $C_2$–$C_{10}$ alkoxycarbonyloxy($C_1$–$C_2$ alkyl)oxy-, $C_2$–$C_{10}$ alkoxycarbonyl($C_1$–$C_2$ alkyl)oxy-, $C_3$–$C_{10}$ cycloalkylcarbonyloxy($C_1$–$C_2$ alkyl)oxy-, $C_3$–$C_{10}$ cycloalkoxycarbonyloxy($C_1$–$C_2$ alkyl)oxy-, $C_3$–$C_{10}$ cycloalkoxycarbonyl($C_1$–$C_2$ alkyl)oxy-, aryloxycarbonyl($C_1$–$C_2$ alkyl)oxy-, aryloxycarbonyloxy($C_1$–$C_2$ alkyl)oxy-, arylcarbonyloxy($C_1$–$C_2$ alkyl)oxy-, $C_1$–$C_5$ alkoxy($C_1$–$C_5$ alkyl)carbonyloxy($C_1$–$C_2$ alkyl)oxy-, (5-($C_1$–$C_5$ alkyl)-1,3-dioxa-cyclopenten-2-one-yl) methyloxy, (5-aryl-1,3-dioxa-cyclopenten-2-one-yl)methyloxy, and ($R^{10}$)($R^{11}$)N—($C_1$–$C_{10}$ alkoxy)-;

$R^{21}$ is selected from:

$C_1$–$C_8$ alkyl, $C_2$–$C_6$ alkenyl, $C_3$–$C_{11}$ cycloalkyl, ($C_3$–$C_{11}$ cycloalkyl)methyl, aryl, aryl($C_1$–$C_4$ alkyl)-, and $C_1$–$C_{10}$ alkyl substituted with 0–2 $R^7$;

Y is selected from:

—$COR^{20}$, —$SO_3H$, —$PO_3H$;

m is 0–2;

n is 0–4;

p is 0–2;
with the following provisos:
(1) n and m are chosen such that the number of atoms connecting $R^1$ and Y is in the range of 8–14;
(2) in W, the alkylene group is substituted with at least one $R^8$ or $R^9$ which is not H;
(3) in the definition of W, when there is only one non-hydrogen substituent on the alkylene group, such substituent may not be an unsubstituted pyridyl radical.

2. A compound of claim 1 of Formula III:

(III)

including stereoisomeric forms thereof, or mixtures of stereoisomeric forms thereof, or pharmaceutically acceptable salt forms thereof wherein:
$R^1$ is selected from:

U is selected from —(CH$_2$)$_n$—, —(CH$_2$)$_n$O(CH$_2$)$_m$—, —NH(CH$_2$)$_n$—, —(CH$_2$)$_n$C(=O)(CH$_2$)$_m$—, —N(R$^{10}$)C(=O)—, and —NHC(=O)(CH$_2$)$_n$—;

$R^2$ and $R^3$ are independently selected from:
H, $C_1$–$C_4$ alkoxy, $NR^{11}R^{12}$, halogen, $NO_2$, CN, $CF_3$, $C_1$–$C_6$ alkyl, $C_3$–$C_6$ alkenyl, $C_3$–$C_7$ cycloalkyl, $C_3$–$C_7$ cycloalkyl($C_1$–$C_4$ alkyl), aryl($C_1$–$C_6$ alkyl)-, ($C_1$–$C_6$ alkyl)carbonyl, ($C_1$–$C_6$ alkoxy)carbonyl, arylcarbonyl, and aryl substituted with 0–4 $R^7$,
alternatively, when $R^2$ and $R^3$ are substituents on adjacent atoms, they can be taken together with the carbon atoms to which they are attached to form a 5–7 membered carbocyclic or 5–7 membered heterocyclic aromatic or nonaromatic ring system, said carbocyclic or heterocyclic ring being substituted with 0–2 groups selected from $C_1$–$C_4$ alkyl, $C_1$–$C_4$ alkoxy, halo, cyano, amino, $CF_3$ and $NO_2$;

$R^4$ is selected from:
H, $C_1$–$C_{10}$ alkyl, ($C_1$–$C_{10}$ alkyl)carbonyl, aryl, aryl($C_1$–$C_4$ alkyl)-, $C_3$–$C_{11}$ cycloalkyl, and $C_3$–$C_{11}$ cycloalkyl($C_1$–$C_4$ alkyl)-;

$R^8$ is selected from:
H, $CO_2R^{18b}$, $C(=O)R^{18b}$, $CONR^{17}R^{18b}$,
$C_1$–$C_{10}$ alkyl substituted with 0–1 $R^6$,
$C_5$–$C_{10}$ alkenyl substituted with 0–1 $R^6$,
$C_5$–$C_{10}$ alkynyl substituted with 0–1 $R^6$,
$C_3$–$C_8$ cycloalkyl substituted with 0–1 $R^6$,
$C_5$–$C_6$ cycloalkenyl substituted with 0–1 $R^6$,
$C_1$–$C_{10}$ alkylcarbonyl,
$C_3$–$C_{10}$ cycloalkyl($C_1$–$C_4$ alkyl)-,
phenyl substituted with 1–3 $R^6$,
naphthyl substituted with 0–3 $R^6$,
a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$;

$R^9$ is selected from:
H, hydroxy, $C_5$–$C_{10}$ alkoxy, nitro, $N(R^{10})R^{11}$, $N(R^{16})R^{17}$, aryl($C_0$–$C_6$ alkyl)carbonyl, aryl($C_3$–$C_6$ alkyl), heteroaryl($C_1$–$C_6$ alkyl), $CONR^{18a}R^{20}$, $SO_2R^{18a}$, $SO_2NR^{18a}R^{20}$,
$C_1$–$C_{10}$ alkyl substituted with 0–1 $R^6$,
$C_5$–$C_{10}$ alkenyl substituted with 0–1 $R^6$,
$C_5$–$C_{10}$ alkynyl substituted with 0–1 $R^6$,
$C_3$–$C_8$ cycloalkyl substituted with 0–1 $R^6$,
$C_5$–$C_6$ cycloalkenyl substituted with 0–1 $R^6$,
$C_1$–$C_{10}$ alkylcarbonyl,
$C_3$–$C_{10}$ cycloalkyl($C_1$–$C_4$ alkyl),
phenyl substituted with 1–3 $R^6$,
naphthyl substituted with 0–3 $R^6$, and
a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$, p2 providing that any of the above alkyl, cycloalkyl, aryl or heteroaryl groups may be unsubstituted or substituted independently with 1–2 $R^7$;

$R^6$ is selected from:
H, $C_1$–$C_{10}$ alkyl, hydroxy, $C_1$–$C_{10}$ alkoxy, nitro, $C_1$–$C_{10}$ alkylcarbonyl, —N(R$^{11}$)R$^{12}$, cyano, halo, $CF_3$, CHO, $CO_2R^{18b}$, $C(=O)R^{18b}$, $CONR^{17}R^{18b}$, $OC(=O)R^{10}$, $OR^{10}$, $OC(=O)NR^{10}R^{11}$, $NR^{10}C(=O)R^{10}$, $NR^{10}C(=O)OR^{21}$, $NR^{10}C(=O)NR^{10}R^{11}$, $NR^{10}SO_2NR^{10}R^{11}$, $NR^{10}SO_2R^{21}$, $S(O)_pR^{11}$, $SO_2NR^{10}R^{11}$,
aryl substituted with 0–3 groups selected from halogen, $C_1$–$C_6$ alkoxy, $C_1$–$C_6$ alkyl, $CF_3$, $S(O)_m$Me, and —NMe$_2$,
aryl($C_1$–$C_4$ alkyl)-, said aryl being substituted with 0–3 groups selected from halogen, $C_1$–$C_6$ alkoxy, $C_1$–$C_6$ alkyl, $CF_3$, $S(O)_p$Me, and —NMe$_2$, and
a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$;

$R^7$ is selected from:
  H, hydroxy, $C_1$–$C_4$ alkyl, $C_1$–$C_4$ alkoxy, aryl, aryl($C_1$–$C_4$ alkyl)-, ($C_1$–$C_4$ alkyl)carbonyl, $CO_2R^{18a}$, $SO_2R^{11}$, $SO_2NR^{10}R^{11}$, $OR^{10}$, and $N(R^{11})R^{12}$;

$R^{10}$ is selected from:
  H, $C_3$–$C_6$ alkenyl, $C_3$–$C_{11}$ cycloalkyl, aryl, ($C_3$–$C_{11}$ cycloalkyl)methyl, aryl($C_1$–$C_4$ alkyl), and $C_1$–$C_{10}$ alkyl substituted with 0–2 $R^6$;

$R^{11}$ is selected from:
  H, hydroxy, $C_1$–$C_8$ alkyl, $C_3$–$C_6$ alkenyl, $C_3$–$C_{11}$ cycloalkyl, ($C_3$–$C_{11}$ cycloalkyl)methyl, $C_1$–$C_6$ alkoxy, benzyloxy, aryl, heteroaryl, heteroaryl($C_1$–$C_4$ alkyl)-, aryl($C_1$–$C_4$ alkyl), adamantylmethyl, and $C_1$–$C_{10}$ alkyl substituted with 0–2 $R^4$,
  alternatively, when $R^{10}$ and $R^{11}$ are both substituents on the same nitrogen atom (as in —$NR^{10}R^{11}$) they may be taken together with the nitrogen atom to which they are attached to form a heterocycle selected from:
    3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl, and 1-piperazinyl;
    said heterocycle being substituted with 0–3 groups selected from: $C_1$–$C_6$ alkyl, aryl, heteroaryl, aryl($C_1$–$C_4$ alkyl)-, ($C_1$–$C_6$ alkyl)carbonyl, ($C_3$–$C_7$ cycloalkyl)carbonyl, ($C_1$–$C_6$ alkoxy)carbonyl, aryl($C_1$–$C_4$ alkoxy)carbonyl, $C_1$–$C_6$ alkylsulfonyl, and arylsulfonyl;

$R^{12}$ is selected from:
  H, $C_1$–$C_6$ alkyl, triphenylmethyl, methoxymethyl, methoxyphenyldiphenylmethyl, trimethylsilylethoxymethyl, ($C_1$–$C_6$ alkyl)carbonyl, ($C_1$–$C_6$ alkoxy)carbonyl, ($C_1$–$C_6$ alkyl)aminocarbonyl, $C_3$–$C_6$ alkenyl, $C_3$–$C_7$ cycloalkyl, $C_3$–$C_7$ cycloalkyl($C_1$–$C_4$ alkyl)-, aryl, heteroaryl ($C_1$–$C_6$ alkyl)carbonyl, heteroarylcarbonyl, aryl($C_1$–$C_6$ alkyl)-, ($C_1$–$C_6$ alkyl)carbonyl, arylcarbonyl, $C_1$–$C_6$ alkylsulfonyl, arylsulfonyl, aryl($C_1$–$C_6$ alkyl)sulfonyl, heteroarylsulfonyl, heteroaryl($C_1$–$C_6$ alkyl)sulfonyl, aryloxycarbonyl, and aryl($C_1$–$C_6$ alkoxy)carbonyl, wherein said aryl groups are substituted with 0–2 substituents selected from the group consisting of $C_1$–$C_4$ alkyl, $C_1$–$C_4$ alkoxy, halo, $CF_3$, and nitro;

$R^{14}$ is selected from H, $C_1$–$C_4$ alkyl, and phenyl($C_1$–$C_4$ alkyl);

$R^{16}$ is selected from —C(=O)$OR^{18a}$, —C(=O)$R^{18b}$, —C(=O)$N(R^{18b})_2$, —$SO_2R^{18a}$, and —$SO_2N(R^{18b})_2$;

$R^{17}$ is selected from:
  H, $C_1$–$C_6$ alkyl, $C_3$–$C_7$ cycloalkyl, $C_3$–$C_7$ cycloalkyl($C_1$–$C_4$ alkyl)-, aryl, aryl($C_1$–$C_6$ alkyl)-, and heteroaryl($C_1$–$C_6$ alkyl);

$R^{18a}$ is selected from:
  $C_7$–$C_8$ alkyl, $C_3$–$C_{11}$ cycloalkyl, aryl($C_1$–$C_6$ alkyl)-, said aryl substituted with 0–4 $R^{19}$, heteroaryl($C_1$–$C_6$ alkyl)-, said heteroaryl substituted with 0–4 $R^{19}$,
  ($C_1$–$C_6$ alkyl)heteroaryl, said heteroaryl substituted with 0–4 $R^{19}$,
  heteroaryl substituted with 0–4 $R^{19}$,
  phenyl substituted with 3–4 $R^{19}$, and
  naphthyl substituted with 0–4 $R^{19}$;

$R^{18b}$ is H or $R^{18a}$;

$R^{19}$ is selected from:
  H, halogen, $CF_3$, $CO_2H$, CN, $NO_2$, —$NR^{11}R^{12}$, $OCF_3$, $C_1$–$C_8$ alkyl, $C_2$–$C_6$ alkenyl, $C_2$–$C_6$ alkynyl, $C_3$–$C_{11}$ cycloalkyl, $C_3$–$C_7$ cycloalkyl($C_1$–$C_4$ alkyl)-, aryl ($C_1$–$C_6$ alkyl)-, $C_1$–$C_6$ alkoxy, $C_1$–$C_4$ alkoxycarbonyl, aryl, aryl-O—, aryl-$SO_2$—, heteroaryl, and heteroaryl-$SO_2$—, wherein said aryl and heteroaryl groups are substituted with 0–4 groups selected from hydrogen, halogen, $CF_3$, $C_1$–$C_3$ alkyl, and $C_1$–$C_3$ alkoxy;

$R^{20}$ is selected from:
  hydroxy, $C_1$–$C_{10}$ alkyloxy, $C_3$–$C_{11}$ cycloalkyloxy, aryloxy, aryl($C_1$–$C_4$ alkyl)oxy,
  $C_2$–$C_{10}$ alkylcarbonyloxy($C_1$–$C_2$ alkyl)oxy-,
  $C_2$–$C_{10}$ alkoxycarbonyloxy($C_1$–$C_2$ alkyl)oxy-,
  $C_2$–$C_{10}$ alkoxycarbonyl($C_1$–$C_2$ alkyl)oxy-,
  $C_3$–$C_{10}$ cycloalkylcarbonyloxy($C_1$–$C_2$ alkyl)oxy-,
  $C_3$–$C_{10}$ cycloalkoxycarbonyloxy($C_1$–$C_2$ alkyl)oxy-,
  $C_3$–$C_{10}$ cycloalkoxycarbonyl($C_1$–$C_2$ alkyl)oxy-,
  aryloxycarbonyl($C_1$–$C_2$ alkyl)oxy-,
  aryloxycarbonyloxy($C_1$–$C_2$ alkyl)oxy-,
  arylcarbonyloxy($C_1$–$C_2$ alkyl)oxy-,
  $C_1$–$C_5$ alkoxy($C_1$–$C_5$ alkyl)carbonyloxy($C_1$–$C_2$ alkyl)oxy-,
  (5-($C_1$–$C_5$ alkyl)-1,3-dioxa-cyclopenten-2-one-yl)methyloxy,
  (5-aryl-1,3-dioxa-cyclopenten-2-one-yl)methyloxy, and
  $(R^{10})(R^{11})N$—($C_1$–$C_{10}$ alkoxy)-;

$R^{21}$ is selected from:
  $C_1$–$C_8$ alkyl, $C_2$–$C_6$ alkenyl, $C_3$–$C_{11}$ cycloalkyl, ($C_3$–$C_{11}$ cycloalkyl)methyl, aryl, aryl($C_1$–$C_4$ alkyl)-, and $C_1$–$C_{10}$ alkyl substituted with 0–2 $R^7$;

m is 0–2;

n is 0–3; and p is 0–2;

with the following provisos:
  (1) n and m are chosen such that the number of atoms connecting $R^1$ and —$COR^{20}$ in Formula (III) is in the range of 10–14,
  (2) if $R^8$ is H, then $R^9$ may not be an unsubstituted pyridyl radical,
  (3) if $R^9$ is H, then $R^8$ may not be an unsubstituted pyridyl radical.

3. A compound of claim 1 of Formula III:

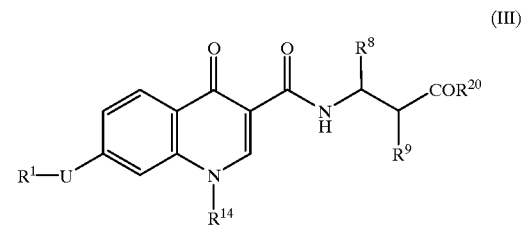

(III)

including stereoisomeric forms thereof, or mixtures of stereoisomeric forms thereof, or pharmaceutically acceptable salt forms thereof wherein:

$R^1$ is selected from:

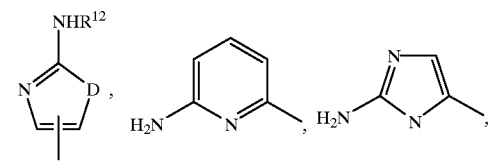

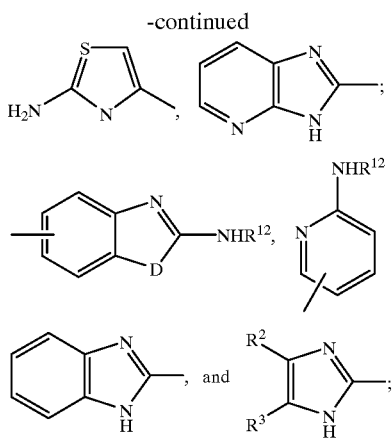

U is selected from —(CH$_2$)$_n$—, —(CH$_2$)$_n$O(CH$_2$)$_m$—, —NH(CH$_2$)$_n$—, —(CH$_2$)$_n$C(=O)(CH$_2$)$_m$—, —N(R$^{10}$)C(=O)—, and —NHC(=O)(CH$_2$)$_n$—;

R$^2$ and R$^3$ are independently selected from:
NR$^{11}$R$^{12}$, NO$_2$, CN, CF$_3$, C$_5$–C$_6$ alkyl, C$_3$–C$_6$ alkenyl, C$_3$–C$_7$ cycloalkyl, aryl(C$_1$–C$_6$ alkyl)-, C$_3$–C$_7$ cycloalkyl(C$_1$–C$_4$ alkyl), (C$_2$–C$_6$ alkyl)carbonyl, (C$_1$–C$_6$ alkoxy)carbonyl, arylcarbonyl, and aryl substituted with 0–4 R$^7$, R$^4$ is selected from:
H, C$_1$–C$_{10}$ alkyl, (C$_1$–C$_{10}$ alkyl)carbonyl, aryl, aryl(C$_1$–C$_4$ alkyl)-, C$_3$–C$_{11}$ cycloalkyl, and C$_3$–C$_{11}$ cycloalkyl(C$_1$–C$_4$ alkyl)-;

R$^8$ is selected from:
H, CO$_2$R$^{18b}$, C(=O)R$^{18b}$, CONR$^{17}$R$^{18b}$,
C$_1$–C$_{10}$ alkyl substituted with 0–1 R$^6$,
C$_5$–C$_{10}$ alkenyl substituted with 0–1 R$^6$,
C$_5$–C$_{10}$ alkynyl substituted with 0–1 R$^6$,
C$_3$–C$_8$ cycloalkyl substituted with 0–1 R$^6$,
C$_5$–C$_6$ cycloalkenyl substituted with 0–1 R$^6$,
C$_1$–C$_{10}$ alkylcarbonyl,
C$_3$–C$_{10}$ cycloalkyl(C$_1$–C$_4$ alkyl)-,
phenyl substituted with 1–3 R$^6$,
naphthyl substituted with 0–3 R$^6$,
a 5–10 membered heterocyclic ring containing 1–3 N, O, or S heteroatoms, wherein said heterocyclic ring may be saturated, partially saturated, or fully unsaturated, said heterocyclic ring being substituted with 0–2 R$^7$;

R$^9$ is selected from:
H, hydroxy, C$_5$–C$_{10}$ alkoxy, nitro, N(R$^{10}$)R$^{11}$, N(R$^{16}$)R$^{17}$, aryl(C$_0$–C$_6$ alkyl)carbonyl, aryl(C$_3$–C$_6$ alkyl), heteroaryl(C$_1$–C$_6$ alkyl), CONR$^{18a}$R$^{20}$, SO$_2$R$^{18a}$, SO$_2$NR$^{18a}$R$^{20}$,
C$_1$–C$_{10}$ alkyl substituted with 0–1 R$^6$,
C$_5$–C$_{10}$ alkenyl substituted with 0–1 R$^6$,
C$_5$–C$_{10}$ alkynyl substituted with 0–1 R$^6$,
C$_3$–C$_8$ cycloalkyl substituted with 0–1 R$^6$,
C$_5$–C$_6$ cycloalkenyl substituted with 0–1 R$^6$,
C$_1$–C$_{10}$ alkylcarbonyl,
C$_3$–C$_{10}$ cycloalkyl(C$_1$–C$_4$ alkyl),
phenyl substituted with 1–3 R$^6$,
naphthyl substituted with 0–3 R$^6$, and
a 5–10 membered heterocyclic ring containing 1–3 N, O, or S heteroatoms, wherein said heterocyclic ring may be saturated, partially saturated, or fully unsaturated, said heterocyclic ring being substituted with 0–2 R$^7$, providing that any of the above alkyl, cycloalkyl, aryl or heteroaryl groups may be unsubstituted or substituted independently with 1–2 R$^7$;

R$^6$ is selected from:
H, C$_1$–C$_{10}$ alkyl, hydroxy, C$_1$–C$_{10}$ alkoxy, nitro, C$_1$–C$_{10}$ alkylcarbonyl, —N(R$^{11}$)R$^{12}$, cyano, halo, CF$_3$, CHO, CO$_2$R$^{18b}$, C(=O)R$^{18b}$, CONR$^{17}$R$^{18b}$, OC(=O)R$^{10}$, OR$^{10}$, OC(=O)NR$^{10}$R$^{11}$, NR$^{10}$C(=O)R$^{10}$, NR$^{10}$C(=O)OR$^{21}$, NR$^{10}$C(=O)NR$^{10}$R$^{11}$, NR$^{10}$SO$_2$NR$^{10}$R$^{11}$, NR$^{10}$SO$_2$R$^{21}$, S(O)$_p$R$^{11}$, SO$_2$NR$^{10}$R$^{11}$,
aryl substituted with 0–3 groups selected from halogen, C$_1$–C$_6$ alkoxy, C$_1$–C$_6$ alkyl, CF$_3$, S(O)$_m$Me, and —NMe$_2$,
aryl(C$_1$–C$_4$ alkyl)-, said aryl being substituted with 0–3 groups selected from halogen, C$_1$–C$_6$ alkoxy, C$_1$–C$_6$ alkyl, CF$_3$, S(O)$_p$Me, and —NMe$_2$, and
a 5–10 membered heterocyclic ring containing 1–3 N, O, or S heteroatoms, wherein said heterocyclic ring may be saturated, partially saturated, or fully unsaturated, said heterocyclic ring being substituted with 0–2 R$^7$;

R$^7$ is selected from:
H, hydroxy, C$_1$–C$_4$ alkyl, C$_1$–C$_4$ alkoxy, aryl, aryl(C$_1$–C$_4$ alkyl)-, (C$_1$–C$_4$ alkyl)carbonyl, CO$_2$R$^{18a}$, SO$_2$R$^{11}$, SO$_2$NR$^{10}$R$^{11}$, OR$^{10}$, and N(R$^{11}$)R$^{12}$;

R$^{10}$ is selected from:
H, C$_3$–C$_6$ alkenyl, C$_3$–C$_{11}$ cycloalkyl, aryl, (C$_3$–C$_{11}$ cycloalkyl)methyl, aryl(C$_1$–C$_4$ alkyl), and C$_1$–C$_{10}$ alkyl substituted with 0–2 R$^6$;

R$^{11}$ is selected from:
H, hydroxy, C$_1$–C$_8$ alkyl, C$_3$–C$_6$ alkenyl, C$_3$–C$_{11}$ cycloalkyl, (C$_3$–C$_{11}$ cycloalkyl)methyl, C$_1$–C$_6$ alkoxy, benzyloxy, aryl, heteroaryl, heteroaryl(C$_1$–C$_4$ alkyl)-, aryl(C$_1$–C$_4$ alkyl), adamantylmethyl, and C$_1$–C$_{10}$ alkyl substituted with 0–2 R$^4$,
alternatively, when R$^{10}$ and R$^{11}$ are both substituents on the same nitrogen atom (as in —NR$^{10}$R$^{11}$) they may be taken together with the nitrogen atom to which they are attached to form a heterocycle selected from:
3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl, and 1-piperazinyl;
said heterocycle being substituted with 0–3 groups selected from: C$_1$–C$_6$ alkyl, aryl, heteroaryl, aryl(C$_1$–C$_4$ alkyl)-, (C$_1$–C$_6$ alkyl)carbonyl, (C$_3$–C$_7$ cycloalkyl)carbonyl, (C$_1$–C$_6$ alkoxy)carbonyl, aryl(C$_1$–C$_4$ alkoxy)carbonyl, C$_1$–C$_6$ alkylsulfonyl, and arylsulfonyl;

R$^{12}$ is selected from:
H, C$_1$–C$_6$ alkyl, triphenylmethyl, methoxymethyl, methoxyphenyldiphenylmethyl, trimethylsilylethoxymethyl, (C$_1$–C$_6$ alkyl)carbonyl, (C$_1$–C$_6$ alkoxy)carbonyl, (C$_1$–C$_6$ alkyl)aminocarbonyl, C$_3$–C$_6$ alkenyl, C$_3$–C$_7$ cycloalkyl, C$_3$–C$_7$ cycloalkyl(C$_1$–C$_4$ alkyl)-, aryl, heteroaryl (C$_1$–C$_6$ alkyl)carbonyl, heteroarylcarbonyl, aryl (C$_1$–C$_6$ alkyl)-, (C$_1$–C$_6$ alkyl)carbonyl, arylcarbonyl, C$_1$–C$_6$ alkylsulfonyl, arylsulfonyl, aryl(C$_1$–C$_6$ alkyl) sulfonyl, heteroarylsulfonyl, heteroaryl(C$_1$–C$_6$ alkyl)sulfonyl, aryloxycarbonyl, and aryl(C$_1$–C$_6$ alkoxy)carbonyl, wherein said aryl groups are substituted with 0–2 substituents selected from the group consisting of C$_1$–C$_4$ alkyl, C$_1$–C$_4$ alkoxy, halo, CF$_3$, and nitro;

$R^{14}$ is selected from H, $C_1$–$C_4$ alkyl, and phenyl($C_1$–$C_4$ alkyl);

$R^{16}$ is selected from —C(=O)O$R^{18a}$, —C(=O)$R^{18b}$, —C(=O)N($R^{18b}$)$_2$, —SO$_2R^{18a}$, and —SO$_2$N($R^{18b}$)$_2$;

$R^{17}$ is selected from:
H, $C_1$–$C_6$ alkyl, $C_3$–$C_7$ cycloalkyl, $C_3$–$C_7$ cycloalkyl($C_1$–$C_4$ alkyl)-, aryl, aryl($C_1$–$C_6$ alkyl)-, and heteroaryl($C_1$–$C_6$ alkyl);

$R^{18a}$ is selected from:
$C_7$–$C_8$ alkyl, $C_3$–$C_{11}$ cycloalkyl,
aryl($C_1$–$C_6$ alkyl)-, said aryl substituted with 0–4 $R^{19}$,
heteroaryl($C_1$–$C_6$ alkyl)-, said heteroaryl substituted with 0–4 $R^{19}$,
($C_1$–$C_6$ alkyl)heteroaryl, said heteroaryl substituted with 0–4 $R^{19}$,
heteroaryl substituted with 0–4 $R^{19}$,
phenyl substituted with 3–4 $R^{19}$, and
naphthyl substituted with 0–4 $R^{19}$;

$R^{18b}$ is H or $R^{18a}$;

$R^{19}$ is selected from:
H, halogen, CF$_3$, CO$_2$H, CN, NO$_2$, —N$R^{11}R^{12}$, OCF$_3$, $C_1$–$C_8$ alkyl, $C_2$–$C_6$ alkenyl, $C_2$–$C_6$ alkynyl, $C_3$–$C_{11}$ cycloalkyl, $C_3$–$C_7$ cycloalkyl($C_1$–$C_4$ alkyl)-, aryl ($C_1$–$C_6$ alkyl)-, $C_1$–$C_6$ alkoxy, $C_1$–$C_4$ alkoxycarbonyl, aryl, aryl-O—, aryl-SO$_2$—, heteroaryl, and heteroaryl-SO$_2$—, wherein said aryl and heteroaryl groups are substituted with 0–4 groups selected from hydrogen, halogen, CF$_3$, $C_1$–$C_3$ alkyl, and $C_1$–$C_3$ alkoxy;

$R^{20}$ is selected from:
hydroxy, $C_1$–$C_{10}$ alkyloxy, $C_3$–$C_{11}$ cycloalkyloxy, aryloxy, aryl($C_1$–$C_4$ alkyl)oxy,
$C_2$–$C_{10}$ alkylcarbonyloxy($C_1$–$C_2$ alkyl)oxy-,
$C_2$–$C_{10}$ alkoxycarbonyloxy($C_1$–$C_2$ alkyl)oxy-,
$C_2$–$C_{10}$ alkoxycarbonyl($C_1$–$C_2$ alkyl)oxy-,
$C_3$–$C_{10}$ cycloalkylcarbonyloxy($C_1$–$C_2$ alkyl)oxy-,
$C_3$–$C_{10}$ cycloalkoxycarbonyloxy($C_1$–$C_2$ alkyl)oxy-,
$C_3$–$C_{10}$ cycloalkoxycarbonyl($C_1$–$C_2$ alkyl)oxy-,
aryloxycarbonyl($C_1$–$C_2$ alkyl)oxy-,
aryloxycarbonyloxy($C_1$–$C_2$ alkyl)oxy-,
arylcarbonyloxy($C_1$–$C_2$ alkyl)oxy-,
$C_1$–$C_5$ alkoxy($C_1$–$C_5$ alkyl)carbonyloxy($C_1$–$C_2$ alkyl)oxy-,
(5-($C_1$–$C_5$ alkyl)-1,3-dioxa-cyclopenten-2-one-yl)methyloxy,
(5-aryl-1,3-dioxa-cyclopenten-2-one-yl)methyloxy, and
($R^{10}$)($R^{11}$)N—($C_1$–$C_{10}$ alkoxy)-;

$R^{21}$ is selected from:
$C_1$–$C_8$ alkyl, $C_2$–$C_6$ alkenyl, $C_3$–$C_{11}$ cycloalkyl, ($C_3$–$C_{11}$ cycloalkyl)methyl, aryl, aryl($C_1$–$C_4$ alkyl)-, and $C_1$–$C_{10}$ alkyl substituted with 0–2 $R^7$;

m is 0–2;
n is 0–3; and
p is 0–2;

with the following provisos:
(1) n and m are chosen such that the number of atoms connecting $R^1$ and —CO$R^{20}$ in Formula (III) is in the range of 10–14,
(2) if $R^8$ is H, then $R^9$ may not be an unsubstituted pyridyl radical,
(3) if $R^9$ is H, then $R^8$ may not be an unsubstituted pyridyl radical.

4. A compound of claim 1 of Formula II:

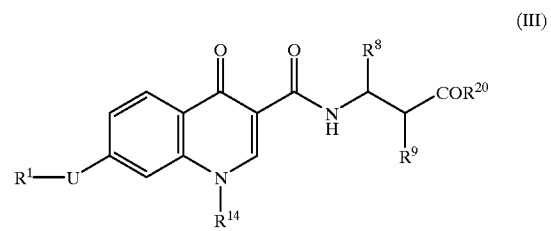

(III)

including stereoisomeric forms thereof, or mixtures of stereoisomeric forms thereof, or pharmaceutically acceptable salt forms thereof wherein:

$R^1$ is selected from:

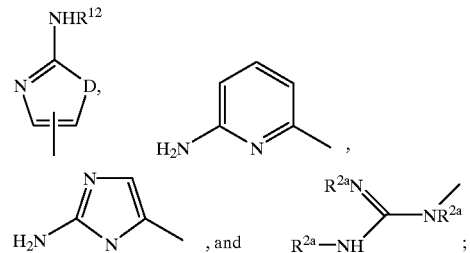

U is selected from —(CH$_2$)$_n$—, —NH(CH$_2$)$_n$—, —N($R^{10}$)C(=O)—, and —NHC(=O)(CH$_2$)$_n$—;

$R^4$ is selected from:
H, $C_1$–$C_4$ alkyl, ($C_1$–$C_4$ alkyl)carbonyl, aryl, aryl ($C_1$–$C_4$ alkyl)-, $C_3$–$C_6$ cycloalkyl, and $C_3$–$C_6$ cycloalkyl($C_1$–$C_4$ alkyl)-;

$R^6$ is H;

$R^7$ is selected from:
H, hydroxy, $C_1$–$C_4$ alkyl, $C_1$–$C_4$ alkoxy, aryl, aryl ($C_1$–$C_4$ alkyl)-, ($C_1$–$C_4$ alkyl)carbonyl, CO$_2R^{18a}$, SO$_2R^{11}$, SO$_2$N$R^{10}R^{11}$, O$R^{10}$, and N($R^{11}$)$R^{12}$;

$R^8$ is H;

$R^9$ is selected from:
H, hydroxy, $C_5$–$C_{10}$ alkoxy, nitro, N($R^{10}$)$R^{11}$, N($R^{16}$) $R^{17}$, aryl($C_0$–$C_6$ alkyl)carbonyl, aryl($C_3$–$C_6$ alkyl), heteroaryl($C_1$–$C_6$ alkyl), CON$R^{18a}R^{20}$, SO$_2R^{18a}$, SO$_2$N$R^{18a}R^{20}$,
providing that any of the above aryl or heteroaryl groups may be unsubstituted or substituted independently with 1–2 $R^7$;

$R^{10}$ is selected from:
H, $C_3$–$C_6$ alkenyl, $C_3$–$C_6$ cycloalkyl, aryl, ($C_3$–$C_6$ cycloalkyl)methyl, aryl($C_1$–$C_4$ alkyl), and $C_1$–$C_4$ alkyl;

$R^{11}$ is selected from:
H, hydroxy, $C_1$–$C_4$ alkyl, $C_3$–$C_6$ alkenyl, $C_3$–$C_6$ cycloalkyl, ($C_3$–$C_6$ cycloalkyl)methyl, $C_1$–$C_6$ alkoxy, benzyloxy, aryl, heteroaryl, heteroaryl ($C_1$–$C_4$ alkyl)-, aryl($C_1$–$C_4$ alkyl), adamantylmethyl, and $C_1$–$C_4$ alkyl substituted with 0–2 $R^4$, $R^{12}$ is selected from:
H, $C_1$–$C_4$ alkyl, ($C_1$–$C_4$ alkyl)carbonyl, ($C_1$–$C_4$ alkoxy)carbonyl, phenyl($C_1$–$C_4$ alkyl)-, phenylsulfonyl, phenyloxycarbonyl, and phenyl ($C_1$–$C_4$ alkoxy)carbonyl, wherein said phenyl groups are substituted with 0–2 substituents selected from the group consisting of $C_1$–$C_4$ alkyl, $C_1$–$C_4$ alkoxy, halo, CF$_3$, and nitro;

$R^{14}$ is selected from H, methyl, ethyl, benzyl and phenylethyl;

$R^{16}$ is selected from $-C(=O)OR^{18a}$, $-C(=O)R^{18b}$, $-C(=O)N(R^{18b})_2$, $-SO_2R^{18a}$, and $-SO_2N(R^{18b})_2$;

$R^{17}$ is selected from:
  H, $C_1-C_6$ alkyl, $C_3-C_7$ cycloalkyl, $C_3-C_7$ cycloalkyl($C_1-C_4$ alkyl)-, aryl, aryl($C_1-C_6$ alkyl)-, and heteroaryl($C_1-C_6$ alkyl);

$R^{18a}$ is selected from:
  $C_7-C_8$ alkyl, $C_3-C_{11}$ cycloalkyl,
  aryl($C_1-C_6$ alkyl)-, said aryl substituted with 0–4 $R^{19}$,
  heteroaryl($C_1-C_6$ alkyl)-, said heteroaryl substituted with 0–4 $R^{19}$,
  ($C_1-C_6$ alkyl)heteroaryl, said heteroaryl substituted with 0–4 $R^{19}$,
  heteroaryl substituted with 0–4 $R^{19}$,
  phenyl substituted with 3–4 $R^{19}$, and
  naphthyl substituted with 0–4 $R^{19}$;

$R^{18b}$ is H or $R^{18a}$;

$R^{19}$ is selected from:
  H, halogen, $CF_3$, $CO_2H$, CN, $NO_2$, $-NR^{11}R^{12}$, $OCF_3$, $C_1-C_8$ alkyl, $C_2-C_6$ alkenyl, $C_2-C_6$ alkynyl, $C_3-C_{11}$ cycloalkyl, $C_3-C_7$ cycloalkyl($C_1-C_4$ alkyl)-, aryl ($C_1-C_6$ alkyl)-, $C_1-C_6$ alkoxy, $C_1-C_4$ alkoxycarbonyl, aryl, aryl-O—, aryl-$SO_2$—, heteroaryl, and heteroaryl-$SO_2$—, wherein said aryl and heteroaryl groups are substituted with 0–4 groups selected from hydrogen, halogen, $CF_3$, $C_1-C_3$ alkyl, and $C_1-C_3$ alkoxy;

$R^{20}$ is selected from:
  hydroxy, $C_1-C_{10}$ alkyloxy, $C_3-C_{11}$ cycloalkyloxy,
  aryloxy, aryl($C_1-C_4$ alkyl)oxy,
  $C_2-C_{10}$ alkylcarbonyloxy($C_1-C_2$ alkyl)oxy-,
  $C_2-C_{10}$ alkoxycarbonyloxy($C_1-C_2$ alkyl)oxy-,
  $C_2-C_{10}$ alkoxycarbonyl($C_1-C_2$ alkyl)oxy-,
  $C_3-C_{10}$ cycloalkylcarbonyloxy($C_1-C_2$ alkyl)oxy-,
  $C_3-C_{10}$ cycloalkoxycarbonyloxy($C_1-C_2$ alkyl)oxy-,
  $C_3-C_{10}$ cycloalkoxycarbonyl($C_1-C_2$ alkyl)oxy-,
  aryloxycarbonyl($C_1-C_2$ alkyl)oxy-,
  aryloxycarbonyloxy($C_1-C_2$ alkyl)oxy-,
  arylcarbonyloxy($C_1-C_2$ alkyl)oxy-,
  $C_1-C_5$ alkoxy($C_1-C_5$ alkyl)carbonyloxy($C_1-C_2$ alkyl)oxy-,
  (5-($C_1-C_5$ alkyl)-1,3-dioxa-cyclopenten-2-one-yl)methyloxy,
  (5-aryl-1,3-dioxa-cyclopenten-2-one-yl)methyloxy, and
  $(R^{10})(R^{11})N-(C_1-C_{10}$ alkoxy)-;

$R^{21}$ is selected from:
  $C_1-C_8$ alkyl, $C_2-C_6$ alkenyl, $C_3-C_{11}$ cycloalkyl, ($C_3-C_{11}$ cycloalkyl)methyl, aryl, aryl($C_1-C_4$ alkyl)-, and $C_1-C_{10}$ alkyl substituted with 0–2 $R^7$;

m is 0–2;
n is 0–3; and
p is 0–2;
with the following provisos:
  (1) n and m are chosen such that the number of atoms connecting $R^1$ and $-COR^{20}$ in Formula (III) is in the range of 10–14,
  (2) $R^9$ is not an unsubstituted pyridyl radical.

5. A compound of claim 1, including enantiomeric and diastereomeric forms thereof, or mixtures of enantiomeric or diastereomeric forms thereof, or pharmaceutically acceptable salt forms thereof selected from the group consisting of:

3-[7-[(imidazol-2-ylamino)methyl]-1-methylquinoline-4-one-3-ylcarbonylamino]-2-(3,5-dimethylisoxazol-4-ylsulfonylamino)propionic acid, 3-[7-[(imidazol-2-ylamino)methyl]-1-methylquinoline-4-one-3-ylcarbonylamino]-2-((2,4,6-trimethylphenyl)sulfonylamino)propionic acid, 3-[7-[(pyridin-2-ylamino)methyl]-1-methylquinoline-4-one-3-ylcarbonylamino]-2-((2,4,6-trimethylphenyl)sulfonylamino)propionic acid, 3-[7-[(imidazol-2-ylamino)methyl]-1-methylquinoline-4-one-3-ylcarbonylamino]-2-((4-phenylbenzene)sulfonylamino)propionic acid, 3-[7-[(benzimidazol-2-ylamino)methyl]-1-methylquinoline-4-one-3-ylcarbonylamino]-2-((2,4,6-trimethylphenyl)sulfonylamino)propionic acid, 3-[7-[(4-methylimidazol-2-ylamino)methyl]-1-methylquinoline-4-one-3-ylcarbonylamino]-2-((2,4,6-trimethylphenyl)sulfonylamino)propionic acid, 3-[7-[(4,5-dimethylimidazol-2-ylamino)methyl]-1-methylquinoline-4-one-3-ylcarbonylamino]-2-((2,4,6-trimethylphenyl)sulfonylamino)propionic acid, 3-[7-[(4,5,6,7-tetrahydrobenzimidazol-2-ylamino)methyl]-1-methylquinoline-4-one-3-ylcarbonylamino]-2-((2,4,6-trimethylphenyl)sulfonylamino)propionic acid, 3-[7-(2-aminopyridin-6-yl)quinoline-4-one-3-ylcarbonylamino]-2-((2,4,6-trimethylphenyl)sulfonylamino)propionic acid, 3-[7-[(7-azabenzimidazol-2-yl)methyl]-1-methylquinoline-4-one-3-ylcarbonylamino]-2-((2,4,6-trimethylphenyl)sulfonylamino)propionic acid, 3-[7-[(benzimidazol-2-ylamino)methyl]-1-(2-phenylethyl)quinoline-4-one-3-ylcarbonylamino]-2-((2,4,6-trimethylphenyl)sulfonylamino)propionic acid, 3-[7-[(pyridin-2-ylamino)methyl]-1-(2-phenylethyl)quinoline-4-one-3-ylcarbonylamino]-2-((2,4,6-trimethylphenyl)sulfonylamino)propionic acid, 3-[7-[(imidazol-2-ylamino)methyl]-1-(2-phenylethyl)quinoline-4-one-3-ylcarbonylamino]-2-((2,4,6-trimethylphenyl)sulfonylamino)propionic acid, 3-[7-[(imidazol-2-ylamino)methyl]-(2-phenylethyl)quinoline-4-one-3-ylcarbonylamino]-2-((2,4,6-trimethylphenyl)sulfonylamino)propionic acid, 3-[7-[(pyridin-2-ylamino)methyl]-(2-phenylethyl)quinoline-4-one-3-ylcarbonylamino]-2 -((2,4,6-trimethylphenyl)sulfonylamino)propionic acid, 3-[7-[(imidazol-2-ylamino)methyl]-1-(2-phenylethyl)quinoline-4-one-3-ylcarbon-ylamino]-2-((4-phenylbenzene)sulfonylamino)propionic acid, 3-[7-[(benzimidazol-2-ylamino)methyl]-1-(2-phenylethyl)quinoline-4-one-3-ylcarbonylamino]-2-((2,4,6-trimethylphenyl)sulfonylamino)propionic acid, 3-[7-[(4-methylimidazol-2-ylamino)methyl]-(2-phenylethyl)quinoline-4-one-3-ylcarbonylamino]-2-((2,4,6-trimethylphenyl)sulfonylamino)propionic acid, 3-[7-[(4,5-dimethylimidazol-2-ylamino)methyl]-(2-phenylethyl)quinoline-4-one-3-ylcarbonylamino]-2-((2,4,6-trimethylphenyl)sulfonylamino)propionic acid, 3-[7-[(4,5,6,7-tetrahydrobenzimidazol-2-ylamino)methyl]-1-(2-phenylethyl)quinoline-4-one-3-ylcarbonylamino]-2-((2,4,6-trimethylphenyl)sulfonylamino)propionic acid, 3-[7-(2-aminopyridin-6-yl)1-(2-phenylethyl)quinoline-4-one-3-ylcarbonylamino]-2-((2,4,6-trimethylphenyl)sulfonylamino)propionic acid, 3-[7-[(7-azabenzimidazol-2-yl)methyl]-1-(2-phenylethyl)quinoline-4-one-3-ylcarbonylamino]-2-((2,4,6-trimethylphenyl)sulfonylamino)propionic acid 3-[7-[(imidazol-2-ylamino)methyl]-1-(2-phenylethyl)quinoline-4-one-3-ylcarbon-ylamino]-2-((2,2-dimethyl-4-phenylbenzene)sulfonylamino)propionic acid, and 3-[7-[(imidazol-2-ylamino)methyl]-1-(2-phenylethyl)quinoline-4-one-3-ylcarbon-ylamino]-2-((2,2-dichloro-4-phenylbenzene)sulfonylamino)propionic acid.

6. A compound of Formula IV:

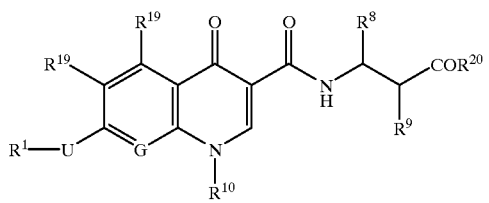

(IV)

including stereoisomeric forms thereof, or mixtures of stereoisomeric forms thereof, or pharmaceutically acceptable salt forms thereof wherein:

$R^1$ is selected from:

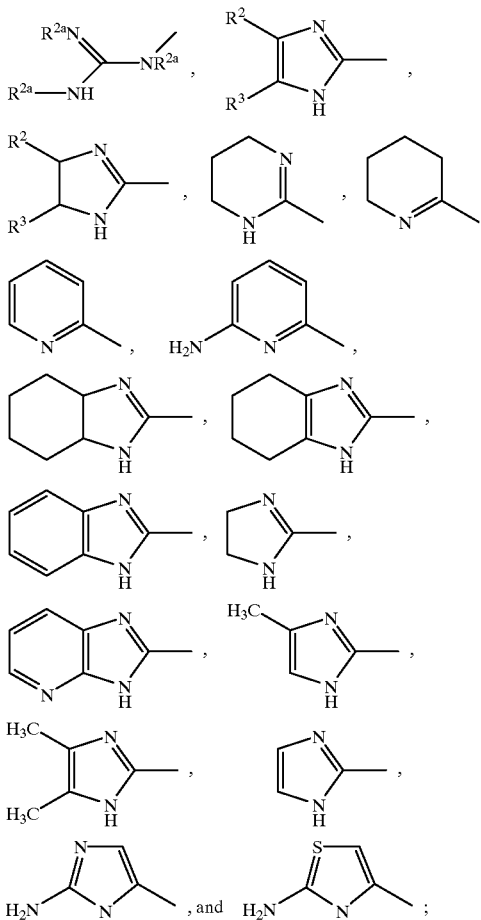

$R^2$ and $R^3$ are independently selected from:
H, $C_1$–$C_4$ alkoxy, $NR^{11}R^{12}$, halogen, $NO_2$, CN, $CF_3$, $C_1$–$C_6$ alkyl, $C_3$–$C_6$ alkenyl, $C_3$–$C_7$ cycloalkyl, $C_3$–$C_7$ cycloalkyl($C_1$–$C_4$ alkyl), aryl($C_1$–$C_6$ alkyl)-, ($C_1$–$C_6$ alkyl)carbonyl, ($C_1$–$C_6$ alkoxy)carbonyl, arylcarbonyl, and aryl substituted with 0–4 $R^7$,
alternatively, when $R^2$ and $R^3$ are substituents on adjacent atoms, they can be taken together with the carbon atoms to which they are attached to form a 5–7 membered carbocyclic or 5–7 membered heterocyclic aromatic or nonaromatic ring system, said carbocyclic or heterocyclic ring being substituted with 0–2 groups selected from $C_1$–$C_4$ alkyl, $C_1$–$C_4$ alkoxy, halo, cyano, amino, $CF_3$ and $NO_2$;

$R^{2a}$ is selected from:
H, $C_1$–$C_{10}$ alkyl, $C_2$–$C_6$ alkenyl, $C_3$–$C_{11}$ cycloalkyl, $C_3$–$C_7$ cycloalkyl($C_1$–$C_4$ alkyl), aryl, aryl($C_1$–$C_4$ alkyl)-, ($C_2$–$C_7$ alkyl)carbonyl, arylcarbonyl, ($C_2$–$C_{10}$ alkoxy)carbonyl, $C_3$–$C_7$ cycloalkoxycarbonyl, $C_7$–$C_{11}$ bicycloalkoxycarbonyl, aryloxycarbonyl, aryl($C_1$–$C_{10}$ alkoxy)carbonyl, $C_1$–$C_6$ alkylcarbonyloxy ($C_1$–$C_4$ alkoxy)carbonyl, arylcarbonyloxy($C_1$–$C_4$ alkoxy)carbonyl, and $C_3$–$C_7$ cycloalkylcarbonyloxy ($C_1$–$C_4$ alkoxy)carbonyl;

$R^4$ is selected from:
H, $C_1$–$C_6$ alkyl, $C_3$–$C_7$ cycloalkyl, $C_3$–$C_7$ cycloalkyl ($C_1$–$C_4$ alkyl)-, aryl, heteroaryl, aryl($C_1$–$C_6$ alkyl)-, and heteroaryl($C_1$–$C_6$ alkyl)-, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$, $R^6$ is selected from:
H, $C_1$–$C_{10}$ alkyl, hydroxy, $C_1$–$C_{10}$ alkoxy, nitro, $C_1$–$C_{10}$ alkylcarbonyl, —$N(R^{11})R^{12}$, cyano, halo, $CF_3$, CHO, $CO_2R^{18b}$, $C(=O)R^{18b}$, $CONR^{17}R^{18b}$, $OC(=O)R^{10}$, $OR^{10}$, $OC(=O)NR^{10}R^{11}$, $NR^{10}C(=O)R^{10}$, $NR^{10}C(=O)OR^{21}$, $NR^{10}C(=O)NR^{10}R^{11}$, $NR^{10}SO_2NR^{10}R^{11}$, $NR^{10}SO_2R^{21}$, $S(O)_pR^{11}$, $SO_2NR^{10}R^{11}$,
aryl substituted with 0–3 groups selected from halogen, $C_1$–$C_6$ alkoxy, $C_1$–$C_6$ alkyl, $CF_3$, $S(O)_m$Me, and —$NMe_2$,
aryl($C_1$–$C_4$ alkyl)-, said aryl being substituted with 0–3 groups selected from halogen, $C_1$–$C_6$ alkoxy, $C_1$–$C_6$ alkyl, $CF_3$, $S(O)_p$Me, and —$NMe_2$, and
a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$;

$R^7$ is selected from:
H, hydroxy, $C_1$–$C_4$ alkyl, $C_1$–$C_4$ alkoxy, aryl, aryl ($C_1$–$C_4$ alkyl)-, ($C_1$–$C_4$ alkyl)carbonyl, $CO_2R^{18a}$, $SO_2R^{11}$, $SO_2NR^{10}R^{11}$, $OR^{10}$, and $N(R^{11})R^{12}$;

U is selected from:
—$(CH_2)_n$—, —$(CH_2)_nO(CH_2)_m$—, —$NH(CH_2)_n$—, —$N(R^{10})C(=O)$—, —$NHC(=O)(CH_2)_n$—, and —$C(=O)N(R^{10})$—;

G is $CR^{19}$;

$R^8$ is selected from:
H, $CO_2R^{18b}$, $C(=O)R^{18b}$, $CONR^{17}R^{18b}$,
$C_1$–$C_{10}$ alkyl substituted with 0–1 $R^6$,
$C_2$–$C_{10}$ alkenyl substituted with 0–1 $R^6$,
$C_2$–$C_{10}$ alkynyl substituted with 0–1 $R^6$,
$C_3$–$C_8$ cycloalkyl substituted with 0–1 $R^6$,
$C_5$–$C_6$ cycloalkenyl substituted with 0–1 $R^6$,
($C_1$–$C_{10}$ alkyl)carbonyl,
$C_3$–$C_{10}$ cycloalkyl($C_1$–$C_4$ alkyl)-,
phenyl substituted with 0–3 $R^6$,
naphthyl substituted with 0–3 $R^6$,
a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$;

$R^9$ is selected from:
$C_1$–$C_{10}$ alkyl substituted with 0–1 $R^6$,
$C_1$–$C_{10}$ alkoxy substituted with 0–2 $R^7$, H, nitro, $N(R^{11})R^{12}$, $OC(=O)R^{10}$, $OR^{10}$, $OC(=O)NR^{10}R^{11}$, $NR^{10}C(=O)R^{10}$, $NR^{10}C(=O)OR^{21}$, $NR^{10}C(=O)NR^{10}R^{11}$, $NR^{10}SO_2NR^{10}R^{11}$, $NR^{10}SO_2R^{21}$, hydroxy, $OR^{22}$, —$N(R^{10})R^{11}$, —$N(R^{16})R^{17}$, aryl($C_0$–$C_6$ alkyl)carbonyl, aryl ($C_1$–$C_6$ alkyl), heteroaryl($C_1$–$C_6$ alkyl), $CONR^{18a}R^{20}$, $SO_2R^{18a}$, and $SO_2NR^{18a}R^{20}$, providing that any of the above alkyl, aryl or heteroaryl groups may be unsubstituted or substituted independently with 1–2 $R^7$;

$R^{10}$ is selected from:

H, $CF_3$, $C_3$–$C_6$ alkenyl, $C_3$–$C_{11}$ cycloalkyl, aryl, ($C_3$–$C_{11}$ cycloalkyl)methyl, aryl($C_1$–$C_4$ alkyl), and $C_1$–$C_{10}$ alkyl substituted with 0–2 $R^6$;

$R^{11}$ is selected from:

H, hydroxy, $C_1$–$C_8$ alkyl, $C_3$–$C_6$ alkenyl, $C_3$–$C_{11}$ cycloalkyl, ($C_3$–$C_{11}$ cycloalkyl)methyl, $C_1$–$C_6$ alkoxy, benzyloxy, aryl, heteroaryl, heteroaryl ($C_1$–$C_4$ alkyl)-, aryl($C_1$–$C_4$ alkyl), adamantylmethyl, and $C_1$–$C_{10}$ alkyl substituted with 0–2 $R^4$;

alternatively, when $R^{10}$ and $R^{11}$ are both substituents on the same nitrogen atom (as in —$NR^{10}R^{11}$) they may be taken together with the nitrogen atom to which they are attached to form a heterocycle selected from:

3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl, and 1-piperazinyl;

said heterocycle being substituted with 0–3 groups selected from: $C_1$–$C_6$ alkyl, aryl, heteroaryl, aryl ($C_1$–$C_4$ alkyl)-, ($C_1$–$C_6$ alkyl)carbonyl, ($C_3$–$C_7$ cycloalkyl)carbonyl, ($C_1$–$C_6$ alkoxy)carbonyl, aryl($C_1$–$C_4$ alkoxy)carbonyl, $C_1$–$C_6$ alkylsulfonyl, and arylsulfonyl;

$R^{12}$ is selected from:

H, $C_1$–$C_6$ alkyl, triphenylmethyl, methoxymethyl, methoxyphenyldiphenylmethyl, trimethylsilylethoxymethyl, ($C_1$–$C_6$ alkyl)carbonyl, ($C_1$–$C_6$ alkoxy)carbonyl, ($C_1$–$C_6$ alkyl)aminocarbonyl, $C_3$–$C_6$ alkenyl, $C_3$–$C_7$ cycloalkyl, $C_3$–$C_7$ cycloalkyl($C_1$–$C_4$ alkyl)-, aryl, heteroaryl ($C_1$–$C_6$ alkyl)carbonyl, heteroarylcarbonyl, aryl ($C_1$–$C_6$ alkyl)-, ($C_1$–$C_6$ alkyl)carbonyl, arylcarbonyl, $C_1$–$C_6$ alkylsulfonyl, arylsulfonyl, aryl($C_1$–$C_6$ alkyl) sulfonyl, heteroarylsulfonyl, heteroaryl($C_1$–$C_6$ alkyl)sulfonyl, aryloxycarbonyl, and aryl($C_1$–$C_6$ alkoxy)carbonyl, wherein said aryl groups are substituted with 0–2 substituents selected from the group consisting of $C_1$–$C_4$ alkyl, $C_1$–$C_4$ alkoxy, halo, $CF_3$, and nitro;

$R^{16}$ is selected from:

—$C(=O)OR^{18a}$, —$C(=O)R^{18b}$, —$C(=O)N(R^{18b})_2$, —$SO_2R^{18a}$, and —$SO_2N(R^{18b})_2$;

$R^{17}$ is selected from:

H, $C_1$–$C_6$ alkyl, $C_3$–$C_7$ cycloalkyl, $C_3$–$C_7$ cycloalkyl ($C_1$–$C_4$ alkyl)-, aryl, aryl($C_1$–$C_6$ alkyl)-, and heteroaryl($C_1$–$C_6$ alkyl);

$R^{18a}$ is selected from:

$C_1$–$C_8$ alkyl, $C_3$–$C_{11}$ cycloalkyl, aryl($C_1$–$C_6$ alkyl)-, said aryl substituted with 0–4 $R^{19}$, heteroaryl($C_1$–$C_6$ alkyl)-, said heteroaryl substituted with 0–4 $R^{19}$, ($C_1$–$C_6$ alkyl)heteroaryl, said heteroaryl substituted with 0–4 $R^{19}$, heteroaryl substituted with 0–4 $R^{19}$, phenyl substituted with 0–4 $R^{19}$, and naphthyl substituted with 0–4 $R^{19}$;

$R^{18b}$ is H or $R^{18a}$;

$R^{19}$ is selected from:

H, halogen, $CF_3$, $CO_2H$, CN, $NO_2$, —$NR^{11}R^{12}$, $OCF_3$, $C_1$–$C_8$ alkyl, $C_2$–$C_6$ alkenyl, $C_2$–$C_6$ alkynyl, $C_3$–$C_{11}$ cycloalkyl, $C_3$–$C_7$ cycloalkyl($C_1$–$C_4$ alkyl)-, aryl ($C_1$–$C_6$ alkyl)-, $C_1$–$C_6$ alkoxy, $C_1$–$C_4$ alkoxycarbonyl, aryl, aryl-O—, aryl-$SO_2$—, heteroaryl, and heteroaryl-$SO_2$—, wherein said aryl and heteroaryl groups are substituted with 0–4 groups selected from hydrogen, halogen, $CF_3$, $C_1$–$C_3$ alkyl, and $C_1$–$C_3$ alkoxy;

$R^{20}$ is selected from:

hydroxy, $C_1$–$C_{10}$ alkyloxy, $C_3$–$C_{11}$ cycloalkyloxy, aryloxy, aryl($C_1$–$C_4$ alkyl)oxy,
$C_2$–$C_{10}$ alkylcarbonyloxy($C_1$–$C_2$ alkyl)oxy-,
$C_2$–$C_{10}$ alkoxycarbonyloxy($C_1$–$C_2$ alkyl)oxy-,
$C_2$–$C_{10}$ alkoxycarbonyl($C_1$–$C_2$ alkyl)oxy-,
$C_3$–$C_{10}$ cycloalkylcarbonyloxy($C_1$–$C_2$ alkyl)oxy-,
$C_3$–$C_{10}$ cycloalkoxycarbonyloxy($C_1$–$C_2$ alkyl)oxy-,
$C_3$–$C_{10}$ cycloalkoxycarbonyl($C_1$–$C_2$ alkyl)oxy-,
aryloxycarbonyl($C_1$–$C_2$ alkyl)oxy-,
aryloxycarbonyloxy($C_1$–$C_2$ alkyl)oxy-,
arylcarbonyloxy($C_1$–$C_2$ alkyl)oxy-,
$C_1$–$C_5$ alkoxy($C_1$–$C_5$ alkyl)carbonyloxy($C_1$–$C_2$ alkyl)oxy-,
(5-($C_1$–$C_5$ alkyl)-1,3-dioxa-cyclopenten-2-one-yl)methyloxy,
(5-aryl-1,3-dioxa-cyclopenten-2-one-yl)methyloxy, and
$(R^{10})(R^{11})N$—($C_1$–$C_{10}$ alkoxy)-;

$R^{21}$ is selected from:

$C_1$–$C_8$ alkyl, $C_2$–$C_6$ alkenyl, $C_3$–$C_{11}$ cycloalkyl, ($C_3$–$C_{11}$ cycloalkyl)methyl, aryl, aryl($C_1$–$C_4$ alkyl)-, and $C_1$–$C_{10}$ alkyl substituted with 0–2 $R^7$;

$R^{22}$ is selected from:

—$C(=O)$—$R^{18b}$, —$C(=O)N(R^{18b})_2$, —$C(=O)NHSO_2R^{18a}$, —$C(=O)NHC(=O)R^{18b}$, —$C(=O)NHC(=O)OR^{18a}$, and —$C(=O)NHSO_2NHR^{18b}$;

m is 0–2;

n is 0–4; and p is 0–2;

with the following provisos:

(1) n and m are chosen such that the number of atoms connecting $R^1$ and —$COR^{20}$ in Formula (IV) is in the range of 10–14, (2) at least one $R^{19}$ group cannot be H.

7. A compound of claim 6 of Formula IV:

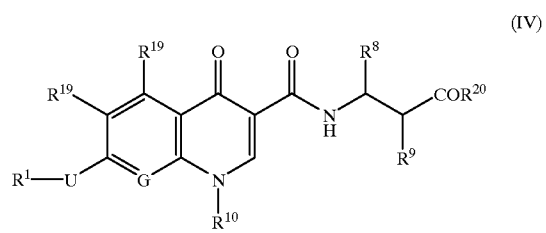

(IV)

including stereoisomeric forms thereof, or mixtures of stereoisomeric forms thereof, or pharmaceutically acceptable salt forms thereof wherein:

$R^1$ is selected from:

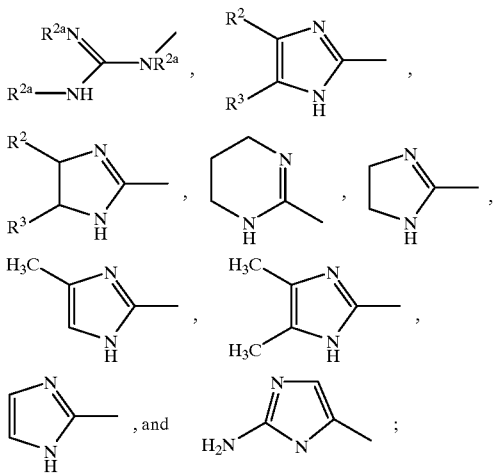

$R^2$ and $R^3$ are independently selected from:
H, $C_1$–$C_4$ alkoxy, $NR^{11}R^{12}$, halogen, $NO_2$, CN, $CF_3$, $C_1$–$C_6$ alkyl, $C_3$–$C_6$ alkenyl, $C_3$–$C_7$ cycloalkyl, $C_3$–$C_7$ cycloalkyl($C_1$–$C_4$ alkyl), aryl($C_1$–$C_6$ alkyl)-, ($C_1$–$C_6$ alkyl)carbonyl, ($C_1$–$C_6$ alkoxy)carbonyl, arylcarbonyl, and aryl substituted with 0–4 $R^7$, alternatively, when $R^2$ and $R^3$ are substituents on adjacent atoms, they can be taken together with the carbon atoms to which they are attached to form a 5–7 membered carbocyclic or 5–7 membered heterocyclic aromatic or nonaromatic ring system, said carbocyclic or heterocyclic ring being substituted with 0–2 groups selected from $C_1$–$C_4$ alkyl, $C_1$–$C_4$ alkoxy, halo, cyano, amino, $CF_3$ and $NO_2$;

$R^{2a}$ is selected from:
H, $C_1$–$C_{10}$ alkyl, $C_2$–$C_6$ alkenyl, $C_3$–$C_{11}$ cycloalkyl, $C_3$–$C_7$ cycloalkyl($C_1$–$C_4$ alkyl), aryl, aryl($C_1$–$C_4$ alkyl)-, ($C_2$–$C_7$ alkyl)carbonyl, arylcarbonyl, ($C_2$–$C_{10}$ alkoxy)carbonyl, $C_3$–$C_7$ cycloalkoxycarbonyl, $C_7$–$C_{11}$ bicycloalkoxycarbonyl, aryloxycarbonyl, aryl($C_1$–$C_{10}$ alkoxy)carbonyl, $C_1$–$C_6$ alkylcarbonyloxy ($C_1$–$C_4$ alkoxy)carbonyl, arylcarbonyloxy($C_1$–$C_4$ alkoxy)carbonyl, and $C_3$–$C_7$ cycloalkylcarbonyloxy ($C_1$–$C_4$ alkoxy)carbonyl;

$R^4$ is selected from:
H, $C_1$–$C_4$ alkyl, $C_3$–$C_7$ cycloalkyl, $C_3$–$C_7$ cycloalkyl ($C_1$–$C_4$ alkyl)-, aryl, heteroaryl, aryl($C_1$–$C_4$ alkyl)-, and heteroaryl($C_1$–$C_4$ alkyl)-, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$, $R^6$ is selected from:
H, $C_1$–$C_4$ alkyl, hydroxy, $C_1$–$C_4$ alkoxy, nitro, $C_1$–$C_4$ alkylcarbonyl, —$N(R^{11})R^{12}$, cyano, halo, $CF_3$, CHO, $CO_2R^{18b}$, $C(=O)$ $R^{18b}$, $CONR^{17}R^{18b}$, $OC(=O)$ $R^{10}$, $OR^{10}$, $OC(=O)NR^{10}R^{11}$, $NR^{10}C$ $(=O)R^{10}$, $NR^{10}C(=O)OR^{21}$, $NR^{10}C(=O)$ $NR^{10}R^{11}$, $NR^{10}SO_2NR^{10}R^{11}$, $NR^{10}SO_2R^{21}$, $S(O)_pR^{11}$, $SO_2NR^{10}R^{11}$, aryl substituted with 0–3 groups selected from halogen, $C_1$–$C_4$ alkoxy, $C_1$–$C_4$ alkyl, $CF_3$, $S(O)_m$Me, and —$NMe_2$, aryl($C_1$–$C_4$ alkyl)-, said aryl being substituted with 0–3 groups selected from halogen, $C_1$–$C_4$ alkoxy, $C_1$–$C_4$ alkyl, $CF_3$, $S(O)_p$Me, and —$NMe_2$, and a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$;

$R^7$ is selected from:
H, hydroxy, $C_1$–$C_4$ alkyl, $C_1$–$C_4$ alkoxy, aryl, aryl ($C_1$–$C_4$ alkyl)-, ($C_1$–$C_4$ alkyl)carbonyl, $CO_2R^{18a}$, $SO_2R^{11}$, $SO_2NR^{10}R^{11}$, $OR^{10}$, and $N(R^{11})R^{12}$;

U is selected from:
—$(CH_2)_n$—, —$NH(CH_2)_n$—, —$N(R^{10})C(=O)$—, and —$NHC(=O)(CH_2)_n$;

G is $CR^{19}$;

$R^8$ is H;

$R^9$ is selected from:
H, nitro, $N(R^{11})R^{12}$, $OC(=O)R^{10}$, $OR^{10}$, $OC(=O)$ $NR^{10}R^{11}$, $NR^{10}C(=O)R^{10}$, $NR^{10}C(=O)OR^{21}$, $NR^{10}C(=O)NR^{10}R^{11}$, $NR^{10}SO_2NR^{10}R^{11}$, $NR^{10}SO_2R^{21}$, hydroxy, $OR^{22}$, —$N(R^{10})R^{11}$, —$N(R^{16})R^{17}$, aryl($C_0$–$C_4$ alkyl)carbonyl, aryl ($C_1$–$C_4$ alkyl), heteroaryl($C_1$–$C_4$ alkyl), $CONR^{18a}R^{20}$, $SO_2R^{18a}$, and $SO_2NR^{18a}R^{20}$, providing that any of the above aryl or heteroaryl groups may be unsubstituted or substituted independently with 1–2 $R^7$;

$R^{10}$ is selected from:
H, $CF_3$, $C_3$–$C_6$ alkenyl, $C_3$–$C_6$ cycloalkyl, aryl, ($C_3$–$C_6$ cycloalkyl)methyl, aryl($C_1$–$C_4$ alkyl), and $C_1$–$C_4$ alkyl substituted with 0–2 $R^6$;

$R^{11}$ is selected from:
H, hydroxy, $C_1$–$C_4$ alkyl, $C_3$–$C_6$ alkenyl, $C_3$–$C_6$ cycloalkyl, ($C_3$–$C_6$ cycloalkyl)methyl, $C_1$–$C_4$ alkoxy, benzyloxy, aryl, heteroaryl, heteroaryl ($C_1$–$C_4$ alkyl)-, aryl($C_1$–$C_4$ alkyl), adamantylmethyl, and $C_1$–$C_4$ alkyl substituted with 0–2 $R^4$;

$R^{12}$ is selected from:
H, $C_1$–$C_4$ alkyl, ($C_1$–$C_4$ alkyl)carbonyl, ($C_1$–$C_4$ alkoxy)carbonyl, phenyl($C_1$–$C_4$ alkyl)-, phenylsulfonyl, phenyloxycarbonyl, and phenyl ($C_1$–$C_4$ alkoxy)carbonyl, wherein said phenyl groups are substituted with 0–2 substituents selected from the group consisting of $C_1$–$C_4$ alkyl, $C_1$–$C_4$ alkoxy, halo, $CF_3$, and nitro;

$R^{16}$ is selected from:
—$C(=O)OR^{18a}$, —$C(=O)R^{18b}$, —$C(=O)N(R^{18b})_2$, —$SO_2R^{18a}$, and —$SO_2N(R^{18b})_2$;

$R^{17}$ is selected from:
H, $C_1$–$C_4$ alkyl, $C_3$–$C_6$ cycloalkyl, $C_3$–$C_6$ cycloalkyl ($C_1$–$C_4$ alkyl)-, aryl, aryl($C_1$–$C_6$ alkyl)-, and heteroaryl($C_1$–$C_6$ alkyl);

$R^{18a}$ is selected from:
$C_1$–$C_4$ alkyl, $C_3$–$C_6$ cycloalkyl,
aryl($C_1$–$C_4$ alkyl)-, said aryl substituted with 0–4 $R^{19}$,
heteroaryl($C_1$–$C_4$ alkyl)-, said heteroaryl substituted with 0–4 $R^{19}$,
($C_1$–$C_4$ alkyl)heteroaryl, said heteroaryl substituted with 0–4 $R^{19}$,
heteroaryl substituted with 0–4 $R^{19}$,
phenyl substituted with 0–4 $R^{19}$, and
naphthyl substituted with 0–4 $R^{19}$;

$R^{18b}$ is H or $R^{18a}$;

$R^{19}$ is selected from:
H, halogen, $CF_3$, $CO_2H$, CN, $NO_2$, —$NR^{11}R^{12}$, $OCF_3$, $C_1$–$C_6$ alkyl, $C_2$–$C_6$ alkenyl, $C_2$–$C_6$ alkynyl, $C_3$–$C_6$ cycloalkyl, $C_3$–$C_6$ cycloalkyl($C_1$–$C_4$ alkyl)-, aryl ($C_1$–$C_4$ alkyl)-, $C_1$–$C_6$ alkoxy, $C_1$–$C_4$ alkoxycarbonyl, aryl, aryl-O—, aryl-$SO_2$—, heteroaryl, and heteroaryl-$SO_2$—, wherein said aryl and heteroaryl groups are substituted with 0–4 groups selected from hydrogen, halogen, $CF_3$, $C_1$–$C_3$ alkyl, and $C_1$–$C_3$ alkoxy;

$R^{20}$ is selected from:
hydroxy, $C_1$–$C_6$ alkyloxy, $C_3$–$C_6$ cycloalkyloxy, aryloxy,
aryl($C_1$–$C_4$ alkyl)oxy,
$C_2$–$C_{10}$ alkylcarbonyloxy($C_1$–$C_2$ alkyl)oxy-,
$C_2$–$C_{10}$ alkoxycarbonyloxy($C_1$–$C_2$ alkyl)oxy-,
$C_2$–$C_{10}$ alkoxycarbonyl($C_1$–$C_2$ alkyl)oxy-,
$C_3$–$C_{10}$ cycloalkylcarbonyloxy($C_1$–$C_2$ alkyl)oxy-,
$C_3$–$C_{10}$ cycloalkoxycarbonyloxy($C_1$–$C_2$ alkyl)oxy-,
$C_3$–$C_{10}$ cycloalkoxycarbonyl($C_1$–$C_2$ alkyl)oxy-,
aryloxycarbonyl($C_1$–$C_2$ alkyl)oxy-,
aryloxycarbonyloxy($C_1$–$C_2$ alkyl)oxy-,
arylcarbonyloxy($C_1$–$C_2$ alkyl)oxy-,
$C_1$–$C_5$ alkoxy($C_1$–$C_5$ alkyl)carbonyloxy($C_1$–$C_2$ alkyl)oxy-,
(5-($C_1$–$C_5$ alkyl)-1,3-dioxa-cyclopenten-2-one-yl) methyloxy,
(5-aryl-1,3-dioxa-cyclopenten-2-one-yl)methyloxy, and
($R^{10}$)($R^{11}$)N—($C_1$–$C_{10}$ alkoxy)-;

$R^{21}$ is selected from:
$C_1$–$C_4$ alkyl, $C_2$–$C_6$ alkenyl, $C_3$–$C_6$ cycloalkyl, ($C_3$–$C_6$ cycloalkyl)methyl, aryl, aryl($C_1$–$C_4$ alkyl)-, and $C_1$–$C_{10}$ alkyl substituted with 0–2 $R^7$;

$R^{22}$ is selected from:
—C(=O)—$R^{18b}$, —C(=O)N($R^{18b}$)$_2$, —C(=O)NHSO$_2$$R^{18a}$, —C(=O)NHC(=O)$R^{18b}$, —C(=O)NHC(=O)O$R^{18a}$, and —C(=O)NHSO$_2$NH$R^{18b}$;

m is 0–2;
n is 0–4; and
p is 0–2;
with the following provisos:
(1) n and m are chosen such that the number of atoms connecting $R^1$ and —COR$^{20}$ in Formula (IV) is in the range of 10–14,
(2) at least one $R^{19}$ group cannot be H.

8. A compound of claim 6, including enantiomeric or diastereomeric forms thereof, or mixtures of enantiomeric or diastereomeric forms thereof, or pharmaceutically acceptable salt forms thereof selected from the group consisting of:

3-[7-[(imidazolin-2-ylamino)methyl]-1-methyl-6,8-difluoroquinoline-4-one-3-ylcarbonylamino]-2-(3,5-dimethylisoxazol-4-ylsulfonylamino)propionic acid, 3-[7-[(imidazolin-2-ylamino)methyl]-1-methyl-6,8-difluoroquinoline-4-one-3-ylcarbonylamino]-2-(benzyloxycarbonylamino)propionic acid, 3-[7-[(imidazolin-2-ylamino)methyl]-1-methyl-6,8-difluoroquinoline-4-one-3-ylcarbonylamino]-2-(n-butyloxycarbonylamino)propionic acid, 3-[7-[(imidazolin-2-ylamino)methyl]-1-methyl-6,8-difluoroquinoline-4-one-3-ylcarbonylamino]-2-(n-butylsulfonylamino)propionic acid, 3-[7-[(tetrahydropyrimid-2-ylamino)methyl]-1-methyl-6,8-difluoroquinoline-4-one-3-ylcarbonylamino]-2-(benzyloxycarbonylamino)propionic acid, 3-[7-[(tetrahydropyrimid-2-ylamino)methyl]-1-methyl-6,8-difluoroquinoline-4-one-3-ylcarbonylamino]-2-(n-butyloxycarbonylamino)propionic acid, 3-[7-[(tetrahydropyrimid-2-ylamino)methyl]-1-methyl-6,8-difluoroquinoline-4-one-3-ylcarbonylamino]-2-(phenylsulfonylamino)propionic acid, 3-[7-[(tetrahydropyrimid-2-ylamino)methyl]-1-methyl-6,8-difluoroquinoline-4-one-3-ylcarbonylamino]-2-(n-butylsulfonyl)aminopropionic acid, 3-[7-[(2-aminothiazol-4-yl)methyl]-1-methyl-6,8-difluoroquinoline-4-one-3-ylcarbonylamino]-2-(benzyloxycarbonylamino)propionic acid, 3-[7-[(imidazolin-2-ylamino)methyl]-1-methyl-6,8-difluoroquinoline-4-one-3-ylcarbonylamino]-2-((2,4,6-trimethylphenyl)sulfonylamino)propionic acid, 3-[7-[(tetrahydropyrimid-2-ylamino)methyl]-1-methyl-6,8-difluoroquinoline-4-one-3-ylcarbonylamino]-2-((2,4,6-trimethylphenyl)sulfonylamino)propionic acid, 3-[7-[(imidazol-2-ylamino)methyl]-1-methyl-6,8-difluoroquinoline-4-one-3-ylcarbonylamino]-2-( 3,5-dimethylisoxazol-4-ylsulfonylamino)propionic acid, 3-[7-[(imidazol-2-ylamino)methyl]-1-methyl-6,8-difluoroquinoline-4-one-3-ylcarbonylamino]-2-(benzyloxycarbonylamino)propionic acid, 3-[7-[(imidazol-2-ylamino)methyl]-1-methyl-6,8-difluoroquinoline-4-one-3-ylcarbonylamino]-2-((2,4,6-trimethylphenyl)sulfonylamino)propionic acid, 3-[7-[(imidazol-2-ylamino)methyl]-1-methyl-6,8-difluoroquinoline-4-one-3-ylcarbonylamino]-2-((4-biphenyl)sulfonylamino)propionic acid, 3-[7-[(imidazol-2-ylamino)methyl]-1-methyl-6,8-difluoroquinoline-4-one-3-ylcarbonylamino]-2-(1-naphthylsulfonylamino)propionic acid, 3-[7-[(benzimidazol-2-ylamino)methyl]-1-methyl-6,8-difluoroquinoline-4-one-3-ylcarbonylamino]-2-((2,4,6-trimethylphenyl)sulfonylamino)propionic acid, 3-[7-[(4-methylimidazol-2-ylamino)methyl]-1-methyl-6,8-difluoroquinoline-4-one-3-ylcarbonylamino]-2-((2,4,6-trimethylphenyl)sulfonylamino)propionic acid, 3-[7-[(4,5-dimethylimidazol-2-ylamino)methyl]-1-methyl-6,8-difluoroquinoline-4-one-3-ylcarbonylamino]-2-((2,4,6-trimethylphenyl)sulfonylamino)propionic acid, 3-[7-[(4,5,6,7-tetrahydrobenzimidazol-2-ylamino)methyl]-1-methyl-6,8-difluoroquinoline-4-one-3-ylcarbonylamino]-2-((2,4,6-trimethylphenyl) sulfonylamino)propionic acid, 3-[7-[(pyridin-2-ylamino)methyl]-1-methyl-6,8-difluoroquinoline-4-one-3-ylcarbonylamino]-2-((2,4,6-trimethylphenyl)sulfonylamino)propionic acid, 3-[7-(2-aminopyridin-6-yl)-1-methyl-6,8-difluoroquinoline-4-one-3-ylcarbonylamino]-2 -((2,4,6-trimethylphenyl)sulfonylamino)propionic acid, 3-[7-[(7-azabenzimidazol-2-yl)methyl]-1-methyl-6,8-difluoroquinoline-4-one-3-ylcarbonylamino]-2-((2,4,6-trimethylphenyl)sulfonylamino)propionic acid, 3-[7-[(benzimidazol-2-ylamino)methyl]-1-(2-phenylethyl)-6,8-difluoroquinoline-4-one-3-ylcarbonylamino] propionic acid, 3-[7-[(pyridin-2-ylamino)methyl]-1-(2-phenylethyl)-6,8-difluoroquinoline-4-one-3-ylcarbonylamino]propionic acid, 3-[7-[(imidazolin-2-ylamino)methyl]-1-(2-phenylethyl)-6,8-difluoroquinoline-4-one-3-ylcarbonylamino]propionic acid, 3-[7-[(imidazol-2-ylamino)methyl]-1-(2-phenylethyl)-6,8-difluoroquinoline-4-one-3-ylcarbonylamino]propionic acid, 3-[7-[(imidazolin-2-ylamino)methyl]-1-(2-phenylethyl)-6,8-difluoroquinoline-4-one-3-ylcarbonylamino]-2-(benzyloxycarbonylamino)propionic acid, 3-[7-[(imidazolin-2-ylamino)methyl]-1-(2-phenylethyl)-6,8-difluoroquinoline-4-one-3-ylcarbonylamino]-2-(n-butyloxycarbonylamino)propionic acid, 3-[7-[(imidazolin-2-ylamino)methyl]-1-(2-phenylethyl)-6,8-difluoroquinoline-4-one-3-ylcarbonylamino]-2-(phenylsulfonylamino)propionic acid, 3-[7-[(imidazolin-2-ylamino)methyl]-1-(2-phenylethyl)-6,8-difluoroquinoline-4-one-3-ylcarbonylamino]-2-(n-butylsulfonylamino)propionic acid, 3-[7-[(tetrahydropyrimid-2-ylamino)methyl]-1-(2-phenylethyl)-6,8-difluoroquinoline-4-one-3-ylcarbonylamino]-2-(benzyloxycarbonylamino)propionic acid, 3-[7-[(tetrahydropyrimid-2-ylamino)methyl]-1-(2-phenylethyl)-6,8-difluoroquinoline-4-one-3-ylcarbonylamino]-2-(n-butyloxycarbonylamino)propionic acid, 3-[7-[(tetrahydropyrimid-2-ylamino)methyl]-1-(2-phenylethyl)-6,8-difluoroquinoline-4-one-3-ylcarbonylamino]-2-(phenylsulfonylamino)propionic acid, 3-[7-[(tetrahydropyrimid-2-ylamino)methyl]-1-(2-phenylethyl)-6,8-difluoroquinoline-4-one-3-ylcarbonylamino]-2-(n-butylsulfonyl)aminopropionic acid, 3-[7-[(2-aminothiazol-4-yl)methyl]-1-(2-phenylethyl)-6,8-difluoroquinoline-4-one-3-ylcarbonylamino]-2-(phenylsulfonylamino)propionic acid, 3-[7-[(2-aminothiazol-4-yl)methyl]-1-(2-phenylethyl)-6,8-difluoroquinoline-4-one-3-ylcarbonylamino]-2-(benzyloxycarbonylamino)propionic acid, 3-[7-[(imidazolin-2-ylamino)methyl]-1-(2-phenylethyl)-6,8-difluoroquinoline-4-one-3-ylcarbonylamino]-2-((2,4,6-trimethylphenyl)sulfonylamino)propionic acid, 3-[7-[(tetrahydropyrimid-2-ylamino)methyl]-1-(2-phenylethyl)-6,8-difluoroquinoline-4-one-3-ylcarbonylamino]-2-((2,4,6-trimethylphenyl)sulfonylamino)propionic acid, 3-[7-[(imidazol-2-ylamino)methyl]-1-(2-phenylethyl)-6,8-difluoroquinoline-4-one-3-ylcarbonylamino]-2-(benzyloxycarbonylamino)propionic acid, 3-[7-[(imidazol-2-ylamino)methyl]-1-(2-phenylethyl)-6,8-difluoroquinoline-4-one-3-ylcarbonylamino]-2-(phenylsulfonylamino)propionic acid, 3-[7-[(imidazol-2-ylamino)methyl]-1-(2-phenylethyl)-6,8-difluoroquinoline-4-one-3-ylcarbonylamino]-2-((2,6-dichlorophenyl)sulfonylamino)propionic acid, 3-[7-[(imidazol-2-ylamino)methyl]-1-(2-phenylethyl)-6,8-difluoroquinoline-4-one-3-ylcarbonylamino]-2-((2,4,6-trimethylphenyl)sulfonylamino)propionic acid, 3-[7-[(imidazol-2-ylamino)methyl]-1-(2-phenylethyl)-6,8-difluoroquinoline-4-one-3-ylcarbonylamino]-2-((4-biphenyl)sulfonylamino)propionic acid, 3-[7-[(benzimidazol-2-ylamino)methyl]-1-(2-phenylethyl)-6,8-difluoroquinoline-4-one-3-ylcarbonylamino]-2-((2,4,6-trimethylphenyl)sulfonylamino)propionic acid, 3-[7-[(4-methylimidazol-2-ylamino)methyl]-1-(2-phenylethyl)-6,8-difluoroquinoline-4-one-3-ylcarbonylamino]-2-((2,4,6-trimethylphenyl)sulfonylamino)propionic acid, 3-[7-[(4,5-dimethylimidazol-2-ylamino)methyl]-1-(2-phenylethyl)-6,8-difluoroquinoline-4-one-3-ylcarbonylamino]-2-((2,4,6-trimethylphenyl)sulfonylamino)propionic acid, 3-[7-[(4,5,6,7-tetrahydrobenzimidazol-2-ylamino)methyl]-1-(2-phenylethyl)-6,8-difluoroquinoline-4-one-3-ylcarbonylamino]-2-((2,4,6-trimethylphenyl)sulfonylamino)propionic acid, 3-[7-[(pyridin-2-ylamino)methyl]-1-(2-phenylethyl)-6,8-difluoroquinoline-4-one-3-ylcarbonylamino]-2-((2,4,6-trimethylphenyl)sulfonylamino)propionic acid, 3-[7-(2-aminopyridin-6-yl)-1-(2-phenylethyl)-6,8-difluoroquinoline-4-one-3-ylcarbonylamino]-2-((2,4,6-trimethylphenyl)sulfonylamino)propionic acid, and 3-[7-[(7-azabenzimidazol-2-yl)methyl]-1-(2-phenylethyl)-6,8-difluoroquinoline-4-one-3-ylcarbonylamino]-2-((2,4,6-trimethylphenyl)sulfonylamino)propionic acid.

9. A compound of Formula IV:

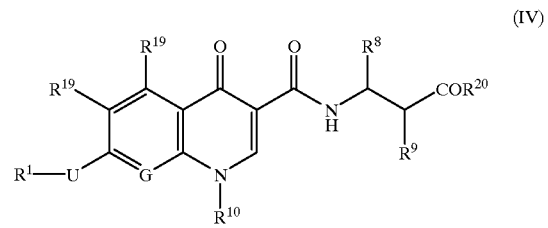

(IV)

including stereoisomeric forms thereof, or mixtures of stereoisomeric forms thereof, or pharmaceutically acceptable salt forms thereof wherein:

$R^1$ is selected from:

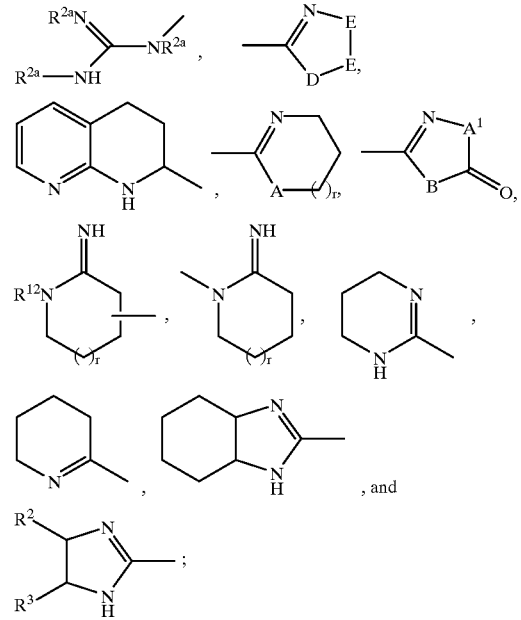

A is —$CH_2$— or —$N(R^{12})$—;

$A^1$ and B are independently —$CH_2$— or —$N(R^{10})$—;

D is —$N(R^{12})$— or —S—;

E—F is —$C(R^2)_2C(R^3)_2$— or —$CH(R^2)CH(R^3)$—;

$R^2$ and $R^3$ are independently selected from:

H, $C_1$–$C_4$ alkoxy, $NR^{11}R^{12}$, halogen, $NO_2$, CN, $CF_3$, $C_1$–$C_6$ alkyl, $C_3$–$C_6$ alkenyl, $C_3$–$C_7$ cycloalkyl, $C_3$–$C_7$ cycloalkyl($C_1$–$C_4$ alkyl), aryl($C_1$–$C_6$ alkyl)-, ($C_1$–$C_6$ alkyl)carbonyl, ($C_1$–$C_6$ alkoxy)carbonyl, arylcarbonyl, and aryl substituted with 0–4 $R^7$, alternatively, when $R^2$ and $R^3$ are substituents on adjacent atoms, they can be taken together with the carbon atoms to which they are attached to form a 5–7 membered carbocyclic or 5–7 membered heterocyclic aromatic or nonaromatic ring system, said carbocyclic or heterocyclic ring being substituted with 0–2 groups selected from $C_1$–$C_4$ alkyl, $C_1$–$C_4$ alkoxy, halo, cyano, amino, $CF_3$ and $NO_2$;

$R^{2a}$ is selected from:
  H, $C_1$–$C_{10}$ alkyl, $C_2$–$C_6$ alkenyl, $C_3$–$C_{11}$ cycloalkyl, $C_3$–$C_7$ cycloalkyl($C_1$–$C_4$ alkyl), aryl, aryl($C_1$–$C_4$ alkyl)-, ($C_2$–$C_7$ alkyl)carbonyl, arylcarbonyl, ($C_2$–$C_{10}$ alkoxy)carbonyl, $C_3$–$C_7$ cycloalkoxycarbonyl, $C_7$–$C_{11}$ bicycloalkoxycarbonyl, aryloxycarbonyl, aryl($C_1$–$C_{10}$ alkoxy)carbonyl, $C_1$–$C_6$ alkylcarbonyloxy ($C_1$–$C_4$ alkoxy)carbonyl, arylcarbonyloxy($C_1$–$C_4$ alkoxy)carbonyl, and $C_3$–$C_7$ cycloalkylcarbonyloxy ($C_1$–$C_4$ alkoxy)carbonyl;

$R^4$ is selected from:
  H, $C_1$–$C_6$ alkyl, $C_3$–$C_7$ cycloalkyl, $C_3$–$C_7$ cycloalkyl($C_1$–$C_4$ alkyl)-, aryl, heteroaryl, aryl($C_1$–$C_6$ alkyl)-, and heteroaryl($C_1$–$C_6$ alkyl)-, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

$R^6$ is selected from:
  H, $C_1$–$C_{10}$ alkyl, hydroxy, $C_1$–$C_{10}$ alkoxy, nitro, $C_1$–$C_{10}$ alkylcarbonyl, —$N(R^{11})R^{12}$, cyano, halo, $CF_3$, CHO, $CO_2R^{18b}$, $C(=O)R^{18b}$, $CONR^{17}R^{18b}$, $OC(=O)R^{10}$, $OR^{10}$, $OC(=O)NR^{10}R^{11}$, $NR^{10}C(=O)R^{10}$, $NR^{10}C(=O)OR^{21}$, $NR^{10}C(=O)NR^{10}R^{11}$, $NR^{10}SO_2NR^{10}R^{11}$, $NR^{10}SO_2R^{21}$, $S(O)_pR^{11}$, $SO_2NR^{10}R^{11}$,
  aryl substituted with 0–3 groups selected from halogen, $C_1$–$C_6$ alkoxy, $C_1$–$C_6$ alkyl, $CF_3$, $S(O)_m$Me, and —$NMe_2$,
  aryl($C_1$–$C_4$ alkyl)-, said aryl being substituted with 0–3 groups selected from halogen, $C_1$–$C_6$ alkoxy, $C_1$–$C_6$ alkyl, $CF_3$, $S(O)_p$Me, and —$NMe_2$, and
  a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$;

$R^7$ is selected from:
  H, hydroxy, $C_1$–$C_4$ alkyl, $C_1$–$C_4$ alkoxy, aryl, aryl($C_1$–$C_4$ alkyl)-, ($C_1$–$C_4$ alkyl)carbonyl, $CO_2R^{18a}$, $SO_2R^{11}$, $SO_2NR^{10}R^{11}$, $OR^{10}$, and $N(R^{11})R^{12}$;

U is selected from:
  —$(CH_2)_n$—, —$(CH_2)_nO(CH_2)_m$—, —$NH(CH_2)_n$—, —$N(R^{10})C(=O)$—, —$NHC(=O)(CH_2)_n$—, and —$C(=O)N(R^{10})$—;

G is $CR^{19}$;

$R^8$ is selected from:
  H, $CO_2R^{18b}$, $C(=O)R^{18b}$, $CONR^{17}R^{18b}$,
  $C_1$–$C_{10}$ alkyl substituted with 0–1 $R^6$,
  $C_2$–$C_{10}$ alkenyl substituted with 0–1 $R^6$,
  $C_2$–$C_{10}$ alkynyl substituted with 0–1 $R^6$,
  $C_3$–$C_8$ cycloalkyl substituted with 0–1 $R^6$,
  $C_5$–$C_6$ cycloalkenyl substituted with 0–1 $R^6$,
  ($C_1$–$C_{10}$ alkyl)carbonyl,
  $C_3$–$C_{10}$ cycloalkyl($C_1$–$C_4$ alkyl)-,
  phenyl substituted with 0–3 $R^6$,
  naphthyl substituted with 0–3 $R^6$,
  a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$;

$R^9$ is selected from:
  $C_1$–$C_{10}$ alkyl substituted with 0–1 $R^6$,
  $C_1$–$C_{10}$ alkoxy substituted with 0–2 $R^7$,
  H, nitro, $N(R^{11})R^{12}$, $OC(=O)R^{10}$, $OR^{10}$, $OC(=O)NR^{10}R^{11}$, $NR^{10}C(=O)R^{10}$, $NR^{10}C(=O)OR^{21}$, $NR^{10}C(=O)NR^{10}R^{11}$, $NR^{10}SO_2NR^{10}R^{11}$, $NR^{10}SO_2R^{21}$, hydroxy, $OR^{22}$, —$N(R^{10})R^{11}$, —$N(R^{16})R^{17}$, aryl($C_0$–$C_6$ alkyl)carbonyl, aryl ($C_1$–$C_6$ alkyl), heteroaryl($C_1$–$C_6$ alkyl), $CONR^{18a}R^{20}$, $SO_2R^{18a}$, and $SO_2NR^{18a}R^{20}$,
  providing that any of the above alkyl, aryl or heteroaryl groups may be unsubstituted or substituted independently with 1–2 $R^7$;

$R^{10}$ is selected from:
  H, $CF_3$, $C_3$–$C_6$ alkenyl, $C_3$–$C_{11}$ cycloalkyl, aryl, ($C_3$–$C_{11}$ cycloalkyl)methyl, aryl($C_1$–$C_4$ alkyl), and $C_1$–$C_{10}$ alkyl substituted with 0–2 $R^6$;

$R^{11}$ is selected from:
  H, hydroxy, $C_1$–$C_8$ alkyl, $C_3$–$C_6$ alkenyl, $C_3$–$C_{11}$ cycloalkyl, ($C_3$–$C_{11}$ cycloalkyl)methyl, $C_1$–$C_6$ alkoxy, benzyloxy, aryl, heteroaryl, heteroaryl ($C_1$–$C_4$ alkyl)-, aryl($C_1$–$C_4$ alkyl), adamantylmethyl, and $C_1$–$C_{10}$ alkyl substituted with 0–2 $R^4$;
  alternatively, when $R^{10}$ and $R^{11}$ are both substituents on the same nitrogen atom (as in —$NR^{10}R^{11}$) they may be taken together with the nitrogen atom to which they are attached to form a heterocycle selected from:
    3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl, and 1-piperazinyl;
    said heterocycle being substituted with 0–3 groups selected from: $C_1$–$C_6$ alkyl, aryl, heteroaryl, aryl ($C_1$–$C_4$ alkyl)-, ($C_1$–$C_6$ alkyl)carbonyl, ($C_3$–$C_7$ cycloalkyl)carbonyl, ($C_1$–$C_6$ alkoxy)carbonyl, aryl($C_1$–$C_4$ alkoxy)carbonyl, $C_1$–$C_6$ alkylsulfonyl, and arylsulfonyl;

$R^{12}$ is selected from:
  H, $C_1$–$C_6$ alkyl, triphenylmethyl, methoxymethyl, methoxyphenyldiphenylmethyl, trimethylsilylethoxymethyl, ($C_1$–$C_6$ alkyl)carbonyl, ($C_1$–$C_6$ alkoxy)carbonyl, ($C_1$–$C_6$ alkyl) aminocarbonyl, $C_3$–$C_6$ alkenyl, $C_3$–$C_7$ cycloalkyl, $C_3$–$C_7$ cycloalkyl($C_1$–$C_4$ alkyl)-, aryl, heteroaryl ($C_1$–$C_6$ alkyl)carbonyl, heteroarylcarbonyl, aryl ($C_1$–$C_6$ alkyl)-, ($C_1$–$C_6$ alkyl)carbonyl, arylcarbonyl, $C_1$–$C_6$ alkylsulfonyl, arylsulfonyl, aryl($C_1$–$C_6$ alkyl) sulfonyl, heteroarylsulfonyl, heteroaryl($C_1$–$C_6$ alkyl)sulfonyl, aryloxycarbonyl, and aryl($C_1$–$C_6$ alkoxy)carbonyl, wherein said aryl groups are substituted with 0–2 substituents selected from the group consisting of $C_1$–$C_4$ alkyl, $C_1$–$C_4$ alkoxy, halo, $CF_3$, and nitro;

$R^{16}$ is selected from:
  —$C(=O)OR^{18a}$, —$C(=O)R^{18b}$, —$C(=O)N(R^{18b})_2$, —$C(=O)NHSO_2R^{18a}$, —$C(=O)NHC(=O)R^{18b}$, —$C(=O)NHC(=O)OR^{18a}$, —$C(=O)NHSO_2NHR^{18b}$, —$SO_2R^{18a}$, —$SO_2N(R^{18b})_2$, and —$SO_2NHC(=O)OR^{18b}$;

$R^{17}$ is selected from:
  H, $C_1$–$C_6$ alkyl, $C_3$–$C_7$ cycloalkyl, $C_3$–$C_7$ cycloalkyl ($C_1$–$C_4$ alkyl)-, aryl, aryl($C_1$–$C_6$ alkyl)-, and heteroaryl($C_1$–$C_6$ alkyl);

$R^{18a}$ is selected from:
  $C_1$–$C_8$ alkyl, $C_3$–$C_{11}$ cycloalkyl,
  aryl($C_1$–$C_6$ alkyl)-, said aryl substituted with 0–4 $R^{19}$,
  heteroaryl($C_1$–$C_6$ alkyl)-, said heteroaryl substituted with 0–4 $R^{19}$, ($C_1$–$C_6$ alkyl)heteroaryl, said heteroaryl substituted with 0–4 $R^{19}$,
heteroaryl substituted with 0–4 $R^{19}$,
phenyl substituted with 0–4 $R^{19}$, and
naphthyl substituted with 0–4 $R^{19}$;

$R^{18b}$ is H or $R^{18a}$;

$R^{19}$ is selected from:
H, halogen, $CF_3$, $CO_2H$, CN, $NO_2$, —$NR^{11}R^{12}$, $OCF_3$, $C_1$–$C_8$ alkyl, $C_2$–$C_6$ alkenyl, $C_2$–$C_6$ alkynyl, $C_3$–$C_{11}$ cycloalkyl, $C_3$–$C_7$ cycloalkyl($C_1$–$C_4$ alkyl)-, aryl ($C_1$–$C_6$ alkyl)-, $C_1$–$C_6$ alkoxy, $C_1$–$C_4$ alkoxycarbonyl, aryl, aryl-O—, aryl-$SO_2$—, heteroaryl, and heteroaryl-$SO_2$—, wherein said aryl and heteroaryl groups are substituted with 0–4 groups selected from hydrogen, halogen, $CF_3$, $C_1$–$C_3$ alkyl, and $C_1$–$C_3$ alkoxy;

$R^{20}$ is selected from:
hydroxy, $C_1$–$C_{10}$ alkyloxy, $C_3$–$C_{11}$ cycloalkyloxy, aryloxy, aryl($C_1$–$C_4$ alkyl)oxy,
$C_2$–$C_{10}$ alkylcarbonyloxy($C_1$–$C_2$ alkyl)oxy-,
$C_2$–$C_{10}$ alkoxycarbonyloxy($C_1$–$C_2$ alkyl)oxy-,
$C_2$–$C_{10}$ alkoxycarbonyl($C_1$–$C_2$ alkyl)oxy-,
$C_3$–$C_{10}$ cycloalkylcarbonyloxy($C_1$–$C_2$ alkyl)oxy-,
$C_3$–$C_{10}$ cycloalkoxycarbonyloxy($C_1$–$C_2$ alkyl)oxy-,
$C_3$–$C_{10}$ cycloalkoxycarbonyl($C_1$–$C_2$ alkyl)oxy-,
aryloxycarbonyl($C_1$–$C_2$ alkyl)oxy-,
aryloxycarbonyloxy($C_1$–$C_2$ alkyl)oxy-,
arylcarbonyloxy($C_1$–$C_2$ alkyl)oxy-,
$C_1$–$C_5$ alkoxy($C_1$–$C_5$ alkyl)carbonyloxy($C_1$–$C_2$ alkyl)oxy-,
(5-($C_1$–$C_5$ alkyl)-1,3-dioxa-cyclopenten-2-one-yl)methyloxy,
(5-aryl-1,3-dioxa-cyclopenten-2-one-yl)methyloxy, and
($R^{10}$)($R^{11}$)N—($C_1$–$C_{10}$ alkoxy)-;

$R^{21}$ is selected from:
$C_1$–$C_8$ alkyl, $C_2$–$C_6$ alkenyl, $C_3$–$C_{11}$ cycloalkyl, ($C_3$–$C_{11}$ cycloalkyl)methyl, aryl, aryl($C_1$–$C_4$ alkyl)-, and $C_1$–$C_{10}$ alkyl substituted with 0–2 $R^7$;

$R^{22}$ is selected from:
—C(=O)$R^{18b}$, —C(=O)N($R^{18b}$)$_2$, —C(=O)NHSO$_2$$R^{18a}$, —C(=O)NHC(=O)$R^{18b}$, and —C(=O)NHC(=O)O$R^{18a}$;

m is 0–2;
n is 0–4;
p is 0–2; and
r is 0–2;

with the proviso that n and m are chosen such that the number of atoms connecting $R^1$ and $COR^{20}$ of Formula (IV) is in the range of 10–14.

10. A compound of claim 9 of Formula IV:

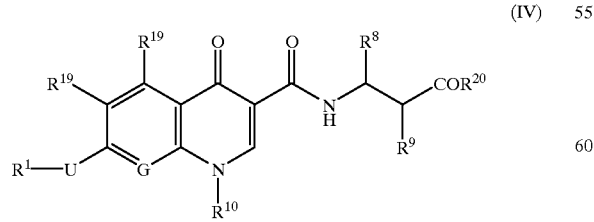

(IV)

including stereoisomeric forms thereof, or mixtures of stereoisomeric forms thereof, or pharmaceutically acceptable salt forms thereof wherein:

$R^1$ is selected from:

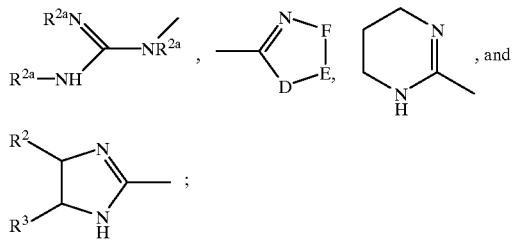

D is —N($R^{12}$)— or —S—;
E—F is —C($R^2$)$_2$C($R^3$)$_2$— or —CH($R^2$)CH($R^3$)$_2$—;
$R^2$ and $R^3$ are independently selected from:
H, $C_1$–$C_4$ alkoxy, $NR^{11}R^{12}$, halogen, $NO_2$, CN, $CF_3$, $C_1$–$C_6$ alkyl, $C_3$–$C_6$ alkenyl, $C_3$–$C_7$ cycloalkyl, $C_3$–$C_7$ cycloalkyl($C_1$–$C_4$ alkyl), aryl($C_1$–$C_6$ alkyl)-, ($C_1$–$C_6$ alkyl)carbonyl, ($C_1$–$C_6$ alkoxy)carbonyl, arylcarbonyl, and aryl substituted with 0–4 $R^7$,
alternatively, when $R^2$ and $R^3$ are substituents on adjacent atoms, they can be taken together with the carbon atoms to which they are attached to form a 5–7 membered carbocyclic or 5–7 membered heterocyclic aromatic or nonaromatic ring system, said carbocyclic or heterocyclic ring being substituted with 0–2 groups selected from $C_1$–$C_4$ alkyl, $C_1$–$C_4$ alkoxy, halo, cyano, amino, $CF_3$ and $NO_2$;

$R^{2a}$ is selected from:
H, $C_1$–$C_{10}$ alkyl, $C_2$–$C_6$ alkenyl, $C_3$–$C_{11}$ cycloalkyl, $C_3$–$C_7$ cycloalkyl($C_1$–$C_4$ alkyl), aryl, aryl($C_1$–$C_4$ alkyl)-, ($C_2$–$C_7$ alkyl)carbonyl, arylcarbonyl, ($C_2$–$C_{10}$ alkoxy)carbonyl, $C_3$–$C_7$ cycloalkoxycarbonyl, $C_7$–$C_{11}$ bicycloalkoxycarbonyl, aryloxycarbonyl, aryl ($C_1$–$C_{10}$ alkoxy)carbonyl, $C_1$–$C_6$ alkylcarbonyloxy ($C_1$–$C_4$ alkoxy)carbonyl, arylcarbonyloxy($C_1$–$C_4$ alkoxy)carbonyl, and $C_3$–$C_7$ cycloalkylcarbonyloxy ($C_1$–$C_4$ alkoxy)carbonyl;

$R^4$ is selected from:
H, $C_1$–$C_6$ alkyl, $C_3$–$C_7$ cycloalkyl, $C_3$–$C_7$ cycloalkyl ($C_1$–$C_4$ alkyl)-, aryl, heteroaryl, aryl($C_1$–$C_6$ alkyl)-, and heteroaryl($C_1$–$C_6$ alkyl)-, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

$R^6$ is selected from:
H, $C_1$–$C_{10}$ alkyl, hydroxy, $C_1$–$C_{10}$ alkoxy, nitro, $C_1$–$C_{10}$ alkylcarbonyl, —N($R^{11}$)$R^{12}$, cyano, halo, $CF_3$, CHO, $CO_2R^{18b}$, C(=O)$R^{18b}$, $CONR^{17}R^{18b}$, OC(=O)$R^{10}$, $OR^{10}$, OC(=O)$NR^{10}R^{11}$, $NR^{10}$C (=O)$R^{10}$, $N^{10}$C(=O)O$R^{21}$, $NR^{10}$C(=O)$NR^{10}R^{11}$, $NR^{10}SO_2NR^{10}R^{11}$, $NR^{10}SO_2R^{21}$, $S(O)_pR^{11}$, $SO_2NR^{10}R^{11}$,
aryl substituted with 0–3 groups selected from halogen, $C_1$–$C_6$ alkoxy, $C_1$–$C_6$ alkyl, $CF_3$, $S(O)_m$Me, and —$NMe_2$,
aryl($C_1$–$C_4$ alkyl)-, said aryl being substituted with 0–3 groups selected from halogen, $C_1$–$C_6$ alkoxy, $C_1$–$C_6$ alkyl, $CF_3$, $S(O)_p$Me, and —$NMe_2$, and
a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$;

$R^7$ is selected from:
  H, hydroxy, $C_1$–$C_4$ alkyl, $C_1$–$C_4$ alkoxy, aryl, aryl($C_1$–$C_4$ alkyl)-, ($C_1$–$C_4$ alkyl)carbonyl, $CO_2R^{18a}$, $SO_2R^{11}$, $SO_2NR^{10}R^{11}$, $OR^{10}$, and $N(R^{11})R^{12}$;

U is selected from:
  —$(CH_2)_n$—, —$(CH_2)_nO(CH_2)_m$—, —$NH(CH_2)_n$—, —$N(R^{10})C(=O)$—, —$NHC(=O)(CH_2)_n$—, and —$C(=O)N(R^{10})$—;

G is $CR^{19}$;

$R^8$ is H;

$R^9$ is selected from:
  H, nitro, $N(R^{11})R^{12}$, $OC(=O)R^{10}$, $OR^{10}$, $OC(=O)NR^{10}R^{11}$, $NR^{10}C(=O)R^{10}$, $NR^{10}C(=O)OR^{21}$, $NR^{10}C(=O)NR^{10}R^{11}$, $NR^{10}SO_2NR^{10}R^{11}$, $NR^{10}SO_2R^{21}$, hydroxy, $OR^{22}$, —$N(R^{10})R^{11}$, —$N(R^{16})R^{17}$, aryl($C_0$–$C_6$ alkyl)carbonyl, aryl($C_1$–$C_6$ alkyl), heteroaryl($C_1$–$C_6$ alkyl), $CONR^{18a}R^{20}$, $SO_2R^{18a}$, and $SO_2NR^{18a}R^{20}$,
  providing that any of the above aryl or heteroaryl groups may be unsubstituted or substituted independently with 1–2 $R^7$;

$R^{10}$ is selected from:
  H, $CF_3$, $C_3$–$C_6$ alkenyl, $C_3$–$C_{11}$ cycloalkyl, aryl, ($C_3$–$C_{11}$ cycloalkyl)methyl, aryl($C_1$–$C_4$ alkyl), and $C_1$–$C_{10}$ alkyl substituted with 0–2 $R^6$;

$R^{11}$ is selected from:
  H, hydroxy, $C_1$–$C_8$ alkyl, $C_3$–$C_6$ alkenyl, $C_3$–$C_{11}$ cycloalkyl, ($C_3$–$C_{11}$ cycloalkyl)methyl, $C_1$–$C_6$ alkoxy, benzyloxy, aryl, heteroaryl, heteroaryl($C_1$–$C_4$ alkyl)-, aryl($C_1$–$C_4$ alkyl), adamantylmethyl, and $C_1$–$C_{10}$ alkyl substituted with 0–2 $R^4$;

$R^{12}$ is selected from:
  H, $C_1$–$C_4$ alkyl, ($C_1$–$C_4$ alkyl)carbonyl, ($C_1$–$C_4$ alkoxy)carbonyl, phenyl($C_1$–$C_4$ alkyl)-, phenylsulfonyl, phenyloxycarbonyl, and phenyl($C_1$–$C_4$ alkoxy)carbonyl, wherein said phenyl groups are substituted with 0–2 substituents selected from the group consisting of $C_1$–$C_4$ alkyl, $C_1$–$C_4$ alkoxy, halo, $CF_3$, and nitro;

$R^{16}$ is selected from:
  —$C(=O)OR^{18a}$, —$C(=O)R^{18b}$, —$C(=O)N(R^{18b})_2$, —$C(=O)NHSO_2R^{18a}$, —$C(=O)NHC(=O)R^{18b}$, —$C(=O)NHC(=O)OR^{18a}$, —$C(=O)NHSO_2NHR^{18b}$, —$SO_2R^{18a}$, —$SO_2N(R^{18b})_2$, and —$SO_2NHC(=O)OR^{18b}$;

$R^{17}$ is selected from:
  H, $C_1$–$C_6$ alkyl, $C_3$–$C_7$ cycloalkyl, $C_3$–$C_7$ cycloalkyl($C_1$–$C_4$ alkyl)-, aryl, aryl($C_1$–$C_6$ alkyl)-, and heteroaryl($C_1$–$C_6$ alkyl);

$R^{18a}$ is selected from:
  $C_1$–$C_8$ alkyl, $C_3$–$C_{11}$ cycloalkyl,
  aryl($C_1$–$C_6$ alkyl)-, said aryl substituted with 0–4 $R^{19}$,
  heteroaryl($C_1$–$C_6$ alkyl)-, said heteroaryl substituted with 0–4 $R^{19}$,
  ($C_1$–$C_6$ alkyl)heteroaryl, said heteroaryl substituted with 0–4 $R^{19}$,
  heteroaryl substituted with 0–4 $R^{19}$,
  phenyl substituted with 0–4 $R^{19}$, and
  naphthyl substituted with 0–4 $R^{19}$;

$R^{18b}$ is H or $R^{18a}$;

$R^{19}$ is selected from:
  H, halogen, $CF_3$, $CO_2H$, CN, $NO_2$, —$NR^{11}R^{12}$, $OCF_3$, $C_1$–$C_8$ alkyl, $C_2$–$C_6$ alkenyl, $C_2$–$C_6$ alkynyl, $C_3$–$C_{11}$ cycloalkyl, $C_3$–$C_7$ cycloalkyl($C_1$–$C_4$ alkyl)-, aryl($C_1$–$C_6$ alkyl)-, $C_1$–$C_6$ alkoxy, $C_1$–$C_4$ alkoxycarbonyl, aryl, aryl-O—, aryl-$SO_2$—, heteroaryl, and heteroaryl-$SO_2$—, wherein said aryl and heteroaryl groups are substituted with 0–4 groups selected from hydrogen, halogen, $CF_3$, $C_1$–$C_3$ alkyl, and $C_1$–$C_3$ alkoxy;

$R^{20}$ is selected from:
  hydroxy, $C_1$–$C_{10}$ alkyloxy, $C_3$–$C_{11}$ cycloalkyloxy, aryloxy, aryl($C_1$–$C_4$ alkyl)oxy,
  $C_2$–$C_{10}$ alkylcarbonyloxy($C_1$–$C_2$ alkyl)oxy-,
  $C_2$–$C_{10}$ alkoxycarbonyloxy($C_1$–$C_2$ alkyl)oxy-,
  $C_2$–$C_{10}$ alkoxycarbonyl($C_1$–$C_2$ alkyl)oxy-,
  $C_3$–$C_{10}$ cycloalkylcarbonyloxy($C_1$–$C_2$ alkyl)oxy-,
  $C_3$–$C_{10}$ cycloalkoxycarbonyloxy($C_1$–$C_2$ alkyl)oxy-,
  $C_3$–$C_{10}$ cycloalkoxycarbonyl($C_1$–$C_2$ alkyl)oxy-,
  aryloxycarbonyl($C_1$–$C_2$ alkyl)oxy-,
  aryloxycarbonyloxy($C_1$–$C_2$ alkyl)oxy-,
  arylcarbonyloxy($C_1$–$C_2$ alkyl)oxy-,
  $C_1$–$C_5$ alkoxy($C_1$–$C_5$ alkyl)carbonyloxy($C_1$–$C_2$ alkyl)oxy-,
  (5-($C_1$–$C_5$ alkyl)-1,3-dioxa-cyclopenten-2-one-yl)methyloxy,
  (5-aryl-1,3-dioxa-cyclopenten-2-one-yl)methyloxy, and
  $(R^{10})(R^{11})N$—$(C_1$–$C_{10}$ alkoxy)-;

$R^{21}$ is selected from:
  $C_1$–$C_8$ alkyl, $C_2$–$C_6$ alkenyl, $C_3$–$C_{11}$ cycloalkyl, ($C_3$–$C_{11}$ cycloalkyl)methyl, aryl, aryl($C_1$–$C_4$ alkyl)-, and $C_1$–$C_{10}$ alkyl substituted with 0–2 $R^7$;

$R^{22}$ is selected from:
  —$C(=O)R^{18b}$, —$C(=O)N(R^{18b})_2$, —$C(=O)NHSO_2R^{18a}$, —$C(=O)NHC(=O)R^{18b}$, and —$C(=O)NHC(=O)OR^{18a}$;

m is 0–2;

n is 0–4;

p is 0–2; and r is 0–2;

with the proviso that n and m are chosen such that the number of atoms connecting $R^1$ and $COR^{20}$ of Formula (IV) is in the range of 10–14.

11. A compound of claim 9, including enantiomeric or diastereomeric forms thereof, or mixtures of enantiomeric or diastereomeric forms thereof, or pharmaceutically acceptable salt forms thereof selected from the group consisting of:

3-[7-[(imidazolin-2-ylamino)methyl]-1-methylquinoline-4-one-3-ylcarbonylamino]-2-(3,5-dimethylisoxazol-4-ylsulfonylamino)propionic acid, 3-[7-[(imidazolin-2-ylamino)methyl]-1-methylquinoline-4-one-3-ylcarbonylamino]-2-(benzyloxycarbonylamino) propionic acid, 3-[7-[(imidazolin-2-ylamino)methyl]-1-methylquinoline-4-one-3- ylcarbonylamino]-2-(n-butyloxycarbonylamino) propionic acid, 3-[7-[(imidazolin-2-ylamino)methyl]-1-methylquinoline-4-one-3-ylcarbonylamino]-2-(n-butylsulfonylamino) propionic acid, 3-[7-[(imidazolin-2-ylamino)methyl]-1-methylquinoline-4-one-3-ylcarbonylamino]-2-((2,4,6-trimethylphenyl)sulfonylamino)propionic acid, 3-[7-[(imidazolin-2-ylamino)methyl]-1-(2-phenylethyl) quinoline-4-one-3-ylcarbonylamino]-2-(benzyloxycarbonylamino)propionic acid, 3-[7-[(imidazolin-2-ylamino)methyl]-1-(2-phenylethyl) quinoline-4-one-3-ylcarbonylamino]-2-(n-butyloxycarbonyl-amino)propionic acid, 3-[7-[(imidazolin-2-ylamino)methyl]-1-(2-phenylethyl) quinoline-4-one-3-ylcarbonylamino]-2-(phenylsulfonylamino)propionic acid, 3-[7-[(imidazolin-2-ylamino)methyl]-1-(2-phenylethyl) quinoline-4-one-3-ylcarbonylamino]-2-(n-butylsulfonylamino)propionic acid, 3-[7-[(imidazolin-2-ylamino)methyl]-1-(2-phenylethyl) quinoline-4-one-3-ylcarbonylamino]-2-((2,4,6-trimethylphenyl)sulfonylamino)propionic acid, 3-[7-[(tetrahydropyrimid-2-ylamino)methyl]-1-methylquinoline-4-one-3-ylcarbonylamino]-2-(benzyloxycarbonylamino)propionic acid, 3-[7-[(tetrahydropyrimid-2-ylamino)methyl]-1-(2-phenylethyl)quinoline-4-one-3-ylcarbonylamino]-2-(n-butyloxycarbonylamino)propionic acid, 3-[7-[(tetrahydropyrimid-2-ylamino)methyl]-1-(2-phenylethyl)quinoline-4-one-3-ylcarbonylamino]-2-(phenylsulfonylamino)propionic acid, 3-[7-[(tetrahydropyrimid-2-ylamino)methyl]-1-methylquinoline-4-one-3-ylcarbonylamino]-2-(n-butylsulfonyl)aminopropionic acid, 3-[7-[(tetrahydropyrimid-2-ylamino)methyl]-1-methylquinoline-4-one-3-ylcarbonylamino]-2-((2,4,6-trimethylphenyl)sulfonylamino)propionic acid, 3-[7-[(tetrahydropyrimid-2-ylamino)methyl]-1-(2-phenylethyl)quinoline-4-one-3-ylcarbonylamino]-2-(benzyloxycarbonylamino)propionic acid, 3-[7-[(tetrahydropyrimid-2-ylamino)methyl]-1-(2-phenylethyl)quinoline-4-one-3-ylcarbonylamino]-2-(n-butyloxycarbonylamino)propionic acid, 3-[7-[(tetrahydropyrimid-2-ylamino)methyl]-1-(2-phenylethyl)quinoline-4-one-3-ylcarbonylamino]-2-(phenylsulfonylamino)propionic acid, 3-[7-[(tetrahydropyrimid-2-ylamino)methyl]-1-(2-phenylethyl)quinoline-4-one-3-ylcarbonylamino]-2-(n-butylsulfonylamino)propionic acid, 3-[7-[(tetrahydropyrimid-2-ylamino)methyl]-1-(2-phenylethyl)quinoline-4-one-3-ylcarbonylamino]-2-((2,4,6-trimethylphenyl)sulfonylamino)propionic acid 3-[7-[(imidazolin-2-ylamino)methyl]-1-methyl-6,8-difluoroquinoline-4-one-3-ylcarbonylamino]-2-(benzyloxycarbonylamino)propionic acid, 3-[7-[(imidazolin-2-ylamino)methyl]-1-methyl-6,8-difluoroquinoline-4-one-3-ylcarbonylamino]-2-(n-butyloxycarbonylamino)propionic acid, 3-[7-[(imidazolin-2-ylamino)methyl]-1-methyl-6,8-difluoroquinoline-4-one-3-ylcarbonylamino]-2-(n-butylsulfonylamino)propionic acid, 3-[7-[(imidazolin-2-ylamino)methyl]-1-methyl-6,8-difluoroquinoline-4-one-3-ylcarbonylamino]-2-((2,4,6-trimethylphenyl)sulfonylamino)propionic acid, 3-[7-[(imidazolin-2-ylamino)methyl]-1-(2-phenylethyl)-6,8-difluoroquinoline-4-one-3-ylcarbonylamino]-2-(benzyloxycarbonylamino)propionic acid, 3-[7-[(imidazolin-2-ylamino)methyl]-1-(2-phenylethyl)-6,8-difluoroquinoline-4-one-3-ylcarbonylamino]-2-(n-butyloxycarbonylamino)propionic acid, 3-[7-[(imidazolin-2-ylamino)methyl]-1-(2-phenylethyl)-6,8-difluoroquinoline-4-one-3-ylcarbonylamino]-2-(phenylsulfonylamino)propionic acid, 3-[7-[(imidazolin-2-ylamino)methyl]-1-(2-phenylethyl)-6,8-difluoroquinoline-4-one-3-ylcarbonylamino]-2-(n-butylsulfonylamino)propionic acid, 3-[7-[(imidazolin-2-ylamino)methyl]-1-(2-phenylethyl)-6,8-difluoroquinoline-4-one-3-ylcarbonylamino]-2-((2,4,6-trimethylphenyl)sulfonylamino)propionic acid, 3-[7-[(tetrahydropyrimid-2-ylamino)methyl]-1-methyl-6,8-difluoroquinoline-4-one-3-ylcarbonylamino]-2-(benzyloxycarbonylamino)propionic acid, 3-[7-[(tetrahydropyrimid-2-ylamino)methyl]-1-(2-phenylethyl)-6,8-difluoroquinoline-4-one-3-ylcarbonylamino]-2-(n-butyloxycarbonylamino)propionic acid, 3-[7-[(tetrahydropyrimid-2-ylamino)methyl]-1-(2-phenylethyl)-6,8-difluoroquinoline-4-one-3-ylcarbonylamino]-2-(phenylsulfonylamino)propionic acid, 3-[7-[(tetrahydropyrimid-2-ylamino)methyl]-1-methylquinoline-4-one-3-ylcarbonylamino]-2-(n-butylsulfonyl)aminopropionic acid, 3-[7-[(tetrahydropyrimid-2-ylamino)methyl]-1-methyl-6,8-difluoroquinoline-4-one-3-ylcarbonylamino]-2-((2,4,6-trimethylphenyl)sulfonylamino)propionic acid, 3-[7-[(tetrahydropyrimid-2-ylamino)methyl]-1-(2-phenylethyl)-6,8-difluoroquinoline-4-one-3-ylcarbonylamino]-2-(benzyloxycarbonylamino)propionic acid, 3-[7-[(tetrahydropyrimid-2-ylamino)methyl]-1-(2-phenylethyl)-6,8-difluoroquinoline-4-one-3-ylcarbonylamino]-2-(n-butyloxycarbonylamino)propionic acid, 3-[7-[(tetrahydropyrimid-2-ylamino)methyl]-1-(2-phenylethyl)-6,8-difluoroquinoline-4-one-3-ylcarbonylamino]-2-(phenylsulfonylamino)propionic acid, 3-[7-[(tetrahydropyrimid-2-ylamino)methyl]-1-(2-phenylethyl)-6,8-difluoroquinoline-4-one-3-ylcarbonylamino]-2-(n-butylsulfonylamino)propionic acid, and 3-[7-[(tetrahydropyrimid-2-ylamino)methyl]-1-(2-phenylethyl)-6,8-difluoroquinoline-4-one-3-ylcarbonylamino]-2-((2,4,6-trimethylphenyl) sulfonylamino)propionic acid.

12. A compound of Formula I:

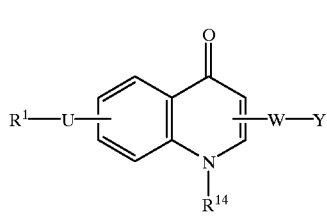

(I)

including stereoisomeric forms thereof, or mixtures of stereoisomeric forms thereof, or pharmaceutically acceptable salt forms thereof wherein:

$R^1$ is selected from:

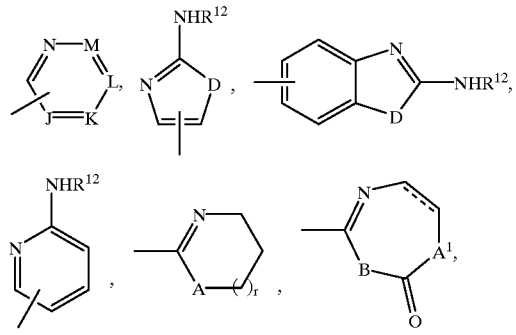

-continued

[chemical structures]

A is —$CH_2$— or —N($R^{12}$)—;
$A^1$ and B are independently —$CH_2$— or —N($R^{10}$)—;
D is —N($R^{12}$)— or —S—;
E—F is —C($R^2$)=C($R^3$)— or —C($R^2$)$_2$C($R^3$)$_2$—;
J is —C($R^2$)— or —N—;
K, L and M are independently —C($R^2$)— or —($R^3$)—;
$R^2$ and $R^3$ are independently selected from:
 H, $C_1$–$C_4$ alkoxy, $NR^{11}R^{12}$, halogen, $NO_2$, CN, $CF_3$, $C_1$–$C_6$ alkyl, $C_3$–$C_6$ alkenyl, $C_3$–$C_7$ cycloalkyl, $C_3$–$C_7$ cycloalkyl($C_1$–$C_4$ alkyl), aryl($C_1$–$C_6$ alkyl)-, ($C_1$–$C_6$ alkyl)carbonyl, ($C_1$–$C_6$ alkoxy)carbonyl, arylcarbonyl, and aryl substituted with 0–4 $R^7$,
 alternatively, when $R^2$ and $R^3$ are substituents on adjacent atoms, they can be taken together with the carbon atoms to which they are attached to form a 5–7 membered carbocyclic or 5–7 membered heterocyclic aromatic or nonaromatic ring system, said carbocyclic or heterocyclic ring being substituted with 0–2 groups selected from $C_1$–$C_4$ alkyl, $C_1$–$C_4$ alkoxy, halo, cyano, amino, $CF_3$ and $NO_2$;
$R^{2a}$ is selected from:
 H, $C_1$–$C_{10}$ alkyl, $C_2$–$C_6$ alkenyl, $C_3$–$C_{11}$ cycloalkyl, $C_3$–$C_7$ cycloalkyl($C_1$–$C_4$ alkyl), aryl, aryl($C_1$–$C_4$ alkyl)-, ($C_2$–$C_7$ alkyl)carbonyl, arylcarbonyl, ($C_2$–$C_{10}$ alkoxy)carbonyl, $C_3$–$C_7$ cycloalkoxycarbonyl, $C_7$–$C_{11}$ bicycloalkoxycarbonyl, aryloxycarbonyl, aryl ($C_1$–$C_{10}$ alkoxy)carbonyl, $C_1$–$C_6$ alkylcarbonyloxy ($C_1$–$C_4$ alkoxy)carbonyl, arylcarbonyloxy($C_1$–$C_4$ alkoxy)carbonyl, and $C_3$–$C_7$ cycloalkylcarbonyloxy ($C_1$–$C_4$ alkoxy)carbonyl;
$R^4$ is selected from:
 H, $C_1$–$C_6$ alkyl, $C_3$–$C_7$ cycloalkyl, $C_3$–$C_7$ cycloalkyl ($C_1$–$C_4$ alkyl)-, aryl, heteroaryl, aryl($C_1$–$C_6$ alkyl)-, and heteroaryl($C_1$–$C_6$ alkyl)-, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$, $R^6$ is selected from:
 H, $C_1$–$C_{10}$ alkyl, hydroxy, $C_1$–$C_{10}$ alkoxy, nitro, $C_1$–$C_{10}$ alkylcarbonyl, —N($R^{11}$)$R^{12}$, cyano, halo, $CF_3$, CHO, $CO_2R^{18b}$, C(=O)$R^{18b}$, $CONR^{17}R^{18b}$, OC(=O)$R^{10}$, $OR^{10}$, OC(=O)$NR^{10}R^{11}$, $NR^{10}$C (=O)$R^{10}$, $NR^{10}$C(=O)O$R^{21}$, $NR^{10}$C(=O) $NR^{10}R^{11}$, $NR^{10}SO_2NR^{10}R^{11}$, $NR^{10}SO_2R^{21}$, S(O)$_pR^{11}$, $SO_2NR^{10}R^{11}$,
 aryl substituted with 0–3 groups selected from halogen, $C_1$–$C_6$ alkoxy, $C_1$–$C_6$ alkyl, $CF_3$, $S(O)_m$Me, and —$NMe_2$,
 aryl($C_1$–$C_4$ alkyl)-, said aryl being substituted with 0–3 groups selected from halogen, $C_1$–$C_6$ alkoxy, $C_1$–$C_6$ alkyl, $CF_3$, $S(O)_p$Me, and —$NMe_2$, and
 a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$;
$R^7$ is selected from:
 H, hydroxy, $C_1$–$C_4$ alkyl, $C_1$–$C_4$ alkoxy, aryl, aryl ($C_1$–$C_4$ alkyl)-, ($C_1$–$C_4$ alkyl)carbonyl, $CO_2R^{18a}$, $SO_2R^{11}$, $SO_2NR^{10}R^{11}$, $OR^{10}$, and $N(R^{11})R^{12}$;
U is selected from:
 —($CH_2$)$_n$—, —($CH_2$)$_n$O($CH_2$)$_m$—, —($CH_2$)$_n$N($R^{12}$) ($CH_2$)$_m$—, —NH($CH_2$)$_n$—, —N($R^{10}$)C(=O)—, —NHC(=O)($CH_2$)$_n$—, —C(=O)N($R^{10}$)—, and —N($R^{10}$)S(O)$_p$—;
W is —(=O)—N($R^{10}$)—($C_2$–$C_3$ alkylene)-, in which the alkylene group is substituted by $R^8$ and by $R^9$:
$R^8$ is selected from:
 H, $C_1$–$C_4$ alkyl, hydroxy, $C_1$–$C_4$ alkoxy, halo, $CF_3$, $CO_2H$, $NR^{10}SO_2R^{21}$, pyridyl, —N($R^{16}$)$R^{17}$,
 phenyl substituted with 0–3 groups selected from halogen, $C_1$–$C_4$ alkoxy, $C_1$–$C_4$ alkyl, $CF_3$, $S(O)_m$Me, and —$NMe_2$;
 phenyl($C_1$–$C_4$ alkyl), said phenyl being substituted with 0–3 groups selected from halogen, $C_1$–$C_4$ alkoxy, $C_1$–$C_4$ alkyl, $CF_3$, $S(O)_p$Me, and —$NMe_2$, and
 carboxy($C_1$–$C_3$ alkyl)-;
$R^9$ is selected from:
 H, $CO_2R^{18b}$, C(=O)$R^{18b}$, $CONR^{17}R^{18b}$,
 $C_1$–$C_6$ alkyl substituted with 0–1 $R^6$,
 $C_2$–$C_4$ alkenyl substituted with 0–1 $R^6$,
 $C_2$–$C_4$ alkynyl substituted with 0–1 $R^6$,
 $C_3$–$C_8$ cycloalkyl substituted with 0–1 $R^6$,
 $C_5$–$C_6$ cycloalkenyl substituted with 0–1 $R^6$,
 ($C_1$–$C_4$ alkyl)carbonyl,
 $C_3$–$C_{10}$ cycloalkyl($C_1$–$C_4$ alkyl)-,
 phenyl substituted with 0–3 $R^6$,
 naphthyl substituted with 0–3 $R^6$,
 a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$,
 $C_1$–$C_4$ alkoxy substituted with 0–2 $R^7$,
 hydroxy, $CO_2H$, nitro, —N($R^{10}$)$R^{11}$, —N($R^{16}$)$R^{17}$, phenyl($C_0$–$C_4$ alkyl)carbonyl, phenyl($C_1$–$C_4$ alkyl)-, heteroaryl($C_1$–$C_6$ alkyl)-, $CONR^{18a}R^{20}$, $SO_2R^{18a}$, and $SO_2NR^{18a}R^{20}$,
 providing that any of the above alkyl, cycloalkyl, phenyl or heteroaryl groups may be unsubstituted or substituted independently with 1–2 $R^7$;

$R^{10}$ is selected from:
  H, $CF_3$, $C_3$–$C_6$ alkenyl, $C_3$–$C_{11}$ cycloalkyl, phenyl, ($C_3$–$C_{11}$ cycloalkyl)methyl, phenyl($C_1$–$C_4$ alkyl), and $C_1$–$C_{10}$ alkyl substituted with 0–2 $R^6$;

$R^{11}$ is selected from:
  H, hydroxy, $C_1$–$C_8$ alkyl, $C_3$–$C_6$ alkenyl, $C_3$–$C_{11}$ cycloalkyl, ($C_3$–$C_{11}$ cycloalkyl)methyl, $C_1$–$C_6$ alkoxy, benzyloxy, aryl, heteroaryl, heteroaryl($C_1$–$C_4$ alkyl)-, aryl($C_1$–$C_4$ alkyl), adamantylmethyl, and $C_1$–$C_{10}$ alkyl substituted with 0–2 $R^4$;
  alternatively, when $R^{10}$ and $R^{11}$ are both substituents on the same nitrogen atom (as in —$NR^{10}R^{11}$) they may be taken together with the nitrogen atom to which they are attached to form a heterocycle selected from:
    3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl, and 1-piperazinyl;
    said heterocycle being substituted with 0–3 groups selected from: $C_1$–$C_6$ alkyl, aryl, heteroaryl, aryl($C_1$–$C_4$ alkyl)-, ($C_1$–$C_6$ alkyl)carbonyl, ($C_3$–$C_7$ cycloalkyl)carbonyl, ($C_1$–$C_6$ alkoxy)carbonyl, aryl($C_1$–$C_4$ alkoxy)carbonyl, $C_1$–$C_6$ alkylsulfonyl, and arylsulfonyl;

$R^{12}$ is selected from:
  H, $C_1$–$C_6$ alkyl, triphenylmethyl, methoxymethyl, methoxyphenyldiphenylmethyl, trimethylsilylethoxymethyl, ($C_1$–$C_6$ alkyl)carbonyl, ($C_1$–$C_6$ alkoxy)carbonyl, ($C_1$–$C_6$ alkyl)aminocarbonyl, $C_3$–$C_6$ alkenyl, $C_3$–$C_7$ cycloalkyl, $C_3$–$C_7$ cycloalkyl($C_1$–$C_4$ alkyl)-, aryl, heteroaryl ($C_1$–$C_6$ alkyl)carbonyl, heteroarylcarbonyl, aryl($C_1$–$C_6$ alkyl)-, ($C_1$–$C_6$ alkyl)carbonyl, arylcarbonyl, $C_1$–$C_6$ alkylsulfonyl, arylsulfonyl, aryl($C_1$–$C_6$ alkyl) sulfonyl, heteroarylsulfonyl, heteroaryl($C_1$–$C_6$ alkyl)sulfonyl, aryloxycarbonyl, and aryl($C_1$–$C_6$ alkoxy)carbonyl, wherein said aryl groups are substituted with 0–2 substituents selected from the group consisting of $C_1$–$C_4$ alkyl, $C_1$–$C_4$ alkoxy, halo, $CF_3$, and nitro;

$R^{14}$ is selected from:
  H, $C_1$–$C_4$ alkyl, and phenyl($C_1$–$C_4$ alkyl);

$R^{16}$ is selected from:
  —C(=O)$OR^{18a}$, —C(=O)$R^{18b}$, —C(=O)N($R^{18b}$)$_2$, —C(=O)$NHSO_2R^{18a}$, —C(=O)NHC(=O)$R^{18b}$, —C(=O)NHC(=O)$OR^{18a}$, —C(=O)$NHSO_2NHR^{18b}$, —$SO_2R^{18a}$, —$SO_2N(R^{18b})_2$, and —$SO_2NHC(=O)OR^{18b}$;

$R^{17}$ is selected from:
  H, $C_1$–$C_6$ alkyl, $C_3$–$C_7$ cycloalkyl, $C_3$–$C_7$ cycloalkyl($C_1$–$C_4$ alkyl)-, aryl, aryl($C_1$–$C_6$ alkyl)-, and heteroaryl($C_1$–$C_6$ alkyl);

$R^{18a}$ is selected from:
  $C_1$–$C_6$ alkyl, aryl-, fluoro ($C_3$–$C_6$ alkyl), aryl($C_1$–$C_4$ alkyl-, di($C_1$–$C_4$ alkyl)amino($C_1$–$C_4$ alkyl)-, morpholino($C_1$–$C_4$ alkyl), piperidino($C_1$–$C_4$ alkyl), N—($C_1$–$C_4$ alkyl)piperidino($C_1$–$C_4$ alkyl), and phenyl substituted by one or two optional groups selected from $C_1$–$C_4$ alkyl, $C_1$–$C_4$ alkoxy, and halogen;

$R^{18b}$ is H or $R^{18a}$;

$R^{20}$ is selected from:
  hydroxy, $C_1$–$C_{10}$ alkyloxy, $C_3$–$C_{11}$ cycloalkyloxy, aryloxy, aryl($C_1$–$C_4$ alkyl)oxy, $C_2$–$C_{10}$ alkylcarbonyloxy($C_1$–$C_2$ alkyl)oxy-, $C_2$–$C_{10}$ alkoxycarbonyloxy($C_1$–$C_2$ alkyl)oxy-, $C_2$–$C_{10}$ alkoxycarbonyl($C_1$–$C_2$ alkyl)oxy-, $C_3$–$C_{10}$ cycloalkylcarbonyloxy($C_1$–$C_2$ alkyl)oxy-, $C_3$–$C_{10}$ cycloalkoxycarbonyloxy($C_1$–$C_2$ alkyl)oxy-, $C_3$–$C_{10}$ cycloalkoxycarbonyl($C_1$–$C_2$ alkyl)oxy-, aryloxycarbonyl($C_1$–$C_2$ alkyl)oxy-, aryloxycarbonyloxy($C_1$–$C_2$ alkyl)oxy-, arylcarbonyloxy($C_1$–$C_2$ alkyl)oxy-, $C_1$–$C_5$ alkoxy($C_1$–$C_5$ alkyl)carbonyloxy($C_1$–$C_2$ alkyl)oxy-, (5-($C_1$–$C_5$ alkyl)-1,3-dioxa-cyclopenten-2-one-yl) methyloxy, (5-aryl-1,3-dioxa-cyclopenten-2-one-yl)methyloxy, and ($R^{10}$)($R^{11}$)N—($C_1$–$C_{10}$ alkoxy)-;

$R^{21}$ is selected from:
  $C_1$–$C_8$ alkyl, $C_2$–$C_6$ alkenyl, $C_3$–$C_{11}$ cycloalkyl, ($C_3$–$C_{11}$ cycloalkyl)methyl, aryl, aryl($C_1$–$C_4$ alkyl)-, and $C_1$–$C_{10}$ alkyl substituted with 0–2 $R^7$;

Y is selected from:
  —$COR^{20}$;

m is 0–2;

n is 0–4;

p is 0–2;

r is 0–2;

with the proviso that n and m are chosen such that the number of atoms connecting $R^1$ and Y is in the range of 8–14.

13. A compound of claim 12 of Formula III:

(III)

including stereoisomeric forms thereof, or mixtures of stereoisomeric forms thereof, or pharmaceutically acceptable salt forms thereof wherein:

$R^1$ is selected from:

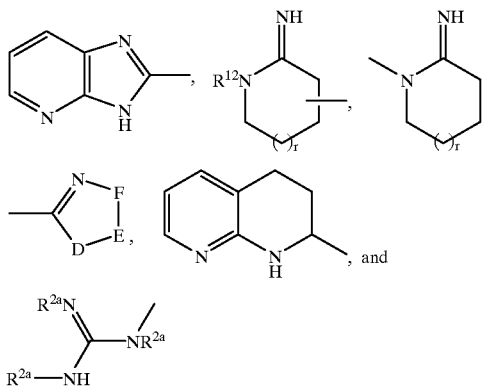

A is —CH$_2$— or —N(R$^{12}$)—;
A$^1$ and B are independently —CH$_2$— or —N(R$^{10}$)—;
D is —N(R$^{12}$)— or —S—;
E—F is —C(R$^2$)=C(R$^3$)— or —C(R$^2$)$_2$C(R$^3$)$_2$—;
R$^2$ and R$^3$ are independently selected from:
  H, C$_1$–C$_4$ alkoxy, NR$^{11}$R$^{12}$, halogen, NO$_2$, CN, CF$_3$, C$_1$–C$_6$ alkyl, C$_3$–C$_6$ alkenyl, C$_3$–C$_7$ cycloalkyl, C$_3$–C$_7$ cycloalkyl(C$_1$–C$_4$ alkyl), aryl(C$_1$–C$_6$ alkyl)-, (C$_1$–C$_6$ alkyl)carbonyl, (C$_1$–C$_6$ alkoxy)carbonyl, arylcarbonyl, and aryl substituted with 0–4 R$^7$,
  alternatively, when R$^2$ and R$^3$ are substituents on adjacent atoms, they can be taken together with the carbon atoms to which they are attached to form a 5–7 membered carbocyclic or 5–7 membered heterocyclic aromatic or nonaromatic ring system, said carbocyclic or heterocyclic ring being substituted with 0–2 groups selected from C$_1$–C$_4$ alkyl, C$_1$–C$_4$ alkoxy, halo, cyano, amino, CF$_3$ and NO$_2$;
R$^{2a}$ is selected from:
  H, C$_1$–C$_{10}$ alkyl, C$_2$–C$_6$ alkenyl, C$_3$–C$_{11}$ cycloalkyl, C$_3$–C$_7$ cycloalkyl(C$_1$–C$_4$ alkyl), aryl, aryl(C$_1$–C$_4$ alkyl)-, (C$_2$–C$_7$ alkyl)carbonyl, arylcarbonyl, (C$_2$–C$_{10}$ alkoxy)carbonyl, C$_3$–C$_7$ cycloalkoxycarbonyl, C$_7$–C$_{11}$ bicycloalkoxycarbonyl, aryloxycarbonyl, aryl (C$_1$–C$_{10}$ alkoxy)carbonyl, C$_1$–C$_6$ alkylcarbonyloxy (C$_1$–C$_4$ alkoxy)carbonyl, arylcarbonyloxy(C$_1$–C$_4$ alkoxy)carbonyl, and C$_3$–C$_7$ cycloalkylcarbonyloxy (C$_1$–C$_4$ alkoxy)carbonyl;
R$^4$ is selected from:
  H, C$_1$–C$_6$ alkyl, C$_3$–C$_7$ cycloalkyl, C$_3$–C$_7$ cycloalkyl (C$_1$–C$_4$ alkyl)-, aryl, heteroaryl, aryl(C$_1$–C$_6$ alkyl)-, and heteroaryl(C$_1$–C$_6$ alkyl)-, wherein said aryl or heteroaryl groups are substituted with 0–2 substituents independently selected from the group consisting of C$_1$–C$_4$ alkyl, C$_1$–C$_4$ alkoxy, F, Cl, Br, CF$_3$, and NO$_2$,
R$^6$ is selected from:
  H, C$_1$–C$_{10}$ alkyl, hydroxy, C$_1$–C$_{10}$ alkoxy, nitro, C$_1$–C$_{10}$ alkylcarbonyl, —N(R$^{11}$)R$^{12}$, cyano, halo, CF$_3$, CHO, CO$_2$R$^{18b}$, C(=O)R$^{18b}$, CONR$^{17}$R$^{18b}$, OC(=O)R$^{10}$, OR$^{10}$, OC(=O)NR$^{10}$R$^{11}$, NR$^{10}$C(=O)R$^{10}$, NR$^{10}$C(=O)OR$^{21}$, NR$^{10}$C(=O) NR$^{10}$R$^{11}$, NR$^{10}$SO$_2$NR$^{10}$R$^{11}$, NR$^{10}$SO$_2$R$^{21}$, S(O)$_p$R$^{11}$, SO$_2$NR$^{10}$R$^{11}$,
  aryl substituted with 0–3 groups selected from halogen, C$_1$–C$_6$ alkoxy, C$_1$–C$_6$ alkyl, CF$_3$, S(O)$_m$Me, and —NMe$_2$,
  aryl(C$_1$–C$_4$ alkyl)-, said aryl being substituted with 0–3 groups selected from halogen, C$_1$–C$_6$ alkoxy, C$_1$–C$_6$ alkyl, CF$_3$, S(O)$_p$Me, and —NMe$_2$, and a 5–10 membered heterocyclic ring containing 1–3 N, O, or S heteroatoms, wherein said heterocyclic ring may be saturated, partially saturated, or fully unsaturated, said heterocyclic ring being substituted with 0–2 R$^7$;
R$^7$ is selected from:
  H, hydroxy, C$_1$–C$_4$ alkyl, C$_1$–C$_4$ alkoxy, aryl, aryl (C$_1$–C$_4$ alkyl)-, (C$_1$–C$_4$ alkyl)carbonyl, CO$_2$R$^{18a}$, SO$_2$R$^{11}$, SO$_2$NR$^{10}$R$^{11}$, OR$^{10}$, and N(R$^{11}$)R$^{12}$;
U is selected from:
  —(CH$_2$)$_n$—, —(CH$_2$)$_n$O(CH$_2$)$_m$—, —(CH$_2$)$_n$N(R$^{12}$) (CH$_2$)$_m$—, —NH(CH$_2$)$_n$—, —N(R$^{10}$)C(=O)—, and —NHC(=O)(CH$_2$)$_n$—;
R$^8$ is H;
R$^9$ is selected from:
  H, CO$_2$R$^{18b}$, C(=O)R$^{18b}$, CONR$^{17}$R$^{18b}$,
  C$_1$–C$_6$ alkyl substituted with 0–1 R$^6$,
  C$_2$–C$_4$ alkenyl substituted with 0–1 R$^6$,
  C$_2$–C$_4$ alkynyl substituted with 0–1 R$^6$,
  C$_3$–C$_8$ cycloalkyl substituted with 0–1 R$^6$,
  C$_5$–C$_6$ cycloalkenyl substituted with 0–1 R$^6$,
  (C$_1$–C$_4$ alkyl)carbonyl,
  C$_3$–C$_{10}$ cycloalkyl(C$_1$–C$_4$ alkyl)-,
  phenyl substituted with 0–3 R$^6$,
  naphthyl substituted with 0–3 R$^6$,
  a 5–10 membered heterocyclic ring containing 1–3 N, O, or S heteroatoms, wherein said heterocyclic ring may be saturated, partially saturated, or fully unsaturated, said heterocyclic ring being substituted with 0–2 R$^7$,
  C$_1$–C$_4$ alkoxy substituted with 0–2 R$^7$,
  hydroxy, CO$_2$H, nitro, —N(R$^{10}$)R$^{11}$, —N(R$^{16}$)R$^{17}$, phenyl(C$_0$–C$_4$ alkyl)carbonyl, phenyl(C$_1$–C$_4$ alkyl)-, heteroaryl(C$_1$–C$_6$ alkyl)-, CONR$^{18a}$R$^{20}$, SO$_2$R$^{18a}$, and SO$_2$NR$^{18a}$R$^{20}$,
  providing that any of the above alkyl, cycloalkyl, phenyl or heteroaryl groups may be unsubstituted or substituted independently with 1–2 R$^7$;
R$^{10}$ is selected from:
  H, CF$_3$, C$_3$–C$_6$ alkenyl, C$_3$–C$_{11}$ cycloalkyl, phenyl, (C$_3$–C$_{11}$ cycloalkyl)methyl, phenyl(C$_1$–C$_4$ alkyl), and C$_1$–C$_{10}$ alkyl substituted with 0–2 R$^6$;
R$^{11}$ is selected from:
  H, hydroxy, C$_1$–C$_8$ alkyl, C$_3$–C$_6$ alkenyl, C$_3$–C$_{11}$ cycloalkyl, (C$_3$–C$_{11}$ cycloalkyl)methyl, C$_1$–C$_6$ alkoxy, benzyloxy, aryl, heteroaryl, heteroaryl (C$_1$–C$_4$ alkyl)-, aryl(C$_1$–C$_4$ alkyl), adamantylmethyl, and C$_1$–C$_{10}$ alkyl substituted with 0–2 R$^4$;
  alternatively, when R$^{10}$ and R$^{11}$ are both substituents on the same nitrogen atom (as in —NR$^{10}$R$^{11}$) they may be taken together with the nitrogen atom to which they are attached to form a heterocycle selected from:
    3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl, and 1-piperazinyl;
    said heterocycle being substituted with 0–3 groups selected from: C$_1$–C$_6$ alkyl, aryl, heteroaryl, aryl (C$_1$–C$_4$ alkyl)-, (C$_1$–C$_6$ alkyl)carbonyl, (C$_3$–C$_7$ cycloalkyl)carbonyl, (C$_1$–C$_6$ alkoxy)carbonyl, aryl(C$_1$–C$_4$ alkoxy)carbonyl, C$_1$–C$_6$ alkylsulfonyl, and arylsulfonyl;
R$^{12}$ is selected from:
  H, C$_1$–C$_6$ alkyl, triphenylmethyl, methoxymethyl, methoxyphenyldiphenylmethyl, trimethylsilylethoxymethyl, ($C_1$–$C_6$ alkyl)carbonyl, ($C_1$–$C_6$ alkoxy)carbonyl, ($C_1$–$C_6$ alkyl)aminocarbonyl, $C_3$–$C_6$ alkenyl, $C_3$–$C_7$ cycloalkyl, $C_3$–$C_7$ cycloalkyl($C_1$–$C_4$ alkyl)-, aryl, heteroaryl ($C_1$–$C_6$ alkyl)carbonyl, heteroarylcarbonyl, aryl ($C_1$–$C_6$ alkyl)-, ($C_1$–$C_6$ alkyl)carbonyl, arylcarbonyl, $C_1$–$C_6$ alkylsulfonyl, arylsulfonyl, aryl($C_1$–$C_6$ alkyl)sulfonyl, heteroarylsulfonyl, heteroaryl($C_1$–$C_6$ alkyl)sulfonyl, aryloxycarbonyl, and aryl($C_1$–$C_6$ alkoxy)carbonyl, wherein said aryl groups are substituted with 0–2 substituents selected from the group consisting of $C_1$–$C_4$ alkyl, $C_1$–$C_4$ alkoxy, halo, $CF_3$, and nitro;

$R^{14}$ is selected from H, $CH_3$, benzyl and phenylethyl;

$R^{16}$ is selected from:
—C(=O)$OR^{18a}$, C(=O)$R^{18b}$, —C(=O)N($R^{18b}$)$_2$, —C(=O)NHSO$_2$$R^{18a}$, —C(=O)NHC(=O)$R^{18b}$, —C(=O)NHC(=O)$OR^{18a}$, —C(=O)NHSO$_2$NHR$^{18b}$, —SO$_2$$R^{18a}$, —SO$_2$N($R^{18b}$)$_2$, and —SO$_2$NHC(=O)$OR^{18b}$;

$R^{17}$ is selected from:
H, $C_1$–$C_6$ alkyl, $C_3$–$C_7$ cycloalkyl, $C_3$–$C_7$ cycloalkyl ($C_1$–$C_4$ alkyl)-, aryl, aryl($C_1$–$C_6$ alkyl)-, and heteroaryl($C_1$–$C_6$ alkyl);

$R^{18a}$ is selected from:
$C_1$–$C_6$ alkyl, aryl-, fluoro($C_3$–$C_6$ alkyl), aryl($C_1$–$C_4$ alkyl-, di($C_1$–$C_4$ alkyl)amino($C_1$–$C_4$ alkyl), morpholino($C_1$–$C_4$ alkyl), piperidino($C_1$–$C_4$ alkyl), N—($C_1$–$C_4$ alkyl)piperidino($C_1$–$C_4$ alkyl), and phenyl substituted by one or two optional groups selected from $C_1$–$C_4$ alkyl, $C_1$–$C_4$ alkoxy, and halogen;

$R^{18b}$ is H or $R^{18a}$;

$R^{20}$ is selected from:
hydroxy, $C_1$–$C_{10}$ alkyloxy, $C_3$–$C_{11}$ cycloalkyloxy, aryloxy, aryl($C_1$–$C_4$ alkyl)oxy,
$C_2$–$C_{10}$ alkylcarbonyloxy($C_1$–$C_2$ alkyl)oxy-,
$C_2$–$C_{10}$ alkoxycarbonyloxy($C_1$–$C_2$ alkyl)oxy-,
$C_2$–$C_{10}$ alkoxycarbonyl($C_1$–$C_2$ alkyl)oxy-,
$C_3$–$C_{10}$ cycloalkylcarbonyloxy($C_1$–$C_2$ alkyl)oxy-,
$C_3$–$C_{10}$ cycloalkoxycarbonyloxy($C_1$–$C_2$ alkyl)oxy-,
$C_3$–$C_{10}$ cycloalkoxycarbonyl($C_1$–$C_2$ alkyl)oxy-,
aryloxycarbonyl($C_1$–$C_2$ alkyl)oxy-,
aryloxycarbonyloxy($C_1$–$C_2$ alkyl)oxy-,
arylcarbonyloxy($C_1$–$C_2$ alkyl)oxy-,
$C_1$–$C_5$ alkoxy($C_1$–$C_5$ alkyl)carbonyloxy($C_1$–$C_2$ alkyl)oxy-,
(5-($C_1$–$C_5$ alkyl)-1,3-dioxa-cyclopenten-2-one-yl)methyloxy,
(5-aryl-1,3-dioxa-cyclopenten-2-one-yl)methyloxy, and
($R^{10}$)($R^{11}$)N—($C_1$–$C_{10}$ alkoxy)-;

$R^{21}$ is selected from:
$C_1$–$C_8$ alkyl, $C_2$–$C_6$ alkenyl, $C_3$–$C_{11}$ cycloalkyl, ($C_3$–$C_{11}$ cycloalkyl)methyl, aryl, aryl($C_1$–$C_4$ alkyl)-, and $C_1$–$C_{10}$ alkyl substituted with 0–2 $R^7$;

m is 0–2;
n is 0–4;
p is 0–2; and
r is 0–2;

with the following provisos:
(1) n and m are chosen such that the number of atoms connecting $R^1$ and $COR^{20}$ of Formula (III) is in the range of 10–14; and
(2) one of the groups $R^8$ or $R^9$ must be hydrogen.

14. A compound of claim 13 of Formula III:

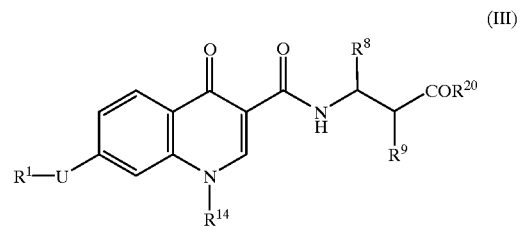

(III)

including stereoisomeric forms thereof, or mixtures of stereoisomeric forms thereof, or pharmaceutically acceptable salt forms thereof wherein:

$R^1$ is selected from:

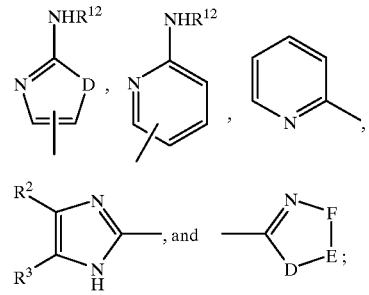

A is —CH$_2$— or —N($R^{12}$)—;
$A^1$ and B are independently —CH$_2$— or —N($R^{10}$)—;
D is —N($R^{12}$)— or —S—;
E—F is —C($R^2$)=C($R^3$)— or —C($R^2$)$_2$C($R^3$)$_2$—;

$R^2$ and $R^3$ are independently selected from:
H, $C_1$–$C_4$ alkoxy, $NR^{11}R^{12}$, halogen, NO$_2$, CN, CF$_3$, $C_1$–$C_6$ alkyl, $C_3$–$C_6$ alkenyl, $C_3$–$C_7$ cycloalkyl, $C_3$–$C_7$ cycloalkyl ($C_1$–$C_4$ alkyl), aryl($C_1$–$C_6$ alkyl)-, ($C_1$–$C_6$ alkyl)carbonyl, ($C_1$–$C_6$ alkoxy)carbonyl, arylcarbonyl, and aryl substituted with 0–4 $R^7$,
alternatively, when $R^2$ and $R^3$ are substituents on adjacent atoms, they can be taken together with the carbon atoms to which they are attached to form a 5–7 membered carbocyclic or 5–7 membered heterocyclic aromatic or nonaromatic ring system, said carbocyclic or heterocyclic ring being substituted with 0–2 groups selected from $C_1$–$C_4$ alkyl, $C_1$–$C_4$ alkoxy, halo, cyano, amino, CF$_3$ and NO$_2$;

$R^4$ is selected from:
H, $C_1$–$C_6$ alkyl, $C_3$–$C_7$ cycloalkyl, $C_3$–$C_7$ cycloalkyl ($C_1$–$C_4$ alkyl)-, aryl, heteroaryl, aryl($C_1$–$C_6$ alkyl)-, and heteroaryl($C_1$–$C_6$ alkyl)-, wherein said aryl or heteroaryl groups are substituted with 0–2 substituents independently selected from the group consisting of $C_1$–$C_4$ alkyl, $C_1$–$C_4$ alkoxy, F, Cl, Br, CF$_3$, and NO$_2$, $R^6$ is selected from:
H, $C_1$–$C_{10}$ alkyl, hydroxy, $C_1$–$C_{10}$ alkoxy, nitro, $C_1$–$C_{10}$ alkylcarbonyl, —N($R^{11}$)$R^{12}$, cyano, halo, CF$_3$, CHO, CO$_2$$R^{18b}$, C(=O)$R^{18b}$, CONR$^{17}$$R^{18b}$, OC(=O)$R^{10}$, $OR^{10}$, OC(=O)NR$^{10}$$R^{11}$, NR$^{10}$C(=O)$R^{10}$, $N^{10}$C(=O)$OR^{21}$, NR$^{10}$C(=O)NR$^{10}$$R^{11}$, NR$^{10}$SO$_2$NR$^{10}$$R^{11}$, NR$^{10}$SO$_2$$R^{21}$, S(O)$_p$$R^{11}$, SO$_2$NR$^{10}$$R^{11}$,
aryl substituted with 0–3 groups selected from halogen, $C_1$–$C_6$ alkoxy, $C_1$–$C_6$ alkyl, CF$_3$, S(O)$_m$Me, and —NMe$_2$, aryl($C_1$–$C_4$ alkyl)-, said aryl being substituted with 0–3 groups selected from halogen, $C_1$–$C_6$ alkoxy, $C_1$–$C_6$ alkyl, $CF_3$, $S(O)_p Me$, and —$NMe_2$, and a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$;

$R^7$ is selected from:

H, hydroxy, $C_1$–$C_4$ alkyl, $C_1$–$C_4$ alkoxy, aryl, aryl($C_1$–$C_4$ alkyl)-, ($C_1$–$C_4$ alkyl)carbonyl, $CO_2 R^{18a}$, $SO_2 R^{11}$, $SO_2 NR^{10} R^{11}$, $OR^{10}$, and $N(R^{11})R^{12}$;

U is selected from:

—$(CH_2)_n$—, —$NH(CH_2)_n$—, —$N(R^{10})C(=O)$—, and —$NHC(=O)(CH_2)_n$—;

$R^8$ is H;

$R^9$ is selected from:

H, hydroxy, $CO_2 H$, nitro, —$N(R^{10})R^{11}$, —$N(R^{16})R^{17}$, phenyl($C_0$–$C_4$ alkyl)carbonyl, phenyl($C_1$–$C_4$ alkyl)-, heteroaryl($C_1$–$C_6$ alkyl)-, $CONR^{18a}R^{20}$, $SO_2 R^{18a}$, and $SO_2 NR^{18a}R^{20}$, providing that any of the above phenyl or heteroaryl groups may be unsubstituted or substituted independently with 1–2 $R^7$;

$R^{10}$ is selected from:

H, $CF_3$, $C_3$–$C_6$ alkenyl, $C_3$–$C_{11}$ cycloalkyl, phenyl, ($C_3$–$C_{11}$ cycloalkyl)methyl, phenyl($C_1$–$C_4$ alkyl), and $C_1$–$C_{10}$ alkyl substituted with 0–2 $R^6$;

$R^{11}$ is selected from:

H, hydroxy, $C_1$–$C_8$ alkyl, $C_3$–$C_6$ alkenyl, $C_3$–$C_{11}$ cycloalkyl, ($C_3$–$C_{11}$ cycloalkyl)methyl, $C_1$–$C_6$ alkoxy, benzyloxy, aryl, heteroaryl, heteroaryl ($C_1$–$C_4$ alkyl)-, aryl($C_1$–$C_4$ alkyl), adamantylmethyl, and $C_1$–$C_{10}$ alkyl substituted with 0–2 $R^4$;

alternatively, when $R^{10}$ and $R^{11}$ are both substituents on the same nitrogen atom (as in —$NR^{10}R^{11}$) they may be taken together with the nitrogen atom to which they are attached to form a heterocycle selected from:

3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl, and 1-piperazinyl;

said heterocycle being substituted with 0–3 groups selected from: $C_1$–$C_6$ alkyl, aryl, heteroaryl, aryl ($C_1$–$C_4$ alkyl)-, ($C_1$–$C_6$ alkyl)carbonyl, ($C_3$–$C_7$ cycloalkyl)carbonyl, ($C_1$–$C_6$ alkoxy)carbonyl, aryl($C_1$–$C_4$ alkoxy)carbonyl, $C_1$–$C_6$ alkylsulfonyl, and arylsulfonyl;

$R^{12}$ is selected from:

H, $C_1$–$C_4$ alkyl, ($C_1$–$C_4$ alkyl)carbonyl, ($C_1$–$C_4$ alkoxy)carbonyl, phenyl($C_1$–$C_4$ alkyl)-, phenylsulfonyl, phenyloxycarbonyl, and phenyl ($C_1$–$C_4$ alkoxy)carbonyl, wherein said phenyl groups are substituted with 0–2 substituents selected from the group consisting of $C_1$–$C_4$ alkyl, $C_1$–$C_4$ alkoxy, halo, $CF_3$, and nitro;

$R^{14}$ is selected from H, $CH_3$, and benzyl;

$R^{16}$ is selected from:

—$C(=O)OR^{18a}$, —$C(=O)R^{18b}$, —$C(=O)N(R^{18b})_2$, —$C(=O)NHSO_2 R^{18a}$, —$C(=O)NHC(=O)R^{18b}$, —$C(=O)NHC(=O)OR^{18a}$, —$C(=O)NHSO_2 NHR^{18b}$, —$SO_2 R^{18a}$, —$SO_2 N(R^{18b})_2$, and —$SO_2 NHC(=O)OR^{18b}$;

$R^{17}$ is selected from:

H, $C_1$–$C_6$ alkyl, $C_3$–$C_7$ cycloalkyl, $C_3$–$C_7$ cycloalkyl ($C_1$–$C_4$ alkyl)-, aryl, aryl($C_1$–$C_6$ alkyl)-, and heteroaryl($C_1$–$C_6$ alkyl);

$R^{18a}$ is selected from:

$C_1$–$C_6$ alkyl, aryl-, fluoro($C_3$–$C_6$ alkyl), aryl($C_1$–$C_4$ alkyl)-, di($C_1$–$C_4$ alkyl)amino($C_1$–$C_4$ alkyl), morpholino($C_1$–$C_4$ alkyl), piperidino($C_1$–$C_4$ alkyl), N—($C_1$–$C_4$ alkyl)piperidino($C_1$–$C_4$ alkyl), and phenyl substituted by one or two optional groups selected from $C_1$–$C_4$ alkyl, $C_1$–$C_4$ alkoxy, and halogen;

$R^{18b}$ is H or $R^{18a}$;

$R^{20}$ is selected from:

hydroxy, $C_1$–$C_{10}$ alkyloxy, $C_3$–$C_{11}$ cycloalkyloxy, aryloxy, aryl($C_1$–$C_4$ alkyl)oxy, $C_2$–$C_{10}$ alkylcarbonyloxy($C_1$–$C_2$ alkyl)oxy-, $C_2$–$C_{10}$ alkoxycarbonyloxy($C_1$–$C_2$ alkyl)oxy-, $C_2$–$C_{10}$ alkoxycarbonyl($C_1$–$C_2$ alkyl)oxy-, $C_3$–$C_{10}$ cycloalkylcarbonyloxy($C_1$–$C_2$ alkyl)oxy-, $C_3$–$C_{10}$ cycloalkoxycarbonyloxy($C_1$–$C_2$ alkyl)oxy-, $C_3$–$C_{10}$ cycloalkoxycarbonyl($C_1$–$C_2$ alkyl)oxy-, aryloxycarbonyl($C_1$–$C_2$ alkyl)oxy-, aryloxycarbonyloxy($C_1$–$C_2$ alkyl)oxy-, arylcarbonyloxy($C_1$–$C_2$ alkyl)oxy-, $C_1$–$C_5$ alkoxy($C_1$–$C_5$ alkyl)carbonyloxy($C_1$–$C_2$ alkyl)oxy-, (5-($C_1$–$C_5$ alkyl)-1,3-dioxa-cyclopenten-2-one-yl)methyloxy, (5-aryl-1,3-dioxa-cyclopenten-2-one-yl)methyloxy, and $(R^{10})(R^{11})N$—$(C_1$–$C_{10}$ alkoxy)-;

$R^{21}$ is selected from:

$C_1$–$C_8$ alkyl, $C_2$–$C_6$ alkenyl, $C_3$–$C_{11}$ cycloalkyl, ($C_3$–$C_{11}$ cycloalkyl)methyl, aryl, aryl($C_1$–$C_4$ alkyl)-, and $C_1$–$C_{10}$ alkyl substituted with 0–2 $R^7$;

m is 0–2;

n is 0–4;

p is 0–2; and r is 0–2;

with the following provisos:

(1) n and m are chosen such that the number of atoms connecting $R^1$ and $COR^{20}$ of Formula (III) is in the range of 10–14; and (2) one of the groups $R^8$ or $R^9$ must be hydrogen.

15. A compound of claim 13 of Formula III:

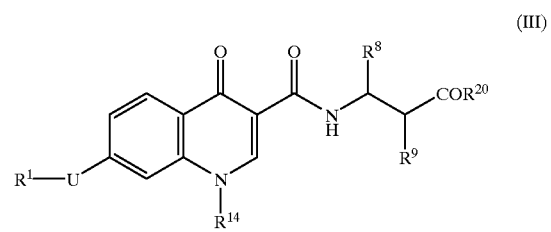

(III)

including stereoisomeric forms thereof, or mixtures of stereoisomeric forms thereof, or pharmaceutically acceptable salt forms thereof wherein:

119

$R^1$ is selected from:

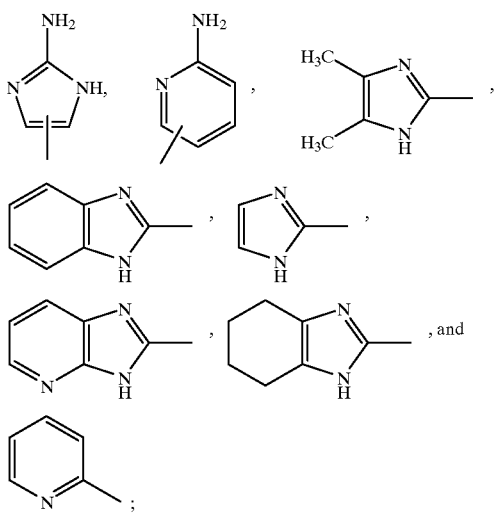

;

$R^4$ is selected from:
H, $C_1$–$C_6$ alkyl, $C_3$–$C_7$ cycloalkyl, $C_3$–$C_7$ cycloalkyl ($C_1$–$C_4$ alkyl)-, aryl, heteroaryl, aryl($C_1$–$C_6$ alkyl)-, and heteroaryl($C_1$–$C_6$ alkyl)-, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$, $R^6$ is selected from:
H, $C_1$–$C_{10}$ alkyl, hydroxy, $C_1$–$C_{10}$ alkoxy, nitro, $C_1$–$C_{10}$ alkylcarbonyl, —N($R^{11}$)$R^{12}$, cyano, halo, $CF_3$, CHO, $CO_2R^{18b}$, C(=O)$R^{18b}$, CONR$^{17}$R$^{18b}$, OC(=O)$R^{10}$, $OR^{10}$, OC(=O)NR$^{10}$R$^{11}$, NR$^{10}$C(=O)$R^{10}$, NR$^{10}$C(=O)OR$^{21}$, NR$^{10}$C(=O)NR$^{10}$R$^{11}$, NR$^{10}$SO$_2$NR$^{10}$R$^{11}$, NR$^{10}$SO$_2$R$^{21}$, S(O)$_p$R$^{11}$, SO$_2$NR$^{10}$R$^{11}$,
aryl substituted with 0–3 groups selected from halogen, $C_1$–$C_6$ alkoxy, $C_1$–$C_6$ alkyl, $CF_3$, S(O)$_m$Me, and —NMe$_2$,
aryl($C_1$–$C_4$ alkyl)-, said aryl being substituted with 0–3 groups selected from halogen, $C_1$–$C_6$ alkoxy, $C_1$–$C_6$ alkyl, $CF_3$, S(O)$_p$Me, and —NMe$_2$, and
a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$;

$R^7$ is selected from:
H, hydroxy, $C_1$–$C_4$ alkyl, $C_1$–$C_4$ alkoxy, aryl, aryl ($C_1$–$C_4$ alkyl)-, ($C_1$–$C_4$ alkyl)carbonyl, $CO_2R^{18a}$, $SO_2R^{11}$, $SO_2NR^{10}R^{11}$, $OR^{10}$, and N($R^{11}$)$R^{12}$;

U is selected from:
—(CH$_2$)$_n$—, —NH(CH$_2$)$_n$—, —N($R^{10}$)C(=O)—, and —NHC(=O)(CH$_2$)$_n$—;

$R^8$ is H;

$R^9$ is selected from:
H, hydroxy, $CO_2H$, —N($R^{10}$)$R^{11}$, —N($R^{16}$)$R^{17}$, phenyl ($C_0$–$C_4$ alkyl)carbonyl, phenyl($C_1$–$C_4$ alkyl)-, heteroaryl($C_1$–$C_6$ alkyl)-, CONR$^{18a}$R$^{20}$, SO$_2$R$^{18a}$, and SO$_2$NR$^{18a}$R$^{20}$,
providing that any of the above phenyl or heteroaryl groups may be unsubstituted or substituted independently with 1–2 $R^7$;

120

$R^{10}$ is selected from:
H, $CF_3$, $C_3$–$C_6$ alkenyl, $C_3$–$C_{11}$ cycloalkyl, phenyl, ($C_3$–$C_{11}$ cycloalkyl)methyl, phenyl($C_1$–$C_4$ alkyl), and $C_1$–$C_{10}$ alkyl substituted with 0–2 $R^6$;

$R^{11}$ is selected from:
H, hydroxy, $C_1$–$C_8$ alkyl, $C_3$–$C_6$ alkenyl, $C_3$–$C_{11}$ cycloalkyl, ($C_3$–$C_{11}$ cycloalkyl)methyl, $C_1$–$C_6$ alkoxy, benzyloxy, aryl, heteroaryl, heteroaryl ($C_1$–$C_4$ alkyl)-, aryl($C_1$–$C_4$ alkyl), adamantylmethyl, and $C_1$–$C_{10}$ alkyl substituted with 0–2 $R^4$;
alternatively, when $R^{10}$ and $R^{11}$ are both substituents on the same nitrogen atom (as in —NR$^{10}$R$^{11}$) they may be taken together with the nitrogen atom to which they are attached to form a heterocycle selected from:
3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl, and 1-piperazinyl;
said heterocycle being substituted with 0–3 groups selected from: $C_1$–$C_6$ alkyl, aryl, heteroaryl, aryl ($C_1$–$C_4$ alkyl)-, ($C_1$–$C_6$ alkyl)carbonyl, ($C_3$–$C_7$ cycloalkyl)carbonyl, ($C_1$–$C_6$ alkoxy)carbonyl, aryl($C_1$–$C_4$ alkoxy)carbonyl, $C_1$–$C_6$ alkylsulfonyl, and arylsulfonyl;

$R^{12}$ is selected from:
H, $C_1$–$C_4$ alkyl, ($C_1$–$C_4$ alkyl)carbonyl, ($C_1$–$C_4$ alkoxy)carbonyl, phenyl($C_1$–$C_4$ alkyl)-, phenylsulfonyl, phenyloxycarbonyl, and phenyl ($C_1$–$C_4$ alkoxy)carbonyl, wherein said phenyl groups are substituted with 0–2 substituents selected from the group consisting of $C_1$–$C_4$ alkyl, $C_1$–$C_4$ alkoxy, halo, $CF_3$, and nitro;

$R^{14}$ is selected from H, $CH_3$, and benzyl;

$R^{16}$ is selected from:
—C(=O)OR$^{18a}$, —C(=O)R$^{18b}$, —C(=O)N(R$^{18b}$)$_2$, —C(=O)NHSO$_2$R$^{18a}$, —C(=O)NHC(=O)R$^{18b}$, —C(=O)NHC(=O)OR$^{18a}$, —C(=O)NHSO$_2$NHR$^{18b}$, —SO$_2$R$^{18a}$, —SO$_2$N(R$^{18b}$)$_2$, and —SO$_2$NHC(=O)OR$^{18b}$;

$R^{17}$ is selected from:
H, $C_1$–$C_6$ alkyl, $C_3$–$C_7$ cycloalkyl, $C_3$–$C_7$ cycloalkyl ($C_1$–$C_4$ alkyl)-, aryl, aryl($C_1$–$C_6$ alkyl)-, and heteroaryl($C_1$–$C_6$ alkyl);

$R^{18a}$ is selected from:
$C_1$–$C_6$ alkyl, aryl-, fluoro($C_3$–$C_6$ alkyl), aryl($C_1$–$C_4$ alkyl-, di($C_1$–$C_4$ alkyl)amino($C_1$–$C_4$ alkyl), morpholino($C_1$–$C_4$ alkyl), piperidino($C_1$–$C_4$ alkyl), N—($C_1$–$C_4$ alkyl)piperidino($C_1$–$C_4$ alkyl), and phenyl substituted by one or two optional groups selected from $C_1$–$C_4$ alkyl, $C_1$–$C_4$ alkoxy, and halogen;

$R^{18b}$ is H or $R^{18a}$;

$R^{20}$ is selected from:
hydroxy, $C_1$–$C_{10}$ alkyloxy, $C_3$–$C_{11}$ cycloalkyloxy, aryloxy, aryl($C_1$–$C_4$ alkyl)oxy,
$C_2$–$C_{10}$ alkylcarbonyloxy($C_1$–$C_2$ alkyl)oxy-,
$C_2$–$C_{10}$ alkoxycarbonyloxy($C_1$–$C_2$ alkyl)oxy-,
$C_2$–$C_{10}$ alkoxycarbonyl($C_1$–$C_2$ alkyl)oxy-,
$C_3$–$C_{10}$ cycloalkylcarbonyloxy($C_1$–$C_2$ alkyl)oxy-,
$C_3$–$C_{10}$ cycloalkoxycarbonyloxy($C_1$–$C_2$ alkyl)oxy-,
$C_3$–$C_{10}$ cycloalkoxycarbonyl($C_1$–$C_2$ alkyl)oxy-,
aryloxycarbonyl($C_1$–$C_2$ alkyl)oxy-,
aryloxycarbonyloxy($C_1$–$C_2$ alkyl)oxy-,
arylcarbonyloxy($C_1$–$C_2$ alkyl)oxy-,
$C_1$–$C_5$ alkoxy($C_1$–$C_5$ alkyl)carbonyloxy($C_1$–$C_2$ alkyl) oxy-, (5-($C_1$–$C_5$ alkyl)-1,3-dioxa-cyclopenten-2-one-yl)
methyloxy,
(5-aryl-1,3-dioxa-cyclopenten-2-one-yl)methyloxy,
and
($R^{10}$)($R^{11}$)N—($C_1$–$C_{10}$ alkoxy)-;

$R^{21}$ is selected from:
$C_1$–$C_8$ alkyl, $C_2$–$C_6$ alkenyl, $C_3$–$C_{11}$ cycloalkyl, ($C_3$–$C_{11}$ cycloalkyl)methyl, aryl, aryl($C_1$–$C_4$ alkyl)-, and $C_1$–$C_{10}$ alkyl substituted with 0–2 $R^7$;

m is 0–2;

n is 0–4;

p is 0–2; and r is 0–2;

with the following provisos:
(1) n and m are chosen such that the number of atoms connecting $R^1$ and $COR^{20}$ in Formula (III) is in the range of 10–14; and
(2) one of the groups $R^8$ or $R^9$ must be hydrogen.

16. A compound of claim 12, including enantiomeric or diastereomeric forms thereof, or mixtures of enantiomeric or diastereomeric forms thereof, or pharmaceutically acceptable salt forms thereof selected from the group consisting of:

3-[7-[(imidazol-2-ylamino)methyl]-1-cyclopropylylquinoline-4-one-3-ylcarbonylamino]-2-((2,4,6-trimethylphenyl)sulfonylamino)propionic acid, 3-[7-[(imidazol-2-ylamino)methyl]-1-cyclopentylquinoline-4-one-3-ylcarbonylamino]-2-((4-phenylbenzene)sulfonylamino)propionic acid, 3-[7-[(benzimidazol-2-ylamino)methyl]-1-methylquinoline-4-one-3-ylcarbonylamino]-2-((2,4,6-trimethylphenyl)sulfonylamino)propionic acid, 3-[7-[(4,5-dimethylimidazol-2-ylamino)methyl]-1-trifluoromethylquinoline-4-one-3-ylcarbonylamino]-2-((2,6-dichlorophenyl)sulfonylamino)propionic acid, 3-[7-(2-aminopyridin-6-yl)-1-phenylquinoline-4-one-3-ylcarbonylamino]-2-((2,4,6-trimethylphenyl)sulfonylamino)propionic acid, 3-[7-[(7-azabenzimidazol-2-yl)methyl]-1-cyclohexylquinoline-4-one-3-ylcarbonylamino]-2-((2,4,6-trimethylphenyl)sulfonylamino)propionic acid, 3-[7-[(imidazol-2-ylamino)methyl]-1-cyclopropylquinoline-4-one-3-ylcarbon-ylamino]-2-((2,2-dichloro-4-phenylbenzene)sulfonylamino)propionic acid.

17. A method for the treatment of cancer metastasis, diabetic retinopathy, neovascular glaucoma, thrombosis, restenosis, osteoporosis, or macular degeneration which comprises administering to a host in need of such treatment a therapeutically effective amount of a compound of claim 1, 2, 3, 4, 5, 6, 7, 8, 9, 10, 11, 12, 13, 14, 15, or 16.

18. A pharmaceutical composition comprising a pharmaceutically acceptable carrier and a compound of claim 1, 2, 3, 4, 5, 7, 8, 9, 11, 10, 11, 12, 13, 14, 15, or 16.

* * * * *